US011084842B2

(12) United States Patent
Gu et al.

(10) Patent No.: US 11,084,842 B2
(45) Date of Patent: Aug. 10, 2021

(54) GLUCOPYRANOSYL DERIVATIVE AND USE THEREOF

(71) Applicant: SUNSHINE LAKE PHARMA CO., LTD., Guangdong (CN)

(72) Inventors: Zheng Gu, Dongguan (CN); Wuyong Wu, Dongguan (CN); Tong Qu, Dongguan (CN); Panpan Kang, Dongguan (CN); Zongyuan Zhang, Dongguan (CN); Weiming Huang, Dongguan (CN); Jianyu Liu, Dongguan (CN); Yingjun Zhang, Dongguan (CN)

(73) Assignee: SUNSHINE LAKE PHARMA CO., LTD., Dongguan (CN)

( * ) Notice: Subject to any disclaimer, the term of this patent is extended or adjusted under 35 U.S.C. 154(b) by 0 days.

(21) Appl. No.: 16/960,488

(22) PCT Filed: Jan. 22, 2019

(86) PCT No.: PCT/CN2019/072666
§ 371 (c)(1),
(2) Date: Jul. 7, 2020

(87) PCT Pub. No.: WO2019/144864
PCT Pub. Date: Aug. 1, 2019

(65) Prior Publication Data
US 2021/0061839 A1 Mar. 4, 2021

(30) Foreign Application Priority Data
Jan. 23, 2018 (CN) .......................... 201810063061.0

(51) Int. Cl.
*C07H 7/04* (2006.01)
*C07H 15/207* (2006.01)

(52) U.S. Cl.
CPC ............. *C07H 15/207* (2013.01); *C07H 7/04* (2013.01)

(58) Field of Classification Search
None
See application file for complete search history.

(56) References Cited

U.S. PATENT DOCUMENTS

| 7,973,012 B2 * | 7/2011 | Kakinuma ........... C07D 405/10 514/23 |
| 8,115,017 B2 | 2/2012 | Kakinuma et al. |
| 8,466,113 B2 | 6/2013 | Kakinuma et al. |
| 9,161,945 B2 | 10/2015 | Kakinuma et al. |
| 9,200,025 B2 | 12/2015 | Carson et al. |
| 9,688,710 B2 | 6/2017 | Carson et al. |
| 10,106,569 B2 | 10/2018 | Carson et al. |

FOREIGN PATENT DOCUMENTS

| WO | 2007/126117 A1 | 11/2007 | |
| WO | WO-2010095768 A1 * | 8/2010 | ............. A61P 43/00 |
| WO | 2012/023582 A1 | 2/2012 | |
| WO | 2017/221886 A1 | 12/2017 | |

OTHER PUBLICATIONS

Wolff, Manfred E. "Burger's Medicinal Chemistry, 5ed, Part I", John Wiley & Sons, 1995, pp. 975-977. (Year: 1995).*
Banker, G.S. et al, "Modern Pharmaceutics, 3ed.", Marcel Dekker, New York, 1996, p. 596 (Year: 1996).*
Adachi et al., Metabolism, vol. 49, No. 8, 2000, 990-995 (Year: 2000).*
Apr. 19, 2019 Search Report issued in International Patent Application No. PCT/CN2019/072666.
Apr. 19, 2019 Written Opinion of the International Searching Authority issued in International Patent Application No. PCT/CN2019/072666.

* cited by examiner

*Primary Examiner* — Traviss C McIntosh, III
(74) *Attorney, Agent, or Firm* — Oliff PLC

(57) ABSTRACT

A glucopyranosyl derivative as a sodium-dependent glucose transporters inhibitor, especially as a SGLT1 inhibitor, a pharmaceutically acceptable salt or a stereoisomer thereof, a pharmaceutical composition thereof, and the uses of the compound and pharmaceutical composition thereof in the preparation of drugs for the treatment of diabetes and diabetes-related diseases.

18 Claims, No Drawings

GLUCOPYRANOSYL DERIVATIVE AND USE THEREOF

CROSS-REFERENCE TO RELATED APPLICATIONS

This application claims priority to Chinese Patent Application Serial No 201810063061.0, filed on Jan. 23, 2018, which is hereby incorporated by reference in its entirety.

FIELD OF THE INVENTION

The present invention belongs to the field of medicine, and in particular relates to a glucopyranosyl derivative as a sodium-dependent glucose transporter (SGLTs) inhibitor especially as a SGLT1 inhibitor a method for preparing them, a pharmaceutical composition containing the derivative, and uses of the derivative and composition thereof. More specifically, it is use of the compound of Formula (I) or a pharmaceutically acceptable salt or a stereoisomer thereof or a pharmaceutical composition containing the compound in the manufacture of medicine for treating diabetes and diabetes related diseases.

BACKGROUND OF THE INVENTION

Diabetes is a common chronic disease, characterized by hyperglycemia. The onset of diabetes associates with insulin resistance in peripheral tissue, reduction of insulin in vivo and increase of gluconeogenesis in liver. When the disease cannot be controlled effectively through diet and exercise, insulin or oral hypoglycemic drugs for treatment are needed. At present, hypoglycemic drugs comprise biguanides, sulfonylureas, insulin sensitizers, glinides, α-glucosidase inhibitors and DPP-IV (dipeptidyl peptidase IV) inhibitors, etc. However, these current hypoglycemic drugs have shortcomings. Biguanides can cause lactic acidosis. Sulfonylureas can result in severe hypoglycemia. Improper use of the glinides can also cause hypoglycemia. Insulin sensitizers can lead to edema, heart failure and weight gain. α-Glucosidase inhibitors can cause abdominal bloating and diarrhea. DPP-IV inhibitors need to combine with metformin to achieve the desired effect of hypoglycemia. Therefore, there is an urgent need to develop safer, more effective and novel hypoglycemic agents.

It has been found by research that glucose transporter proteins are a class of carrier proteins embedded in the cell membrane for transporting glucose. Glucose must be in virtue of glucose transporter proteins to cross lipid bilayer structure of cell membranes. Glucose transporter proteins are divided into two categories. The first category is sodium-dependent glucose transporters (SGLTs), and the other category is glucose transporters (GLUTs). The two main family members of the SGLTs are SGLT1 and SGLT2. SGLT1 is mainly distributed in small intestine, kidney, heart and windpipe, predominantly expressed in the intestinal brush border and the distal S3 segment of the renal proximal tubule, and a few expressed in heart and windpipe, and transports glucose and galactose with a sodium to glucose ratio of 2:1. While SGLT2 is mainly distributed in kidney, predominantly expressed in the S1 segment of the renal proximal tubule, and transports glucose with a sodium to glucose ratio of 1:1. In biological bodies, glucose is transported by SGLTs through active transport against a concentration gradient with simultaneous energy consumption. While glucose is transported by GLUTs through facilitated diffusion along a concentration gradient without energy consumption in the transport process. Research indicates that normally plasma glucose is filtered in the kidney glomeruli in which 90% of glucose in the proximal S1 segment of the renal tubule is actively transported to epithelial cells by SGLT2 and 10% of glucose in the distal S3 segment of the renal tubule is actively transported to epithelial cells by SGLT1, and then transported to peripheral capillary network by GLUT of epithelial basement membrane accomplishing reabsorption of glucose by renal tubules. Hence, SGLTs is the first stage in regulation of glucose metabolism in cells, and an ideal target for treating diabetes effectively. Inhibiting SGLTs would not influence the normal anti-regulatory mechanism of glucose, which may cause the risk of hypoglycemia. Meanwhile, lowering blood glucose through an increase of renal glucose excretion could promote weight loss in obese patients. It has also been found by research that the mechanism of action of SGLTs inhibitors is independent of pancreatic β cell dysfunction or the degree of insulin resistance. Therefore, the efficacy of SGLTs inhibitors will not decrease with the severe insulin resistance or β-cell failure. It can be used alone or in combination with other hypoglycemic agents to better exert hypoglycemic effects through complementary mechanisms. Therefore, SGLTs inhibitors are ideal and novel hypoglycemic agents.

In addition, it has also been found by research that SGLTs inhibitors can be used for treating diabetes-related complications. Such as retinopathy, neuropathy, kidney disease, insulin resistance caused by glucose metabolic disorder, hyperinsulinemia, hyperlipidemia, obesity, and so on. Meanwhile, SGLTs inhibitors can also be used in combination with current therapeutic drugs, such as sulphonamides, thiazolidinedione, metformin, and insulin, etc, which can reduce the dose without impacting on the effectiveness of the medicine, and thereby avoid or reduce side effects, and improve patient compliance.

Currently, the research focuses on the discovery of selective SGLT2 inhibitors. Most of the SGLTs inhibitors currently in clinical trials, such as Dapagliflozin, canagliflozin, and empagliflozin, are selective SGLT2 inhibitors. However, results of the recent clinical trial indicate that SGLT1 inhibitors may exhibit greater benefits by inhibiting glucose reabsorption (U.S. Patent Application Publication No. US20110218159). It has been reported that there is insufficient absorption of glucose and galactose in patients with congenital SGLT1 abnormalities, which provides a factual basis for reducing the absorption of carbohydrates by inhibiting SGLT1 activity. In addition, in OLETF rats and rats with symptoms of streptozoon-induced diabetes, the mRNA and protein of SGLT1 increased, and absorption of glucose accelerated. Thus, blocking SGLT1 activity can inhibit the absorption of carbohydrates such as glucose in the small intestine, and subsequently prevent the rise of blood glucose level. In particular, postprandial hyperglycemia can be effectively normalized by delaying the absorption of glucose based on the above mechanism. In addition, SGLT1 inhibitors can also increase the level of glucagon-like peptide-1 (GLP-1) (Moriya, R. et al., Am J Physiol Endorinol Metab, 297: E1358-E1365 (2009)).

In summary, SGLTs inhibitors, especially compounds with excellent inhibitory activities of SGLT1, have good development prospects as novel therapeutic drugs for diabetes.

SUMMARY OF THE INVENTION

The present invention provides a compound having SGLTs inhibitory activity, especially having obvious SGLT1 inhibitory activity for the treatment of diabetes, insulin resistance, hyperglycemia, hyperinsulinemia, hyperlipidemia, obesity, X syndrome, atherosclerosis, cardiovascular disease, congestive heart failure, hypomagnesemia, hyponatremia, renal failure, disorders associated with blood concentration, constipation or hypertension, and their complications. The present invention also provides a method of preparing the compound, the pharmaceutical composition comprising the compound, and a method of using the compound and composition to prepare a drug for treating the above-mentioned diseases in mammals, particularly humans. Compared to existing analogous compounds, the compound of the present invention not only has better pharmacological activity, but also has more excellent metabolic kinetic properties in vivo and pharmacodynamic properties in vivo. Specifically, the compound of the present invention has excellent SGLT1 inhibitory activity and excellent hypoglycemic and urinary glucose excretion effects. Therefore, the compound provided by the present invention has more excellent druggability than the existing analogous compound.

In one aspect, the present invention relates to a compound having Formula (I) or a stereoisomer, a geometric isomer, a tautomer, an N-oxide, a solvate, a metabolite, a pharmaceutically acceptable salt, a dimer, a trimer or a prodrug thereof, cycloalkyl or 3-6 membered heterocyclyl, wherein each of the $C_{1-6}$ alkyl, $C_{2-6}$ alkenyl, $C_{2-6}$ alkynyl, $C_{1-6}$ alkoxy, $C_{1-6}$ alkylthiol, $C_{1-6}$ alkylamino, $C_{3-6}$ cycloalkyl and 3-6 membered heterocyclyl is independently unsubstituted or substituted with 1, 2, 3 or 4 substituents independently selected from D, F, Cl, Br, I, CN, $NO_2$, OH, $NH_2$, —C(=O)OH, —SH, =O, $C_{1-6}$ alkyl, $C_{1-6}$ haloalkyl, $C_{1-6}$ alkoxy, $C_{1-6}$ alkylamino or $C_{1-6}$ haloalkoxy;

$R^3$ is H, D, CN, =O, $C_{1-6}$ alkyl, $C_{2-6}$ alkenyl, $C_{2-6}$ alkynyl, $C_{1-6}$ alkoxy, $C_{1-6}$ alkylthio, $C_{1-6}$ alkylamino, $C_{3-6}$ cycloalkyl or 3-6 membered heterocyclyl, wherein each of the $C_{1-6}$ alkyl, $C_{2-6}$ alkenyl, $C_{2-6}$ alkynyl, $C_{1-6}$ alkoxy, $C_{1-6}$ alkylthiol, $C_{1-6}$ alkylamino, $C_{3-6}$ cycloalkyl and 3-6 membered heterocyclyl is independently unsubstituted or substituted with 1, 2, 3 or 4 substituents independently selected from D, F, Cl, Br, I, CN, $NO_2$, OH, $NH_2$, —C(=O)OH, —SH, =O, $C_{1-6}$ alkyl, $C_{1-6}$ haloalkyl, $C_{1-6}$ alkoxy, $C_{1-6}$ alkylamino or $C_{1-6}$ haloalkoxy;

or $R^2$ and $R^3$, together with the carbon atom they are attached to, form a $C_{3-6}$ carbocycle or 3-6 membered heterocyclic ring, wherein each of the $C_{3-6}$ carbocycle and the 3-6 membered heterocyclic ring is independently unsubstituted or substituted with 1, 2, 3 or 4 substituents independently selected from D, F, Cl, Br, I, CN, $NO_2$, OH, $NH_2$,

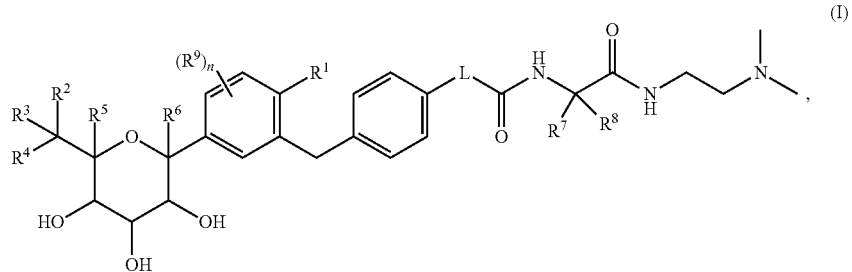

(I)

wherein,

L is $C_{1-8}$ alkylene or —Y—Z—, wherein the $C_{1-8}$ alkylene is unsubstituted or substituted with 1, 2, 3 or 4 substituents independently selected from D, F, Cl, Br, I, CN, $NO_2$, OH, $NH_2$, —C(=O)OH, —SH, $C_{1-6}$ alkyl, $C_{1-6}$ haloalkyl, $C_{1-6}$ alkoxy, $C_{1-6}$ alkylamino or $C_{1-6}$ haloalkoxy;

Y is —O—, —NH—, —S—, —S(=O)— or —S(=O)$_2$—;

Z is $C_{1-8}$ alkylene, wherein the $C_{1-8}$ alkylene is unsubstituted or substituted with 1, 2, 3 or 4 substituents independently selected from D, F, Cl, Br, I, CN, $NO_2$, OH, $NH_2$, —C(=O)OH, —SH, $C_{1-6}$ alkyl, $C_{1-6}$ haloalkyl, $C_{1-6}$ alkoxy, $C_{1-6}$ alkylamino or $C_{1-6}$ haloalkoxy;

$R^1$ is H, D, F, Cl, Br, I, OH, CN, $NO_2$, $NH_2$, $C_{1-6}$ alkyl, $C_{2-6}$ alkenyl, $C_{2-6}$ alkynyl, $C_{1-6}$ alkoxy, $C_{1-6}$ hydroxyalkyl, $C_{1-6}$ haloalkyl, $C_{1-6}$haloalkoxy, $C_{1-6}$ alkylamino, $C_{1-6}$ alkylthio, $C_{3-6}$ cycloalkyl or $C_{3-6}$ cycloalkyl-$C_{1-4}$ alkylene, wherein each of the $C_{1-6}$ alkyl, $C_{2-6}$ alkenyl, $C_{2-6}$ alkynyl, $C_{1-6}$ alkoxy, $C_{1-6}$ hydroxyalkyl, $C_{1-6}$ haloalkyl, $C_{1-6}$ haloalkoxy, $C_{1-6}$ alkylamino, $C_{1-6}$ alkylthio, $C_{3-6}$ cycloalkyl and $C_{3-6}$ cycloalkyl-$C_{1-4}$ alkylene is independently unsubstituted or substituted with 1, 2, 3 or 4 substituents independently selected from D, F, Cl, Br, I, CN, $NO_2$, OH, $NH_2$, —C(=O)OH, —SH, $C_{1-6}$ alkyl, $C_{1-6}$ haloalkyl, $C_{1-6}$ alkoxy, $C_{1-6}$ alkylamino or $C_{1-6}$ haloalkoxy;

$R^2$ is H, D, CN, =O, $C_{1-6}$ alkyl, $C_{2-6}$ alkenyl, $C_{2-6}$ alkynyl, $C_{1-6}$ alkoxy, $C_{1-6}$ alkylthio, $C_{1-6}$ alkylamino, $C_{3-6}$ —C(=O)OH, —SH, =O, $C_{1-6}$ alkyl, $C_{1-6}$ haloalkyl, $C_{1-6}$ alkoxy, $C_{1-6}$ alkylamino or $C_{1-6}$ haloalkoxy;

$R^4$ is H, D or —$OR^{4a}$;

$R^{4a}$ is H, D, $C_{1-6}$ alkyl, $C_{3-6}$ cycloalkyl, 3-6 membered heterocyclyl, $C_{6-10}$ aryl, 5-8 membered heteroaryl, $C_{3-6}$ cycloalkyl-$C_{1-4}$ alkylene, (3-6 membered heterocyclyl)-$C_{1-4}$ alkylene, $C_{6-10}$ aryl-$C_{1-4}$ alkylene or (5-8 membered heteroaryl)-$C_{1-4}$ alkylene, wherein each of the $C_{1-6}$ alkyl, $C_{3-6}$ cycloalkyl, 3-6 membered heterocyclyl, $C_{6-10}$ aryl, 5-8 membered heteroaryl, $C_{3-6}$ cycloalkyl-$C_{1-4}$ alkylene, (3-6 membered heterocyclyl)-$C_{1-4}$ alkylene, $C_{6-10}$ aryl-$C_{1-4}$ alkylene and (5-8 membered heteroaryl)-$C_{1-4}$ alkylene is independently unsubstituted or substituted with 1, 2, 3 or 4 substituents independently selected from D, F, Cl, Br, I, CN, $NO_2$, OH, $NH_2$, —C(=O)OH, —SH, =O, $C_{1-6}$ alkyl, $C_{1-6}$ haloalkyl, $C_{1-6}$ alkoxy, $C_{1-6}$ alkylamino or $C_{1-6}$ haloalkoxy;

each of $R^5$ and $R^6$ is independently H, D, F, Cl, Br, I, OH, CN, $NO_2$, $NH_2$, $C_{1-6}$ alkyl, $C_{1-6}$ alkoxy, $C_{3-6}$ cycloalkyl, $C_{3-6}$ cycloalkoxy, 3-6 membered heterocyclyl, $C_{6-10}$ aryl or 5-8 membered heteroaryl, wherein each of the $C_{1-6}$ alkyl, $C_{1-6}$ alkoxy, $C_{3-6}$ cycloalkyl, $C_{3-6}$ cycloalkoxy, 3-6 membered heterocyclyl, $C_{6-10}$ aryl, and 5-8 membered heteroaryl is independently unsubstituted or substituted with 1, 2, 3 or 4 substituents independently selected from D, F, Cl, Br, I, OH, CN, $NH_2$, =O, $C_{1-6}$ alkyl, $C_{2-6}$ alkenyl, $C_{2-6}$ alkynyl, $C_{1-6}$ haloalkyl, $C_{1-6}$ alkoxy or $C_{1-6}$ alkylamino;

or $R^5$ and $R^6$, together with the carbon atom they are attached to respectively, form a 5 membered heterocyclyl ring or 6 membered heterocyclyl ring, wherein each of the 5 membered heterocyclyl ring and 6 membered heterocyclyl ring is independently unsubstituted or substituted with 1, 2, 3 or 4 substituents independently selected from D, F, Cl, Br, I, OH, CN, NH$_2$, =O, C$_{1-6}$ alkyl, C$_{2-6}$ alkenyl, C$_{2-6}$ alkynyl, C$_{1-6}$ haloalkyl, C$_{1-6}$ alkoxy or C$_{1-6}$ alkylamino;

R$^9$ is H, D, F, Cl, Br, I, OH, CN, NO$_2$, NH$_2$, C$_{1-6}$ alkyl or C$_{1-6}$ alkoxy; each of R$^7$ and R$^8$ is independently H, D, F, Cl, Br, I, CN, NO$_2$, OH, NH$_2$, C$_{1-6}$ alkyl, C$_{1-6}$ alkoxy, C$_{1-6}$ alkylamino, C$_{1-6}$ haloalkyl, C$_{1-6}$ haloalkoxy, C$_{3-8}$ cycloalkyl, C$_{3-8}$ cycloalkyl-C$_{1-4}$ alkylene, 3-8 membered heterocyclyl, (3-8 membered heterocyclyl)-C$_{1-4}$ alkylene, C$_{6-10}$ aryl, C$_{6-10}$ aryl-C$_{1-4}$ alkylene, 5-8 membered heteroaryl or (5-8 membered heteroaryl)-C$_{1-4}$ alkylene, wherein each of the C$_{1-6}$ alkyl, C$_{1-6}$ alkoxy, C$_{1-6}$ alkylamino, C$_{1-6}$ haloalkyl, C$_{1-6}$ haloalkoxy, C$_{3-8}$ cycloalkyl, C$_{3-8}$ cycloalkyl-C$_{1-4}$ alkylene, 3-8 membered heterocyclyl, (3-8 membered heterocyclyl)-C$_{1-4}$ alkylene, C$_{6-10}$ aryl, C$_{6-10}$ aryl-C$_{1-4}$ alkylene, 5-8 membered heteroaryl and (5-8 membered heteroaryl)-C$_{1-4}$ alkylene is independently unsubstituted or substituted with 1, 2, 3 or 4 substituents independently selected from D, F, Cl, Br, I, CN, NO$_2$, OH, NH$_2$, =O, —C(=O)OH, —C(=O)NH$_2$, C$_{1-6}$ alkyl, C$_{2-6}$ alkenyl, C$_{2-6}$ alkynyl, C$_{1-6}$ haloalkyl, C$_{1-6}$ alkoxy, C$_{1-6}$ alkylamino or C$_{1-6}$ haloalkoxy;

or R$^7$ and R$^8$, together with the carbon atom they are attached to respectively, form a C$_{3-8}$ carbocycle, 3-8 membered heterocyclyl ring, a C$_{6-10}$ aromatic ring or a 5-8 membered heteroaryl ring, wherein each of the C$_{3-8}$ carbocycle, 3-8 membered heterocyclyl ring, C$_{6-10}$ aromatic ring or 5-8 membered heteroaryl ring is independently unsubstituted or substituted with 1, 2, 3 or 4 substituents independently selected from D, F, Cl, Br, I, CN, NO$_2$, OH, NH$_2$, =O, —C(=O)OH, —C(=O)NH$_2$, C$_{1-6}$ alkyl, C$_{2-6}$ alkenyl, C$_{2-6}$ alkynyl, C$_{1-6}$ haloalkyl, C$_{1-6}$ alkoxy, C$_{1-6}$ alkylamino or C$_{1-6}$ haloalkoxy;

n is 0, 1, 2 or 3.

In other embodiments, the present invention relates to a compound having Formula (II) or a stereoisomer, a geometric isomer, a tautomer, an N-oxide, a solvate, a metabolite, a pharmaceutically acceptable salt, a dimer, a trimer or a prodrug thereof, dently selected from D, F, Cl, Br, I, CN, NO$_2$, OH, NH$_2$, —C(=O)OH, —SH, C$_{1-4}$ alkyl, C$_{1-4}$ haloalkyl, C$_{1-4}$ alkoxy, C$_{1-4}$ alkylamino or C$_{1-4}$ haloalkoxy;

In still other embodiments, L is —CH$_2$—, —CH$_2$CH$_2$—, —CH$_2$CH$_2$CH$_2$—, —CH(CH$_3$)CH$_2$—, —CH$_2$(CH$_2$)$_2$CH$_2$—, —C(CH$_3$)$_2$CH$_2$—, —CH$_2$(CH$_2$)$_3$CH$_2$— or —CH$_2$(CH$_2$)$_4$CH$_2$—, wherein each of the —CH$_2$—, —CH$_2$CH$_2$—, —CH$_2$CH$_2$CH$_2$—, —CH(CH$_3$)CH$_2$—, —CH$_2$(CH$_2$)$_2$CH$_2$—, —C(CH$_3$)$_2$CH$_2$—, —CH$_2$(CH$_2$)$_3$CH$_2$— or —CH$_2$(CH$_2$)$_4$CH$_2$— is independently unsubstituted or substituted with 1, 2, 3 or 4 substituents independently selected from D, F, Cl, Br, I, CN, NO$_2$, OH, NH$_2$, —C(=O)OH, —SH, methyl, ethyl, n-propyl, isopropyl, trifluoromethyl, methoxy, ethoxy, methylamino, trifluoromethoxy or difluoromethoxy.

Y is —O—, —NH—, —S—, —S(=O)— or —S(=O)$_2$—;

Z is —CH$_2$—, —CH$_2$CH$_2$—, —CH$_2$CH$_2$CH$_2$—, —CH(CH$_3$)CH$_2$—, —CH$_2$(CH$_2$)$_2$CH$_2$—, —C(CH$_3$)$_2$CH$_2$—, —CH$_2$(CH$_2$)$_3$CH$_2$— or —CH$_2$(CH$_2$)$_4$CH$_2$—, wherein each of the —CH$_2$—, —CH$_2$CH$_2$—, —CH$_2$CH$_2$CH$_2$—, —CH(CH$_3$)CH$_2$—, —CH$_2$(CH$_2$)$_2$CH$_2$—, —C(CH$_3$)$_2$CH$_2$—, —CH$_2$(CH$_2$)$_3$CH$_2$— or —CH$_2$(CH$_2$)$_4$CH$_2$— is independently unsubstituted or substituted with 1, 2, 3 or 4 substituents independently selected from D, F, Cl, Br, I, CN, NO$_2$, OH, NH$_2$, —C(=O)OH, —SH, methyl, ethyl, n-propyl, isopropyl, trifluoromethyl, methoxy, ethoxy, methylamino, trifluoromethoxy or difluoromethoxy.

In some embodiments, le is H, D, F, Cl, Br, I, OH, CN, NO$_2$, NH$_2$, methyl, ethyl, n-propyl, isopropyl, propenyl, propynyl, methoxy, ethoxy, hydroxymethyl, trifluoromethyl, trifluoroethyl, monofluoromethyl, trifluoromethoxy, difluoromethoxy, methylamino, cyclopropyl, cyclobutyl, cyclopentyl, cyclohexyl or cyclopropyl-methylene, wherein each of the methyl, ethyl, n-propyl, isopropyl, propenyl, propynyl, methoxy, ethoxy, hydroxymethyl, trifluoroethyl, monofluoromethyl, difluoromethoxy, methylamino, cyclopropyl, cyclobutyl, cyclopentyl, cyclohexyl and cyclopropyl-methylene is independently unsubstituted or substituted with 1, 2, 3 or 4 substituents independently selected from D, F, Cl, Br, I, CN, NO$_2$, OH, NH$_2$, —C(=O)OH, —SH, methyl, ethyl,

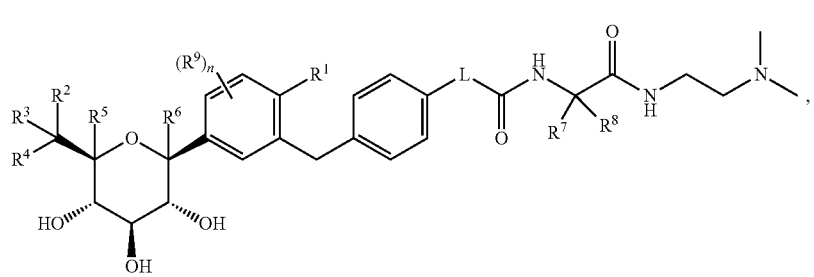

(II)

wherein R$^1$, R$^2$, R$^3$, R$^4$, R$^5$, R$^6$, R$^7$, R$^8$, R$^9$, L and n are as defined herein.

In other embodiments, L is C$_{1-6}$ alkylene or —Y—Z—, wherein the C$_{1-6}$ alkylene is unsubstituted or substituted with 1, 2, 3 or 4 substituents independently selected from D, F, Cl, Br, I, CN, NO$_2$, OH, NH$_2$, —C(=O)OH, —SH, C$_{1-4}$ alkyl, C$_{1-4}$ haloalkyl, C$_{1-4}$ alkoxy, C$_{1-4}$ alkylamino or C$_{1-4}$ haloalkoxy;

Y is —O—, —NH—, —S—, —S(=O)— or —S(=O)$_2$—;

Z is C$_{1-6}$ alkylene, wherein the C$_{1-6}$ alkylene is unsubstituted or substituted with 1, 2, 3 or 4 substituents indepenn-propyl, isopropyl, trifluoromethyl, methoxy, ethoxy, methylamino, trifluoromethoxy or difluoromethoxy.

In some embodiments, R$^2$ is H, D, CN, =O, C$_{1-4}$ alkyl, C$_{2-4}$ alkenyl, C$_{2-4}$ alkynyl, C$_{1-4}$ alkoxy, C$_{1-4}$ alkylthio, C$_{1-4}$ alkylamino, C$_{3-6}$ cycloalkyl or 5-6 membered heterocyclyl, wherein each of the C$_{1-4}$ alkyl, C$_{2-4}$ alkenyl, C$_{2-4}$ alkynyl, C$_{1-4}$ alkoxy, C$_{1-4}$ alkylthio, C$_{1-4}$ alkylamino, C$_{3-6}$ cycloalkyl or 5-6 membered heterocyclyl is independently unsubstituted or substituted with 1, 2, 3 or 4 substituents independently selected from D, F, Cl, Br, I, CN, NO$_2$, OH, NH$_2$, —C(=O)OH, —SH, =O, C$_{1-4}$ alkyl, C$_{1-4}$ haloalkyl, C$_{1-4}$ alkoxy, C$_{1-4}$ alkylamino or C$_{1-4}$ haloalkoxy;

$R^3$ is H, D, CN, =O, $C_{1-4}$ alkyl, $C_{2-4}$ alkenyl, $C_{2-4}$ alkynyl, $C_{1-4}$ alkoxy, $C_{1-4}$ alkylthio, $C_{1-4}$ alkylamino, $C_{3-6}$ cycloalkyl or 5-6 membered heterocyclyl, wherein each of the $C_{1-4}$ alkyl, $C_{2-4}$ alkenyl, $C_{2-4}$ alkynyl, $C_{1-4}$ alkoxy, $C_{1-4}$ alkylthio, $C_{1-4}$ alkylamino, $C_{3-6}$ cycloalkyl or 5-6 membered heterocyclyl is independently unsubstituted or substituted with 1, 2, 3 or 4 substituents independently selected from D, F, Cl, Br, I, CN, $NO_2$, OH, $NH_2$, —C(=O)OH, —SH, =O, $C_{1-4}$ alkyl, $C_{1-4}$ haloalkyl, $C_{1-4}$ alkoxy, $C_{1-4}$ alkylamino or $C_{1-4}$ haloalkoxy;

or $R^2$ and $R^3$, together with the carbon atom they are attached to, form a $C_{3-6}$ carbocycle or 5-6 membered heterocyclic ring, wherein each of the $C_{3-6}$ carbocycle and 5-6 membered heterocyclic ring is independently unsubstituted or substituted with 1, 2, 3 or 4 substituents independently selected from D, F, Cl, Br, I, CN, $NO_2$, OH, $NH_2$, —C(=O)OH, —SH, =O, $C_{1-4}$ alkyl, $C_{1-4}$ haloalkyl, $C_{1-4}$ alkoxy, $C_{1-4}$ alkylamino or $C_{1-4}$ haloalkoxy;

In still other embodiments, $R^2$ is H, D, CN, =O, methyl, ethyl, n-propyl, isopropyl, vinyl, propynyl, methoxy, ethoxy, methylthio, methylamino, cyclopropyl, cyclobutyl, cyclopentyl, cyclohexyl or 5-6 membered heterocyclyl, wherein each of the methyl, ethyl, n-propyl, isopropyl, vinyl, propynyl, methoxy, ethoxy, methylthio, methylamino, cyclopropyl, cyclobutyl, cyclopentyl, cyclohexyl or 5-6 membered heterocyclyl is independently unsubstituted or substituted with 1, 2, 3 or 4 substituents independently selected from D, F, Cl, Br, I, CN, $NO_2$, OH, $NH_2$, —C(=O)OH, —SH, =O, methyl, ethyl, n-propyl, isopropyl, trifluoromethyl, methoxy, ethoxy, methylamino, trifluoromethoxy or difluoromethoxy;

$R^3$ is H, D, CN, =O, methyl, ethyl, n-propyl, isopropyl, vinyl, propynyl, methoxy, ethoxy, methylthio, methylamino, cyclopropyl, cyclobutyl, cyclopentyl, cyclohexyl or 5-6 membered heterocyclyl, wherein each of the methyl, ethyl, n-propyl, isopropyl, vinyl, propynyl, methoxy, ethoxy, methylthio, methylamino, cyclopropyl, cyclobutyl, cyclopentyl, cyclohexyl or 5-6 membered heterocycly is independently unsubstituted or substituted with 1, 2, 3 or 4 substituents independently selected from D, F, Cl, Br, I, CN, $NO_2$, OH, $NH_2$, —C(=O)OH, —SH, =O, methyl, ethyl, n-propyl, isopropyl, trifluoromethyl, methoxy, ethoxy, methylamino, trifluoromethoxy or difluoromethoxy;

or $R^2$ and $R^3$, together with the carbon atom they are attached to, form a cyclopropane, cyclobutane, cyclopentane, cyclohexane or 5-6 membered heterocyclic ring, wherein each cyclopropane, cyclobutane, cyclopentane, cyclohexane or 5-6 membered heterocyclic ring is independently unsubstituted or substituted with 1, 2, 3 or 4 substituents independently selected from D, F, Cl, Br, I, CN, $NO_2$, OH, $NH_2$, —C(=O)OH, —SH, =O, methyl, ethyl, n-propyl, isopropyl, trifluoromethyl, methoxy, ethoxy, methyl amino, trifluoromethoxy or difluoromethoxy.

In other embodiments, $R^4$ is H, D or —$OR^{4a}$;

$R^{4a}$ is H, D, methyl, ethyl, n-propyl, isopropyl, cyclopropyl, cyclobutyl, cyclopentyl, cyclohexyl, tetrahydrofuranyl, tetrahydrothiophenyl, tetrahydropyranyl, piperidyl, morpholinyl, thiomorpholinyl, piperazinyl, phenyl, furyl, pyrrolyl, pyridyl, pyrazolyl, imidazolyl, triazolyl, tetrazolyl, oxazolyl, isoxazolyl, oxadiazolyl, 1,3,5-triazinyl, thiazolyl, thienyl, pyrazinyl, pyridazinyl, pyrimidinyl, $C_{3-6}$ cycloalkyl-$C_{1-2}$ alkylene, (5-6 membered heterocyclyl)-$C_{1-2}$ alkylene, phenyl-$C_{1-2}$ alkylene or (5-6 membered heteroaryl)-$C_{1-2}$ alkylene, wherein each of the methyl, ethyl, n-propyl, isopropyl, cyclopropyl, cyclobutyl, cyclopentyl, cyclohexyl, tetrahydrofuranyl, tetrahydrothiophenyl, tetrahydropyranyl, piperidyl, morpholinyl, thiomorpholinyl, piperazinyl, phenyl, furyl, pyrrolyl, pyridyl, pyrazolyl, imidazolyl, triazolyl, tetrazolyl, oxazolyl, isoxazolyl, oxadiazolyl, 1,3,5-triazinyl, thiazolyl, thienyl, pyrazinyl, pyridazinyl, pyrimidinyl, $C_{3-6}$ cycloalkyl-$C_{1-2}$ alkylene, (5-6 membered heterocyclyl)-$C_{1-2}$ alkylene, phenyl-$C_{1-2}$ alkylene or (5-6 membered heteroaryl)-$C_{1-2}$ alkylene is independently unsubstituted or substituted with 1, 2, 3 or 4 substituents independently selected from D, F, Cl, Br, I, CN, $NO_2$, OH, $NH_2$, —C(=O)OH, —SH, =O, methyl, ethyl, n-propyl, isopropyl, trifluoromethyl, methoxy, ethoxy, methylamino, trifluoromethoxy or difluoromethoxy.

In other embodiments, $R^9$ is H, D, F, Cl, Br, I, OH, CN, $NO_2$, $NH_2$, methyl, ethyl, n-propyl, isopropyl, methoxy or ethoxy.

In other embodiments, each of $R^7$ and $R^8$ is independently H, D, F, Cl, Br, I, CN, $NO_2$, OH, $NH_2$, $C_{1-4}$ alkyl, $C_{1-4}$ alkoxy, $C_{1-4}$ alkylamino, $C_{1-4}$ haloalkyl, $C_{1-4}$ haloalkoxy, $C_{3-6}$ cycloalkyl, $C_{3-6}$ cycloalkyl-$C_{1-2}$alkylene, 5-6 membered heterocyclyl, (5-6 membered heterocyclyl)-$C_{1-2}$ alkylene, $C_{6-10}$ aryl, $C_{6-10}$ aryl-$C_{1-2}$ alkylene, 5-6 membered heteroaryl or (5-6 membered heteroaryl)-$C_{1-2}$ alkylene, wherein each of the $C_{1-4}$ alkyl, $C_{1-4}$ alkoxy, $C_{1-4}$ alkylamino, $C_{1-4}$ haloalkyl, $C_{1-4}$ haloalkoxy, $C_{3-6}$ cycloalkyl, $C_{3-6}$ cycloalkyl-$C_{1-2}$ alkylene, 5-6 membered heterocyclyl, (5-6 membered heterocyclyl)-$C_{1-2}$ alkylene, $C_{6-10}$ aryl, $C_{6-10}$ aryl-$C_{1-2}$ alkylene, 5-6 membered heteroaryl or (5-6 membered heteroaryl)-$C_{1-2}$ alkylene is independently unsubstituted or substituted with 1, 2, 3 or 4 substituents independently selected from D, F, Cl, Br, I, CN, $NO_2$, OH, $NH_2$, =O, —C(=O)OH, —C(=O)$NH_2$, $C_{1-4}$ alkyl, $C_{2-4}$ alkenyl, $C_{2-4}$ alkynyl, $C_{1-4}$ haloalkyl, $C_{1-4}$ alkoxy, $C_{1-4}$ alkylamino or $C_{1-4}$ haloalkoxy;

or $R^7$ and $R^8$, together with the carbon atom they are attached to respectively, form a $C_{3-6}$ carbocycle, 5-6 membered heterocyclyl ring, $C_{6-10}$ aromatic ring or 5-6 membered heteroaryl ring, wherein each of the $C_{3-6}$ carbocycle, 5-6 membered heterocyclyl ring, $C_{6-10}$ aromatic ring or 5-6 membered heteroaryl ring is independently unsubstituted or substituted with 1, 2, 3 or 4 substituents independently selected from D, F, Cl, Br, I, CN, $NO_2$, OH, $NH_2$, =O, —C(=O)OH, —C(=O)$NH_2$, $C_{1-4}$ alkyl, $C_{2-4}$ alkenyl, $C_{2-4}$ alkynyl, $C_{1-4}$ haloalkyl, $C_{1-4}$ alkoxy, $C_{1-4}$ alkylamino or $C_{1-4}$ haloalkoxy.

In still other embodiments, each of $R^7$ and $R^8$ is independently H, D, F, Cl, Br, I, CN, $NO_2$, OH, $NH_2$, methyl, ethyl, n-propyl, isopropyl, n-butyl, tert-butyl, methoxy, ethoxy, methylamino, trifluoromethyl, trifluoromethoxy, difluoromethoxy, cyclopropyl, cyclobutyl, cyclopentyl, cyclohexyl, $C_{3-6}$ cycloalkyl-$C_{1-2}$ alkylene, pyrrolidinyl, tetrahydrofuranyl, tetrahydrothiophenyl, tetrahydropyranyl, tetrahydrothiopyranyl, piperidinyl, morpholinyl, thiomorpholinyl, piperazinyl, (5-6 membered heterocyclyl)-$C_{1-2}$ alkylene, phenyl, phenyl-$C_{1-2}$ alkylene, furyl, pyrrolyl, pyridyl, pyrazolyl, imidazolyl, triazolyl, tetrazolyl, oxazolyl, oxadiazolyl, 1,3,5-triazinyl, thiazolyl, thienyl, pyrazinyl, pyridazinyl, pyrimidinyl or (5-6 membered heteroaryl)-$C_{1-2}$ alkylene, wherein each of the methyl, ethyl, n-propyl, isopropyl, n-butyl, tert-butyl, methoxy, ethoxy, methylamino, trifluoromethyl, trifluoromethoxy, difluoromethoxy, cyclopropyl, cyclobutyl, cyclopentyl, cyclohexyl, $C_{3-6}$ cycloalkyl-$C_{1-2}$ alkylene, pyrrolidinyl, tetrahydrofuranyl, tetrahydrothiophenyl, tetrahydropyranyl, tetrahydrothiopyranyl, piperidinyl, morpholinyl, thiomorpholinyl, piperazinyl, (5-6 membered heterocyclyl)-$C_{1-2}$ alkylene, phenyl, phenyl-$C_{1-2}$ alkylene, furyl, pyrrolyl, pyridyl, pyrazolyl, imidazolyl, triazolyl, tetrazolyl, oxazolyl, oxadiazolyl, 1,3,5-triazinyl, thiazolyl, thienyl, pyrazinyl, pyridazinyl, pyrimidinyl or (5-6 membered heteroaryl)-$C_{1-2}$ alkylene is independently unsubstituted or substituted with 1, 2, 3 or 4 substituents independently selected from D, F, Cl, Br, I, CN, $NO_2$, OH, $NH_2$, =O, —C(=O)OH, —C(=O)$NH_2$, methyl, ethyl, n-propyl, isopropyl, vinyl, ethynyl, trifluoromethyl, methoxy, ethoxy, methyl amino, trifluoromethoxy or difluoromethoxy;

or $R^7$ and $R^8$, together with the carbon atom they are attached to respectively, form a cyclopropyl, cyclobutyl, cyclopentyl, cyclohexyl, pyrrolidine, tetrahydrofuran, tetrahydrothiophene, tetrahydropyran, tetrahydrothiopyran, piperidine, morpholine, thiomorpholine, piperazine, benzene ring, furan, pyrrole, pyridine, pyrazole, imidazole, triazole, tetrazole, oxazole, oxadiazole, 1,3,5-triazine, thiazole, thiophene, pyrazine, pyridazine or pyrimidine, wherein each of the cyclopropyl, cyclobutyl, cyclopentyl, cyclohexyl, pyrrolidine, tetrahydrofuran, tetrahydrothiophene, tetrahydropyran, tetrahydrothiopyran, piperidine, morpholine, thiomorpholine, piperazine, benzene ring, furan, pyrrole, pyridine, pyrazole, imidazole, triazole, tetrazole, oxazole, oxadiazole, 1,3,5-triazine, thiazole, thiophene, pyrazine, pyridazine or pyrimidine is independently unsubstituted or substituted with 1, 2, 3 or 4 substituents independently selected from D, F, Cl, Br, I, CN, $NO_2$, OH, $NH_2$, =O, —C(=O)OH, —C(=O)$NH_2$, methyl, ethyl, n-propyl, isopropyl, vinyl, ethynyl, trifluoromethyl, methoxy, ethoxy, methyl amino, trifluoromethoxy or difluoromethoxy.

In other embodiments, the present invention relates to a compound having Formula (III) or a stereoisomer, a geometric isomer, a tautomer, an N-oxide, a solvate, a metabolite, a pharmaceutically acceptable salt, a dimer, a trimer or a prodrug thereof,

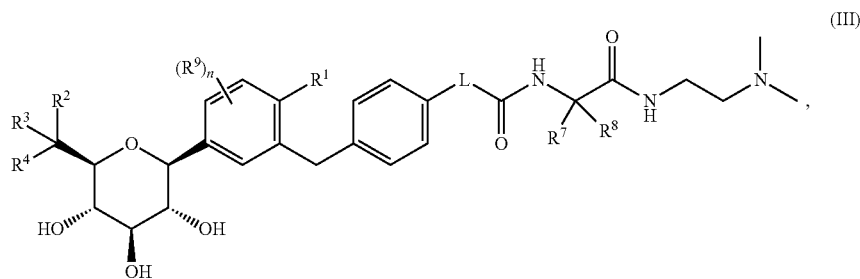

(III)

wherein $R^1$, $R^2$, $R^3$, $R^4$, $R^7$, $R^8$, $R^9$, L and n are as defined herein.

In other embodiments, the present invention relates to a compound having Formula (IV) or a stereoisomer, a geometric isomer, a tautomer, an N-oxide, a solvate, a metabolite, a pharmaceutically acceptable salt, a dimer, a trimer or a prodrug thereof,

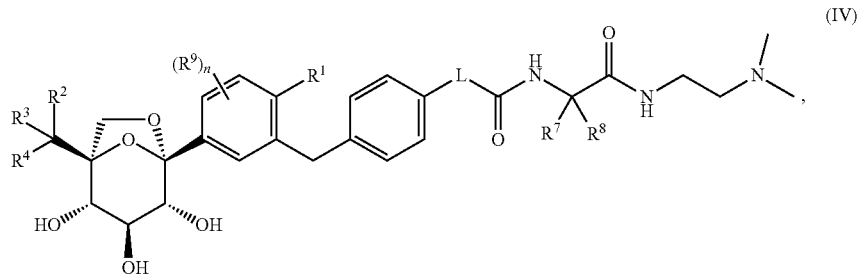

(IV)

wherein $R^1$, $R^2$, $R^3$, $R^4$, $R^7$, $R^8$, $R^9$, L and n are as defined herein.

In a further aspect, provided herein is a pharmaceutical composition comprising the compound disclosed herein.

In some embodiments, the pharmaceutical composition disclosed herein further comprises a pharmaceutically acceptable carrier, excipient, adjuvant, vehicle or any combination thereof.

In some embodiments, the pharmaceutical composition disclosed herein further comprises one or more additional therapeutic agents, wherein the additional therapeutic agent is selected from an anti-diabetic agent, an antihyperglycemic agent, an antiobesity agent, an antihypertensive agent, an appetite suppressant, a lipid-lowering agent or a combination thereof.

In other embodiments, the anti-diabetic agent and antihyperglycemic agent disclosed herein are independently selected from a SGLT2 inhibitor a biguanide, a sulfonylurea, a glucosidase inhibitor a PPAR agonist(a peroxisome proliferator activation receptor agonist), an αP2 inhibitor(an adipocyte fatty acid binding protein inhibitor), a PPARα/γ dual activator(a peroxisome proliferator-activated receptor α/γ double activator), a dipeptidyl peptidase IV inhibitor a glinide, an insulin, a glucagon-like peptide-1(GLP-1) inhibitor a PTP1B inhibitor(a protein tyrosine phosphatase 1B inhibitor), a glycogen phosphorylase inhibitor a glucose-6-phosphatase inhibitor or a combination thereof.

In other embodiments, the anti-obesity agent disclosed herein is selected from a central anti-obesity agent, a MCH (melanin-concentrating hormone) receptor antagonist, a neuropeptide Y receptor antagonist, and a cannabinoid receptor antagonist, a brain-gut peptide antagonist, a lipase inhibitor a β3 agonist, a 11β-HSD1 (11β hydroxysteroid dehydrogenase 1) inhibitor a DGAT-1 (diacylglycerol acyl transferase 1) inhibitor a cholecystokinin agonist, a feeding inhibitor or a combination thereof.

In other embodiments, the lipid-lowering agent disclosed herein is selected from an MTP inhibitor (microsomal triglyceride transfer protein inhibitor), an EIMGCoA reductase inhibitor (hydroxymethylglutaryl coenzyme A reductase inhibitor), a squalene synthase inhibitor a lipid-lowering agent of betabutyric acid (also known as a fibrate lipid-lowering agent), an ACAT inhibitor (an acetylcholesteryl acetyl transferase inhibitor), a lipoxygenase inhibitor a cholesterol absorption inhibitor an ileal Na (+)/bile acid cotransporter inhibitor an upregulator of LDL receptor activity, a lipid-lowering agent of niacin, a bile acid chelate or a combination thereof.

In still other embodiments, the lipid-lowering agent disclosed herein is pravastatin, simvastatin, atorvastatin, fluvastatin, cerivastatin, atavastatin, rosuvastatin or a combination thereof.

In other aspect, the invention relates to use of the compound or the pharmaceutical composition disclosed herein in the preparation of a medicament, wherein the medicament is used to inhibit SGLT1.

In a further aspect, the invention relates to use of the compound or the pharmaceutical composition disclosed herein in the preparation of a medicament, wherein the medicament is used to improve the intestinal environment.

In a further aspect, the invention relates to use of the compound or the pharmaceutical composition disclosed herein in the preparation of a medicament, wherein the medicament is used for preventing or treating diseases, lessening symptoms of the diseases or delaying progression or onset of the diseases, wherein the diseases are diabetes, diabetic complications, insulin resistance, hyperglycemia, hyperinsulinemia, hyperlipidemia, obesity, syndrome X, atherosclerosis, cardiovascular disease, congestive heart failure, hypomagnesemia, hyponatremia, renal failure, disorders associated with blood concentration, or hypertension.

In a further aspect, the invention relates to the compound or the pharmaceutical composition disclosed herein for use in inhibiting SGLT1, or improving the intestinal environment, or preventing or treating a disease, lessening symptoms of the disease or delaying progression or onset of the disease, wherein the disease is diabetes, diabetic complications, insulin resistance, hyperglycemia, hyperinsulinemia, hyperlipidemia, obesity, syndrome X, atherosclerosis, cardiovascular disease, congestive heart failure, hypomagnesemia, hyponatremia, renal failure, disorders associated with blood concentration, constipation or hypertension.

In a further aspect, the invention relates to a method of inhibiting SGLT1, or improving the intestinal environment, or preventing or treating a disease, lessening symptoms of the disease or delaying progression or onset of the disease, comprising administering a therapeutically effective amount of the compound or the pharmaceutical composition disclosed herein to the patient, wherein the disease is diabetes, diabetic complications, insulin resistance, hyperglycemia, hyperinsulinemia, hyperlipidemia, obesity, syndrome X, atherosclerosis, cardiovascular disease, congestive heart failure, hypomagnesemia, hyponatremia, renal failure, disorders associated with blood concentration, constipation or hypertension; wherein the diabetic complications are diabetic retinopathy, diabetic neuropathy or diabetic nephropathy; the hyperlipidemia is hypertriglyceridemia.

In some embodiments, the diabetic complications disclosed herein are diabetic retinopathy, diabetic neuropathy or diabetic nephropathy.

In some embodiments, the hyperlipidemia disclosed herein is hypertriglyceridemia.

The foregoing merely summarizes certain aspects disclosed herein and is not intended to be limiting in nature. These aspects and other aspects are described more fully below.

DETAILED DESCRIPTION OF THE INVENTION

The present invention provides a glucopyranosyl derivative, a preparation method thereof and application thereof in medicine. One Skilled in the art can learn from this article and make proper modification of the process parameters. Of particular note is that all similar substitutions and modifications to the skilled in the art is obvious, and they are deemed to be included in the present invention.

Definitions and General Terminology

Reference will now be made in detail to certain embodiments of the invention, examples of which are illustrated in the accompanying structures and formulas. The invention is intended to cover all alternatives, modifications, and equivalents which may be included within the scope of the present invention. One skilled in the art will recognize many methods and materials similar or equivalent to those described herein, which could be used in the practice of the present invention. The present invention is in no way limited to the methods and materials described herein. In the event that one or more of the incorporated literature, patents, and similar materials differs from or contradicts this application, including but not limited to defined terms, term usage, described techniques, or the like, this application controls.

It is further appreciated that certain features of the invention, which are, for clarity, described in the context of separate embodiments, can also be provided in combination in a single embodiment. Conversely, various features of the invention which are, for brevity, described in the context of a single embodiment, can also be provided separately or in any suitable subcombination.

Unless defined otherwise, all technical and scientific terms used herein have the same meaning as is commonly understood by one skilled in the art to which this invention belongs. All patents and publications referred to herein are incorporated by reference in their entirety. As used herein, the following definitions shall apply unless otherwise indicated. For purposes of this invention, the chemical elements are identified in accordance with the *Periodic Table of the Elements, CAS version, and the Handbook of Chemistry and Physics,* 75th Ed. 1994. Additionally, *general principles of organic chemistry* can be referred to "Organic Chemistry", Thomas Sorrell, University Science Books, Sausalito: 1999 and "*March's Advanced Organic Chemistry*", by Michael B. Smith and Jerry March, John Wiley & Sons, New York: 2007, the entire contents of which are hereby incorporated by reference.

The grammatical articles "a", "an" and "the", as used herein, are intended to include "at least one" or "one or more" unless otherwise indicated herein or clearly contradicted by the context. Thus, the articles used herein refer to the article of one or more than one (i.e., at least one) grammatical objects. By way of example, "a component" means one or more components, and thus, possibly, more than one component is contemplated and may be employed or used in an implementation of the described embodiments.

Unless otherwise stated, the terms used in the specification and claims of the invention have the following definitions.

The term "comprise" is an open expression, it means comprising the contents disclosed herein, but don't exclude other contents.

As described herein, compounds disclosed herein may optionally be substituted with one or more substituents, such as illustrated generally above, or as exemplified by particular classes, subclasses, and species of the invention. It should be understood that the terms "optionally substituted", "unsubstituted or substituted with a substituent" and "substituted or unsubstituted" can be used interchangeably. The term "optionally" or "optional" refers to an event or condition described subsequently may, but may not necessarily occur, and the description includes the circumstances in which the event or condition occurs and the circumstances in which the event or condition does not occur.

In general, the term "optionally" whether or not preceded by the term "substituted" means that one or more hydrogen atoms in the given structure are unsubstituted or substituted with specific substituents. Unless otherwise indicated, an optionally substituted group may have a substituent at each substitutable position of the group. When more than one position in a given structure can be substituted with more than one substituent selected from a specified group, the substituent may be either the same or different at each position. Wherein the substituent may be, but is not limited to, D, F, Cl, Br, I, CN, $NO_2$, OH, $NH_2$, OXO(=O), —C(=O)OH, —C(=O)$NH_2$, —SH, alkyl, haloalkyl, alkoxy, alkylamino, alkylthio, haloalkoxy, alkenyl, alkynyl, hydroxyalkyl, cycloalkyl, cycloalkoxy, cycloalkyl-alkylene, carbocyclyl, carbocyclyl-alkylene, heterocyclyl, heterocyclyl-alkylene, aryl, aryl-alkylene, heteroaryl or heteroaryl-alkylene.

Furthermore, what need to be explained is that the phrase "each . . . is independently", "each of . . . and . . . is independently" and " . . . is independent", unless otherwise stated, should be interchangeable and broadly understood. The specific options expressed by the same symbol are independent of each other in different groups; or the specific options expressed by the same symbol are independent of each other in same groups.

At various places in the present specification, substituents of compounds disclosed herein are disclosed in groups or in ranges. It is specifically intended that the invention include each and every individual subcombination of the members of such groups and ranges. For example, the term "$C_{1-6}$ alkyl" specifically refers to independently disclosed $C_1$ alkyl (methyl), $C_2$ alkyl (ethyl), $C_3$ alkyl, $C_4$ alkyl, $C_5$ alkyl, and $C_6$ alkyl; "$C_{3-8}$ cycloalkyl" refers to independently disclosed $C_3$ cycloalkyl (cyclopropyl), $C_4$ cycloalkyl (cyclobutyl), $C_5$ cycloalkyl (cyclopentyl), $C_6$ cycloalkyl (cyclohexyl), C cycloalkyl (cycloheptyl) and $C_8$ cycloalkyl (cyclooctyl).

At various places in the present specification, linking substituents are described. Where the structure clearly requires a linking group, the Markush variables listed for that group are understood to be linking groups. For example, if the structure requires a linking group and the Markush group definition for that variable lists "alkyl" or "aryl" then it is understood that the "alkyl" or "aryl" represents a linking alkylene group or arylene group, respectively.

As used herein, the term "alkyl" or "alkyl group" refers to a saturated linear or branched-chain monovalent hydrocarbon radical of 1 to 20 carbon atoms. Unless otherwise specified, the alkyl group contains 1 to 20 carbon atoms; in some embodiments, the alkyl group contains 1 to 12 carbon atoms; in some embodiments, the alkyl group contains 1 to 10 a carbon atoms; in other embodiments, the alkyl group contains 1 to 9 carbon atoms; in other embodiments, the alkyl group contains 1 to 8 carbon atoms, i.e., $C_{1-4}$ alkyl; in other embodiments, the alkyl group contains 1 to 6 carbon atoms, i.e., $C_{1-8}$ alkyl; in other embodiments, the alkyl group contains 1 to 4 carbon atoms, i.e., $C_{1-4}$ alkyl; in other embodiments, the alkyl group contains 1 to 3 carbon atoms, i.e., $C_{1-3}$ alkyl; in other embodiments, the alkyl group contains 1 to 2 carbon atoms, i.e., $C_{1-2}$ alkyl. Some non-limiting examples of the alkyl group include, methyl (Me, —$CH_3$), ethyl (Et, —$CH_2CH_3$), n-propyl (n-Pr, —$CH_2CH_2CH_3$), isopropyl (i-Pr, —$CH(CH_3)_2$), n-butyl (n-Bu, —$CH_2CH_2CH_2CH_3$), isobutyl (i-Bu, —$CH_2CH(CH_3)_2$), sec-butyl (s-Bu, —$CH(CH_3)CH_2CH_3$), tert-butyl (t-Bu, —$C(CH_3)_3$), n-pentyl (—$CH_2CH_2CH_2CH_2CH_3$), 2-pentyl (—$CH(CH_3)CH_2CH_2CH_3$), 3-pentyl (—$CH(CH_2CH_3)_2$), 2-methyl-2-butyl (—$C(CH_3)_2CH_2CH_3$), 3-methyl-2-butyl (—$CH(CH_3)CH(CH_3)_2$), 3-methyl-1-butyl (—$CH_2CH_2CH(CH_3)_2$), 2-methyl-1-butyl (—$CH_2CH(CH_3)CH_2CH_3$), n-hexyl (—$CH_2CH_2CH_2CH_2CH_2CH_3$), 2-hexyl (—$CH(CH_3)CH_2CH_2CH_2CH_3$), 3-hexyl (—$CH(CH_2CH_3)(CH_2CH_2CH_3)$), 2-methyl-2-pentyl (—$C(CH_3)_2CH_2CH_2CH_3$), 3-methyl-2-pentyl (—$CH(CH_3)CH(CH_3)CH_2CH_3$), 4-methyl-2-pentyl (—$CH(CH_3)CH_2CH(CH_3)_2$), 3-methyl-3-pentyl (—$C(CH_3)(CH_2CH_3)_2$), 2-methyl-3-pentyl (—$CH(CH_2CH_3)CH(CH_3)_2$), 2,3-dimethyl-2-butyl (—$C(CH_3)_2CH(CH_3)_2$), 3,3-dimethyl-2-butyl (—$CH(CH_3)C(CH_3)_3$, n-heptyl, n-octyl, etc. Wherein, the alkyl group may be optionally substituted with one or more substituents disclosed herein.

As used herein, the term "alkyl" or the prefix "alk-" is inclusive of both straight chain and branched saturated carbon chain.

The term "alkylene" refers to a saturated divalent hydrocarbon group derived from saturated straight or branched-chain hydrocarbon radical by the removal of two hydrogen atoms. Unless otherwise specified, the alkylene group contains 1 to 12 carbon atoms. In some embodiments, the alkylene group contains 1 to 8 carbon atoms; in other embodiments, the alkylene group contains 1 to 6 carbon atoms; in still other embodiments, the alkylene group contains 1 to 4 carbon atoms; in still other embodiments, the alkylene group contains 1 to 3 carbon atoms; in yet other embodiments, the alkylene group contains 1 to 2 carbon atoms. Such embodiments include methylene (—CH$_2$—), ethylidene (including —CH$_2$CH$_2$— or —CH(CH$_3$)—), isopropylidene (including —CH(CH$_3$)CH$_2$— or —C(CH$_3$)$_2$—), n-propylidene (including —CH$_2$CH$_2$CH$_2$—, —CH(CH$_2$CH$_3$)— or —CH$_2$CH(CH$_3$)—), n-butylidene (including —CH$_2$(CH$_2$)$_2$CH$_2$—, —CH(CH$_2$CH$_2$CH$_3$)—, —CH$_2$CH(CH$_2$CH$_3$)—, —CH$_2$CH$_2$CH(CH$_3$)— or —CH(CH$_3$)CH(CH$_3$)—), tert-butylidene(including —CH(CH(CH$_3$)$_2$)—, —CH$_2$CH(CH$_3$)CH$_2$— or —CH$_2$C(CH$_3$)$_2$—), pentylidene (e.g., —CH$_2$(CH$_2$)$_3$CH$_2$—), hexylidene (e.g., —CH$_2$(CH$_2$)$_4$CH$_2$—), and the like. Wherein, the alkylene may be optionally substituted with one or more substituents disclosed herein.

The term "alkenyl" refers to a linear or branched-chain monovalent hydrocarbon radical of 2 to 12 carbon atoms with at least one site of unsaturation, i.e., a carbon-carbon sp$^2$ double bond, wherein the alkenyl group may be optionally substituted independently with one or more substituents described herein, and includes radicals having "cis" and "trans" orientations, or alternatively, "F" and "Z" orientations. In some embodiments, the alkenyl group contains 2 to 8 carbon atoms; in other embodiments, the alkenyl group contains 2 to 6 carbon atoms; in still other embodiments, the alkenyl group contains 2 to 4 carbon atoms. Examples of the alkenyl group include, but are not limited to, vinyl (—CH=CH$_2$), propenyl (—CH$_2$CH=CH$_2$, —CH=CHCH$_3$), butenyl (—CH=CHCH$_2$CH$_3$, —CH$_2$CH=CHCH$_3$, —CH$_2$CH$_2$CH=CH$_2$, —CH=C(CH$_3$)$_2$, —CH=C(CH$_3$)$_2$, —CH$_2$C(CH$_3$)=CH$_2$), pentenyl (—CH$_2$CH$_2$CH$_2$CH=CH$_2$, —CH$_2$CH$_2$CH=CHCH$_3$, —CH$_2$CH$_2$CH=CHCH$_3$, —CH$_2$CH=CHCH$_2$CH$_3$, —CH=CHCH$_2$CH$_2$CH$_3$, —CH$_2$CH$_2$C(CH$_3$)=CH$_2$, —CH$_2$CH=C(CH$_3$)$_2$, —CH=CHCH(CH$_3$)$_2$, —C(CH$_2$CH$_3$)=CHCH$_3$, —CH(CH$_2$CH$_3$)CH=CH$_2$), etc.

The term "alkynyl" refers to a linear or branched-chain monovalent hydrocarbon radical of 2 to 12 carbon atoms with at least one site of unsaturation, i.e., a carbon-carbon, sp triple bond. In some embodiments, the alkynyl group contains 2 to 8 carbon atoms; in other embodiments, the alkynyl contains 2 to 6 carbon atoms; in still other embodiments, the alkynyl contains 2 to 4 carbon atoms. Some non-limiting examples of the alkynyl group include ethynyl (—C≡CH), 1-propynyl (CH$_3$C≡C—), propargyl (—CH$_2$C≡CH), 1-butynyl, 2-butynyl, 1-pentynyl, 2-pentynyl, 3-methyl-1-butynyl, 1-hexynyl, 1-heptynyl and 1-octynyl, etc. The alkynyl group may be optionally and independently substituted with one or more substituents disclosed herein.

The term "alkoxy" or "alkyl-oxy" refers to an alkyl group attached to the rest of the molecule via an oxygen atom, i.e., alkyl-O—, wherein the alkyl group are as defined herein. In some embodiments, the alkoxy group contains 1 to 20 carbon atoms; in other embodiments, the alkoxy group contains 1 to 10 carbon atoms; in still other embodiments, the alkoxy group contains 1 to 8 carbon atoms; in still other embodiments, the alkoxy group contains 1 to 6 carbon atoms; in still other embodiments, the alkoxy group contains 1 to 4 carbon atoms; in still other embodiments, the alkoxy group contains 1-3 carbon atoms; in still other embodiments, the alkoxy group contains 1-2 carbon atoms.

Some non-limiting examples of the alkoxy group include methoxy (MeO, —OCH$_3$), ethoxy (EtO, —OCH$_2$CH$_3$), 1-propoxy (n-PrO, n-propoxy, —OCH2CH$_2$CH$_3$), 2-propoxy (i-PrO, i-propoxy, —OCH(CH$_3$)$_2$), 1-butoxy (n-BuO, n-butoxy, —OCH$_2$CH$_2$CH$_2$CH$_3$), 2-methyl-1-propoxy (i-BuO, i-butoxy, —OCH$_2$CH(CH$_3$)$_2$), 2-butoxy (s-BuO, s-butoxy, —OCH(CH$_3$)CH$_2$CH$_3$), 2-methyl-2-propoxy (t-BuO, t-butoxy, —OC(CH$_3$)$_3$), 1-pentoxy (n-pentoxy, —OCH$_2$CH$_2$CH$_2$CH$_2$CH$_3$), 2-pentoxy (—OCH(CH$_3$)CH$_2$CH$_2$CH$_3$), 3-pentoxy (—OCH(CH$_2$CH$_3$)$_2$), 2-methyl-2-butoxy (—OC(CH$_3$)$_2$CH$_2$CH$_3$), 3-methyl-2-butoxy (—OCH(CH$_3$)CH(CH$_3$)$_2$), 3-methyl-1-butoxy (—OCH$_2$CH$_2$CH(CH$_3$)$_2$), 2-methyl-1-butoxy (—OCH$_2$CH(CH$_3$)CH$_2$CH$_3$), and the like, wherein the alkoxy group may be independently unsubstituted or substituted with one or more substituents described herein.

The term "alkylthio" refers to an alkyl group attached to the rest of the molecule via a sulfur atom, i.e., alkyl-S—, wherein the alkyl group has the meaning as described herein. In some embodiments, the alkylthio group contains 1-6 carbon atoms; in other embodiments, the alkylthio group contains 1 to 4 carbon atoms; in still other embodiments, the alkylthio group contains 1 to 3 carbon atoms; in still other embodiments, the alkylthio group contains 1 to 2 carbon atoms. Some non-limiting examples of the alkylthio group include methylthio, ethylthio, etc. The alkylthio group may be optionally substituted with one or more substituents disclosed herein.

The term "alkylamino" or "alkyl amino" refers to "N-alkylamino" and "N,N-dialkylamino", wherein the amino groups are independently substituted with one or two alkyl radicals, respectively. In some embodiments, the alkylamino is a lower alkyl amino group having one or two $C_{1-6}$ alkyl attached to nitrogen atom. In other embodiments, the alkylamino is a lower $C_{1-4}$ alkyl amino group. In other embodiments, the alkylamino is a lower $C_{1-3}$ alkyl amino group. In other embodiments, the alkylamino is a lower $C_{1-2}$ alkyl amino group. Some examples of suitable alkylamino radical include monoalkylamino or dialkylamino, but are not limited to, N-methylamino, N-ethylamino, N,N-dimethylamino and N,N-diethylamino, and the like. Wherein the alkylamino group may be optionally substituted with one or more substituents disclosed herein.

The term "haloalkyl" refers to an alkyl group substituted with one or more halogen atoms. In some embodiments, the haloalkyl group contains 1 to 10 carbon atoms. In other embodiments, the haloalkyl group contains 1 to 8 carbon atoms. In still other embodiments, the haloalkyl group contains 1 to 6 carbon atoms. In still other embodiments, the haloalkyl group contains 1 to 4 carbon atoms. In yet other embodiments, the haloalkyl group contains 1 to 3 carbon atoms. In yet other embodiments, the haloalkyl group contains 1 to 2 carbon atoms. Some non-limiting examples of the haloalkyl include fluoromethyl (—CH$_2$F), difluoromethyl (—CHF$_2$), trifluoromethyl (—CF$_3$), fluoroethyl (—CHFCH$_3$, —CH$_2$CH$_2$F), difluoroethyl (—CF$_2$CH$_3$, —CFHCFH$_2$, —CH$_2$CHF$_2$), perfluoroethyl, fluoropropyl (—CHFCH$_2$CH$_3$, —CH$_2$CHFCH$_3$, —CH$_2$CH$_2$CH$_2$F), difluoropropyl (—CF$_2$CH$_2$CH$_3$, —CFHCFHCH$_3$, —CH$_2$CH$_2$CHF$_2$, —CH$_2$CF$_2$CH$_3$, —CH$_2$CHFCH$_2$F), trifluoropropyl, 1,1-dichloroethyl, 1,2-dichloropropyl, and the like. The haloalkyl group is optionally substituted with one or more substituents described herein.

The term "haloalkoxy" refers to an alkoxy group substituted with one or more halogen substitutes. In some embodiments, the haloalkoxy group contains 1 to 10 carbon atoms. In other embodiments, the haloalkoxy group contains 1 to 8 carbon atoms. In still other embodiments, the haloalkoxy group contains 1 to 6 carbon atoms. In still other embodiments, the haloalkoxy group contains 1 to 4 carbon atoms. In yet other embodiments, the haloalkoxy group contains 1 to 3 carbon atoms. In yet other embodiments, the haloalkoxy group contains 1 to 2 carbon atoms. Some non-limiting examples of the haloalkoxy group include trifluoromethoxy, difluoromethoxy, etc. The haloalkoxy group is optionally substituted with one or more substituents described herein.

The term "hydroxy alkyl" or "hydroxyalkyl" refers to an alkyl group having one or more hydroxy substituents, wherein the alkyl group are as defined herein. In some embodiments, the hydroxyalkyl group contains 1 to 6 carbon atoms. In other embodiments, the hydroxy alkyl group contains 1 to 4 carbon atoms. In still other embodiments, the hydroxy alkyl group contains 1 to 3 carbon atoms. In yet other embodiments, the hydroxy alkyl group contains 1 to 2 carbon atoms. Some non-limiting examples of the hydroxyalkyl include hydroxymethyl, 2-hydroxyethyl (—$CH_2CH_2OH$), 1-hydroxyethyl (—$CHOHCH_3$), 1,2-dihydroxyethyl (—$CHOHCH_2OH$), 2,3-dihydroxypropyl (—$CH_2CHOHCH_2OH$), 1-hydroxypropyl (—$CH_2CH_2CH_2OH$), 2-hydroxypropyl, 3-hydroxypropyl, hydroxybutyl, and the like. The hydroxyalkyl group is optionally substituted with one or more substituents described herein.

The term "cycloalkyl" refers to a saturated monocyclic, bicyclic or tricyclic ring system having one or more attachment points attached to the rest of the molecule and 3 to 12 ring carbon atoms. Wherein, in some embodiments, the cycloalkyl is a ring system containing 3 to 10 ring carbon atoms; in other embodiments, the cycloalkyl is a ring system containing 3 to 8 ring carbon atoms; in other embodiments, the cycloalkyl is a ring system containing 5 to 8 ring carbon atoms; in other embodiments, the cycloalkyl group is a ring system containing 3 to 6 ring carbon atoms; in other embodiments, the cycloalkyl is a ring system containing 5 to 6 ring carbon atoms. Some non-limiting examples of the cycloalkyl include cyclopropyl, cyclobutyl, cyclopentyl and cyclohexyl. The cycloalkyl group may be optionally substituted with one or more substituents disclosed herein.

The term "cycloalkyloxy" refers to a cycloalkyl group attached to the rest of the molecule through an oxygen atom, i.e., cycloalkyl-O—, wherein the cycloalkyl is as defined herein. In some embodiments, the cycloalkoxy group contains 3 to 12 ring carbon atoms; in other embodiments, the cycloalkoxy group contains 3 to 8 ring carbon atoms; in still other embodiments, the cycloalkoxy group contains 3 to 6 ring carbon atoms. Some non-limiting examples of the cycloalkoxy include cyclopropoxy, cyclobutoxy, and the like. The cycloalkoxy group may be optionally substituted with one or more substituents disclosed herein.

The term "carbocyclyl" as used alone or as a large part of "carbocyclylalkyl" or "carbocyclylalkoxy" refers to a non-aromatic carbocyclic ring system which is saturated or contains one or more unsaturated units, 3 to 14 ring carbon atoms, but not any aromatic ring. The terms "carbocyclic ring", "carbocyclyl" or "carbocyclic" are used interchangeably herein. In some embodiments, the number of ring carbon atoms of the carbocyclic ring is 3 to 12; in other embodiments, the number of ring carbon atoms of the carbocyclic ring is 3 to 10; in other embodiments, the number of ring carbon atoms of the carbocyclic ring is 3 to 8; in other embodiments, the number of ring carbon atoms of the carbocyclic ring is 3 to 6; in other embodiments, the number of ring carbon atoms of the carbocyclic ring is 5 to 6; in other embodiments, the number of ring carbon atoms of the carbocyclic ring is 5 to 8. In other embodiments, the number of ring carbon atoms of the carbocyclic ring is 6 to 8. The "carbocyclyl" includes monocyclic, bicyclic or polycyclic fused, spiro or bridged carbocyclic ring systems, and also includes polycyclic ring systems in which the carbon ring can fuse with one or more non-aromatic carbon rings or one or more aromatic rings or combination thereof, wherein the connected atom groups or points are on the carbon ring. The bicyclic carbocyclyl group includes a bridged bicyclic carbocyclyl, a fused bicyclic carbocyclyl and a spiro bicyclic carbocyclyl, and the "fused" bicyclic ring systems contain two rings sharing two adjacent ring atoms. The bridged bicyclic group includes two rings that share 2, 3 or 4 adjacent ring atoms. The spiro-ring system shares one ring atom. The suitable carbocyclyl group includes, but is not limited to, cycloalkyl, cycloalkenyl and cycloalkynyl. Some non-limiting examples of the carbocyclyl group include cyclopropyl, cyclobutyl, cyclopentyl, 1-cyclopent-1-enyl, 1-cyclopent-2-enyl, 1-cyclopent-3-enyl, cyclohexyl, 1-cyclohex-1-enyl, 1-cyclohex-2-enyl, 1-cyclohex-3-enyl, cyclohexadienyl, cycloheptyl, cyclooctyl, cyclononyl, cyclodecyl, cycloundecyl, cyclododecyl, and the like. The bridged carbocyclyl group includes, but is not limited to, bicyclo [2.2.2] octyl, bicyclo [2.2.1] heptyl, bicyclo [3.3.1] nonyl, bicyclo [3.2.3] nonyl, and the like. The carbocyclyl group is optionally substituted with one or more substituents described herein.

The term "heterocyclyl" as used alone or as a large part of "heterocyclylalkyl" or "heterocyclylalkoxy" refers to a saturated or partially unsaturated, non-aromatic monocyclic, bicyclic or tricyclic ring system containing 3 to 12 ring atoms of which at least one ring atom is selected from nitrogen, sulfur and oxygen atoms, wherein the heterocyclic group is non-aromatic and does not contain an aromatic ring, and the ring system has one or more connection points connected to the rest of the molecule. The term "heterocyclyl" includes monocyclic, bicyclic or polycyclic fused, spiro or bridged heterocyclic ring systems. The bicyclic heterocyclyl includes a bridged bicyclic heterocyclyl, a fused bicyclic heterocyclyl and a spiro bicyclic heterocyclyl. The terms "heterocyclyl" and "heterocycle" are used interchangeably herein. Unless otherwise specified, the heterocyclyl may be carbon-based or nitrogen-based, and the —$CH_2$— group can be optionally replaced by —C(=O)—. The sulfur atom of the ring can be optionally oxidized to an S-oxide. The nitrogen atom of the ring can be optionally oxidized to an N-oxygen compound. In some embodiments, the heterocyclyl is a ring system of 3-8 ring atoms; in other embodiments, the heterocyclyl is a ring system of 3-6 ring atoms; in other embodiments, the heterocyclyl is a ring system of 5 to 7 ring atoms; in other embodiments, the heterocyclyl is a ring system of 5 to 10 ring atoms; in other embodiments, the heterocyclyl is a ring system of 5 to 8 ring atoms; in other embodiments, the heterocyclyl is a ring system of 6 to 8 ring atoms; in other embodiments, the heterocyclyl is a ring system of 5 to 6 ring atoms; in other embodiments, the heterocyclyl is a ring system of 4 ring atoms; in other embodiments, the heterocyclyl is a ring system of 5 ring atoms; in other embodiments, the heterocyclyl is a ring system composed of 6 ring atoms; in other embodiments, the heterocyclyl is a ring system of 7 ring atoms; in other embodiments, the heterocyclyl is a ring system of 8 ring atoms.

Some non-limiting examples of the heterocyclyl include oxiranyl, azetidinyl, oxetanyl, thioheterobutyl, pyrrolidinyl, 2-pyrrolinyl, 3-pyrrolinyl, pyrazolinyl, pyrazolidinyl, imidazolinyl, imidazolidinyl, tetrahydrofuranyl, dihydrofuranyl, tetrahydrothiophenyl, dihydrothienyl, 1,3-dioxocyclopentyl, dithiacyclopentyl, tetrahydropyranyl, dihydrogenpyranyl, 2H-pyranyl, 4H-pyranyl, tetrahydrothiopyranyl, piperidinyl, morpholinyl, thiomorpholinyl, piperazinyl, dioxoalkyl, dithiaalkyl, thioxanyl, homopiperazinyl, homopiperidinyl, oxepanyl, thiacycloheptanyl, tetrahydropyrrolyl, dihydropyrrolyl, tetrahydropyridyl, tetrahydropyrimidinyl, tetra hydropyrazinyl, tetrahydropyridazinyl. Some non-limiting examples of —CH$_2$— group in the heterocyclyl include 2-oxopyrrolidinyl, oxo-1,3-thiazolidinyl, 2-piperidinonyl, 3,5-dioxopiperidinyl, pyrimidinedionyl, and the like. Some non-limited examples of the sulfur atom oxidized in the heterocyclyl include sulfolanyl and 1,1-dioxothiomorpholinyl. The bridged heterocyclyl groups include, but are not limited to, 2-oxabicyclo[2.2.2]octyl, 1-azabicyclo[2.2.2]octyl, 3-azabicyclo[3.2.1]octyl, and the like. The heterocyclyl group may be optionally substituted with one or more substituents disclosed herein.

The term "m-membered", wherein m is an integer, typically describes the number of ring-forming atoms in a moiety which the number of ring-forming atoms is m. For example, piperidinyl is a heterocyclyl consisting of 6 ring atoms and 1,2,3,4-tetralyl is a carbocyclyl group consisting of 10 ring atoms.

The term "aryl" as used alone or as a large part of "arylalkyl" or "arylalkoxy" refers to monocyclic, bicyclic and tricyclic, aromatic carbocyclic ring systems, having a total of 6 to 14 ring atoms, or 6 to 12 ring atoms, or 6 to 10 ring atoms, wherein each ring contains 3 to 7 ring atoms and has one or more attachment points attached to the rest of the molecule. The term "aryl" may be used interchangeably with the term "aryl ring" or "aromatic ring". For example, the aryl group may include phenyl, naphthyl and anthryl. The aryl group may be optionally substituted with one or more substituents disclosed herein.

The term "heteroaryl" as used alone or as a large part of "heteroarylalkyl" or "heteroarylalkoxy" refers to monocyclic, bicyclic and tricyclic, aromatic systems having a total of 5 to 16 ring atoms, wherein each ring contains 5 to 7 ring atoms and at least one ring in the system is aromatic. Meanwhile, the heteroaryl has one or more attachment points attached to the rest of the molecule. Unless otherwise stated, the heteroaryl group can be attached to the rest of the molecule (e.g., the major structure in the formula) through any reasonable site (which can be C in CH, or N in NH). When the heteroaryl group contains —CH$_2$— group, the —CH$_2$— group can be optionally replaced by —C(=O)— group. The term "heteroaryl" and "heteroaromatic ring" or "heteroaromatic compound" can be used interchangeably herein. In some embodiments, the heteroaryl is a 5 to 14 membered heteroaryl containing 1, 2, 3 or 4 heteroatoms independently selected from O, S and N. In other embodiments, the heteroaryl is a 5 to 12 membered heteroaryl containing 1, 2, 3 or 4 heteroatoms independently selected from O, S and N; in other embodiments, the heteroaryl is a 5 to 10 membered heteroaryl containing 1, 2, 3 or 4 heteroatoms independently selected from O, S and N; in other embodiments, the heteroaryl is a 5 to 8 membered heteroaryl containing 1, 2, 3 or 4 heteroatoms independently selected from O, S and N; in other embodiments, the heteroaryl is a 5 to 7 membered heteroaryl containing 1, 2, 3 or 4 heteroatoms independently selected from O, S and N; in other embodiments, the heteroaryl is a 5 to 6 membered heteroaryl containing 1, 2, 3 or 4 heteroatoms independently selected from O, S and N; in other embodiments, the heteroaryl is a 5 membered heteroaryl containing 1, 2, 3 or 4 heteroatoms independently selected from O, S and N; in other embodiments, the heteroaryl is a 6 membered heteroaryl containing 1, 2, 3 or 4 heteroatoms independently selected from O, S and N.

Some non-limiting examples of the heteroaryl group include 2-furanyl, 3-furanyl, N-imidazolyl, 2-imidazolyl, 4-imidazolyl, 5-imidazolyl, 3-isoxazolyl, 4-isoxazolyl, 5-isoxazolyl, 2-oxazolyl, 4-oxazolyl, 5-oxazolyl, N-pyrrolyl, 2-pyrrolyl, 3-pyrrolyl, 2-pyridyl, 3-pyridyl, 4-pyridyl, 2-pyrimidinyl, 4-pyrimidinyl, 5-pyrimidinyl, pyridazinyl (e.g., 3-pyridazinyl), 2-thiazolyl, 4-thiazolyl, 5-thiazolyl, tetrazolyl (e.g., 5H-tetrazolyl, 2H-tetrazolyl), triazolyl (e.g., 2-triazolyl, 5-triazolyl, 4H-1,2,4-triazolyl, 1H-1,2,4-triazolyl, 1,2,3-triazolyl), 2-thienyl, 3-thienyl, pyrazolyl (e.g., 2-pyrazolyl and 3-pyrazolyl), isothiazolyl, 1,2,3-oxadiazolyl, 1,2,5-oxadiazolyl, 1,2,4-oxadiazolyl, 1,3,4-oxadiazolyl, 1,2,3-thiadiazolyl, 1,3,4-thiadiazolyl, 1,2,5-thiadiazolyl, pyrazinyl, 1,3,5-triazinyl; and also include, but are not limited to the following bicyclo: benzimidazolyl, benzofuryl, benzothiophenyl, indolyl (e.g., 2-indolyl), purinyl, quinolinyl (e.g., 2-quinolinyl, 3-quinolinyl, 4-quinolinyl), and isoquinolinyl (e.g., 1-isoquinolinyl, 3-isoquinolinyl or 4-isoquinolinyl), imidazo[1,2-a]pyridyl, pyrazolo[1,5-a]pyridyl, pyrazolo[1,5-a]pyrimidyl, imidazo[1,2-b]pyridazinyl, [1,2,4]triazolo[4,3-b]pyridazinyl, [1,2,4]triazolo[1,5-a]pyrimidinyl, or [1,2,4]triazolo[1,5-a]pyridyl, and the like. The heteroaryl group is optionally substituted with one or more substituents disclosed herein.

The term "heteroatom" refers to O, S, N, P and Si, including any oxidized form of S, N and P; a form of primary, secondary, tertiary and quaternary ammonium salts; or a form of which hydrogen of the nitrogen atom is substituted, for example, N (as in 3,4-dihydro-2H-pyrrolyl), NH (as in pyrrolidinyl) or NR (as in N-substituted pyrrolidinyl, R is a substituent described herein).

The term "halogen" refers to fluoro (F), chloro (Cl), bromo (Br), or iodo (I).

The term "nitro" refers to —NO$_2$.

The term "mercapto" refers to —SH.

The term "hydroxy" refers to —OH.

The term "amino" refers to —NH$_2$.

The term "cyano" refers to —CN.

The term "carboxy" refers to —C(=O)OH.

The term "carbonyl", whether used alone or in conjunction with other terms, denotes—(C=O)—.

The term "D" refers to deuteration, i.e., $^2$H.

As described herein, the ring system formed by connecting substituents to the center of the ring through a bond represents that substituents can be substituted at any substitutable position in the ring system. For example, the Formula a represents that any possible substituted position on the A ring may be optionally substituted with n R; when the A ring is a bicyclic structure, R may substitute at any substitutable positions on any ring; also for example, the Formula b represents that the substituent R may substitute at any possible substituted position on the phenyl ring, as shown in Formulas b-1 to b-3:

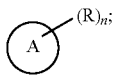

Formula a

Formula b

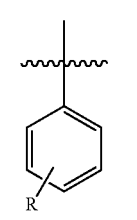

Formula b-1

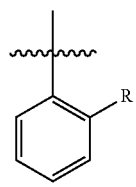

Formula b-2

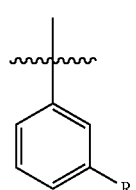

Formula b-3

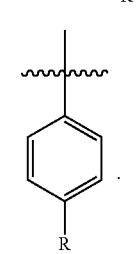

The term "protecting group" or "PG" refers to a substituent group that is employed to block or protect a particular functionality while other functional groups of the compound react. For example, an "amino-protecting group" refers to a substituent attached to an amino group that blocks or protects the amino functionality in the compound. Suitable amino-protecting groups include acetyl, trifluoroacetyl, t-butoxy-carbonyl (BOC, Boc), benzyloxycarbonyl (CBZ, Cbz) and 9-fluorenylmethylenoxy-carbonyl (Fmoc). Similarly, a "hydroxy-protecting group" refers to a substituent of a hydroxy group that blocks or protects the hydroxy functionality. Suitable protecting groups include, but are not limited to acetyl, benzoyl, benzyl, p-methoxybenzyl, silyl group, and the like. A "carboxy-protecting group" refers to a substituent of the carboxy group that blocks or protects the carboxy functionality. Common carboxy-protecting groups include —$CH_2CH_2SO_2Ph$, cyanoethyl, 2-(trimethylsilyl) ethyl, 2-(trimethylsilyl) ethoxy-methyl, 2-(p-toluenesulfonyl) ethyl, 2-(p-nitrophenylsulfonyl)-ethyl, 2-(diphenylphosphino)-ethyl, nitroethyl and the like. For a general description of protecting groups can be referred to in the literature: T. W. Greene, *Protective Groups in Organic Synthesis*, John Wiley & Sons, New York, 1991; and P. J. Kocienski, *Protecting Groups*, Thieme, Stuttgart, 2005.

The term "leaving group" or "LG" refers to an atom or a functional group that is detached from a larger molecule in a chemical reaction and is a term used in the nucleophilic substitution reaction and elimination reaction. In a nucleophilic substitution reaction, a reactant attacked by a nucleophile is referred to as a substrate, and an atom or group that are cleaved from a substrate molecule with a pair of electrons is referred to as a leaving group. Common leaving groups include, for example but are not limited to, halogen atom, ester group, sulfonate group, nitro group, azide group or hydroxyl group, and the like.

The term "pharmaceutically acceptable" means that the substance or composition must be chemically and/or toxicologically compatible with the other ingredients containing the formulation and/or the mammal treated therewith. Preferably, as used herein, the term "pharmaceutically acceptable" means approved by a regulatory agency of the Federal or a state government or listed in the U.S. Pharmacopeia or other generally recognized pharmacopeia for use in animals, and more particularly in humans.

The term "carrier" includes any solvent, dispersion medium, coating, surfactant, antioxidant, preservative (e.g., antibacterial, antifungal), isotonic agent, salt, drug stabilizer, binder, excipient, dispersing agents, lubricant, sweetener, flavoring agent, coloring agent, or combination thereof, which are known to those skilled in the art (e.g., *Remington's Pharmaceutical Sciences*, 18th Ed. Mack Printing Company, 1990, pp. 1289-1329). The use thereof in a therapeutic or pharmaceutical composition is encompassed except that any conventional carrier is incompatible with the active ingredient.

The term "pharmaceutical composition" refers to a mixture of one or more of the compounds described herein, or physiologically/pharmaceutically acceptable salts or prodrugs thereof, and other chemical components, wherein other chemical components are, for example physiologically/pharmaceutically acceptable carriers, excipients, diluents, binders, adjuvants and additional therapeutic agents like antidiabetic agents, antihyperglycemic agents, antiadipositas agents, antihypertensive agents, antiplatelet agents, antiatheroaclerotic agents, lipid-lowering agents and etc. The purpose of the pharmaceutical composition is to facilitate administration of a compound to an organism.

The term "prodrug" refers to a compound that is transformed in vivo into a compound of Formula (I). Such a transformation can be affected, for example, by hydrolysis of the prodrug form in blood or enzymatic transformation to the parent form in blood or tissue. The prodrug of the compound disclosed herein may be, for example, esters. Some common esters which have been utilized as prodrugs are phenyl esters, aliphatic ($C_1$-$C_{24}$) esters, acyloxymethyl esters, carbonates, carbamates and amino acid esters. For example, the compound disclosed herein that contains a hydroxy group may be acylated at this position in its prodrug form. Other prodrug forms include phosphates, such as, those phosphate compounds derived from the phosphonation of a hydroxy group on the parent compound. A thorough discussion of prodrugs can be referred to the following literature: Higuchi et al., *Pro-drugs as Novel Delivery Systems*, Vol. 14, A.C.S. Symposium Series; Roche, et al., *Bioreversible Carriers in Drug Design*, American Pharmaceutical Association and Pergamon Press, 1987; Rautio et al., *Prodrugs: Design and Clinical Applications*, Nature Reviews Drug Discovery, 2008, 7, 255-270, and Hecker et al., *Prodrugs of Phosphates and Phosphonates*, J. Med. Chem., 2008, 51, 2328-2345.

The term "metabolite" refers to a product produced by a specified compound or salt thereof through metabolism in vivo. The metabolites of a compound may be identified using routine techniques known in the art and their activities characterized using tests such as those described herein. Such products may result for example from oxidation, reduction, hydrolysis, amidation, deamidation, esterification, deesterification, enzyme cleavage, and the like, of the administered compound. Accordingly, the invention includes metabolites of the compound disclosed herein, including metabolites produced by contacting a compound disclosed herein with a mammal for a sufficient time period.

The term "pharmaceutically acceptable salt" refers to organic or inorganic salts of the compound disclosed herein. Pharmaceutically acceptable salts are well known in the art. For example, Berge et al., describe pharmaceutically acceptable salts in detail in J. Pharmacol Sci, 1977, 66: 1-19. Some non-limiting examples of the pharmaceutically salts include salts of an amino group formed with inorganic acids such as hydrochloric acid, hydrobromic acid, phosphoric acid, metaphosphoric acid, sulfuric acid, nitric acid and perchloric acid or with organic acids such as methanesulfonic acid, ethanesulfonic acid, acetic acid, trifluoroacetic acid, glycolic acid, 2-hydroxyethanesulfonic acid, oxalic acid, maleic acid, tartaric acid, citric acid, succinic acid, malonic acid, benzenesulfonic acid, p-toluenesulfonic acid, malic acid, fumaric acid, lactic acid and lactobionic acid or salts obtained by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, laurate, laurylsulfate, malonate, 2-naphthalenesulfonate, nicotinate, nitrate, oleate, palmitate, pamoate, pectinate, persulfate, 3-phenylpropionate, picrate, pivalate, propionate, stearate, thiocyanate, undecanoate, valerate, and the like. Salts derived from appropriate bases include alkali metal, alkaline earth metal, ammonium and $N^+(C_{1-4}$ alkyl$)_4$ salts. This invention also envisions the quaternization of any basic nitrogen-containing groups of the compound disclosed herein. Water or oil soluble or dispersable products may be obtained by such quaternization. Representative alkali or alkaline earth metal salts include sodium, lithium, potassium, calcium, magnesium, and the like. Further pharmaceutically acceptable salts include appropriate, nontoxic ammonium, counterions formed by quaternary ammonium and amine cations, such as halide, hydroxide, carboxylate, sulfate, phosphate, nitrate, $C_{1-8}$ sulfonate or aryl sulfonate.

The term "solvate" refers to an association or complex of one or more solvent molecules and a compound disclosed herein. Some non-limiting examples of the solvent that form solvates include water, isopropanol, ethanol, methanol, dimethylsulfoxide (DMSO), ethyl acetate, acetic acid and ethanolamine. The term "hydrate" refers to the complex where the solvent molecule is water.

The term "N-oxide" refers to one or more than one nitrogen atoms oxidised to form an N-oxide when a compound contains several amine functions. Particular examples of N-oxides are the N-oxides of a tertiary amine or a nitrogen atom of a nitrogen-containing heterocycle. N-oxides can be formed by treatment of the corresponding amine with an oxidizing agent such as hydrogen peroxide or a per-acid (e.g. a peroxycarboxylic acid) (See, *Advanced Organic Chemistry*, by Jerry March, 4th Edition, Wiley Interscience, pages). More particularly, N-oxides can be made by the procedure of L. W. Deady (Syn. Comm. 1977, 7, 509-514) in which the amine compound is reacted with m-chloroperoxybenzoic acid (MCPBA), for example, in an inert solvent such as dichloromethane.

Any asymmetric atom (e.g., carbon or the like) of the compound(s) disclosed herein can be present in racemic or enantiomerically enriched, such as (R)-, (S)-, (R, S)- or (S, S)-configuration. In some embodiments, each asymmetric atom has at least 50% enantiomeric excess, at least 60% enantiomeric excess, at least 70% enantiomeric excess, at least 80% enantiomeric excess, at least 90% enantiomeric excess, at least 95% enantiomeric excess, or at least 99% enantiomeric excess in the (R)- or (S)-configuration. If possible, the substituent on the atom having an unsaturated double bond may exist in the form of cis-(Z)- or trans-(E)-.

Thus, as described herein, the compound of the invention may exist in a form of possible isomers, rotamers, atropisomers, tautomers, or mixtures thereof. For example, it is substantially pure geometric (cis or trans) isomers, diastereomers, optical isomers (enantiomers), racemates or mixtures thereof.

Any resulting mixture of stereoisomers can be separated on the basis of the physicochemical differences of the constituents, into the pure or substantially pure geometric or optical isomers, enantiomers, diastereomers, for example, by chromatography and/or fractional crystallization.

Any resulting racemates of final products or intermediates can be resolved into the optical antipodes by methods known to those skilled in the art, e.g., by separation of the diastereomeric salts thereof. Racemic products can also be resolved by chiral chromatography, e.g., high performance liquid chromatography (HPLC) using a chiral adsorbent. Particularly, enantiomers can also be prepared by asymmetric syntheses. See, for example, Jacques, et al., Enantiomers, *Racemates and Resolutions* (Wiley Interscience, New York, 1981); *Principles of Asymmetric Synthesis* (2nd Ed. Robert E. Gawley, Jeffrey Aubé, Elsevier, Oxford, UK, 2012); Eliel, E. L. *Stereochemistry of Carbon Compounds* (McGraw-Hill, N.Y., 1962); and Wilen, S. H. *Tables of Resolving Agents and Optical Resolutions* p. 268 (E. L. Eliel, Ed., Univ. of Notre Dame Press, Notre Dame, Ind. 1972).

The invention also includes isotopically-labeled compound of the invention which are identical to those described herein except that one or more atoms are replaced by an atom having an atomic mass or mass number different from the natural common atomic mass or mass number. Exemplary isotopes that can be incorporated into the compound of the invention include isotopes of hydrogen, carbon, nitrogen, oxygen, phosphorous, sulfur, fluorine, and chlorine, such as $^2H$, $^3H$, $^{13}C$, $^{14}C$, $^{15}N$, $^{16}O$, $^{17}O$, $^{31}P$, $^{32}P$, $^{36}S$, $^{18}F$ and $^{37}Cl$.

The compound of the invention comprising the aforementioned isotopes and/or other isotopes of other atoms, as well as pharmaceutically acceptable salts of the compound are included within the scope of the invention. The isotopically-labeled compound of the present invention, for example those into which radioactive isotopes such as $^3H$ or $^{14}C$ are incorporated, are useful in drug and/or substrate tissue distribution assays. Deuterated Isotopes are particularly preferred because of its ease of preparation and detection, i.e., $^3H$, and carbon-14, i.e., $^{14}C$. In addition, substitution with heavy isotopes such as deuterium, i.e., 2H, may provide some therapeutic advantages derived from greater metabolic stability, such as increased in vivo half-life or reduced dosage requirements. Therefore, it may be preferable in some cases.

Stereochemical definitions and conventions used herein generally follow S. P. Parker, Ed., *McGraw-Hill Dictionary of Chemical Terms* (1984) McGraw-Hill Book Company, New York; and Eliel, E. and Wilen, S., "*Stereochemistry of Organic Compounds*", John Wiley & Sons, Inc., New York, 1994. The compound of the present invention may contain asymmetric or chiral centers and therefore may exist in different stereoisomeric forms. It is intended that all stereoisomeric forms of the compound disclosed herein include, but are not limited to, diastereomers, enantiomers and atropisomers, while mixtures thereof such as racemic mixtures, are also included in the scope of the present invention. Many organic compounds exist in optically active forms, i.e., they have the ability to rotate the plane of plane-polarized light. In describing an optically active compound, the prefixes D and L, or R and S, are used to denote the absolute configuration of the molecule about its chiral center(s). The prefixes d and l or (+) and (−) are employed to designate the sign of rotation of plane-polarized light by the compound, with (−) or l meaning that the compound is levorotatory. A compound prefixed with (+) or d is dextrorotatory. For a given chemical structure, these stereoisomers are identical except that these stereoisomers are mirror images of one another. A specific stereoisomer is referred to as an enantiomer, and a mixture of such isomers is often called an enantiomeric mixture. A 50:50 mixture of enantiomers is referred to as a racemic mixture or a racemate, which may occur when there is no stereoselection or stereospecificity in a chemical reaction or process.

Depending on the choice of the starting materials and procedures, the compound of the invention can be present in the form of one of the possible stereoisomers or as mixtures thereof, such as racemates and diastereoisomer mixtures, depending on the number of asymmetric carbon atoms. Optically active (R)- and (S)- isomers may be prepared using chiral synthons or chiral reagents, or resolved using conventional techniques. If the compound contains a double bond, the substituent may be E or Z configuration. If the compound contains a disubstituted cycloalkyl, the substituent of the cycloalkyl may have a cis- or trans-configuration.

The compound of the present invention may contain asymmetric or chiral centers and therefore may exist in different stereoisomeric forms. It is intended that all stereoisomeric forms of the compound disclosed herein include, but are not limited to, diastereomers, enantiomers and atropisomers, as well as mixtures thereof such as racemic mixtures, are also included in the scope of the present invention.

Unless otherwise indicated, structures described herein also meant to all isomers (e.g., enantiomers, diastereomeric atropisomers, and geometric (or conformation)) forms including these structures; such as R and S configurations of each asymmetric center, the (Z) and (E) double bond isomers, and the (Z) and (E) conformers. Therefore, the single stereochemical isomer and enantiomeric mixture, diastereomeric mixture and geometric isomer (or conformational isomer) mixture of the present compound are within the scope disclosed herein.

The term "tautomer" or "tautomeric form" refers to structural isomers of different energies which are interconvertible via a low energy barrier. If tautomerization is possible (e.g. in solution), a chemical equilibrium of tautomers can be reached. For example, proton tautomers (also known as prototropic tautomers) include interconversions via migration of a proton, such as keto-enol and imine-enamine isomerizations. Valence tautomers include interconversions by reorganization of some of the bonding electrons. A specific example of keto-enol tautomerization is the interconversion of pentane-2,4-dione and 4-hydroxypent-3-en-2-one tautomers. Another example of tautomerization is phenol-keto tautomerization. The specific example of phenol-keto tautomerisms is pyridin-4-ol and pyridin-4(1H)-one tautomerism. Unless otherwise stated, all tautomeric forms of the compound disclosed herein are within the scope of the invention.

The term "geometric isomer" is also referred to as "cis-trans isomer", which is caused by a double bond (including a double bond of an olefin, a C=N double bond, and a N=N double bond) or a single bond of a ring carbon atom that cannot be freely rotated.

The term "dimer" refers to the same or the same kind of substance that appears in a double form and may have properties or functions that are not present in a single state. Common examples include dicyclopentadiene, dimerized cuprous chloride, sucrose, and the like.

The term "trimer" refers to three identical or identical species substances polymerize into a new molecule, and the new molecule is considered to be a trimer, which is a polymer with low molecular weight.

As used herein, the term "subject" refers to an animal. Typically the animal is a mammal. The subject also refers to primates (e.g., humans), cattle, sheep, goats, horses, dogs, cats, rabbits, rats, mice, fish, birds, and the like. In certain embodiments, the subject is a primate. In yet other embodiments, the subject is a human.

The terms "subject" and "patient" as used herein are used interchangeably. The terms "subject" and "patient" refer to animals (e.g., birds or mammals such as chickens, quails, or turkeys), particularly "mammals" including non-primates (e.g., cows, pigs, horses, sheep, rabbits, guinea pigs, rats, cats, dogs, and mice) and primates (e.g., monkeys, chimpanzees, and humans), especially human beings. In one embodiment, the subject is a non-human animal, such as a domestic animal (e.g., a horse, cow, pig or sheep) or a pet (e.g., a dog, cat, guinea pig or rabbit). In other embodiments, the "patient" refers to a human.

The term "syndrome X", also known as conditions, diseases of metabolic syndrome, the disorders are detailed in Johannsson et al., J. Clin. Endocrinol. Metab., 1997; 82, 727-734.

The term "intestinal improvement" refers to the increase of beneficial bacteria such as *Bifidobacterium* and *Lactobacillus*, the increase of organic acids in the intestine, and the decrease of spoilage products in the intestine.

The terms "cancer" and "cancerous" refer to or describe the physiological condition in mammals that is typically characterized by unregulated cell growth. A "tumor" comprises one or more cancerous cells. Examples of cancer include, but are not limited to, carcinoma, lymphoma, blastoma, sarcoma, and leukemia or lymphoid malignancies. More particular examples of such cancers include squamous cell cancer (e.g., epithelial squamous cell cancer), lung cancer including small-cell lung cancer, non-small cell lung cancer ("NSCLC"), adenocarcinoma of the lung and squamous carcinoma of the lung, cancer of the peritoneum, hepatocellular cancer, gastric or stomach cancer including gastrointestinal cancer, pancreatic cancer, glioblastoma, cervical cancer, ovarian cancer, liver cancer, bladder cancer, hepatoma, breast cancer, colon cancer, rectal cancer, colorectal cancer, endometrial or uterine carcinoma, salivary gland carcinoma, kidney or renal cancer, prostate cancer, vulval cancer, thyroid cancer, hepatic carcinoma, anal carcinoma, penile carcinoma, as well as head and neck cancer.

Additionally, unless otherwise stated, structures depicted herein are also meant to include compounds that differ only in the presence of one or more isotopically enriched atoms.

As used herein, the term "treat", "treating" or "treatment" of any disease or disorder refers in one embodiment, to ameliorating the disease or disorder (i.e., slowing or arresting or reducing the development of the disease or at least one of the clinical symptoms thereof). In another embodiment "treat", "treating" or "treatment" refers to alleviating or ameliorating at least one physical parameter including those which may not be discernible by the patient. In yet another embodiment, "treat", "treating" or "treatment" refers to modulating the disease or disorder, either physically, (e.g., stabilization of a discernible symptom), physiologically, (e.g., stabilization of a physical parameter), or both. In yet another embodiment, "treat", "treating" or "treatment" refers to preventing or delaying the onset or development or progression of the disease or disorder.

Description of the Compound of the Invention

The present invention provides a compound having better SGLTs inhibitory activity, especially SGLT1 inhibitory activity for the preparation of a drug for the treatment of diabetes, insulin resistance, hyperglycemia, hyperinsulinemia, hyperlipidemia, obesity, X syndrome, atherosclerosis, cardiovascular disease, congestive heart failure, hypomagnesemia, hyponatremia, renal failure, disorders associated with blood concentration, constipation or hypertension. The compound of the invention may also be used to improve the intestinal environment. The present invention also provides a method of preparing the compound, a pharmaceutical composition comprising the compound, and a method of using the compound and composition to prepare a drug for the treatment of the above-mentioned diseases in mammals, particularly humans. Compared to existing analogous compounds, the compound of the present invention not only has better pharmacological activity, but also has more excellent metabolic kinetic properties in vivo and pharmacodynamic properties in vivo. At the same time, the preparation method is simple and easy, and the process method is stable, which is suitable for industrial production. Therefore, the compound provided by the present invention has more excellent druggability than the existing analogous compounds.

Specifically speaking: in one aspect, the present invention relates to a compound having Formula (I) or a stereoisomer, a geometric isomer, a tautomer, an N-oxide, a solvate, a metabolite, a pharmaceutically acceptable salt, a dimer, a trimer or a prodrug thereof, $R^1$ is H, D, F, Cl, Br, I, OH, CN, $NO_2$, $NH_2$, $C_{1-6}$ alkyl, $C_{2-6}$ alkenyl, $C_{2-6}$ alkynyl, $C_{1-6}$ alkoxy, $C_{1-6}$ hydroxyalkyl, $C_{1-6}$ haloalkyl, $C_{1-6}$ haloalkoxy, $C_{1-6}$ alkylamino, $C_{1-6}$ alkylthio, $C_{3-6}$ cycloalkyl or $C_{3-6}$ cycloalkyl-$C_{1-4}$ alkylene, wherein each of the $C_{1-6}$ alkyl, $C_{2-6}$ alkenyl, $C_{2-6}$ alkynyl, $C_{1-6}$ alkoxy, $C_{1-6}$ hydroxyalkyl, $C_{1-6}$ haloalkyl, $C_{1-6}$ haloalkoxy, $C_{1-6}$ alkylamino, $C_{1-6}$ alkylthio, $C_{3-6}$ cycloalkyl and $C_{3-6}$ cycloalkyl-$C_{1-4}$ alkylene is independently unsubstituted or substituted with 1, 2, 3 or 4 substituents independently selected from the group consisting of D, F, Cl, Br, I, CN, $NO_2$, OH, $NH_2$, —C(=O)OH, —SH, $C_{1-6}$ alkyl, $C_{1-6}$ haloalkyl, $C_{1-6}$ alkoxy, $C_{1-6}$ alkylamino or $C_{1-6}$ haloalkoxy;

$R^2$ is H, D, CN, =O, $C_{1-6}$ alkyl, $C_{2-6}$ alkenyl, $C_{2-6}$ alkynyl, $C_{1-6}$ alkoxy, $C_{1-6}$ alkylthio, $C_{1-6}$ alkylamino, $C_{3-6}$ cycloalkyl or 3-6 membered heterocyclyl, wherein each of the $C_{1-6}$ alkyl, $C_{2-6}$ alkenyl, $C_{2-6}$ alkynyl, $C_{1-6}$ alkoxy, $C_{1-6}$ alkylthiol, $C_{1-6}$ alkylamino, $C_{3-6}$ cycloalkyl and 3-6 membered heterocyclyl is independently unsubstituted or substituted with 1, 2, 3 or 4 substituents independently selected from D, F, Cl, Br, I, CN, $NO_2$, OH, $NH_2$, —C(=O)OH, —SH, =O, $C_{1-6}$ alkyl, $C_{1-6}$ haloalkyl, $C_{1-6}$ alkoxy, $C_{1-6}$ alkylamino or $C_{1-6}$ haloalkoxy;

$R^3$ is H, D, CN, =O, $C_{1-6}$ alkyl, $C_{2-6}$ alkenyl, $C_{2-6}$ alkynyl, $C_{1-6}$ alkoxy, $C_{1-6}$ alkylthio, $C_{1-6}$ alkylamino, $C_{3-6}$ cycloalkyl or 3-6 membered heterocyclyl, wherein each of the $C_{1-6}$ alkyl, $C_{2-6}$ alkenyl, $C_{2-6}$ alkynyl, $C_{1-6}$ alkoxy, $C_{1-6}$ alkylthiol, $C_{1-6}$ alkylamino, $C_{3-6}$ cycloalkyl and 3-6 membered heterocyclyl is independently unsubstituted or substituted with 1, 2, 3 or 4 substituents independently selected from D, F, Cl, Br, I, CN, $NO_2$, OH, $NH_2$, —C(=O)OH, —SH, =O, $C_{1-6}$ alkyl, $C_{1-6}$ haloalkyl, $C_{1-6}$ alkoxy, $C_{1-6}$ alkylamino or $C_{1-6}$ haloalkoxy;

or $R^2$ and $R^3$, together with the carbon atom they are attached to, form a $C_{3-6}$ carbocycle or 3-6 membered heterocyclic ring, wherein each of the $C_{3-6}$ carbocycle and the 3-6 membered heterocyclic ring is independently unsubstituted or substituted with 1, 2, 3 or 4 substituents independently selected from D, F, Cl, Br, I, CN, $NO_2$, OH, $NH_2$,

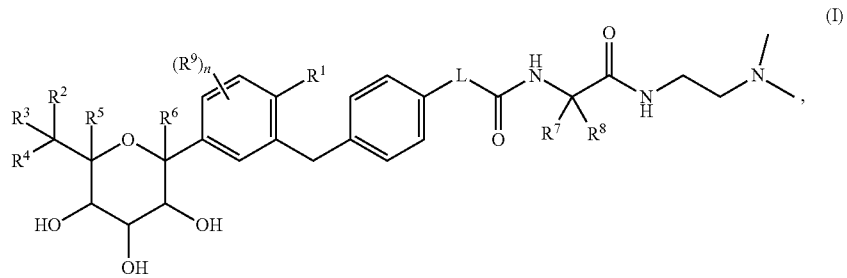

(I)

wherein $R^1$, $R^2$, $R^3$, $R^4$, $R^5$, $R^6$, $R^7$, $R^8$, $R^9$, L and n are as defined herein.

In some embodiments, L is $C_{1-8}$ alkylene or —Y—Z—, wherein the $C_{1-8}$ alkylene is unsubstituted or substituted with 1, 2, 3 or 4 substituents independently selected from D, F, Cl, Br, I, CN, $NO_2$, OH, $NH_2$, —C(=O)OH, —SH, $C_{1-6}$ alkyl, $C_{1-6}$ haloalkyl, $C_{1-6}$ alkoxy, $C_{1-6}$ alkylamino or $C_{1-6}$ haloalkoxy;

Y is —O—, —NH—, —S—, —S(=O)— or —S(=O)$_2$—;

Z is $C_{1-8}$ alkylene, wherein the $C_{1-8}$ alkylene is unsubstituted or substituted with 1, 2, 3 or 4 substituents independently selected from D, F, Cl, Br, I, CN, $NO_2$, OH, $NH_2$, —C(=O)OH, —SH, $C_{1-6}$ alkyl, $C_{1-6}$ haloalkyl, $C_{1-6}$ alkoxy, $C_{1-6}$ alkylamino or $C_{1-6}$ haloalkoxy;

—C(=O)OH, —SH, =O, $C_{1-6}$ alkyl, $C_{1-6}$ haloalkyl, $C_{1-6}$ alkoxy, $C_{1-6}$ alkylamino or $C_{1-6}$ haloalkoxy;

$R^4$ is H, D or —$OR^{4a}$;

$R^{4a}$ is H, D, $C_{1-6}$ alkyl, $C_{3-6}$ cycloalkyl, 3-6 membered heterocyclyl, $C_{6-10}$ aryl, 5-8 membered heteroaryl, $C_{3-6}$ cycloalkyl-$C_{1-4}$ alkylene, (3-6 membered heterocyclyl)-$C_{1-4}$ alkylene, $C_{6-10}$ aryl-$C_{1-4}$ alkylene or (5-8 membered heteroaryl)-$C_{1-4}$ alkylene, wherein each of the $C_{1-6}$ alkyl, $C_{3-6}$ cycloalkyl, 3-6 membered heterocyclyl, $C_{6-10}$ aryl, 5-8 membered heteroaryl, $C_{3-6}$ cycloalkyl-$C_{1-4}$ alkylene, (3-6 membered heterocyclyl)-$C_{1-4}$ alkylene, $C_{6-10}$ aryl-$C_{1-4}$ alkylene and (5-8 membered heteroaryl)-$C_{1-4}$ alkylene is independently unsubstituted or substituted with 1, 2, 3 or 4 substituents independently selected from D, F, Cl, Br, I, CN, NO₂, OH, NH₂, —C(=O)OH, —SH, =O, $C_{1-6}$ alkyl, $C_{1-6}$ haloalkyl, $C_{1-6}$ alkoxy, $C_{1-6}$ alkylamino or $C_{1-6}$ haloalkoxy;

each of $R^5$ and $R^6$ is independently H, D, F, Cl, Br, I, OH, CN, NO₂, NH₂, $C_{1-6}$ alkyl, $C_{1-6}$ alkoxy, $C_{3-6}$ cycloalkyl, $C_{3-6}$ cycloalkoxy, 3-6 membered heterocyclyl, $C_{6-10}$ aryl or 5-8 membered heteroaryl, wherein each of the $C_{1-6}$ alkyl, $C_{1-6}$ alkoxy, $C_{3-6}$ cycloalkyl, $C_{3-6}$ cycloalkoxy, 3-6 membered heterocyclyl, $C_{6-10}$ aryl, and 5-8 membered heteroaryl is independently unsubstituted or substituted with 1, 2, 3 or 4 substituents independently selected from D, F, Cl, Br, I, OH, CN, NH₂, =O, $C_{1-6}$ alkyl, $C_{2-6}$ alkenyl, $C_{2-6}$ alkynyl, $C_{1-6}$ haloalkyl, $C_{1-6}$ alkoxy or a $C_{1-6}$ alkylamino;

or $R^5$ and $R^6$, together with the carbon atom they are attached to respectively, form a 5 membered heterocyclyl ring or 6 membered heterocyclyl ring, wherein each of the 5 membered heterocyclyl ring and 6 membered heterocyclyl ring is independently unsubstituted or substituted with 1, 2, 3 or 4 substituents independently selected from D, F, Cl, Br, I, OH, CN, NH₂, =O, $C_{1-6}$ alkyl, $C_{2-6}$ alkenyl, $C_{2-6}$ alkynyl, $C_{1-6}$ haloalkyl, $C_{1-6}$ alkoxy or $C_{1-6}$ alkylamino;

$R^9$ is H, D, F, Cl, Br, I, OH, CN, NO₂, NH₂, $C_{1-6}$ alkyl or $C_{1-6}$ alkoxy; each of $R^7$ and $R^8$ is independently H, D, F, Cl, Br, I, CN, NO₂, OH, NH₂, $C_{1-6}$ alkyl, $C_{1-6}$ alkoxy, $C_{1-6}$ alkylamino, $C_{1-6}$ haloalkyl, $C_{1-6}$ haloalkoxy, $C_{3-8}$ cycloalkyl, $C_{3-8}$ cycloalkyl-$C_{1-4}$ alkylene, 3-8 membered heterocyclyl, (3-8 membered heterocyclyl)-$C_{1-4}$ alkylene, $C_{6-10}$ aryl, $C_{6-10}$ aryl-$C_{1-4}$ alkylene, 5-8 membered heteroaryl or (5-8 membered heteroaryl)-$C_{1-4}$ alkylene, wherein each of the $C_{1-6}$ alkyl, $C_{1-6}$ alkoxy, $C_{1-6}$ alkylamino, $C_{1-6}$ haloalkyl, $C_{1-6}$ haloalkoxy, $C_{3-8}$ cycloalkyl, $C_{3-8}$ cycloalkyl-$C_{1-4}$ alkylene, 3-8 membered heterocyclyl, (3-8 membered heterocyclyl)-$C_{1-4}$ alkylene, $C_{6-10}$ aryl, $C_{6-10}$ aryl-$C_{1-4}$ alkylene, 5-8 membered heteroaryl and (5-8 membered heteroaryl)-$C_{1-4}$ alkylene is independently unsubstituted or substituted with 1, 2, 3 or 4 substituents independently selected from D, F, Cl, Br, I, CN, NO₂, OH, NH₂, =O, —C(=O)OH, —C(=O)NH₂, $C_{1-6}$ alkyl, $C_{2-6}$ alkenyl, $C_{2-6}$ alkynyl, $C_{1-6}$ haloalkyl, $C_{1-6}$ alkoxy, $C_{1-6}$ alkylamino or $C_{1-6}$ haloalkoxy;

or $R^7$ and $R^8$, together with the carbon atom they are attached to respectively, form a $C_{3-8}$ carbocycle, 3-8 membered heterocyclyl ring, $C_{6-10}$ aromatic ring or 5-8 membered heteroaryl ring, wherein each of the $C_{3-8}$ carbocycle, 3-8 membered heterocyclyl ring, $C_{6-10}$ aromatic ring or 5-8 membered heteroaryl ring is independently unsubstituted or substituted with 1, 2, 3 or 4 substituents independently selected from D, F, Cl, Br, I, CN, NO₂, OH, NH₂, =O, —C(=O)OH, —C(=O)NH₂, $C_{1-6}$ alkyl, $C_{2-6}$ alkenyl, $C_{2-6}$ alkynyl, $C_{1-6}$ haloalkyl, $C_{1-6}$ alkoxy, $C_{1-6}$ alkylamino or $C_{1-6}$ haloalkoxy;

n is 0, 1, 2 or 3.

In other embodiments, the present invention relates to a compound having Formula (II) or a stereoisomer, a geometric isomer, a tautomer, an N-oxide, a solvate, a metabolite, a pharmaceutically acceptable salt, a dimer, a trimer or a prodrug thereof,

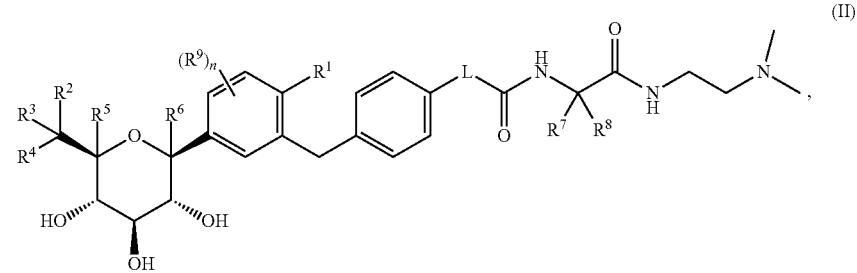

(II)

wherein $R^1$, $R^2$, $R^3$, $R^4$, $R^5$, $R^6$, $R^7$, $R^8$, $R^9$, L and n are as defined herein.

In other embodiments, L is $C_{1-6}$ alkylene or —Y—Z—, wherein the $C_{1-6}$ alkylene is unsubstituted or substituted with 1, 2, 3 or 4 substituents independently selected from D, F, Cl, Br, I, CN, $NO_2$, OH, $NH_2$, —C(=O)OH, —SH, $C_{1-4}$ alkyl, $C_{1-4}$ haloalkyl, $C_{1-4}$ alkoxy, $C_{1-4}$ alkylamino or $C_{1-4}$ haloalkoxy.

In still other embodiments, L is —$CH_2$—, —$CH_2CH_2$—, —$CH_2CH_2CH_2$—, —$CH(CH_3)CH_2$—, —$CH_2(CH_2)_2CH_2$—, —$C(CH_3)_2CH_2$—, —$CH_2(CH_2)_3CH_2$— or —$CH_2(CH_2)_4CH_2$—, wherein each of the —$CH_2$—, —$CH_2CH_2$—, —$CH_2CH_2CH_2$—, —$CH(CH_3)CH_2$—, —$CH_2(CH_2)_2CH_2$—, —$C(CH_3)_2CH_2$—, —$CH_2(CH_2)_3CH_2$— or —$CH_2(CH_2)_4CH_2$— is independently unsubstituted or substituted with 1, 2, 3 or 4 substituents independently selected from D, F, Cl, Br, I, CN, $NO_2$, OH, $NH_2$, —C(=O)OH, —SH, methyl, ethyl, n-propyl, isopropyl, trifluoromethyl, methoxy, ethoxy, methylamino, trifluoromethoxy or difluoromethoxy.

In other embodiments, Y is —O—, —NH—, —S—, —S(=O)— or —S(=O)$_2$—;

Z is $C_{1-6}$ alkylene, wherein the $C_{1-6}$ alkylene is unsubstituted or substituted with 1, 2, 3 or 4 substituents independently selected from D, F, Cl, Br, I, CN, $NO_2$, OH, $NH_2$, —C(=O)OH, —SH, $C_{1-4}$ alkyl, $C_{1-4}$ haloalkyl, $C_{1-4}$ alkoxy, $C_{1-4}$ alkylamino or $C_{1-4}$ haloalkoxy.

In still other embodiments, Y is —O—, —NH—, —S—, —S(=O)— or —S(=O)$_2$—;

Z is —$CH_2$—, —$CH_2CH_2$—, —$CH_2CH_2CH_2$—, —$CH(CH_3)CH_2$—, —$CH_2(CH_2)_2CH_2$—, —$C(CH_3)_2CH_2$—, —$CH_2(CH_2)_3CH_2$— or —$CH_2(CH_2)_4CH_2$—, wherein each of the —$CH_2$—, —$CH_2CH_2$—, —$CH_2CH_2CH_2$—, —$CH(CH_3)CH_2$—, —$CH_2(CH_2)_2CH_2$—, —$C(CH_3)_2CH_2$—, —$CH_2(CH_2)_3CH_2$— or —$CH_2(CH_2)_4CH_2$— is independently unsubstituted or substituted with 1, 2, 3 or 4 substituents independently selected from D, F, Cl, Br, I, CN, $NO_2$, OH, $NH_2$, —C(=O)OH, —SH, methyl, ethyl, n-propyl, isopropyl, trifluoromethyl, methoxy, ethoxy, methylamino, trifluoromethoxy or difluoromethoxy.

In other embodiments, le is H, D, F, Cl, Br, I, OH, CN, $NO_2$, $NH_2$, $C_{1-4}$ alkyl, $C_{2-4}$ alkenyl, $C_{2-4}$ alkynyl, $C_{1-4}$ alkoxy, $C_{1-4}$ hydroxyalkyl, $C_{1-4}$ haloalkyl, $C_{1-4}$ haloalkoxy, $C_{1-4}$ alkylamino, $C_{1-4}$ alkylthio, $C_{3-6}$ cycloalkyl or $C_{3-6}$ cycloalkyl-$C_{1-2}$ alkylene, wherein each of the $C_{1-4}$ alkyl, $C_{2-4}$ alkenyl, $C_{2-4}$ alkynyl, $C_{1-4}$ alkoxy, $C_{1-4}$ hydroxyalkyl, $C_{1-4}$ haloalkyl, $C_{1-4}$ haloalkoxy, $C_{1-4}$ alkylamino, $C_{1-4}$ alkylthio, $C_{3-6}$ cycloalkyl and $C_{3-6}$ cycloalkyl-$C_{1-2}$ alkylene is independently unsubstituted or substituted with 1, 2, 3 or 4 substituents independently selected from D, F, Cl, Br, I, CN, $NO_2$, OH, $NH_2$, —C(=O)OH, —SH, $C_{1-4}$ alkyl, $C_{1-4}$ haloalkyl, $C_{1-4}$ alkoxy, $C_{1-4}$ alkylamino or $C_{1-6}$ haloalkoxy.

In still other embodiments, $R^1$ is H, D, F, Cl, Br, I, OH, CN, $NO_2$, $NH_2$, methyl, ethyl, n-propyl, isopropyl, propenyl, propynyl, methoxy, ethoxy, hydroxymethyl, trifluoromethyl, trifluoroethyl, monofluoromethyl, trifluoromethoxy, difluoromethoxy, methylamino, cyclopropyl, cyclobutyl, cyclopentyl, cyclohexyl or cyclopropyl-methylene, wherein each of the methyl, ethyl, n-propyl, isopropyl, propenyl, propynyl, methoxy, ethoxy, hydroxymethyl, trifluoroethyl, monofluoromethyl, difluoromethoxy, methylamino, cyclopropyl, cyclobutyl, cyclopentyl, cyclohexyl and cyclopropyl-methylene is independently unsubstituted or substituted with 1, 2, 3 or 4 substituents independently selected from D, F, Cl, Br, I, CN, $NO_2$, OH, $NH_2$, —C(=O)OH, —SH, methyl, ethyl, n-propyl, isopropyl, trifluoromethyl, methoxy, ethoxy, methylamino, trifluoromethoxy or difluoromethoxy.

In other embodiments, $R^2$ is H, D, CN, =O, $C_{1-4}$ alkyl, $C_{2-4}$ alkenyl, $C_{2-4}$ alkynyl, $C_{1-4}$ alkoxy, $C_{1-4}$ alkylthio, $C_{1-4}$ alkylamino, $C_{3-6}$ cycloalkyl or 5-6 membered heterocyclyl, wherein each of the $C_{1-4}$ alkyl, $C_{2-4}$ alkenyl, $C_{2-4}$ alkynyl, $C_{1-4}$ alkoxy, $C_{1-4}$ alkylthio, $C_{1-4}$ alkylamino, $C_{3-6}$ cycloalkyl or 5-6 membered heterocyclyl is independently unsubstituted or substituted with 1, 2, 3 or 4 substituents independently selected from D, F, Cl, Br, I, CN, $NO_2$, OH, $NH_2$, —C(=O)OH, —SH, =O, $C_{1-4}$ alkyl, $C_{1-4}$ haloalkyl, $C_{1-4}$ alkoxy, $C_{1-4}$ alkylamino or $C_{1-4}$ haloalkoxy.

In still other embodiments, $R^2$ is H, D, CN, =O, methyl, ethyl, n-propyl, isopropyl, vinyl, acetonyl, methoxy, ethoxy, methylthio, methylamino, cyclopropyl, cyclobutyl, cyclopentyl, cyclohexyl or 5-6 membered heterocyclyl, wherein each of the methyl, ethyl, n-propyl, isopropyl, vinyl, acetonyl, methoxy, ethoxy, methylthio, methylamino, cyclopropyl, cyclobutyl, cyclopentyl, cyclohexyl or 5-6 membered heterocycly is independently unsubstituted or substituted with 1, 2, 3 or 4 substituents independently selected from D, F, Cl, Br, I, CN, $NO_2$, OH, $NH_2$, —C(=O)OH, —SH, =O, methyl, ethyl, n-propyl, isopropyl, trifluoromethyl, methoxy, ethoxy, methylamino, trifluoromethoxy or difluoromethoxy.

In other embodiments, $R^3$ is H, D, CN, =O, $C_{1-4}$ alkyl, $C_{2-4}$ alkenyl, $C_{2-4}$ alkynyl, $C_{1-4}$ alkoxy, $C_{1-4}$ alkylthio, $C_{1-4}$ alkylamino, $C_{3-6}$ cycloalkyl or 5-6 membered heterocyclyl, wherein each of the $C_{1-4}$ alkyl, $C_{2-4}$ alkenyl, $C_{2-4}$ alkynyl, $C_{1-4}$ alkoxy, $C_{1-4}$ alkylthio, $C_{1-4}$ alkylamino, $C_{3-6}$ cycloalkyl or 5-6 membered heterocyclyl is independently unsubstituted or substituted with 1, 2, 3 or 4 substituents independently selected from D, F, Cl, Br, I, CN, $NO_2$, $NH_2$, —C(=O)OH, —SH, =O, $C_{1-4}$ alkyl, $C_{1-4}$ haloalkyl, $C_{1-4}$ alkoxy, $C_{1-4}$ alkylamino or $C_{1-4}$ haloalkoxy.

In still other embodiments, $R^3$ is H, D, CN, =O, methyl, ethyl, n-propyl, isopropyl, vinyl, acetonyl, methoxy, ethoxy, methylthio, methylamino, cyclopropyl, cyclobutyl, cyclopentyl, cyclohexyl or 5-6 membered heterocyclyl, wherein each of the methyl, ethyl, n-propyl, isopropyl, vinyl, acetonyl, methoxy, ethoxy, methylthio, methylamino, cyclopropyl, cyclobutyl, cyclopentyl, cyclohexyl or 5-6 membered heterocycly is independently unsubstituted or substituted with 1, 2, 3 or 4 substituents independently selected from D, F, Cl, Br, I, CN, $NO_2$, OH, $NH_2$, —C(=O)OH, —SH, =O, methyl, ethyl, n-propyl, isopropyl, trifluoromethyl, methoxy, ethoxy, methylamino, trifluoromethoxy or difluoromethoxy.

In other embodiments, $R^2$ and $R^3$ together with the carbon atom they are attached to, form a $C_{3-6}$ carbocycle or 5-6 membered heterocyclic ring, wherein each of the $C_{3-6}$ carbocycle and 5-6 membered heterocyclic ring is independently unsubstituted or substituted with 1, 2, 3 or 4 substituents independently selected from D, F, Cl, Br, I, CN, $NO_2$, OH, $NH_2$, —C(=O)OH, —SH, =O, $C_{1-4}$ alkyl, $C_{1-4}$ haloalkyl, $C_{1-4}$ alkoxy, $C_{1-4}$ alkylamino or $C_{1-4}$ haloalkoxy.

In still other embodiments, $R^2$ and $R^3$, together with the carbon atom they are attached to, form a cyclopropane, cyclobutane, cyclopentane, cyclohexane or 5-6 membered heterocyclic ring, wherein each of the cyclopropane, cyclobutane, cyclopentane, cyclohexane or 5-6 membered heterocyclic ring is independently unsubstituted or substituted with 1, 2, 3 or 4 substituents independently selected from D, F, Cl, Br, I, CN, $NO_2$, OH, $NH_2$, —C(=O)OH, —SH, =O, methyl, ethyl, n-propyl, isopropyl, trifluoromethyl, methoxy, ethoxy, methylamino, trifluoromethoxy or difluoromethoxy.

In other embodiments, $R^4$ is H, D or —$OR^{4a}$;

$R^{4a}$ is H, D, $C_{1-4}$ alkyl, $C_{3-6}$ cycloalkyl, 5-6 membered heterocyclyl, $C_{6-10}$ aryl, 5-6 membered heteroaryl, $C_{3-6}$ cycloalkyl-$C_{1-2}$ alkylene, (5-6 membered heterocyclyl)-$C_{1-4}$ alkylene, $C_{6-10}$ aryl—$C_{1-2}$ alkylene or (5-6 membered heteroaryl)-$C_{1-4}$ alkylene, wherein each of the $C_{1-4}$ alkyl, $C_{3-6}$ cycloalkyl, 5-6 membered heterocyclyl, $C_{6-10}$ aryl, 5-6 membered heteroaryl, $C_{3-6}$ cycloalkyl-$C_{1-4}$ alkylene, (5-6 membered heterocyclyl)-$C_{1-2}$ alkylene, $C_{6-10}$ aryl-$C_{1-2}$ alkylene and (5-6 membered heteroaryl)-$C_{1-2}$ alkylene is independently unsubstituted or substituted by 1, 2, 3 or 4 substituents independently selected from D, F, Cl, Br, I, CN, $NO_2$, OH, $NH_2$, —C(=O)OH, —SH, =O, $C_{1-4}$ alkyl, $C_{1-4}$ haloalkyl, $C_{1-4}$ alkoxy, $C_{1-4}$ alkylamino or $C_{1-4}$ haloalkoxy.

In still other embodiments, $R^4$ is H, D or —$OR^{4a}$;

$R^{4a}$ is H, D, methyl, ethyl, n-propyl, isopropyl, cyclopropyl, cyclobutyl, cyclopentyl, cyclohexyl, tetrahydrofuranyl, tetrahydrothiophenyl, tetrahydropyranyl, piperidyl, morpholinyl, thiomorpholinyl, piperazinyl, phenyl, furyl, pyrrolyl, pyridyl, pyrazolyl, imidazolyl, triazolyl, tetrazolyl, oxazolyl, isoxazolyl, oxadiazolyl, 1,3,5-triazinyl, thiazolyl, thienyl, pyrazinyl, pyridazinyl, pyrimidinyl, $C_{3-6}$ cycloalkyl-$C_{1-2}$ alkylene, (5-6 membered heterocyclyl)-$C_{1-2}$ alkylene, phenyl-$C_{1-2}$ alkylene or (5-6 membered heteroaryl)-$C_{1-2}$ alkylene, wherein each of the methyl, ethyl, n-propyl, isopropyl, cyclopropyl, cyclobutyl, cyclopentyl, cyclohexyl, tetrahydrofuranyl, tetrahydrothiophenyl, tetrahydropyranyl, piperidyl, morpholinyl, thiomorpholinyl, piperazinyl, phenyl, furyl, pyrrolyl, pyridyl, pyrazolyl, imidazolyl, triazolyl, tetrazolyl, oxazolyl, isoxazolyl, oxadiazolyl, 1,3,5-triazinyl, thiazolyl, thienyl, pyrazinyl, pyridazinyl, pyrimidinyl, $C_{3-6}$ cycloalkyl-$C_{1-2}$ alkylene, (5-6 membered heterocyclyl)-$C_{1-2}$ alkylene, phenyl-$C_{1-2}$ alkylene or (5-6 membered heteroaryl)-$C_{1-2}$alkylene is independently unsubstituted or substituted with 1, 2, 3 or 4 substituents independently selected from D, F, Cl, Br, I, CN, $NO_2$, OH, $NH_2$, —C(=O)OH, —SH, =O, methyl, ethyl, n-propyl, isopropyl, trifluoromethyl, methoxy, ethoxy, methylamino, trifluoromethoxy or difluoromethoxy.

In other embodiments, each of $R^5$ and $R^6$ is independently H, D, F, Cl, Br, I, OH, CN, $NO_2$, $NH_2$, $C_{1-4}$ alkyl, $C_{1-4}$ alkoxy, $C_{3-6}$ cycloalkyl, $C_{3-6}$ cycloalkoxy, 5-6 membered heterocyclyl, $C_{6-10}$ aryl or 5-6 membered heteroaryl, wherein each of the $C_{1-4}$ alkyl, $C_{1-4}$ alkoxy, $C_{3-6}$ cycloalkyl, $C_{3-6}$ cycloalkoxy, 5-6 membered heterocyclyl, $C_{6-10}$ aryl, and 5-6 membered heteroaryl is independently unsubstituted or substituted with 1, 2, 3 or 4 substituents independently selected from D, F, Cl, Br, I, OH, CN, $NH_2$, =O, $C_{1-4}$ alkyl, $C_{2-4}$ alkenyl, $C_{2-4}$ alkynyl, $C_{1-4}$ haloalkyl, $C_{1-4}$ alkoxy or $C_{1-4}$ alkylamino.

In still other embodiments, each of $R^5$ and $R^6$ is independently H, D, F, Cl, Br, I, OH, CN, $NO_2$, $NH_2$, methyl, ethyl, n-propyl, isopropyl, methoxy, ethoxy, cyclopropyl, cyclobutyl, cyclopropoxy, 5-6 membered heterocyclyl, phenyl, 5-6 membered heteroaryl, wherein each of the methyl, ethyl, n-propyl, isopropyl, methoxy, ethoxy, cyclopropyl, cyclobutyl, cyclopropoxy, 5-6 membered heterocyclyl, phenyl, 5-6 membered heteroaryl is independently unsubstituted or substituted with 1, 2, 3 or 4 substituents independently selected from D, F, Cl, Br, I, OH, CN, $NH_2$, =O, methyl, ethyl, n-propyl, isopropyl, vinyl, ethynyl, trifluoromethyl, methoxy, ethoxy or methylamino.

In other embodiments, $R^5$ and $R^6$, together with the carbon atom they are attached to respectively, form a 5 membered heterocyclyl ring or 6 membered heterocyclyl ring, wherein each of the 5 membered heterocyclyl ring and 6 membered heterocyclyl ring is independently unsubstituted or substituted with 1, 2, 3 or 4 substituents independently selected from D, F, Cl, Br, I, OH, CN, $NH_2$, =O, $C_{1-4}$ alkyl, $C_{2-4}$ alkenyl, $C_{2-4}$ alkynyl, $C_{1-4}$ haloalkyl, $C_{1-4}$ alkoxy or $C_{1-4}$ alkylamino.

In still other embodiments, $R^5$ and $R^6$, together with the carbon atom they are attached to respectively, form tetrahydrofuran, dihydrofuran, tetrahydropyran, dihydropyran, 1,3-oxathiolane, 1,3-dioxacyclopentane, dioxane, 1,4-dioxane or morpholine, wherein each of the tetrahydrofuran, dihydrofuran, tetrahydropyran, dihydropyran, 1,3-oxathiolane, 1,3-dioxacyclopentane, dioxane, 1,4-dioxane or morpholine, is independently unsubstituted or substituted with 1, 2, 3 or 4 substituents independently selected from D, F, Cl, Br, I, OH, CN, $NH_2$, =O, methyl, ethyl, n-propyl, isopropyl, vinyl, ethynyl, trifluoromethyl, methoxy, ethoxy or methylamino.

In other embodiments, $R^9$ is H, D, F, Cl, Br, I, OH, CN, $NO_2$, $NH_2$, $C_{1-4}$ alkyl or $C_{1-4}$ alkoxy.

In still other embodiments, $R^9$ is H, D, F, Cl, Br, I, OH, CN, $NO_2$, $NH_2$, methyl, ethyl, n-propyl, isopropyl, methoxy or ethoxy.

In other embodiments, each of $R^7$ and $R^8$ is independently H, D, F, Cl, Br, I, CN, $NO_2$, OH, $NH_2$, $C_{1-4}$ alkyl, $C_{1-4}$ alkoxy, $C_{1-4}$ alkylamino, $C_{1-4}$ haloalkyl, $C_{1-4}$ haloalkoxy, $C_{3-6}$ cycloalkyl, $C_{3-6}$ cycloalkyl-$C_{1-2}$ alkylene, 5-6 membered heterocyclyl, (5-6 membered heterocyclyl)-$C_{1-2}$ alkylene, $C_{6-10}$ aryl, $C_{6-10}$ aryl-$C_{1-2}$ alkylene, 5-6 membered heteroaryl or (5-6 membered heteroaryl)-$C_{1-2}$ alkylene, wherein each of the $C_{1-4}$ alkyl, $C_{1-4}$ alkoxy, $C_{1-4}$ alkylamino, $C_{1-4}$ haloalkyl, $C_{1-4}$ haloalkoxy, $C_{3-6}$ cycloalkyl, $C_{3-6}$ cycloalkyl-$C_{1-2}$ alkylene, 5-6 membered heterocyclyl, (5-6 membered heterocyclyl)-$C_{1-2}$ alkylene, $C_{6-10}$ aryl, $C_{6-10}$ aryl-$C_{1-2}$ alkylene, 5-6 membered heteroaryl or (5-6 membered heteroaryl)-$C_{1-2}$ alkylene is independently unsubstituted or substituted with 1, 2, 3 or 4 substituents independently selected from D, F, Cl, Br, I, CN, $NO_2$, OH, $NH_2$, =O, —C(=O)OH, —C(=O)$NH_2NH_2$, $C_{1-4}$ alkyl, $C_{2-4}$ alkenyl, $C_{2-4}$ alkynyl, $C_{1-4}$ haloalkyl, $C_{1-4}$ alkoxy, $C_{1-4}$ alkylamino or $C_{1-4}$ haloalkoxy.

In still other embodiments, each of $R^7$ and $R^8$ is independently H, D, F, Cl, Br, I, CN, $NO_2$, OH, $NH_2$, methyl, ethyl, n-propyl, isopropyl, n-butyl, tert-butyl, methoxy, ethoxy, methylamino, trifluoromethyl, trifluoromethoxy, difluoromethoxy, cyclopropyl, cyclobutyl, cyclopentyl, cyclohexyl, $C_{3-6}$ cycloalkyl-$C_{1-2}$ alkylene, pyrrolidinyl, tetrahydrofuranyl, tetrahydrothiophenyl, tetrahydropyranyl, tetrahydrothiopyranyl, piperidinyl, morpholinyl, thiomorpholinyl, piperazinyl, (5-6 membered heterocyclyl)-$C_{1-2}$ alkylene, phenyl, phenyl-$C_{1-2}$ alkylene, furyl, pyrrolyl, pyridyl, pyrazolyl, imidazolyl, triazolyl, tetrazolyl, oxazolyl, oxadiazolyl, 1,3,5-triazinyl, thiazolyl, thienyl, pyrazinyl, pyridazinyl, pyrimidinyl or (5-6 membered heteroaryl)-$C_{1-2}$ alkylene, wherein each of the methyl, ethyl, n-propyl, isopropyl, n-butyl, tert-butyl, methoxy, ethoxy, methylamino, trifluoromethyl, trifluoromethoxy, difluoromethoxy, cyclopropyl, cyclobutyl, cyclopentyl, cyclohexyl, $C_{3-6}$ cycloalkyl-$C_{1-2}$ alkylene, pyrrolidinyl, tetrahydrofuranyl, tetrahydrothiophenyl, tetrahydropyranyl, tetrahydrothiopyranyl, piperidinyl, morpholinyl, thiomorpholinyl, piperazinyl, (5-6 membered heterocyclyl)-$C_{1-2}$ alkylene, phenyl, phenyl-$C_{1-2}$ alkylene, furyl, pyrrolyl, pyridyl, pyrazolyl, imidazolyl, triazolyl, tetrazolyl, oxazolyl, oxadiazolyl, 1,3,5-triazinyl, thiazolyl, thienyl, pyrazinyl, pyridazinyl, pyrimidinyl or (5-6 membered heteroaryl)-$C_{1-2}$ alkylene is independently unsubstituted or substituted with 1, 2, 3 or 4 substituents independently selected from D, F, Cl, Br, I, CN, $NO_2$, OH, $NH_2$, =O, —C(=O)OH, —C(=O)$NH_2$, methyl, ethyl, n-propyl, isopropyl, vinyl, ethynyl, trifluoromethyl, methoxy, ethoxy, methyl amino, trifluoromethoxy or difluoromethoxy.

In other embodiments, or $R^7$ and $R^8$, together with the carbon atom they are attached to respectively, form a $C_{3-6}$ carbocycle, 5-6 membered heterocyclyl ring, $C_{6-10}$ aromatic ring or 5-6 membered heteroaryl ring, wherein each of the $C_{3-6}$ carbocycle, 5-6 membered heterocyclyl ring, $C_{6-10}$ aromatic ring or 5-6 membered heteroaryl ring is independently unsubstituted or substituted with 1, 2, 3 or 4 substituents independently selected from D, F, Cl, Br, I, CN, $NO_2$, OH, $NH_2$, =O, —C(=O)OH, —C(=O)$NH_2$, $C_{1-4}$ alkyl, $C_{2-4}$ alkenyl, $C_{2-4}$ alkynyl, $C_{1-4}$ haloalkyl, $C_{1-4}$ alkoxy, $C_{1-4}$ alkylamino or $C_{1-4}$ haloalkoxy.

In still other embodiments, $R^7$ and $R^8$, together with the carbon atom they are attached to respectively, form a cyclopropyl, cyclobutyl, cyclopentyl, cyclohexyl, pyrrolidine, tetrahydrofuran, tetrahydrothiophene, tetrahydropyran, tetrahydrothiopyran, piperidine, morpholine, thiomorpholine, piperazine, benzene ring, furan, pyrrole, pyridine, pyrazole, imidazole, triazole, tetrazole, oxazole, oxadiazole, 1,3,5-triazine, thiazole, thiophene, pyrazine, pyridazine or pyrimidine, wherein each of the cyclopropyl, cyclobutyl, cyclopentyl, cyclohexyl, pyrrolidine, tetrahydrofuran, tetrahydrothiophene, tetrahydropyran, tetrahydrothiopyran, piperidine, morpholine, thiomorpholine, piperazine, benzene ring, furan, pyrrole, pyridine, pyrazole, imidazole, triazole, tetrazole, oxazole, oxadiazole, 1,3,5-triazine, thiazole, thiophene, pyrazine, pyridazine or pyrimidine is independently unsubstituted or substituted with 1, 2, 3 or 4 substituents independently selected from D, F, Cl, Br, I, CN, $NO_2$, OH, $NH_2$, =O, —C(=O)OH, —C(=O)$NH_2$, methyl, ethyl, n-propyl, isopropyl, vinyl, ethynyl, trifluoromethyl, methoxy, ethoxy, methyl amino, trifluoromethoxy or difluoromethoxy.

In other embodiments, the present invention relates to a compound having Formula (III) or a stereoisomer, a geometric isomer, a tautomer, an N-oxide, a solvate, a metabolite, a pharmaceutically acceptable salt, a dimer, a trimer or a prodrug thereof,

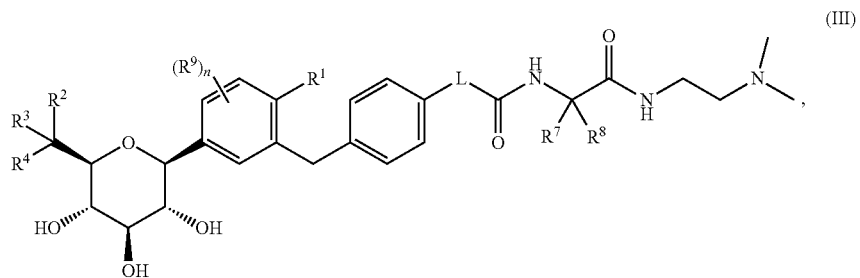

(III)

wherein $R^1$, $R^2$, $R^3$, $R^4$, $R^7$, $R^8$, $R^9$, L and n are as defined herein.

In other embodiments, the present invention relates to a compound having Formula (IV) or a stereoisomer, a geometric isomer, a tautomer, an N-oxide, a solvate, a metabolite, a pharmaceutically acceptable salt, a dimer, a trimer or a prodrug thereof,

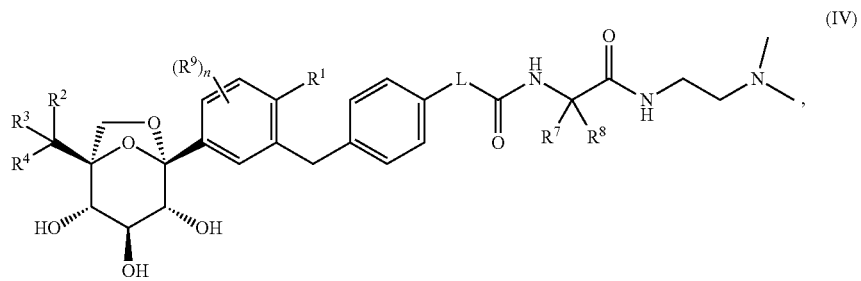

(IV)

wherein $R^1$, $R^2$, $R^3$, $R^4$, $R^7$, $R^8$, $R^9$, L and n are as defined herein.
In still other embodiments, the present invention relates to a structure of one of the following, or a stereoisomer, a geometric isomer, a tautomer, an N-oxide, a solvate, a metabolite, a pharmaceutically acceptable salt, a dimer, a trimer or a prodrug thereof,
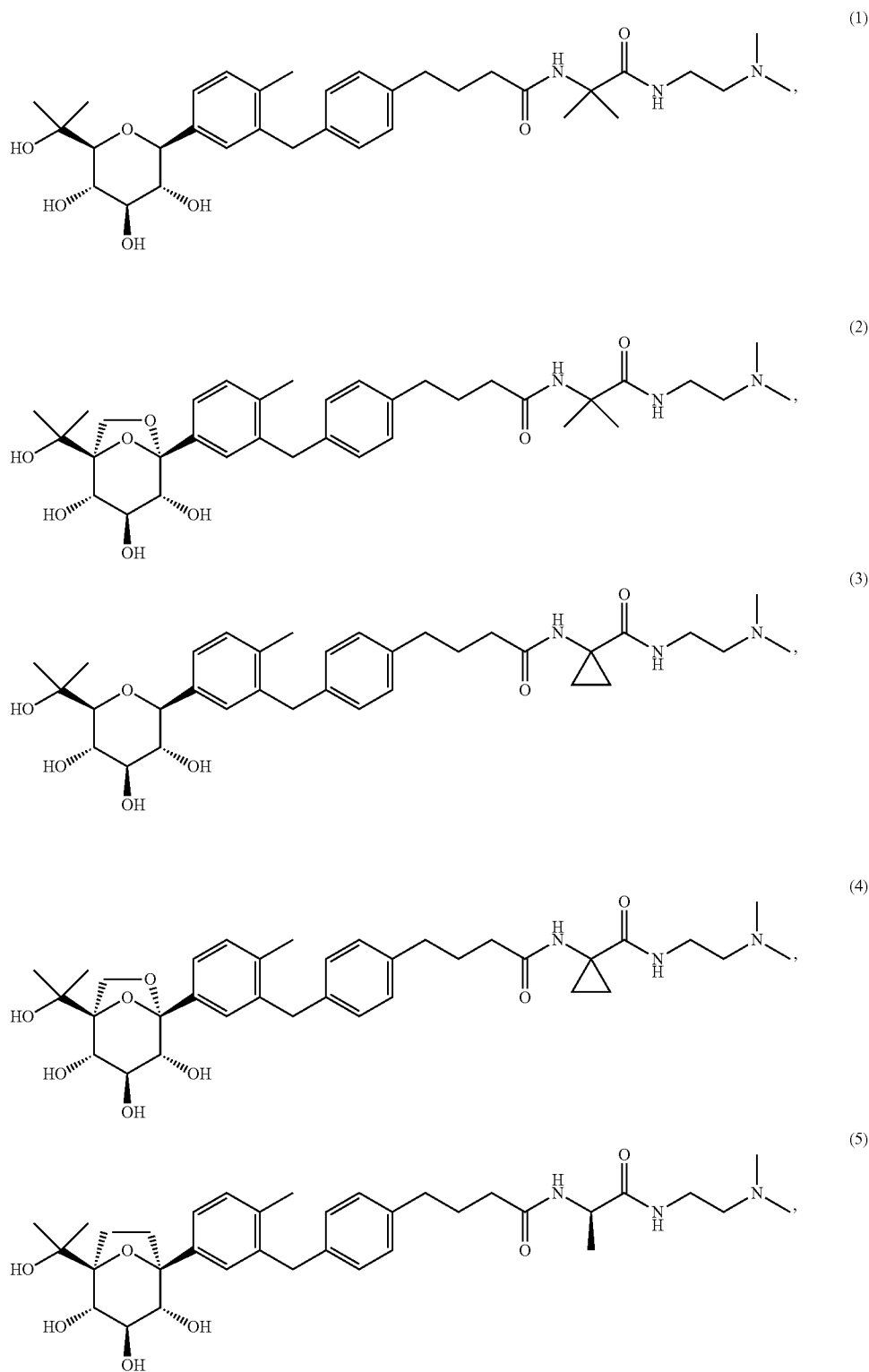

-continued
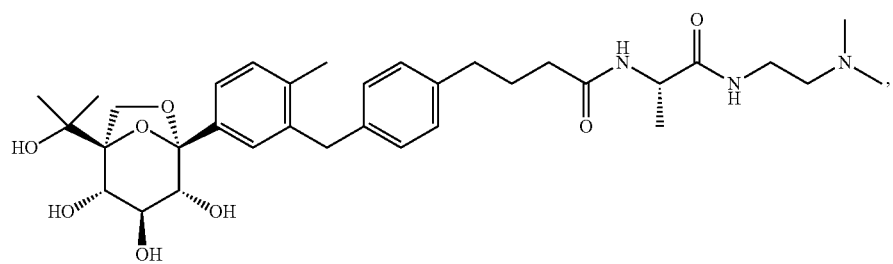
(6)
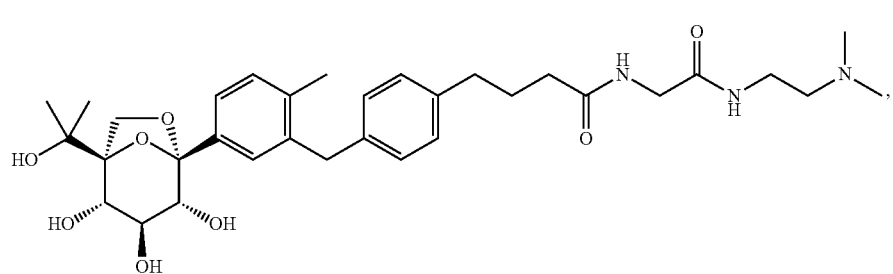
(7)
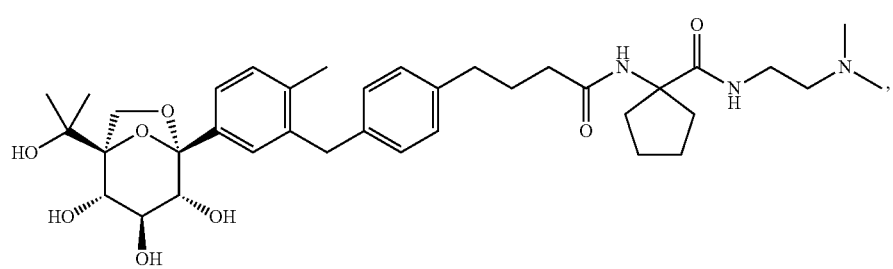
(8)
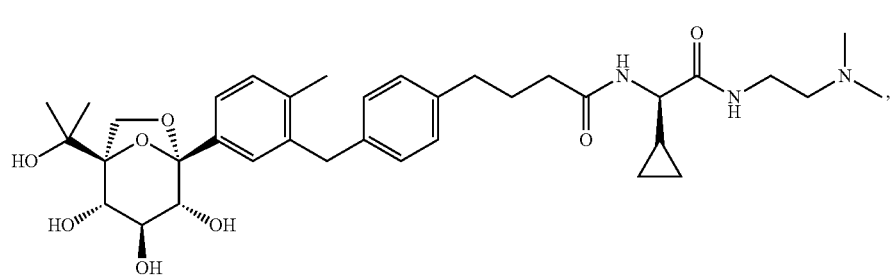
(9)
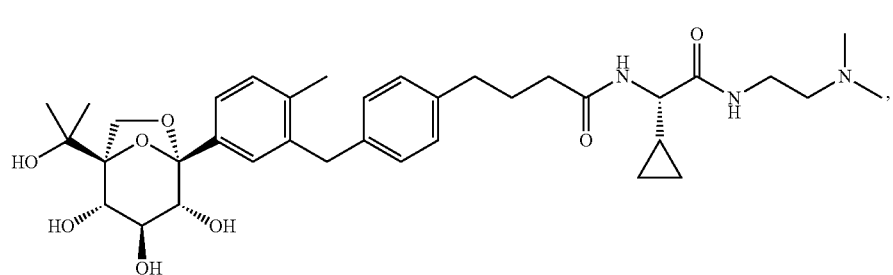
(10)
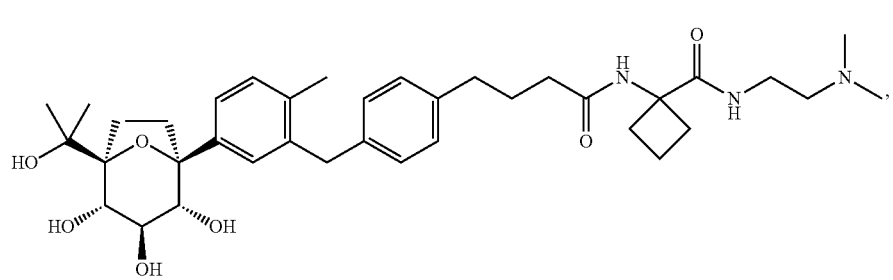
(11)

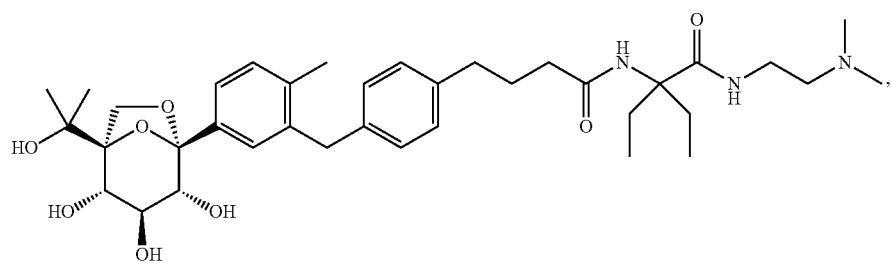
(12)
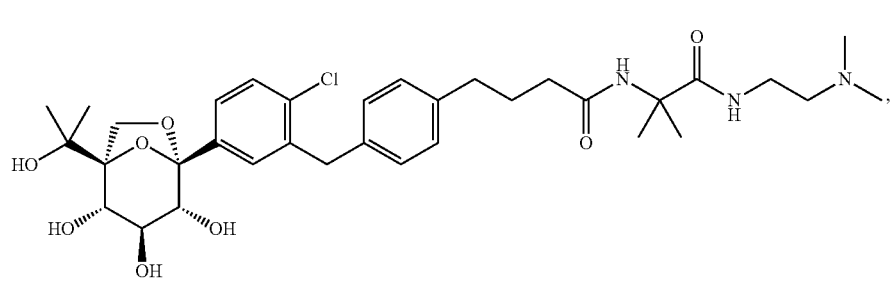
(13)
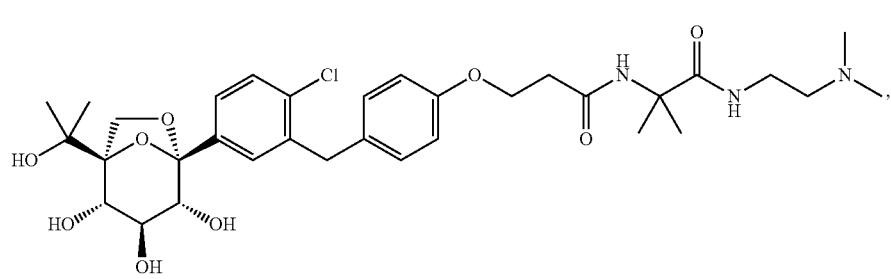
(14)
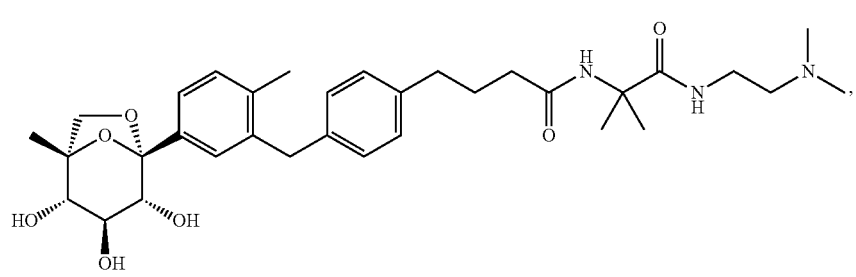
(15)
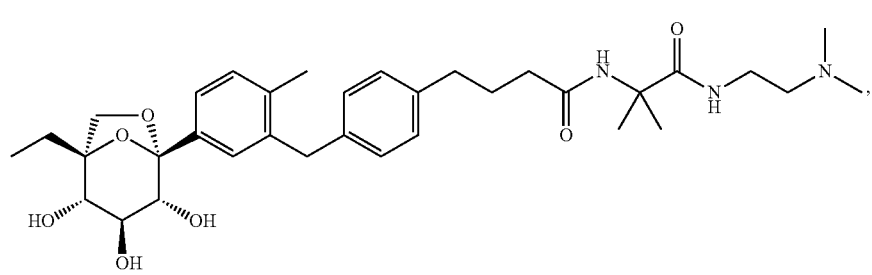
(16)
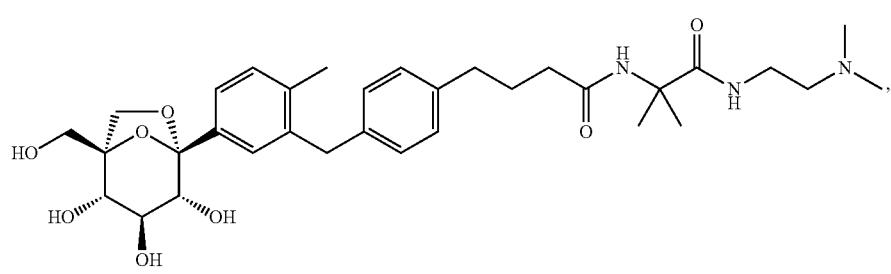
(17)

-continued
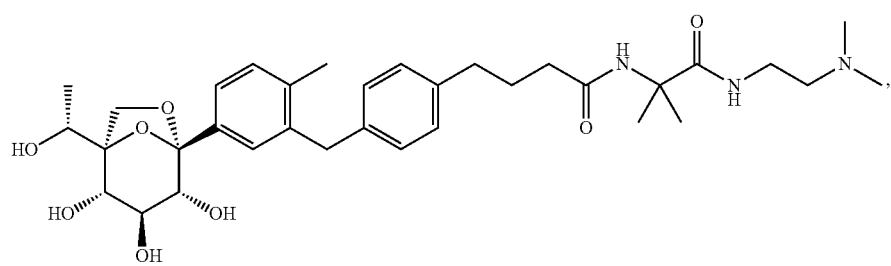
(18)
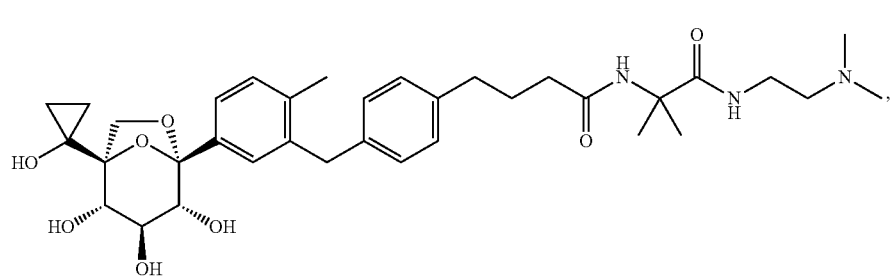
(19)
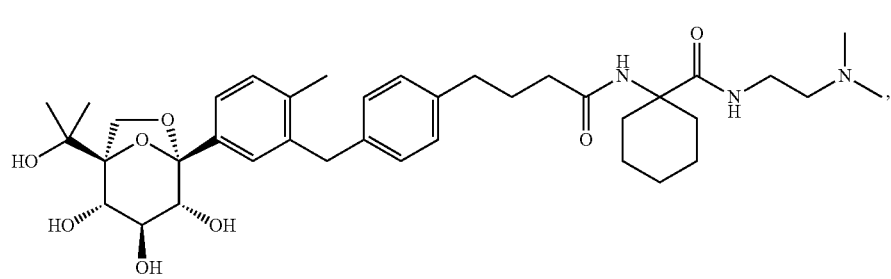
(20)
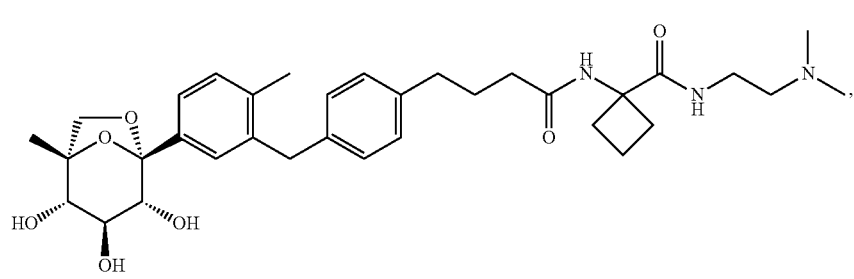
(21)
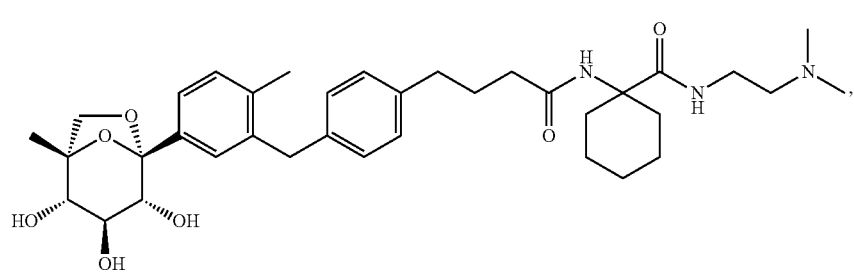
(22)
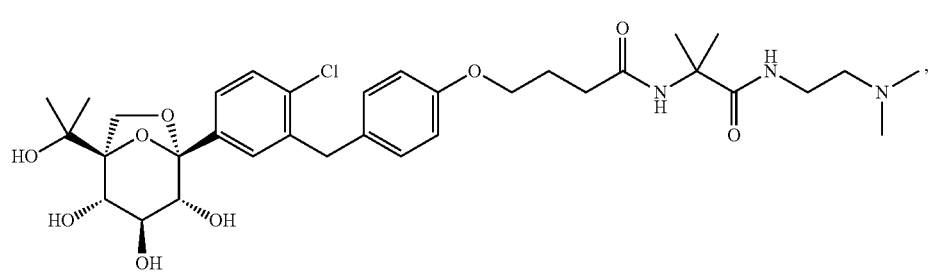
(23)

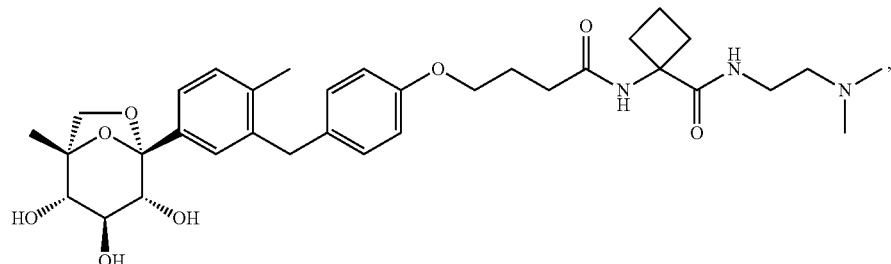

(24)

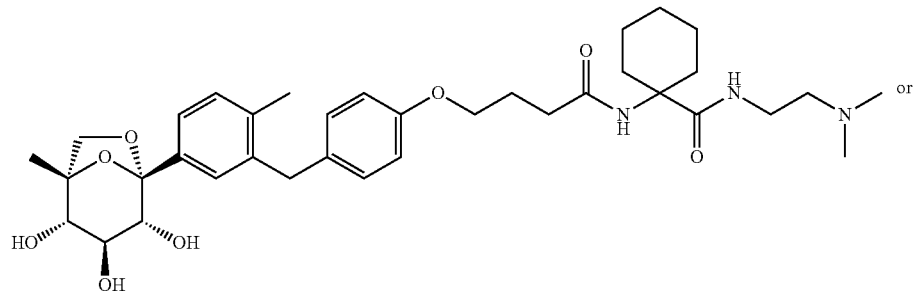

(25)

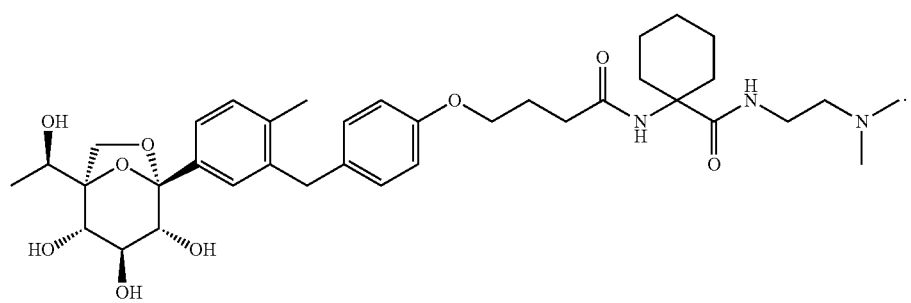

(26)

In a further aspect, provided herein is a pharmaceutical composition comprising the compound disclosed herein.

In some embodiments, the pharmaceutical composition disclosed herein further comprises a pharmaceutically acceptable carrier, excipient, adjuvant and vehicle or any combination thereof.

In some embodiments, the pharmaceutical composition disclosed herein further comprises one or more additional therapeutic agents, wherein the additional therapeutic agent is selected from an anti-diabetic agent, an antihyperglycemic agent, an antiobesity agent, an antihypertensive agent, an appetite suppressant, a lipid-lowering agent or a combination thereof.

In other embodiments, the pharmaceutical composition can be in the form of liquid, solid, semi-solid, gel or spray.

In other embodiments, the anti-diabetic agent and antihyperglycemic agent disclosed herein are independently selected from a SGLT2 inhibitor a biguanide, a sulfonylurea, a glucosidase inhibitor a PPAR agonist (a peroxisome proliferator activation receptor agonist), an αP2 inhibitor (an adipocyte fatty acid binding protein inhibitor), a PPARα/γ dual activator(a peroxisome proliferator-activated receptor α/γ double activator), a dipeptidyl peptidase IV inhibitor a glinide, an insulin, a glucagon-like peptide-1(GLP-1) inhibitor a PTP1B inhibitor (a protein tyrosine phosphatase 1B inhibitor), a glycogen phosphorylase inhibitor a glucose-6-phosphatase inhibitor or a combination thereof.

In other embodiments, the anti-obesity agent disclosed herein is selected from the group consisting of a central anti-obesity agent, a MCH (melanin-concentrating hormone) receptor antagonist, a neuropeptide Y receptor antagonist, and a cannabinoid receptor antagonist, a brain-gut peptide antagonist, a lipase inhibitor a β3 agonist, a 11β-HSD1 (11β hydroxysteroid dehydrogenase 1) inhibitor a DGAT-1 (diacylglycerol acyl transferase 1) inhibitor a cholecystokinin agonist, a feeding inhibitor or a combination thereof.

In other embodiments, the antihypertensive agent of the present invention is selected from an angiotensin converting enzyme inhibitor an angiotensin II receptor antagonist, a calcium channel antagonist, a potassium channel opener, a diuretic, or a combination thereof.

In other embodiments, the lipid-lowering agent disclosed herein is selected from an MTP inhibitor (microsomal triglyceride transfer protein inhibitor), an HMGCoA reductase inhibitor (hydroxymethylglutaryl coenzyme A reductase inhibitor), a squalene synthase inhibitor a lipid-lowering agent of betabutyric acid (also known as a fibrate lipid-lowering agent), an ACAT inhibitor(an acetylcholesteryl acetyl transferase inhibitor), a lipoxygenase inhibitor a cholesterol absorption inhibitor an ileal Na(+)/bile acid cotransporter inhibitor an upregulator of LDL receptor activity, a lipid-lowering agent of niacin, a bile acid chelate or a combination thereof.

In still other embodiments, the lipid-lowering agent disclosed herein is pravastatin, simvastatin, atorvastatin, fluvastatin, cerivastatin, atavastatin, rosuvastatin or a combination thereof.

In other aspect, the invention relates to the use of the compound or the pharmaceutical composition disclosed herein in the preparation of a medicament, wherein the medicament is used to inhibit SGLT1.

In other aspect, the invention relates to the use of the compound or the pharmaceutical composition disclosed herein in the preparation of a medicament, wherein the medicament is used to improve the intestinal environment.

In a further aspect, the invention relates to the use of the compound or the pharmaceutical composition disclosed herein in the preparation of a drug, wherein the drug is used for preventing or treating a disease, lessening symptoms of the disease or delaying progression or onset of the disease, wherein the disease is diabetes, diabetic complications, insulin resistance, hyperglycemia, hyperinsulinemia, hyperlipidemia, obesity, syndrome X, atherosclerosis, cardiovascular disease, congestive heart failure, hypomagnesemia, hyponatremia, renal failure, disorders associated with blood concentration, constipation or hypertension.

In some embodiments, the diabetic complications disclosed herein are diabetic retinopathy, diabetic neuropathy or diabetic nephropathy.

In some embodiments, the hyperlipidemia disclosed herein is hypertriglyceridemia.

In other aspect, the invention relates to a method of inhibiting SGLT1 activity using the compound or pharmaceutical composition of the invention, the method comprising administering to a patient a therapeutically effective amount of the compound or the pharmaceutical composition.

In other aspect, the invention relates to a method of improving the intestinal environment using the compound or pharmaceutical composition of the invention, the method comprising administering to a patient a therapeutically effective amount of the compound or the pharmaceutical composition.

In other aspect, the invention relates to a method of preventing or treating the following diseases using the compound or pharmaceutical composition of the invention, which comprises administering an effective therapeutical dose of the compound or pharmaceutical composition of the invention to a patient, wherein the diseases are diabetes, diabetic complications, insulin resistance, hyperglycemia, hyperinsulinemia, hyperlipidemia, obesity, syndrome X, atherosclerosis, cardiovascular disease, congestive heart failure, hypomagnesemia, hyponatremia, renal failure, disorders associated with blood concentration, constipation or hypertension. Furthermore, the above compound or pharmaceutical composition thereof provided herein may be co-administered with other therapies or therapeutic agents. The mode of administration can be carried out simultaneously, sequentially or at a certain time interval.

The dosage of the compound or pharmaceutical composition that required to perform a therapeutic, prophylactic or prolonged effects generally depends on the specific compound administered, the patient, the specific disease or condition and its severity, the route of administration and frequency, and the like, and needs to be determined by the attending physician according to the specific circumstances. For example, the compound or pharmaceutical composition provided herein can be applied once a week or even at a longer interval when applied intravenously.

In other aspect, the invention relates to the application of the compound or the pharmaceutical composition disclosed herein to inhibit the activity of SGLT1.

In other aspect, the invention relates to the application of the compound or the pharmaceutical composition disclosed herein to improve the intestinal environment.

In other aspect, the invention relates to the application of the compound or the pharmaceutical composition disclosed herein to prevent or treat the following diseases, lessen symptoms of the diseases or delay progression or onset of the diseases, wherein the diseases are diabetes, diabetic complications, insulin resistance, hyperglycemia, hyperinsulinemia, hyperlipidemia, obesity, syndrome X, atherosclerosis, cardiovascular disease, congestive heart failure, hypomagnesemia, hyponatremia, renal failure, disorders associated with blood concentration, or hypertension.

In some embodiments, the salt refers to a pharmaceutically acceptable salt. The term "pharmaceutically acceptable" means that the substance or composition must be chemically and/or toxicologically compatible with the other ingredients containing the formulation and/or the mammal treated therewith.

The compound of the invention also includes other salts of such compound which are not necessarily pharmaceutically acceptable salts, and may be used to prepare and/or purify the compound of the invention and/or used to separate an intermediate of enantiomer of the compound of the invention.

Pharmaceutically acceptable acid addition salts can be formed with inorganic acids and organic acids, e.g., acetate, aspartate, benzoate, besylate, bromide/hydrobromide, bicarbonate/carbonate, bisulfate/sulfate, camphorsulfonate, chloride/hydrochloride, chlortheophyllonate, citrate, ethandisulfonate, fumarate, gluceptate, gluconate, glucuronate, hippurate, hydroiodide/iodide, isethionate, lactate, lactobionate, laurylsulfate, malate, maleate, malonate, mandelate, mesylate, methylsulphate, naphthoate, napsylate, nicotinate, nitrate, octadecanoate, oleate, oxalate, palmitate, pamoate, phosphate/hydrogen phosphate/dihydrogen phosphate, polygalacturonate, propionate, stearate, succinate, subsalicylate, tartrate, tosylate and trifluoroacetate salts.

Inorganic acids from which salts can be derived include, for example, hydrochloric acid, hydrobromic acid, sulfuric acid, nitric acid, phosphoric acid, and the like.

Organic acids from which salts can be derived include, for example, acetic acid, propionic acid, glycolic acid, oxalic acid, maleic acid, malonic acid, succinic acid, fumaric acid, tartaric acid, citric acid, benzoic acid, mandelic acid, methanesulfonic acid, ethanesulfonic acid, toluenesulfonic acid, sulfosalicylic acid, and the like.

Pharmaceutically acceptable base addition salts can be formed with inorganic and organic bases.

Inorganic bases from which salts can be derived include, for example, ammonium salts and metals from columns I to XII of the periodic table. In certain embodiments, the salts are derived from sodium, potassium, ammonium, calcium, magnesium, iron, silver, zinc, and copper; particularly suitable salts include ammonium, potassium, sodium, calcium and magnesium salts.

Organic bases from which salts can be derived include, for example, primary, secondary, and tertiary amines, substituted amines including naturally occurring substituted amines, cyclic amines, basic ion exchange resins, and the like. Certain organic amines include, such as isopropylamine, benzathine, cholanate, diethanolamine, diethylamine, lysine, meglumine, piperazine and tromethamine.

The pharmaceutically acceptable salts of the present invention can be synthesized from a parent compound, a basic or acidic moiety, by conventional chemical methods. Generally, such salts can be prepared by reacting free acid forms of these compounds with a stoichiometric amount of the appropriate base (such as Na, Ca, Mg, or K hydroxide, carbonate, bicarbonate or the like), or by reacting free base forms of these compounds with a stoichiometric amount of the appropriate acid. Such reactions are typically carried out in water or in an organic solvent, or in a mixture of the two. Generally, use of non-aqueous media like ether, ethyl acetate, ethanol, isopropanol, or acetonitrile is desirable, where practicable. Lists of additional suitable salts can be found, e.g., in "Remington's Pharmaceutical Sciences", 20th ed., Mack Publishing Company, Easton, Pa., (1985); and in "Handbook of Pharmaceutical Salts: Properties, Selection, and Use" by Stahl and Wermuth (Wiley-VCH, Weinheim, Germany, 2002).

Moreover, the compound of the present invention, including the salt thereof, may also be obtained in the form of hydrates thereof or include other solvents for their crystallization. The compound of the present invention may inherently or by design form solvates with pharmaceutically acceptable solvents (including water); therefore, the compound of the invention includes both solvated and unsolvated forms.

Any formula given herein is also intended to represent isotopically unenriched forms as well as isotopically enriched forms of the compound. The isotopically enriched compound has the structure depicted by the general formula given herein except that one or more atoms are replaced by an atom having a selected atomic mass or mass number. Exemplary isotopes that can be incorporated into the compound of the invention include isotopes of hydrogen, carbon, nitrogen, oxygen, phosphorus, sulfur, fluorine, and chlorine, such as $^{2}$H, $^{3}$H, $^{11}$C, $^{13}$C, $^{14}$C, $^{15}$N, $^{18}$F, $^{31}$P, $^{32}$P, $^{36}$S, $^{37}$Cl and $^{125}$I.

In other aspect, the compound of the invention include isotopically enriched compound as defined herein, for example those into which radioactive isotopes, such as $^{3}$H, $^{14}$C and $^{18}$F, or those into which non-radioactive isotopes, such as $^{2}$H and $^{13}$C are present. Such isotopically enriched compounds are useful in metabolic studies (with $^{14}$C), reaction kinetic studies (with, for example $^{2}$H or $^{3}$H), detection or imaging techniques, such as positron emission tomography (PET) or single-photon emission computed tomography (SPECT) including drug or substrate tissue distribution assays, or in radioactive treatment of patients. In particular, the $^{18}$F-enriched compound may be particularly desirable for PET or SPECT studies. Isotopically-enriched compounds of Formula (I) can generally be prepared by conventional techniques known to those skilled in the art or by processes analogous to those described in the accompanying examples and preparations using an appropriate isotopically-labeled reagent in place of the non-labeled reagent previously employed.

Further, substitution with heavier isotopes, particularly deuterium (i.e., 2H or D) may afford certain therapeutic advantages resulting from greater metabolic stability, for example, increased in vivo half-life or reduced dosage requirements or an improvement in therapeutic index. It is understood that deuterium in this context is regarded as a substituent of the compound of Formula (I). The concentration of such a heavier isotope, specifically deuterium, may be defined by the isotopic enrichment factor. The term "isotopic enrichment factor" as used herein means the ratio between the isotopic abundance and the natural abundance of a specified isotope. If a substituent of the compound of the invention is designated as deuterium, such compound has an isotopic enrichment factor for each designated deuterium atom of at least 3500 (52.5% deuterium incorporation at each designated deuterium atom), at least 4000 (60% deuterium incorporation), at least 4500 (67.5% deuterium incorporation), at least 5000 (75% deuterium incorporation), at least 5500 (82.5% deuterium incorporation), at least 6000 (90% deuterium incorporation), at least 6333.3 (95% deuterium incorporation), at least 6466.7 (97% deuterium incorporation), at least 6600 (99% deuterium incorporation), or at least 6633.3 (99.5% deuterium incorporation). Pharmaceutically acceptable solvates of the invention include those wherein the solvent of crystallization may be isotopically substituted, such as $D_2O$, $d_6$-acetone, DMSO-$d_6$.

The foregoing merely summarizes certain aspects disclosed herein and is not limited to these aspects. Other aspects will be described more fully below.

Pharmaceutical Composition and Formulation and Administration of the Compound of the Invention The present invention relates to a pharmaceutical composition, which comprises the compound of the invention or the compound of the structure shown in the examples, or a stereoisomer, a geometric isomer, a tautomer, an N-oxide, a solvate, a metabolite, a dimer, a trimer, and a pharmaceutically acceptable salt or a prodrug thereof. The pharmaceutical composition further comprises at least one pharmaceutically acceptable carrier, adjuvant, excipient, vehicle or combination thereof, and optionally, other therapeutic and/or prophylactic ingredients. The amount of the compound in the pharmaceutical composition disclosed herein is effective and detectable for inhibiting the activity of sodium-dependent glucose transporter 1 (SGLT1) in biological samples or patients.

It will also be appreciated that the compound disclosed herein has a free form, or appropriate, as a pharmaceutically acceptable derivative. Some non-limiting examples of the pharmaceutically acceptable derivative include pharmaceutically acceptable prodrugs, salts, esters, salts of such esters, or any other adducts or derivatives which upon administration to a patient in need is capable of providing, directly or indirectly, a compound as otherwise described herein, or a metabolite or residue thereof.

The pharmaceutically acceptable carrier may contain inert ingredients that do not unduly inhibit the biological activity of the compound. The pharmaceutically acceptable carrier should be biocompatible, such as non-toxic, non-inflammatory, non-immunogenic or otherwise free of other adverse effects or side effects once administered to the patient. Standard pharmaceutical technology can be used.

As described herein, the pharmaceutical composition disclosed herein or pharmaceutically acceptable composition further comprise a pharmaceutically acceptable carrier, an adjuvant, or an excipient, which, as used herein, includes any and all solvents, diluents, or other liquid vehicle, dispersion or suspension aids, surface active agents, isotonic agents, thickening or emulsifying agents, preservatives, solid binders, lubricants and the like, as suited to the particular dosage form desired. Remington: The Science and Practice of Pharmacy, 21st edition, 2005, ed. D. B. Troy, Lippincott Williams & Wilkins, Philadelphia, and Encyclopedia of Pharmaceutical Technology, eds. J. Swarbrick and J. C. Boylan, 1988-1999, Marcel Dekker, New York, the contents of each of which is incorporated by reference herein, are disclosed various carriers used in formulating pharmaceutically acceptable compositions and known techniques for the preparation thereof. Except insofar as any conventional carrier medium incompatible with the compound disclosed herein, such as by producing any undesirable biological effect or otherwise interacting in a deleterious manner with any other components of the pharmaceutically acceptable composition, any other conventional carrier medium and use thereof are contemplated to be within the scope of this invention.

Some non-limiting examples of substances that can be used as pharmaceutically acceptable carriers include ion exchangers, alumina, aluminium stearate, lecithin, serum albumin (e.g., human serum albumin), buffer substances (e.g., tween 80, phosphate, glycine, sorbic acid or potassium sorbate), metaglyceride mixtures of saturated vegetable fatty acids, water, salts or electrolytes (e.g., protamine sulfate, disodium hydrogen phosphate, potassium hydrogen phosphate, sodium chloride or zinc salt), silica gel, magnesium trisilicate, polyvinylpyrrolidone, polyacrylate, wax, polyethylene-polypropylene oxide-block copolymer, methyl cellulose, hydroxypropyl methyl cellulose, lanolin, sugars (e.g., lactose, glucose and sucrose), starch (e.g., corn starch and potato starch), cellulose and derivatives thereof (e.g., sodium carboxymethyl cellulose, ethyl cellulose and cellulose acetate), powdered gum, malt, gelatin, talc, excipients (e.g., cocoa oil and suppository wax), oil (e.g., peanut oil, cottonseed oil, safflower oil, sesame oil, olive oil, corn oil and soybean oil), ethylene glycol (e.g., propylene glycol or polyethylene glycol), ester (e.g., ethyl oleate and ethyl dodecanoate), agar, buffer (e.g., magnesium hydroxide and aluminium hydroxide), alginic acid, non-pyrogenic water, isotonic brine, Ringer's solution, ethanol and phosphate buffers, and other non-toxic compatible Lubricants (such as sodium lauryl sulfate and magnesium stearate), as well as colouring agents, anti-sticking agents, coating agents, sweeteners and flavoring enhancers, preservatives and antioxidants, can also exist in the composition according to the judgement of the formulator.

The compound or composition of the invention can be administered in any suitable manner and can be administered to a human or other animals orally, rectally, parenterally, intrasternally, intravaginally, intraperitoneally, topically (as through powder, ointment or drops), orally as oral or nasal spray, etc., according to the severity of the infection.

Liquid dosage forms for oral administration include, but are not limited to, pharmaceutically acceptable emulsions, microemulsions, solutions, suspensions, syrups and elixirs. In addition to the active compound, the liquid dosage forms may contain inert diluent commonly used in the art, such as, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, dimethyl formamide, oils (in particular, cottonseed, groundnut, corn, germ, olive, castor and sesame oils), glycerol, tetrahydrofuryl alcohol, polyethylene glycol and fatty acid ester of sorbitan, and mixtures thereof. In addition to the inert diluent, the oral compositions may also contain adjuvants such as wetting agents, emulsifying or suspending agents, sweetening agents, flavoring agents and flavor enhancers.

Injectable preparations, such as sterile injectable water or oil suspensions, can be prepared using suitable dispersants or wetting agents and suspensions according to known techniques. The sterile injectable preparation may also be a sterile injectable solution, suspension or emulsion in a non-toxic parenterally acceptable diluent or solvent, such as a solution in 1,3-butanediol. The acceptable vehicles and solvents that include water, Ringer's solution, U. S. P. and isotonic sodium chloride solution. In addition, sterile and nonvolatile oils are conventionally employed as a solvent or suspending medium. For this purpose, any odorless, fixed oil may be employed including synthetic monoglycerides or diglycerides. In addition, fatty acids, such as oleic acid, are used to prepare injections.

For example, the injectable preparation which is previously dissolved or dispersible in sterile water or other sterile injectable medium can be sterilized by filtration through a bacterial retention filter or by the addition of a sterile solid composition.

To prolong the action of the compound or composition of the invention, it is often desirable to slow the absorption of the compound by subcutaneous or intramuscular injection. This may be accomplished by use of a liquid suspension of crystalline or amorphous material having poor water solubility. The rate of absorption of the compound then depends upon its rate of dissolution which, in turn, may depend upon crystal size and crystalline form. Alternatively, delayed absorption of the parenterally administered compound can be achieved by dissolving or suspending the compound in an oil vehicle. Injectable depot forms are made by forming a microcapsule matrix of a compound in a biodegradable polymer such as polylactide-polyglycolic acid. The releasing rate of the compound can be controlled based on the ratio of the compound to the polymer and the nature of the particular polymer employed. Examples of other biodegradable polymers include polyorthoesters and polyanhydrides. Injectable depot formulations are also prepared by entrapping the compound in liposomes or microemulsions which are compatible with body tissues.

Composition for rectal or vaginal administration is especially a suppository which can be prepared by admixing the compound of the invention and a suitable non-irritating excipient or carrier, such as cocoa butter, polyethylene glycol or suppository wax. The excipient or the carrier is solid at ambient temperature but liquid at body temperature and thus melts in the rectum or vaginal cavity and releases the active compound.

Solid dosage forms for oral administration include capsules, tablets, pills, powders and granules. In these dosage forms, the active compound is mixed with at least one pharmaceutically acceptable inert excipient or carrier such as sodium citrate or calcium phosphate and/or a) filler or bulking agent such as starch, lactose, sucrose, glucose, mannitol and silicic acid, b) a binder such as carboxymethylcellulose, alginates, gelatin, polyvinylpyrrolidone, sucrose and acacia, c) a humectant such as glycerol, d) a disintegrating agent such as agar, calcium carbonate, potato starch or tapioca starch, alginic acid, certain silicates and sodium carbonate, e) a blocker solution such as paraffin, f) an absorption enhancer such as quaternary amines, g) a wetting agent such as cetyl alcohol and glyceryl monostearate, h) a absorbent such as kaolin and bentonite, i) a lubricant such as talc, calcium stearate, magnesium stearate, solid polyethylene glycol, sodium lauryl sulfate, and a mixture thereof. In the case of capsules, tablets and pills, the dosage forms may also comprise buffering agents.

Solid compositions of a similar type may also be employed as fillers of soft and hard gel capsules using excipients such as lactose or milk sugar as well as high molecular weight polyethylene glycol. Solid dosage forms of tablets, dragees, capsules, pills, and granules can be prepared with coatings and shells such as enteric coating and other coatings well known in the pharmaceutical art. They may optionally contain emulsifiers and may also have the properties of compositions, so that they may optionally only release active ingredients in a delayed manner, or preferably in a part of the intestine. Examples of embedding compositions that can be used include polymeric substances and waxes. Solid compositions of a similar type may also be employed as fillers of soft and hard gel capsules using excipients such as lactose or milk sugar as well as high molecular weight polyethylene glycol.

The active compound can also be presented in microencapsulated form with one or more of the above-mentioned excipients. Solid dosage forms of tablets, dragees, capsules, pills, and granules can be prepared with coatings and shells such as enteric coating, controlled release coating and other coatings well known in the pharmaceutical art. In these solid dosage forms, the active compound may be mixed with at least one inert diluent, such as sucrose, lactose or starch. In general, such dosage forms may also contain additional materials other than inert diluents, such as tableting lubricants and other tableting adjuvants, such as magnesium stearate and microcrystalline cellulose. In the case of capsules, tablets and pills, the dosage forms may also comprise buffering agents. They may optionally contain emulsifiers and may also have the properties of compositions, so that they may optionally only release active ingredients in a delayed manner, or preferably in a part of the intestine. Examples of embedding compositions that can be used include polymeric substances and waxes.

Topical or transdermal administration forms of the compound of the invention include ointments, ointments, creams, lotions, gels, powders, solutions, sprays, inhalants or patches. The active compound is admixed under sterile conditions with pharmaceutically acceptable carriers and any required preservatives or buffers which may be required. Ophthalmic formulations, ear drops, and eye drops are also considered within the scope of the invention. Additionally, the present invention contemplates the use of a dermal patch that provides the additional advantage of controlling the delivery of the compound to the body. The dosage form can be made by dissolving or dispersing the compound in the proper medium. Absorption enhancers can also be used to increase the flux of the compound through the skin. The rate can be controlled by providing a rate controlling membrane or by dispersing the compound in a polymer matrix or gel.

The composition of invention may also be administered orally, parenterally, by inhalation spray through topically, rectally, nasally, orally, vaginally or by implantation of a kit. The term "parenteral" as used in the present invention includes, but is not limited to, subcutaneous, intravenous, intramuscular, intra-articular, intrasynovial, intrasternal, intrathecal, intrahepatic, intralesional, and intracranial injection or infusion techniques. In particular, the composition is administered orally, intraperitoneally or intravenously.

The sterile injectable form of the composition of the invention may be aqueous or oily suspensions. These suspensions can be prepared with techniques known in the art using suitable dispersing or wetting agents and suspending agents. The sterile injectable preparation may also be a sterile injectable solution or suspension in a non-toxic parenterally acceptable diluent or solvent, such as a solution in 1,3-butanediol. The acceptable vehicles and solvents include water, Ringer's solution, U. S. P. and isotonic sodium chloride solution. In addition, sterile and nonvolatile oils are conventionally employed as a solvent or suspending medium. For this purpose, any odorless, fixed oil may be employed including synthetic monoglycerides or diglycerides. Further, as with natural pharmaceutically acceptable oils, especially in the form of polyoxyethylenated, such as olive oil or castor oil, fatty acids such as oleic acid and glyceride derivatives thereof are used in the preparation of injections. These oil solutions or suspensions may also contain a long-chain alcohol diluent or dispersing agent, such as carboxymethylcellulose or similar dispersing agents which are conventionally employed in the formulation of pharmaceutically acceptable formulations, including emulsions and suspensions. Other commonly used surfactants, such as Tweens, Spans, and other emulsifiers or bioavailability enhancers commonly used in the manufacture of pharmaceutically acceptable solid, liquid or other dosage forms may also be used for the purpose of formulation.

The pharmaceutical composition of the present invention can be orally administered in any orally acceptable dosage form including, but not limited to, capsules, tablets, aqueous suspensions or solutions. In the case of oral tablets, conventional carriers include, but are not limited to, lactose and starch. A lubricant such as magnesium stearate is usually also added. For oral administration in capsule form, useful diluents include lactose and dried cornstarch. When an aqueous suspension is required orally, the active ingredient is combined with emulsifying and suspending agents. Some sweeteners, flavor enhancers or colorants may also be added if desired.

Alternatively, the pharmaceutical composition of the invention may be administered in the form of a suppository for rectal use. The pharmaceutical composition can be prepared by mixing agents and non-irritating excipients which are solid at room temperature but liquid at the rectal temperature and therefore will melt in the rectum to release the drug. Such substances include, but are not limited to, cocoa butter, beeswax, and polyethylene glycol.

The pharmaceutical composition of the present invention may also be administered topically, especially when the therapeutic target includes areas or organs that are readily accessible by topical administration, including ocular, cutaneous or low intestinal diseases. It is easy to prepare suitable topical formulations for each of the areas or organs.

Topical administration to the lower intestinal tract can be achieved in a rectal suppository formulation (see above) or a suitable enema formulation. A topical skin patch can also be used.

For topical administration, the pharmaceutical composition may be formulated as a suitable ointment containing the active component suspended or dissolved in one or more carriers. Carriers of the compound of the present invention suitable for topical administration include, but are not limited to, mineral oil, petroleum jelly, white petrolatum, propylene glycol, polyoxyethylene, polyoxypropylene, emulsified waxes and water. Alternatively, the pharmaceutical composition may be formulated as a suitable lotion or cream containing the active component suspended or dissolved in one or more pharmaceutically acceptable carriers. Suitable carriers include, but are not limited to, mineral oil, sorbitan monostearate, polysorbate 60, cetyl ester wax, cetearyl alcohol, 2-octyl dodecanol, benzyl alcohol and water.

For ophthalmic use, the pharmaceutical composition may be formulated into a micronized suspension in sterile saline with isotonic pH regulation, or especially a sterile saline solution with isotonic pH regulation, with or without a preservative such as benzalkonium chloride. Alternatively, for ophthalmic use, the pharmaceutical composition can be formulated as a cream, such as petrolatum.

The pharmaceutical composition can also be administered by nasal aerosol or inhalation. The composition is prepared according to techniques well known in the pharmaceutical arts and is prepared into a solution in brine using benzyl alcohol and other suitable preservatives, bioavailability absorption enhancers, fluorocarbons and/or other conventional solubilizers or dispersants.

The compound used in the method of the invention can be formulated into a unit dosage form. The term "unit dosage form" refers to physically discrete units suitable as unit dose of the subject, each unit containing a predetermined amount of active substance which is calculated to produce the desired therapeutic effect, optionally in association with a suitable pharmaceutical carrier. The unit dosage form can be administered as once of a single daily dose or multiple daily doses (e.g., about 1 to 4 times or more per day). When multiple daily doses are used, the unit dosage form for each dose may be the same or different.

The compound disclosed herein can be administered as the sole pharmaceutical agent or in combination with one or more other additional therapeutic (pharmaceutical) agents wherein the combination causes no unacceptable adverse effects. This may be of particular relevance for the treatment of diabetes, diabetic complications and other related diseases. Some non-limiting examples of these diseases include diabetes type I, diabetes type II, diabetic retinopathy, diabetic neuropathy, diabetic nephropathy, insulin resistance, hyperglycemia, hyperinsulinemia, elevated blood levels of fatty acids or glycerol, hyperlipidemia, obesity, hypertriglyceridemia, syndrome X, diabetic complications, atherosclerosis, cardiovascular disease, congestive heart failure, hypomagnesemia, hyponatremia, renal failure, disorders associated with blood concentration, and hypertension. As used herein, the additional therapeutic agents include antidiabetic drugs, antihyperglycemic drugs, antiobesity drugs, antihypertensive drugs, appetite suppressant drugs, lipid-lowering drugs, or combinations thereof.

Wherein, the anti-diabetic agents of the present invention include, but are not limited to, SGLT-2 inhibitors (e.g., dapagliflozin, canagliflozin, tofogliflozin, ipragliflozin, luseogliflozin, empagliflozin), biguanides (e.g., phenformin, metformin), sulfonylureas (e.g., acetohexamide, chlorpropamide, glibenclamide, glipizide, gliclazide, glimepiride, glipentide, gliquidone, tolazamide and tolbutamide), meglitinide, glinides (e.g., repaglinide, nateglinide), α-glucosidase inhibitor (e.g., acarbose), α-glucosidase inhibitors (esterase, camiglibose, emiglitate, miglitol, voglibose, pradimicin, salbostatin), PPAR agonists (e.g., balaglitazone, ciglitazone, darglitazone, englitazone, isaglitazone, pioglitazone, rosiglitazone and troglitazone), PPARα/γ dual agonists (such as CLX-0940, GW-1536, GW-1929, GW-2433, KRP-297, L-796449, LR-90, MK-0767 and SB-219994), DPP-IV inhibitors (e.g., sitagliptin, vidagliptin, alogliptin, linagliptin and saxagliptin), glucagon-like peptide-1(GLP-1) agonists (e.g., exendin-3 and exendin-4), protein tyrosine phosphatases-1B (PTP-1B) inhibitors (e.g., trodusquemine, hyrtiosal extract and compounds disclosed by Zhang, S. et al., *Drug Discovery Today*, 12(9/10), 373-381, 2007), insulin, insulin mimics, hepatic glycogen phosphorylase inhibitors, VPAC2 receptor agonists, glucokinase activators, glycogen phosphorylase inhibitors or glucose-6-phosphatase inhibitors, αP2 inhibitors, acetyl-CoA carboxylase-2 (ACC-2) inhibitors, phosphodiesterase (PDE)-10 inhibitors, diacylglycerol acyltransferase (DGAT) 1 or 2 inhibitors, glucose transporter 4 (GLUT4) regulators and glutamine-fructose-6-phosphate amidotransferase (GFAT) inhibitors.

Wherein, the antihyperglycemic agents include, but are not limited to, SGLT-2 inhibitors (e.g.,dapagliflozin, canagliflozin, tofogliflozin, ipragliflozin, luseogliflozin, empagliflozin), biguanides (e.g., phenformin, metformin), sulfonylureas (e.g., acetohexamide, chlorpropamide, glibenclamide, glipizide, gliclazide, glimepiride, glipentide, gliquidone, tolazamide and tolbutamide), meglitinide, glinides (e.g., repaglinide, nateglinide), α-glucosidase inhibitor (e.g., acarbose), α-glucosidase inhibitors(esterase, camiglibose, emiglitate, miglitol, voglibose, pradimicin, salbostatin), PPAR agonists (e.g., balaglitazone, ciglitazone, darglitazone, englitazone, isaglitazone, pioglitazone, rosiglitazone and troglitazone), PPARα/γ dual agonists (such as CLX-0940, GW-1536, GW-1929, GW-2433, KRP-297, L-796449, LR-90, MK-0767 and SB-219994), DPP-IV inhibitors (e.g., sitagliptin, vidagliptin, alogliptin, linagliptin and saxagliptin), glucagon-like peptide-1(GLP-1) agonists (e.g., exendin-3 and exendin-4), protein tyrosine phosphatases-1B (PTP-1B) inhibitors(e.g., trodusquemine, hyrtiosal extract and compounds disclosed by Zhang, S. et al., *Drug Discovery Today*, 12(9/10), 373-381, 2007), insulin, insulin mimics, hepatic glycogen phosphorylase inhibitors, VPAC2 receptor agonists, glucokinase activators, glycogen phosphorylase inhibitors or glucose-6-phosphatase inhibitors, αP2 inhibitors, acetyl-CoA carboxylase-2 (ACC-2) inhibitors, phosphodiesterase (PDE)-10 inhibitors, diacylglycerol acyltransferase (DGAT) 1 or 2 inhibitors, glucose transporter 4 (GLUT4) regulators and glutamine-fructose-6-phosphate amidotransferase (GFAT) inhibitors.

Wherein, the anti-obesity drugs include, but are not limited to, central anti-obesity drugs (e.g., dexfenfluramine, fenfluramine, phentermine, sibutramine, amphepramone, d-amphetamine, mazindol, phenylpropanolamine, clobenzorex, MCH receptor agonists (e.g., compounds described in WO06035967, SB-568849; SNAP-7941, T-226296), neuropeptide Y receptor antagonists (e.g., CP-422935), cannabinoid receptor antagonists (e.g., rimonabant), SR-147778), brain gut peptide antagonists, lipase inhibitors (e.g., orlistat, ATL-962), β3 agonists (e.g., AJ-9677, AZ40140), 11β-HSD1 inhibitors (e.g., BVT-3498, INCB13739), DGAT-1 inhibitors, peptide appetite suppressants (e.g., leptin, CNTF (ciliary neurotrophic factor)), cholecystokinin agonists (e.g., lintitript)), feeding inhibitors (e.g., P-57).

Wherein, the lipid-lowering agents include, but are not limited to, MTP inhibitors, EIMGCoA reductase inhibitors, squalene synthase inhibitors, a fibric acid derivatives, ACAT inhibitors, lipoxygenase inhibitors, cholesterol absorption inhibitors, ileal Na(+)/bile acid cotransporter inhibitors, upregulators of LDL receptor activity, bile acid sequestrants or niacin hypolipidemic drugs. In some embodiments, the lipid-lowering agents are selected from pravastatin, simvastatin, atorvastatin, fluvastatin, cerivastatin, atavastatin or rosuvastatin. Wherein, the antiobesity agents include CB-1 antagonists (e.g., rimonabant, taranabant, surinabant, otenabant, SLV319 and AVE1625), gut-selective MTP inhibitors (e.g., dirlotapide, mitratapide and implitapide), CCKa agonists, 5-HT2c agonists (e.g., lorcaserin), MCR4 agonists, lipase inhibitors (e.g., cetilistat), PYY3-36, opioid antagonist (e.g., naltrexone), oleoyl-estrone, obinepitide, pramlintide, tesofensine, lepaconine, liraglutide, bromocriptine, orlistat, exenatide, AOD-9604 and sibutramine.

Wherein, the suitable anti-inflammatory agents include drugs for prevention and treatment of genital/urethral infection, such as Vaccinium macrocarpon and derivatives thereof, e.g., cranberry juice, cranberry extracts or flavanols of cranberries. Moreover, other suitable anti-inflammatory agents include, but are not limited to, aspirin, non-steroidal anti-inflammatory drugs, glucocorticosteroid, sulfasalazine and cyclooxygenase II selective inhibitor etc.

Use of the Compound and Pharmaceutical Composition of the Invention

The amount of the compound or the compound in the composition disclosed herein is effective and detectable for inhibiting sodium-dependent glucose transporters (SGLTs)

activity, especially significant inhibition of SGLT1 activity. Hence, the compound of the invention would be used for preventing and treating diabetes and related diseases or improving symptoms of these diseases.

The compound of the invention would be useful for but are not limited to, preventing or treating diabetes or related diseases, or lessening diabetes or related diseases, or delaying the progression or onset of diabetes or related diseases or increasing HDL levels in a patient by administering to the patient a compound or a composition disclosed herein in an effective amount. The diseases include, but are not limited to, diabetes, especially type II diabetes, and insulin resistance, hyperglycemia, hyperinsulinemia, hyperlipidemia such as hypertriglyceridemia, diabetic complications such as diabetic retinopathy, diabetic neuropathy or diabetic nephropathy, obesity, X syndrome, atherosclerosis, cardiovascular disease, congestive heart failure, hypomagnesemia, hyponatremia, renal failure, disorders associated with blood concentration, constipation or hypertension.

The compound of the invention has excellent intestinal environment-improving effect, and can increase beneficial bacteria such as bifidobacteria and lactobacilli, increase organic acid in the intestine, and reduce spoilage products in the intestine. By covering the intestinal environment, diseases associated with changes in the intestinal environment can be improved. Wherein, the "diseases associated with changes in the intestinal environment" includes, but is not limited to, chronic kidney disease, pseudomembranous colitis/hemorrhagic enteritis, infectious enteritis, ulcerative colitis, Crohn's disease, irritable bowel Syndrome, obesity, arteriosclerosis, hypertension, Guillain-Barre syndrome, allergic disease, diabetes, multiple sclerosis, autoimmune disease, alcoholic liver dysfunction, nonalcoholic fatty liver disease, nonalcoholic fatty hepatitis, enteritis caused by non-steroidal anti-inflammatory drugs, stress, depression, influenza, periodontal disease, cancer, hay fever, functional dyspepsia, pruritus, etc.

Moreover, the compound or the pharmaceutical composition disclosed herein also suit for preventing or treating the damage of diabetes in later stages, such as nephropathy, retinopathy, neuropathy, myocardial infarction, peripheral arterial occlusive disease, thrombosis, arteriosclerosis, inflammation, immune disease, autoimmune diseases such as AIDS, asthma, osteoporosis, cancer, psoriasis, Alzheimer's disease, schizophrenia and infectious diseases. An "effective amount" or "effective dose" of the compound or pharmaceutically acceptable composition is an amount that is effective in treating or lessening the severity of one or more of the aforementioned disorders. The compound or pharmaceutically acceptable composition is effective administered in a fairly wide dose range. For example, the daily dose is from about 0.1 mg to 1000 mg per person, which can be administered in a single dose or in several divided doses. The compound and composition, according to the method disclosed herein, may be administered with any amount and any route of administration which is effective for treating or lessening the severity of the disorder or disease. The exact amount required will vary from subject to subject, depending on the species, age, and general condition of the subject, the severity of the infection, the particular agent, its mode of administration, and the like. A compound or composition can also be administered with one or more other therapeutic agents as discussed above.

General Synthesis and Detection Methods

For the purpose of describing the invention, the examples are listed below. It is to be understood that the invention is not limited to the embodiments, merely provides a method of practicing the invention.

In the present invention, if the chemical name of the compound doesn't match the corresponding structure, the compound is characterized by the corresponding structure.

Generally, the compound disclosed herein may be prepared by the method described herein, unless otherwise stated, wherein the substituents are as defined for Formula (I), Formula (II), Formula (III) or Formula (IV) above. The following schemes and examples are presented to further exemplify the invention.

One skilled in the art will recognize that the chemical reactions described may be readily adapted to prepare a number of other compounds disclosed herein, and alternative methods for preparing the compounds disclosed herein are deemed to be within the scope disclosed herein. For example, the synthesis of non-exemplified compounds according to the invention may be successfully performed by modifications apparent to those skilled in the art, e.g., by appropriately protecting interfering groups, by utilizing other suitable reagents known in the art other than those described, and/or by making routine modifications of reaction conditions. Alternatively, other reactions disclosed herein or known in the art will be recognized as having applicability for preparing other compounds disclosed herein.

The structures of the compound were identified by nuclear magnetic resonance (e.g., $^1$H-NMR, $^{11}$C-NMR and/or $^{19}$F-NMR). $^1$H-NMR, $^{13}$C-NMR, $^{19}$F-NMR chemical shifts (δ) were recorded as ppm ($10^{-6}$). $^1$H-NMR, $^{13}$C-NMR and $^{19}$F-NMR were determined by Bruker Ultrashield-400 NMR spectrometer and Bruker Avance III HD 600 NMR spectrometer. The solvents were deuterated chloroform ($CDCl_3$), deuterated methanol ($CD_3OD$ or MeOH-$d_4$) or deuterated dimethyl sulfoxide (DMSO-$d^6$). TMS (0 ppm) or chloroform (7.25 ppm) was used as a reference standard. When peak multiplicities are reported, the following abbreviations are used: s (singlet), d (doublet), t (triplet), m (multiplet), br (broadened), dd (doublet of doublets), dt (doublet of triplets), td (triplet of doublets), brs (broadened singlet). Coupling constants J were reported in Hertz (Hz).

Novasep pump 250 high performance liquid chromatography is commonly used for preparation of purification or preparation of split.

Agilen-6120 Quadrupole LC/MS mass spectrometer is used for determination of LC-MS.

The silica gel used in column chromatography generally was Qingdao Ocean Chemical Factory 300 to 400 mesh silica gel.

The staring materials of the present invention were known or purchased from Shanghai Accela Company, Energy Company, J&K, Tianjin Alfa Company and the like, or they could be prepared by the conventional synthesis methods in the prior art.

Unless otherwise stated, the reactions disclosed herein were carried out in a nitrogen atmosphere.

The term "nitrogen atmosphere" refers to such an atmosphere that a reaction flask was equipped with a balloon or a stainless steel autoclave filled with about 1 L nitrogen.

The term "hydrogen atmosphere" refers to such an atmosphere that a reaction flask was equipped with a balloon or a stainless steel autoclave filled with about 1 L hydrogen.

Unless otherwise stated, the solution used in the examples disclosed herein was an aqueous solution.

Unless otherwise stated, the reaction temperature was room temperature.

Unless otherwise stated, the room temperature was from 20° C. to 30° C.

The reaction process in the examples was monitored by thin layer chromatography (TLC). The solvent system for development of a TLC plate comprised dichloromethane and methanol, dichloromethane and ethyl acetate, petroleum ether and ethyl acetate. The volume ratio of the solvents in the solvent system was adjusted according to the polarity of the compound.

The elution system of column chromatography comprised: A: petroleum ether and ethyl acetate; B: dichloromethane and ethyl acetate; C: dichloromethane and methanol. The volume ratio of the solvents in the elution system was adjusted according to the polarity of the compound, and sometimes it was also adjusted by adding a basic agent such as aqueous ammonia or an acidic agent such as acetic acid.

The following abbreviations are used throughout the specification:
DMSO-$d_6$ deuterated dimethyl sulfoxide
$CDCl_3$ deuterated chloroform
$CD_3OD$ deuterated methanol
Br bromine
Mg magnesium
Cbz Carboxybenzyl
Ac acetyl
Bn benzyl
Et ethyl
Me methyl
Ms methanesulfonyl
Boc tert-butoxycarbonyl
PMB p-methoxybenzyl
HBTU O-benzotriazole-tetramethylurea hexafluorophosphate
HATU O-(7-azabenzotriazol-1-yl)-N,N,N',N'-tetramethylurea hexafluorophosphate
DBU 1,8-diazabicyclo[5.4.0]undec-7-ene
DCM dichloromethane
HCl hydrogen chloride
mL milliliter
μL microlitre
M, mol/L mole/liter
mol mole
mmol millimole
g gram
h hour
$H_2$ hydrogen
min minute
$N_2$ nitrogen
MPa mega pascal
atm standard atmospheric pressure General Synthetic Procedures Typical synthetic procedures for the preparation of the compound disclosed herein are shown in the following synthesis schemes 1 to 11. Unless otherwise stated, $R^2$, $R^3$, $R^7$ and $R^8$ have the definitions as described herein.

Scheme 1

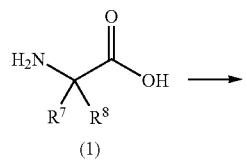

(1)

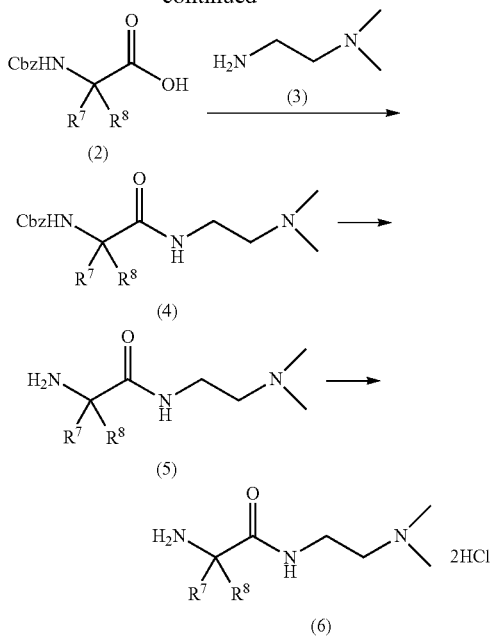

The intermediate of Formula (6) can be synthesized by the method disclosed in Synthesis Scheme 1. Firstly, compound (1) reacts with benzyl chloroformate to give compound (2). Condensation reaction of compound (2) and compound (3) can give compound (4). Then compound (4) can be subjected to catalytic hydrogenation to remove the protective group on the amino group to give compound (5). Finally, compound (5) is salted with hydrogen chloride to give compound (6).

Scheme 2

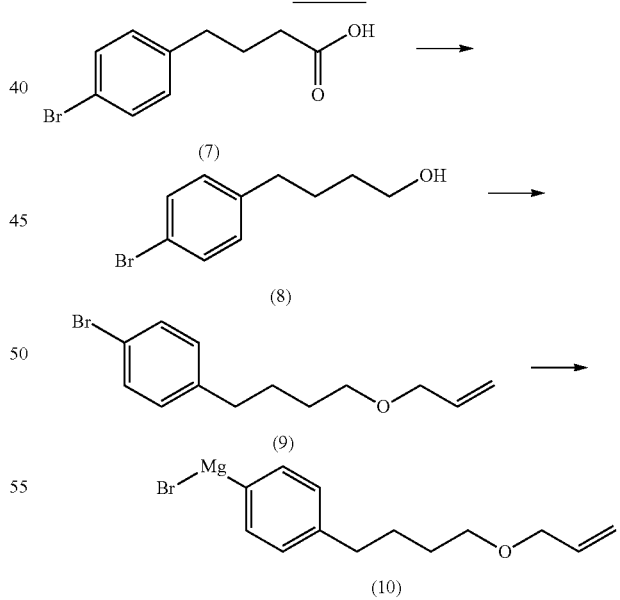

The intermediate of Formula (10) can be synthesized by the method disclosed in Synthesis Scheme 2. Firstly, compound (7) is reduced by a reducing agent to give compound (8). Then compound (9) is obtained by substitution reaction of compound (8) and allyl bromide under basic conditions. Finally, compound (10) is obtained by reaction of compound (9) and Mg.

Scheme 3

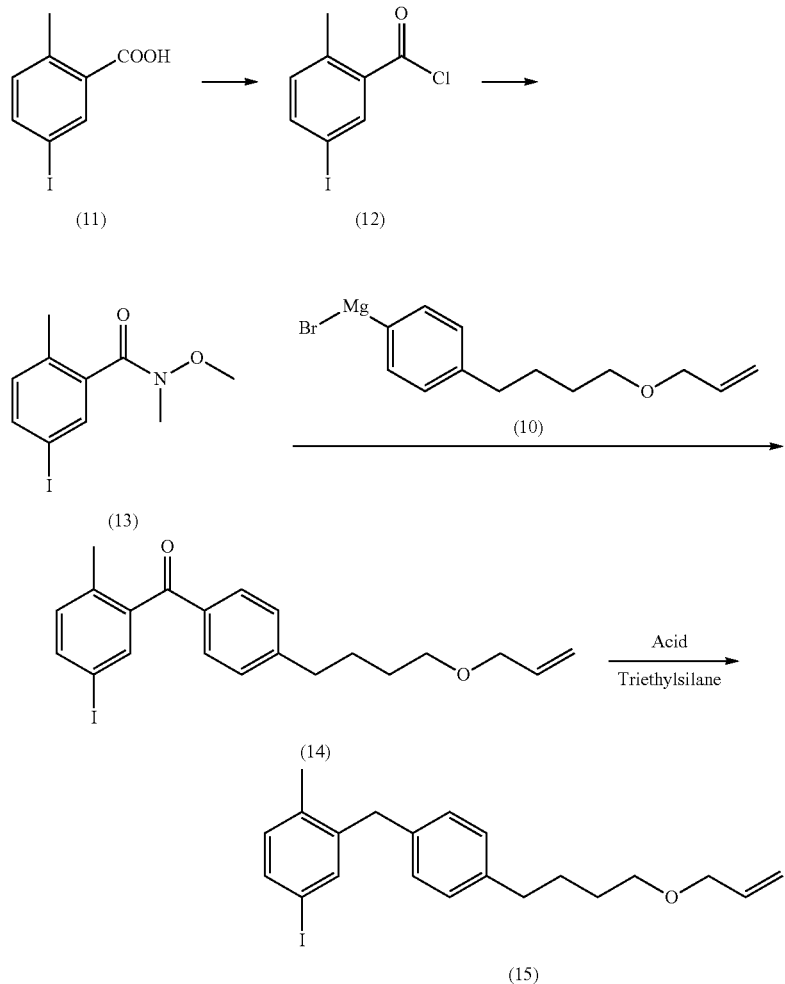

The intermediate of Formula (15) can be synthesized by the method disclosed in Synthesis Scheme 3. Firstly, compound (12) is given by reaction of compound (11) and oxalyl chloride. Then compound (13) is given by reaction of compound (12) and dimethylhydroxylamine hydrochloride under basic conditions. Grignard Reaction of compound (13) and compound (10) can give compound (14). Finally, compound (14) is reduced by the action of acid and triethylsilane to give compound (15).

Scheme 4

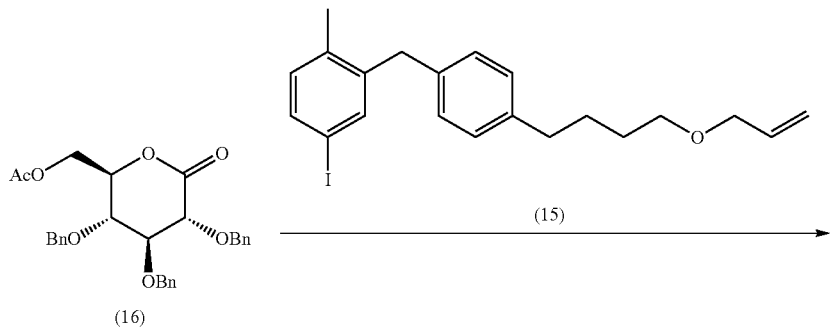

-continued
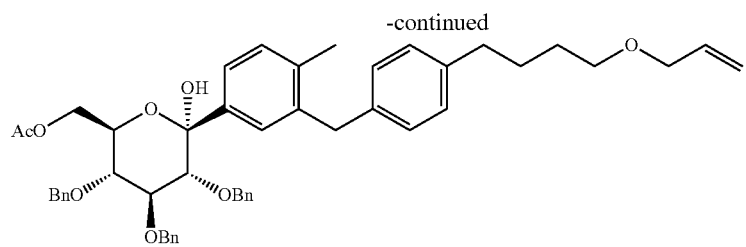
(17)
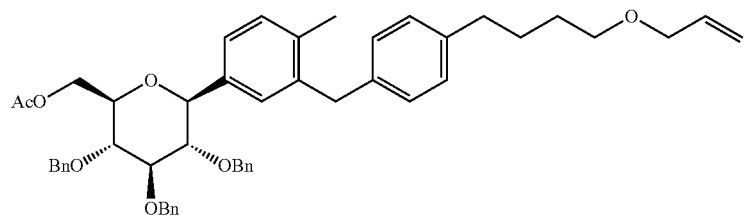
(18)
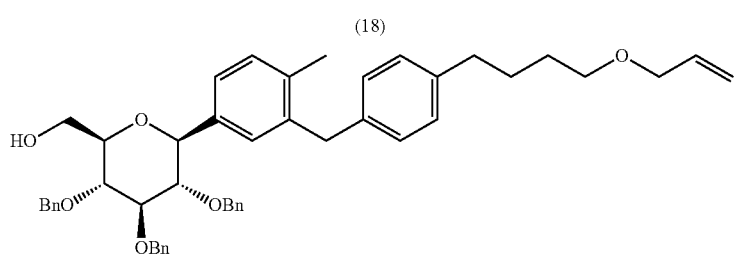
(19)
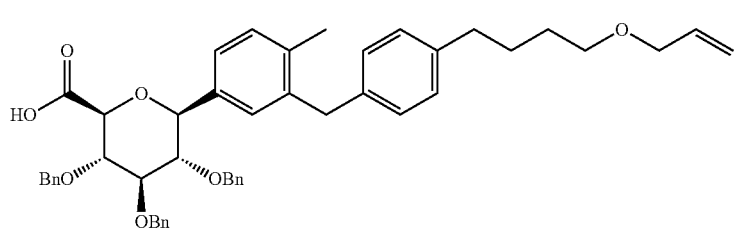
(20)
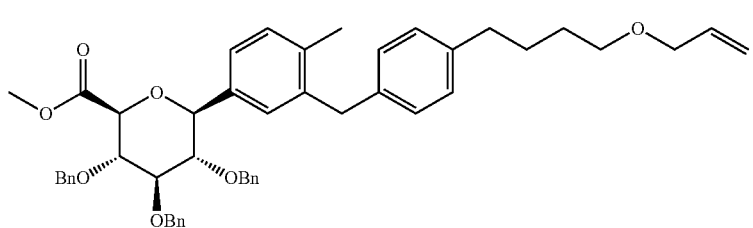
(21)
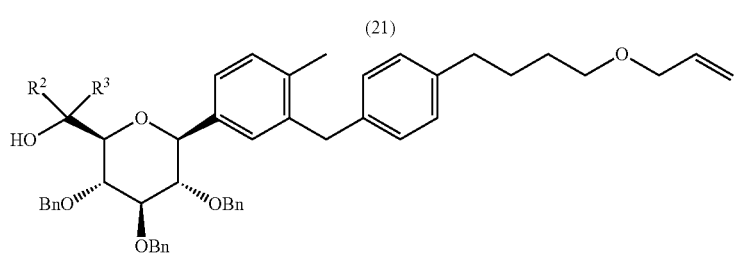
(22)

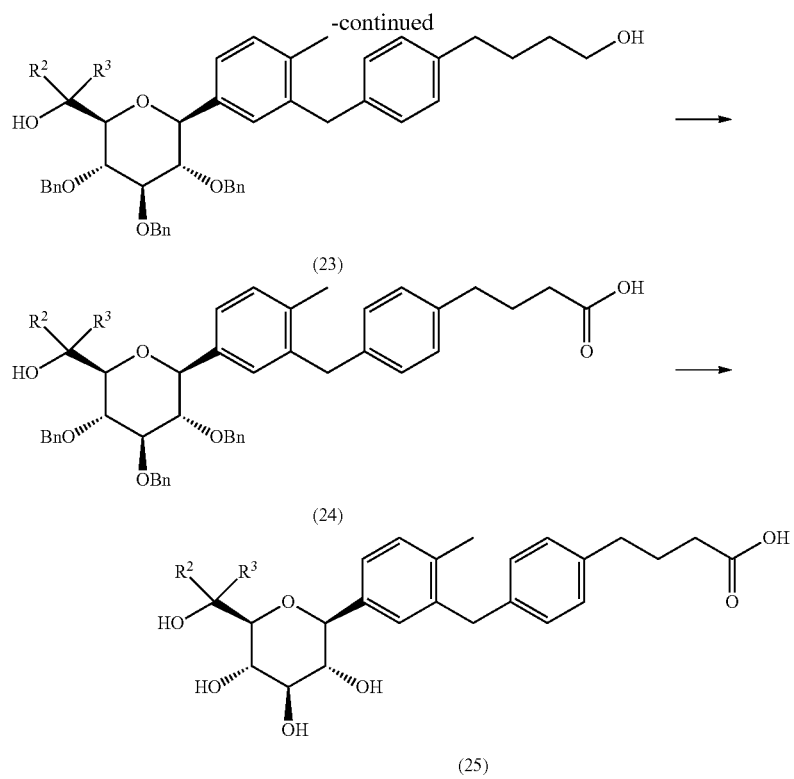

The intermediate of Formula (24) or the intermediate of Formula (25) can be synthesized by the method disclosed in Synthesis Scheme 4. Firstly, compound (15) reacting with isopropyl magnesium chloride is subjected to Grignard reaction with compound (16) to give compound (17). Compound (17) is subjected to reduction reaction with triethylsilane under a condition of boron trifluoride etherate to give compound (18). Compound (18) can be suffered from deprotection of hydroxy protecting group Ac to give compound (19). Then, Oxidation reaction of compound (19) and Dess-Martin periodinane can give compound (20). Reaction of compound (20) and methanol under acidic conditions can give compound (21). Then reaction of compound (21) and Grignard reagent under low temperature conditions can give compound (22). Compound (22) can be suffered from deprotection of hydroxy protecting group allyl under a condition of catalyst to give compound (23). Finally, compound (24) is given by oxidation reaction of compound (23) and iodobenzene diacetat under a condition of catalyst 2,2,6,6-tetramethylpiperidine oxide. Compound (24) can be suffered from deprotection of hydroxy protecting group Bn to give compound (25).

Scheme 5

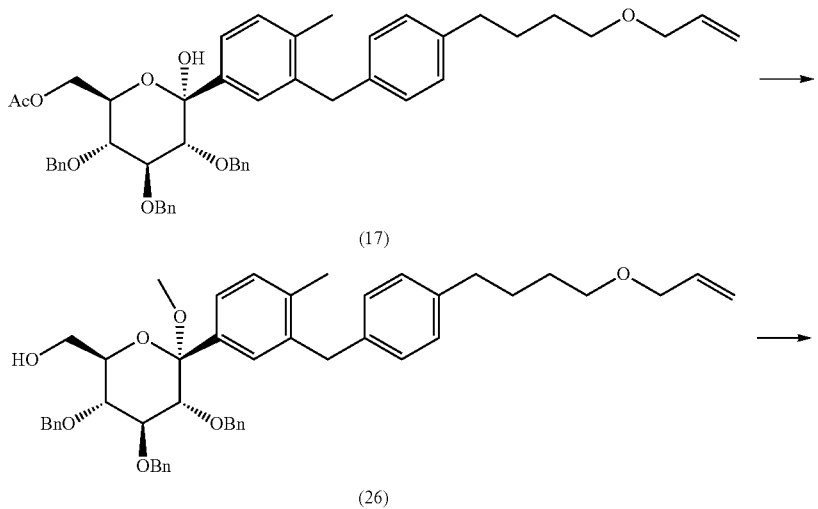

-continued
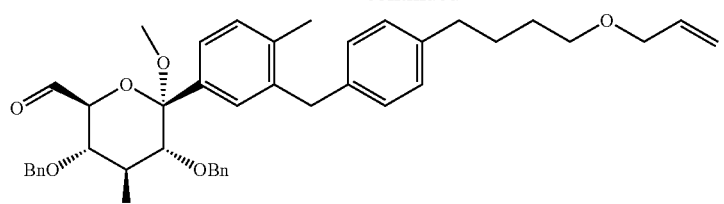
(27)
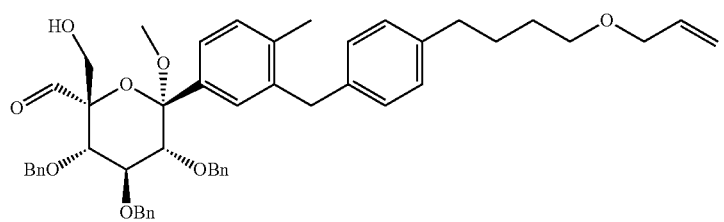
(28)
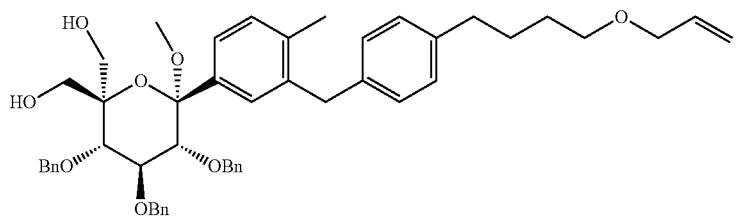
(29)
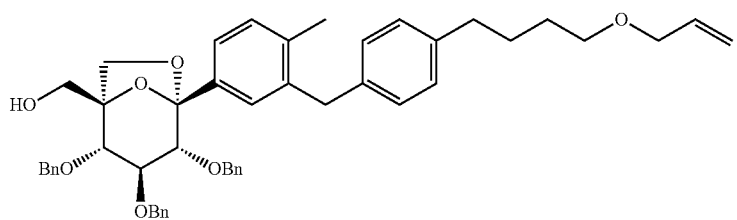
(30)
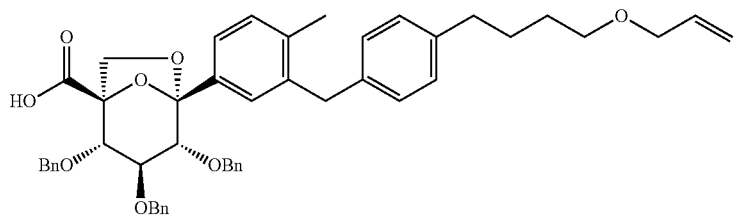
(31)
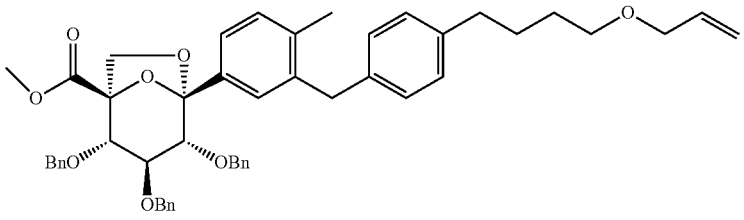
(32)

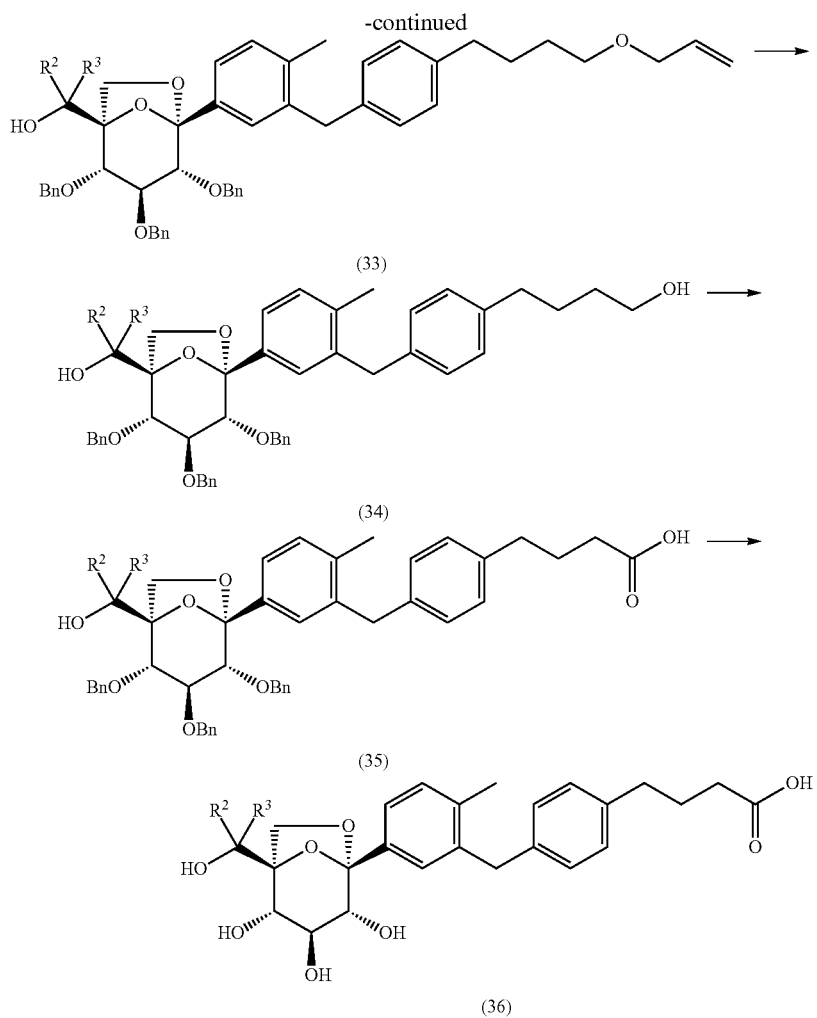

The intermediate shown in Formula (35) or the intermediate shown in Formula (36) can be synthesized by the method disclosed in Synthesis Scheme 5. Reaction of compound (17) and methanol under acidic conditions can give compound (26). Compound (26) is oxidized by oxidizing agents to give compound (27). Reaction of compound (27) and formaldehyde under a condition of DBU can give compound (28). Reduction reaction of compound (28) and sodium borohydride can give compound (29). Compound (29) is subjected to ring closure under acidic conditions to give compound (30). Oxidation reaction of compound (30) and Dess-Martin periodinane can give compound (31). Reaction of compound (31) and methanol under acidic conditions can give compound (32). Then reaction of compound (32) and Grignard reagent under low temperature conditions can give compound (33). Compound (33) can be suffered from deprotection of hydroxy protecting group allyl under a condition of catalyst to give compound (34). Finally, compound (35) is given by oxidation reaction of compound (34) and iodobenzene diacetat under a condition of catalyst 2,2,6,6-tetramethylpiperidine oxide. Compound (35) can be subjected to catalytic hydrogenation to remove the hydroxy protecting group Bn to give compound (36).

Scheme 6

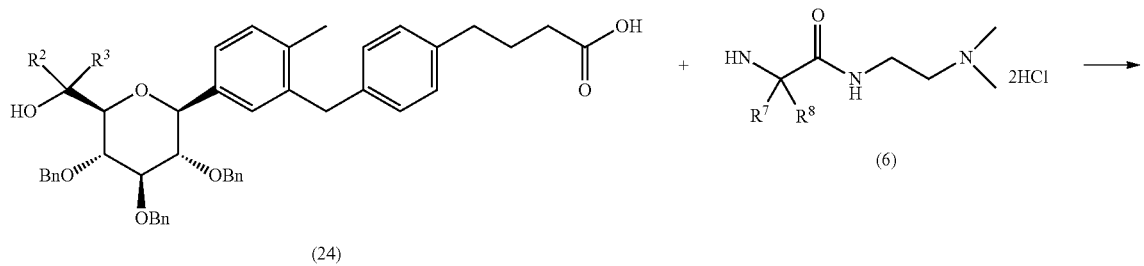

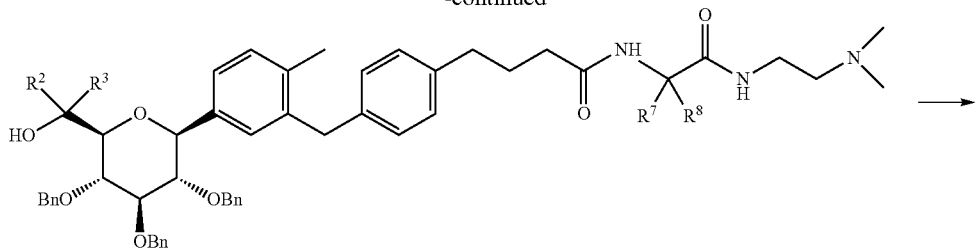
(37)
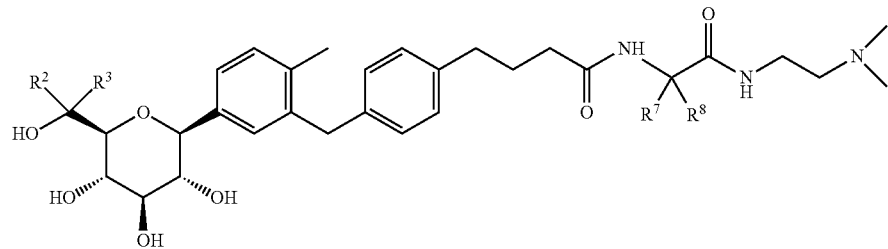
(38)
The intermediate shown in Formula (38) can be synthesized by the method disclosed in Synthesis Scheme 6. Firstly, condensation reaction of compound (24) and compound (6) can give compound (37). Then, compound (37) can be subjected to catalytic hydrogenation to remove the hydroxy protecting group Bn to give compound (38).
Scheme 7
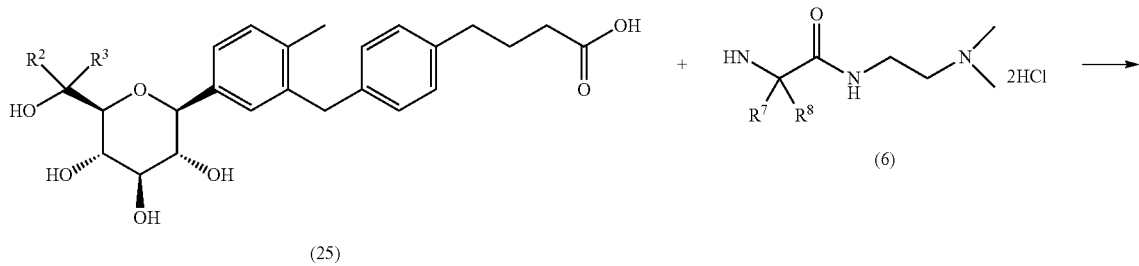
(25)        (6)
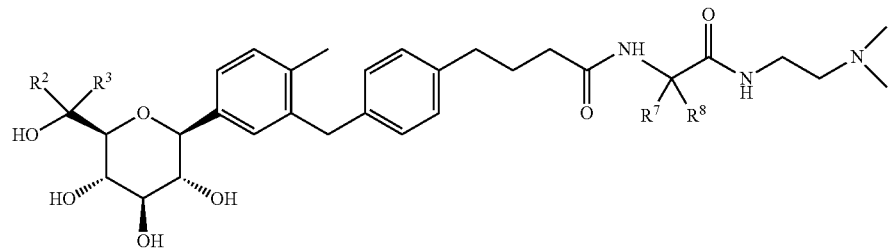
(38)

The intermediate shown in Formula (38) can also be synthesized by the method disclosed in Synthesis Scheme 7. Condensation reaction of compound (25) and compound (6) can give compound (38).

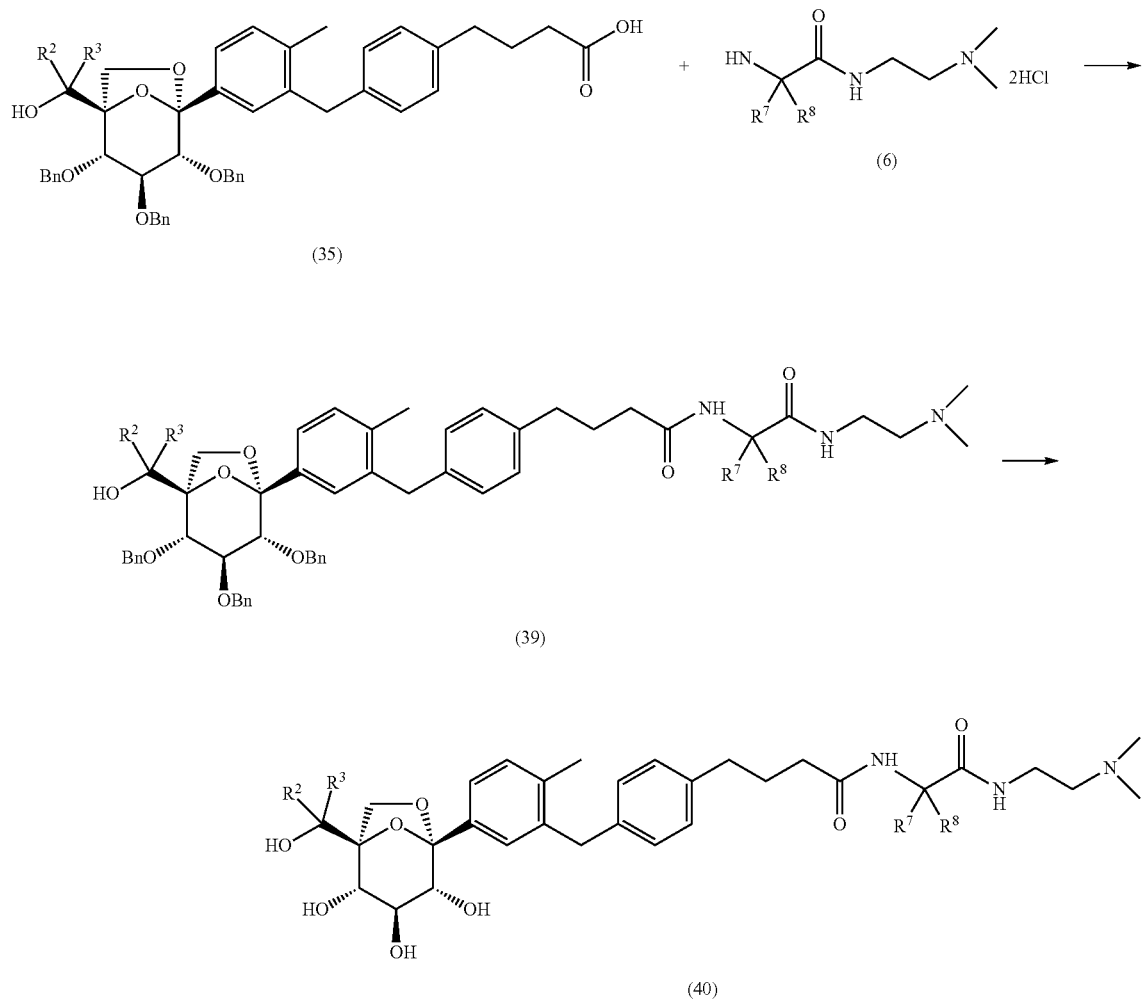

The intermediate shown in Formula (40) can be synthesized by the method disclosed in Synthesis Scheme 8. Firstly, condensation reaction of compound (35) and compound (6) can give compound (39). Then, compound (39) can be subjected to catalytic hydrogenation to remove the hydroxy protecting group Bn to give compound (40).

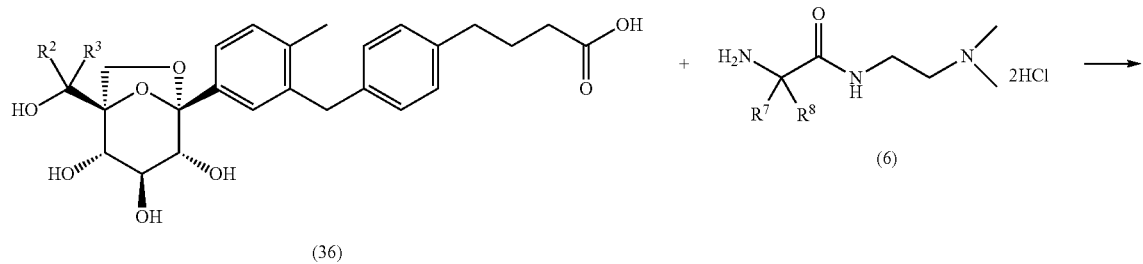

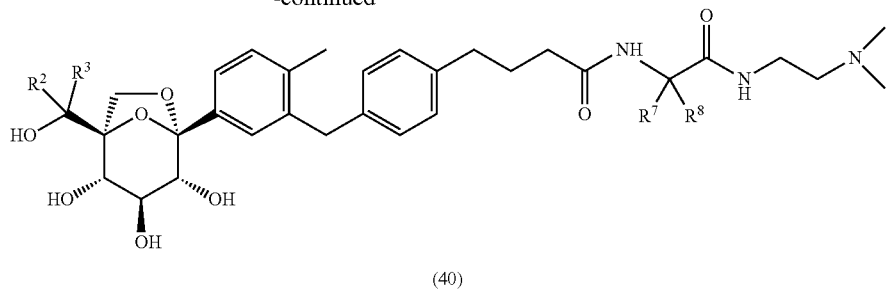

(40)

The intermediate shown in Formula (40) can also be synthesized by the method disclosed in Synthesis Scheme 9. Condensation reaction of compound (36) and compound (6) can give compound (40).

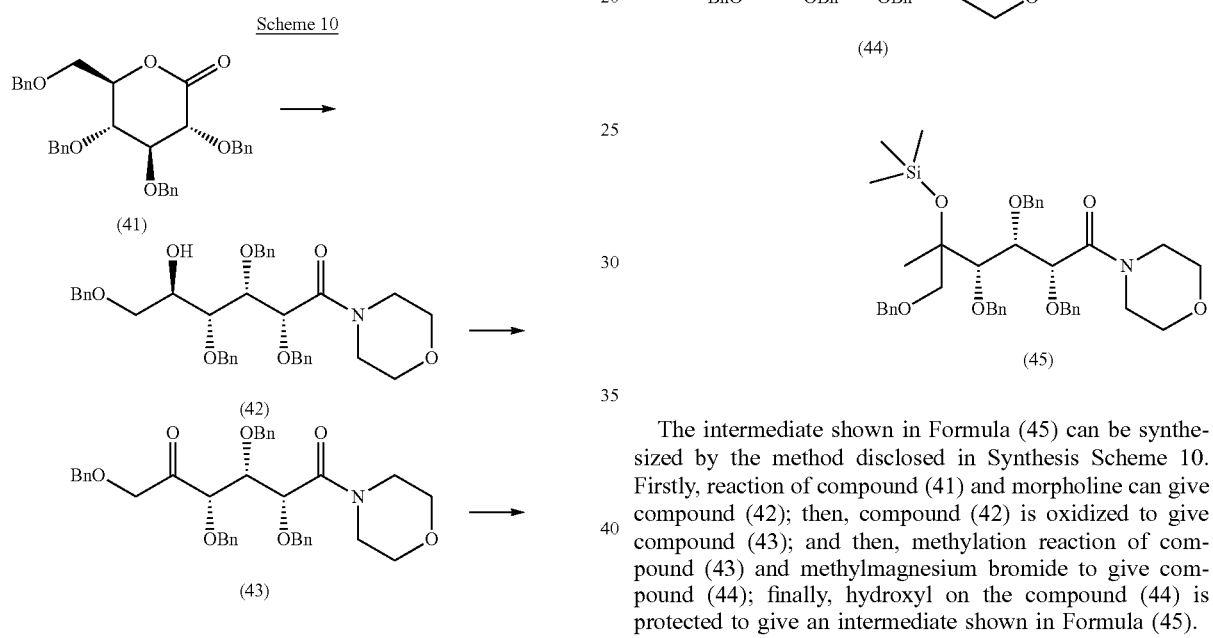

The intermediate shown in Formula (45) can be synthesized by the method disclosed in Synthesis Scheme 10. Firstly, reaction of compound (41) and morpholine can give compound (42); then, compound (42) is oxidized to give compound (43); and then, methylation reaction of compound (43) and methylmagnesium bromide to give compound (44); finally, hydroxyl on the compound (44) is protected to give an intermediate shown in Formula (45).

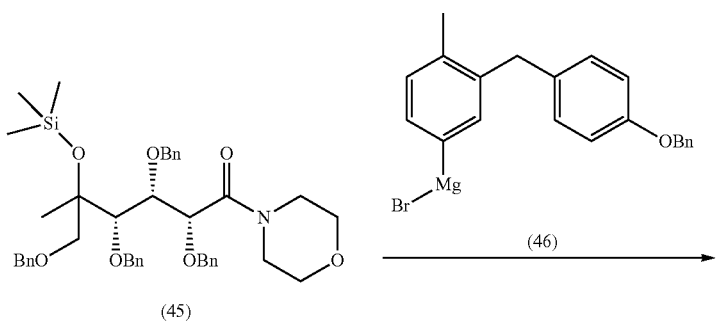

77
-continued
78
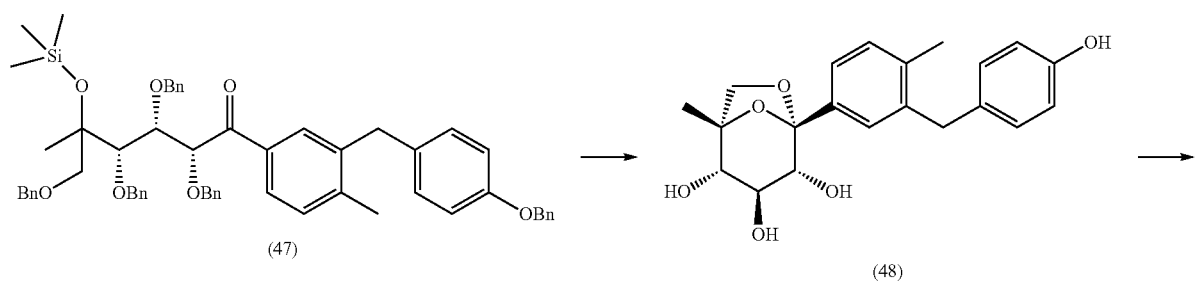
(47) → (48) →
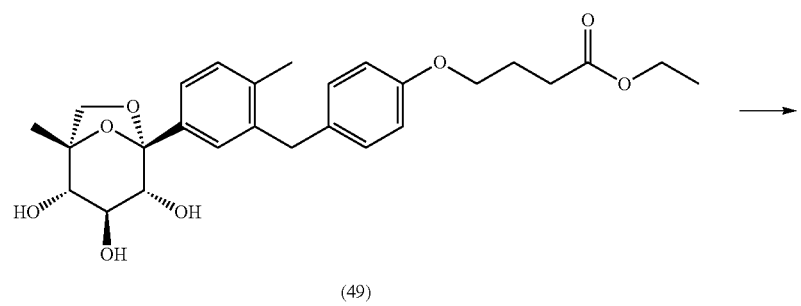
(49) →
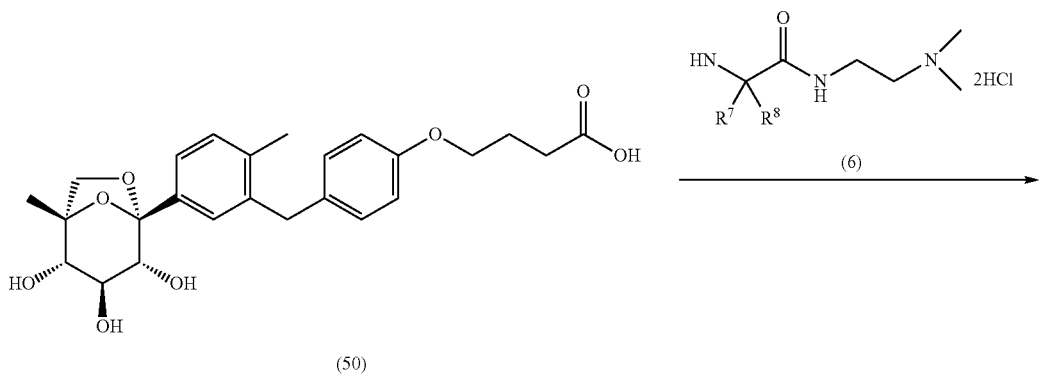
(50) (6) →
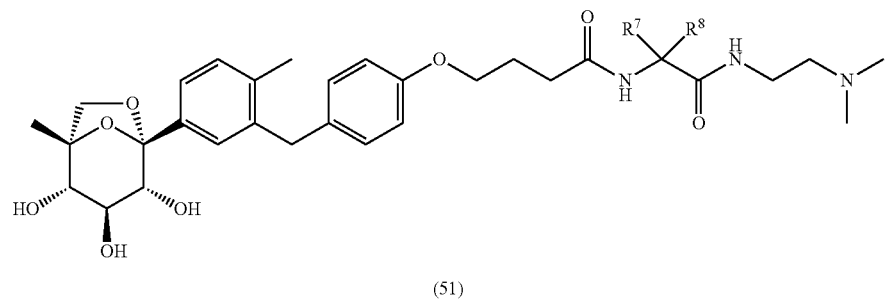
(51)

The compound shown in Formula (51) can be synthesized by the method disclosed in Synthesis Scheme 11. Firstly, Grignard reaction of compound (45) and compound (46) can give compound (47); compound (47) is hydrogenated and reduced under acidic conditions to give compound (48); then, reaction of compound (48) and ethyl 4-bromobutyrate under basic conditions can give compound (49); then, compound (49) is hydrolyzed to give compound (50); finally, condensation reaction of compound (50) and compound (6) can give compound (51).

EXAMPLES

Example 1

N-(2-dimethylaminoethyl)-2-methyl-2-[4-[4-[[2-methyl-5-[(2S,3R,4R,5S,6S)-3,4,5-trihydroxy-6-(1-hydroxy-1-methyl-ethyl)tetrahydropyran-2-yl]phenyl]methyl]phenyl]butanamido]propanamide

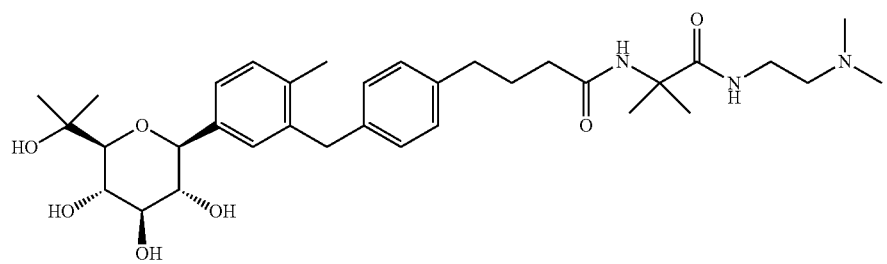 [SMILES: Cc1ccc([C@@H]2O[C@H](C(C)(C)O)[C@@H](O)[C@H](O)[C@H]2O)cc1Cc1ccc(CCCC(=O)NC(C)(C)C(=O)NCCN(C)C)cc1]

Step 1

4-(4-bromophenyl)butyl-1-ol

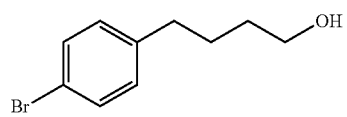 [SMILES: OCCCCc1ccc(Br)cc1]

4-(4-Bromophenyl)butanoic acid (50.0 g, 150 mmol) was dissolved in tetrahydrofuran (250 mL) at room temperature, and the mixture was cooled to −10° C. under nitrogen. Then borane in tetrahydrofuran (1.0 M, 300 mL, 300 mmol) was added dropwise. The mixture was heated to room temperature and stirred for 2 hours. The reaction mixture was poured into ice water (500 mL), and extracted with ethyl acetate (500 mL). The organic phase was washed with saturated salt water (200 mL), dried over anhydrous sodium sulfate and subjected to suction filtration and concentration to give the title compound as colorless oil (47.0 g, 98%).

Step 2

1-(4-allyloxybutyl)-4-bromo-benzene

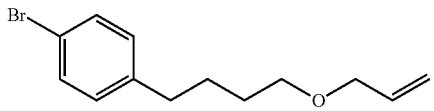

4-(4-bromophenyl)butyl-1-ol (47.0 g, 205 mmol) was dissolved in tetrahydrofuran (500 mL) at room temperature, and the mixture was cooled to −10° C. under nitrogen. Sodium hydride (11.0 g, 275 mmol) was added in batches and stirred for 30 minutes. To the mixture was added allyl bromide (33.6 g, 288 mmol) dropwise. Then the mixture was heated to room temperature and stirred overnight. The reaction mixture was quenched with pouring into ice water (1.0 L), and extracted with ethyl acetate (500 mL). The organic phase was washed with saturated salt water (200 mL), dried over anhydrous sodium sulfate, and subjected to suction filtration and concentration. The residue was purified by a silica gel column chromatography (EtOAc/PE(v/v)=1/40) to give the title compound as colorless oil (33.0 g, 60%).

Step 3

[4-(4-allyloxybutyl)phenyl]-magnesium bromide

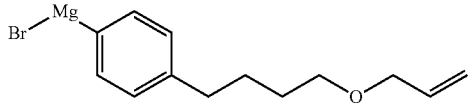

To a reaction flask were added magnesium strips (6.4 g, 0.26 mol) and iodine (0.6 g, 2 mmol) in turn at room temperature. 1-(4-allyloxybutyl)-4-bromo-benzene (59.0 g, 219 mmol) was dissolved in tetrahydrofuran (300 mL), and 10 ml of the solution was added under nitrogen. The mixture was heated to the initiation of the reaction (the color of iodine disappeared), then the remaining solution was added dropwise and stirred for 20 minutes at 65° C. to give the title compound as a brown solution (65 g, 100%). And the next step proceeded directly.

Step 4

5-iodo-2-methyl-benzoyl chloride

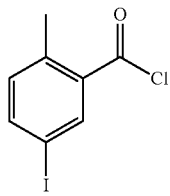

5-Iodo-2-methyl-benzoic acid (50.0 g, 191 mmol) was dissolved in dichloromethane (500 mL) at room temperature, and the mixture was cooled to −10° C. under nitrogen. Then oxalyl chloride (25 mL, 0.29 mol) and N,N-dimethylformamide (1.5 mL, 19 mmol) was added dropwise. The mixture was stirred at room temperature overnight, and concentrated to give the title compound as a yellow solid (53 g, 100%).

Step 5

5-iodo-N-methoxy-N,2-dimethyl-benzamide

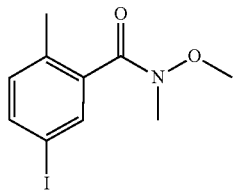

To a reaction flask were added 5-iodo-2-methyl-benzoyl chloride (53.0 g, 189 mmol), dimethylhydroxylamine hydrochloride (37.0 g, 379 mmol) and dichloromethane (500 mL) in turn at room temperature, and the mixture was cooled to −10° C. under nitrogen. Then triethylamine (106 mL, 761 mmol) was added dropwise and stirred for 3.5 hours at room temperature. The reaction mixture was washed with saturated brine (500 mL). The organic phase was dried over anhydrous sodium sulfate, subjected to suction filtration and concentration to give the title compound as yellow oil (54 g, 93%).

MS (ESI, pos. ion) m/z: 306.0 [M+H]$^+$.

Step 6

[4-(4-allyloxybutyl)phenyl]-5-iodo-2-methyl-phenyl)methyl ketone

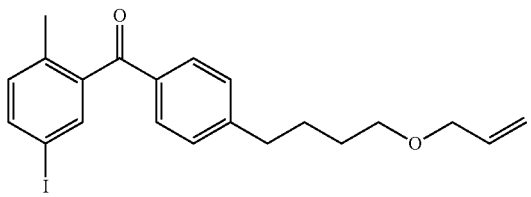 [SMILES: C=CCOCCCCc1ccc(C(=O)c2cc(I)ccc2C)cc1]

5-Iodo-N-methoxy-N,2-dimethyl-benzamide (50.0 g, 164 mmol) in tetrahydrofuran (200 mL) was cooled to −20° C. at room temperature. [4-(4-Allyloxybutyl)phenyl]-magnesium bromide (63.0 g, 215 mmol) synthesized in Step 3 was added dropwise under nitrogen. The mixture was stirred at −20° C. for 1 hour, and then stirred at room temperature overnight. The reaction mixture was cooled to 0° C., and quenched with dropwise saturated aqueous ammonium chloride (400 mL). The resulting mixture was extracted with ethyl acetate (300 mL×2). The combined organic layers were washed with saturated brine (300 mL), dried over ahydrous sodium sulfate and filtered. The filtrate was concentrated, and the residue was purified by a silica gel column chromatography (EtOAc/PE(v/v)=1/30) to give the title compound as colorless oil (59.0 g, 83%).

Step 7

2-[[4-(4-allyloxybutyl)phenyl]methyl]-4-iodo-1-methyl-benzene

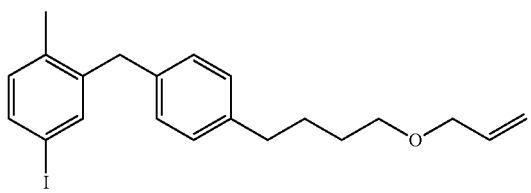 [SMILES: C=CCOCCCCc1ccc(Cc2cc(I)ccc2C)cc1]

To a reaction flask were added [4-(4-allyloxybutyl)phenyl]-5-iodo-2-methyl-phenyl)methyl ketone (59.0 g, 136 mmol) and trifluoroacetic acid (150 mL) in turn at room temperature. The reaction mixture was cooled to 0° C. under nitrogen. Then triethylsilane (174 mL, 1.09 mol) and trifluoromethanesulfonic acid (12.5 mL, 141 mmol) were added dropwise in turn, and the mixture was stirred at room temperature for 1 hour. The resulting mixture was concentrated. The residue was dissolved in ethyl acetate (600 mL). The combined organic layers were washed with water (500 mL), saturated sodium bicarbonate (500 mL) and saturated brine (500 mL), dried over ahydrous sodium sulfate and filtered. The filtrate was concentrated, and the residue was purified by a silica gel column chromatography (petroleum ether) to give the title compound as yellow oil (57 g, 99%).

$^1$H NMR (400 MHz, CDCl$_3$) δ (ppm): 7.52-7.47 (m, 2H), 7.13 (d, 2H), 7.04 (d, 2H), 6.92 (d, 1H), 5.95 (m, 1H), 5.30 (dd, 1H), 5.20 (dd, 1H), 4.02-3.97 (m, 2H), 3.91 (s, 2H), 3.48 (t, 2H), 2.64 (t, 2H), 2.21 (s, 3H), 1.76-1.63 (m, 4H).

Step 8

Benzyl N-[2-(2-dimethylaminoethylamino)-1,1-dimethyl-2-oxo-ethyl]carbamate

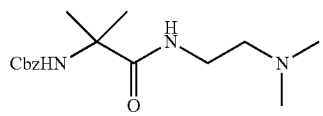 [SMILES: CN(C)CCNC(=O)C(C)(C)NC(=O)OCc1ccccc1]

To a reaction flask were added 2-(Benzyloxycarboxamido)-2-methyl-propionic acid (10.0 g, 42.1 mmol), carbonyldiimidazole (10.5 g, 64.8 mmol) and chloroform (100 mL) in turn at room temperature. The mixture was stirred for 45 minutes under nitrogen. To the mixture was added N,N-dimethyl-1,2-ethanediamine (5.6 g, 64 mmol). The reaction mixture was continuously stirred overnight. The reaction mixture was washed with water (200 mL) and dried over anhydrous sodium sulfate, subjected to suction filtration and concentration to give the title compound as a yellow oil (13 g, 100%).

Step 9

2-amino-N-(2-dimethylaminoethyl)-2-methyl-propanamide

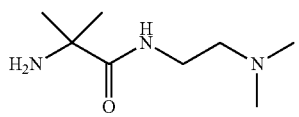

To a reaction flask were added benzyl N-[2-(2-dimethylaminoethylamino)-1,1-dimethyl-2-oxo-ethyl]carbamate (13.0 g, 42.3 mmol), 10% palladium/carbon (0.60 g, 0.57 mmol), tetrahydrofuran (50 mL) and anhydrous methanol (70 mL) in turn room temperature. The mixture was stirred for 2 hours under hydrogen. The mixture was filtered and concentrated to give the title compound as yellow oil (7.0 g, 96%).

Step 10

2-amino-N-(2-dimethylaminoethyl)-2-methyl-propanamide dihydrochloride

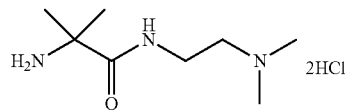

2-Amino-N-(2-dimethylaminoethyl)-2-methyl-propanamide (8.0 g, 46 mmol) was dissolved in ethyl acetate (80 mL) at room temperature. To the mixture was added a solution of HCl in isopropyl alcohol (20 mL, 5 M). The reaction mixture was stirred for 10 minutes, then cooled to 0° C. and stirred for 30 minutes. The mixture was filtered, and the filter cake was washed with ethyl acetate (20 mL) and dried in vacuo to give the title compound as a white solid (10.5 g, 92%).

Step 11

(3R,4S,5R,6R)-3,4,5-tribenzoyloxy-6-(benzyloxymethyl)tetrahydropyran-2-one

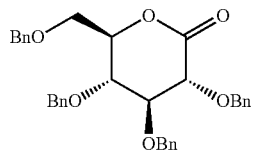 [SMILES: O=C1O[C@H](COCc2ccccc2)[C@@H](OCc2ccccc2)[C@H](OCc2ccccc2)[C@H]1OCc1ccccc1]

To a reaction flask were added (3R,4S,5R,6R)-3,4,5-tribenzoyloxy-6-(benzyloxymethyl)tetrahydropyran-2-ol (130 g, 240 mmol), sodium bicarbonate (80.0 g, 952 mmol), dichloromethane (1000 mL) and water (800 mL) in turn at room temperature. The mixture was cooled to 0° C. To the mixture were added potassium bromide (18.0 g, 151 mmol) and 2,2,6,6-tetramethylpiperidine oxide (5.6 g, 36 mmol), then sodium hypochlorite solution (360 g, available chlorine 6.2%, available chlorine 629 mmol) was once added into the mixture. The mixture was stirred for 20 minitues. The reaction mixture was separated. The organic phase was washed with saturated brine (500 mL), dried over anhydrous sodium sulfate, filtered, and concentrated to give the title compound as yellow oil (129 g, 100%).

Step 12 acetate[(2R,3R,4S,5R)-3,4,5-tribenzoyloxy-6-oxo-tetrahydropyran-2-yl]methyl

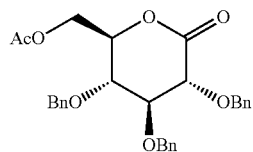

To a mixture of (3R,4S,5R,6R)-3,4,5-tribenzoyloxy-6-(benzyloxymethyl)tetrahydropyran-2-one (130 g, 241 mmol) in acetic anhydride (200 mL, 2.12 mol) was added glacial acetic acid (350 mL) at room temperature. The reaction mixture was cooled to −15° C. under nitrogen, then concentrated sulfuric acid (14.0 mL, 263 mmol) was added dropwise, and the resulting mixture was stirred at −15-10° C. for 2.5 hours. The mixture was poured into ice-water (1.5 L). The resulting mixture was extracted with ethyl acetate (1.0 L). The organic phase was washed with water (500 mL), saturated sodium bicarbonate (1.0 L) and saturated brine (500 mL) in turn, dried over ahydrous sodium sulfate and filtered. The filtrate was concentrated, and the residue was purified by a silica gel column chromatography (EtOAc/PE (v/v)=1/4) to give the title compound as colorless oil (85 g, 71%).

Step 13 acetate[(2R,3R,4S,5R,6S)-6-[3-[[4-(4-allyloxybutyl)phenyl]methyl]-4-methyl-phenyl]-3,4,5-tribenzoyloxy-6-hydroxy-tetrahydropyran-2-yl]methyl

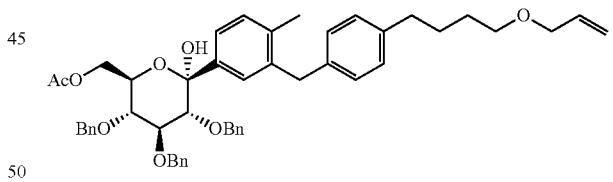

2-[[4-(4-Allyloxybutyl)phenyl]methyl]-4-iodo-1-methylbenzene (30.0 g, 71.4 mmol) was dissolved in tetrahydrofuran (150 mL) at room temperature. The mixture was cooled to −10° C. under nitrogen, then isopropylmagnesium chloride in tetrahydrofuran (39 mL, 78 mmol, 2.0 M) was added and the mixture was stirred for 1.5 hours which was then added dropwise into acetate[(2R,3R,4S,5R)-3,4,5-tribenzoyloxy-6-oxo-tetrahydropyran-2-yl]methyl (25.0 g, 50.9 mmol) in tetrahydrofuran (150 mL) of −10° C. under nitrogen. The resulting mixture was stirred for 2.5 hours. The reaction mixture was quenched with saturated aqueous ammonium chloride (200 mL). The resulting mixture was extracted with ethyl acetate (300 mL×2). The combined organic layers were washed with saturated brine (500 mL), dried over ahydrous sodium sulfate and filtered. The filtrate was concentrated, and the residue was purified by a silica gel column chromatography (EtOAc/PE(v/v)=1/4) to give the title compound as yellow oil (32.1 g, 80%).

Step 14 acetate[(2R,3R,4R,5S,6S)-6-[3-[[4-(4-allyloxybutyl)phenyl]methyl]-4-methyl-phenyl]-3,4,5-tribenzyloxy-tetrahydropyran-2-yl]methyl

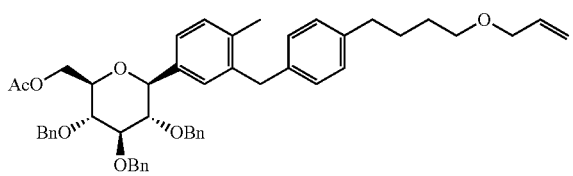 [SMILES: C=CCOCCCCc1ccc(Cc2cc([C@@H]3O[C@H](COC(C)=O)[C@@H](OCc4ccccc4)[C@H](OCc4ccccc4)[C@H]3OCc3ccccc3)ccc2C)cc1]

[(2R,3R,4S,5R,6S)-6-[3-[[4-(4-allyloxybutyl)phenyl]methyl]-4-methyl-benzene]-3,4,5-tribenzyloxy-6-hydroxy-tetrahydropyran-2-yl]methyl acetate (32.0 g, 40.7 mmol) was dissolved in a mixed solvent of acetonitrile (100 mL) and dichloromethane (100 mL), then triethylsilane (23.0 mL, 144 mmol) was added. The mixture was cooled to −10° C. under nitrogen, and a solution of boron trifluoride in diethyl ether (13 mL, 0.10 mol) was added dropwise. The resulting mixture was stirred for 30 minutes and then stirred at room temperature for 30 minutes. The mixture was cooled to 0° C., quenched with saturated sodium bicarbonate solution (100 mL) and separated. The organic phase was dried over anhydrous sodium sulfate, filtered and concentrated to give the title compound as yellow oil (29 g, 92%).

Step 15

[(2R,3R,4R,5S,6S)-6-[3-[[4-(4-allyloxybutyl)phenyl]methyl]-4-methyl-phenyl]-3,4,5-tribenzyloxy-tetrahydropyran-2-yl]methanol

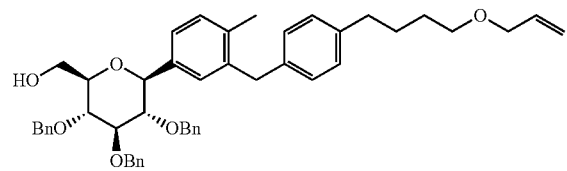

Acetate[(2R,3R,4R,5S,6S)-6-[3-[[4-(4-allyloxybutyl)phenyl]methyl]-4-methyl-benzene]-3,4,5-tribenzyloxy-tetrahydropyran-2-yl]methyl (28.0 g, 36.4 mmol) was dissolved in anhydrous methanol (120 mL), then 30% sodium methoxide solution (6.0 mL) was added dropwise. The mixture was stirred for 20 min. The mixture was concentrated. To the residue was added ethyl acetate (300 mL). The resulting mixture was washed with water (100 mL), hydrochloric acid solution (1 M, 100 mL), saturated sodium bicarbonate (100 mL) and saturated brine (100 mL), dried over ahydrous sodium sulfate and filtered. The filtrate was concentrated, and the residue was purified by a silica gel column chromatography (EtOAc/PE(v/v)=1/8) to give the title compound as yellow oil (8.0 g, 30%).

Step 16

(2R,3R,4R,5S,6S)-6-[3-[[4-(4-allyloxybutyl)phenyl]methyl]-4-methyl-phenyl]-3,4,5-tribenzyloxy-tetrahydropyran-2-formic acid

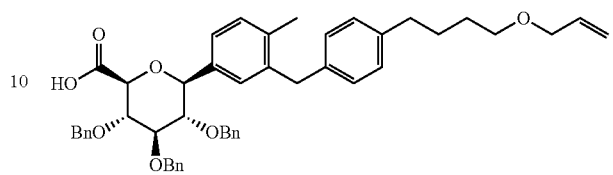

[(2R,3R,4R,5S,6S)-6-[3-[[4-(4-allyloxybutyl)phenyl]methyl]-4-methyl-phenyl]-3,4,5-tribenzyloxy-tetrahydropyran-2-yl]methanol (13.5 g, 18.6 mmol) was dissolved in dichloromethane (140 mL), then cooled to 0° C. Dess-Martin Periodinane (58.0 g, 136 mmol) was added. The reaction mixture was heated to 40° C. and stirred for 2 hours. The mixture was concentrated. The residue was purified by a silica gel column chromatography (EtOAc/PE(v/v)=1/1) to give the title compound as a white solid (11.5 g, 84%).

Step 17 methyl(2S,3S,4R,5S,6S)-6-[3-[[4-(4-allyloxybutyl)phenyl]methyl]-4-methyl-phenyl]-3,4,5-tribenzyloxy-tetrahydropyran-2-formate

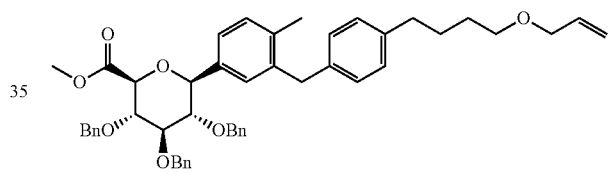

(2S,3S,4R,5S,6S)-6-[3-[[4-(4-allyloxybutyl)phenyl]methyl]-4-methyl-phenyl]-3,4,5-tribenzyloxy-tetrahydropyran-2-formic acid (11.5 g, 15.5 mmol) was dissolved in anhydrous methanol (100 mL), then concentrated sulphuric acid (1.0 mL, 19 mmol) was added. The mixture was heated to 40° C. and stirred overnight. Then the mixture was concentrated. The resulting mixture was washed with ethyl acetate (200 mL), saturated sodium bicarbonate (100 mL), dried over ahydrous sodium sulfate and filtered. The filtrate was concentrated, and the residue was purified by a silica gel column chromatography (EtOAc/PE(v/v)=1/10) to give the title compound as colorless oil (8.8 g, 75%).

Step 18

2-[(2S,3S,4R,5S,6S)-6-[3-[[4-(4-allyloxybutyl)phenyl]methyl]-4-methyl-phenyl]-3,4,5-tribenzyloxy-tetrahydropyran-2-yl]propan-2-ol

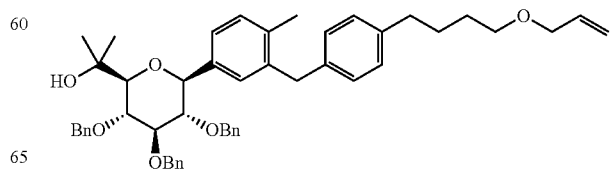

Methyl(2S,3S,4R,5S,6S)-6-[3-[[4-(4-allyloxybutyl)phenyl]methyl]-4-methyl-phenyl]-3,4,5-tribenzyloxy-tetrahydropyran-2-formate (8.8 g, 12 mmol) was dissolved in tetrahydrofuran (80 mL), then cooled to 0° C. under nitrogen. Methylmagnesium bromide in diethyl ether solution (25 mL, 75 mmol, 3.0 M) was added dropwise and the resulting mixture was stirred at room temperature for 4 hours. The mixture was cooled to 0° C., quenched with dropwise saturated ammonium chloride solution (100 mL) and extracted with ethyl acetate (100 mL×2). The mixture was dried over anhydrous sodium sulfate and subjected to suction filtration and concentration to give the title compound as colorless oil (8.8 g, 100%).

Step 19

(2S,3R,4S,5S,6S)-3,4,5-tribenzyloxy-2-[4-methyl-3-[[4-(4-hydroxybutyl)phenyl]methyl]phenyl]-6-(1-hydroxy-1-methyl-ethyl)tetrahydropyran-2-ol

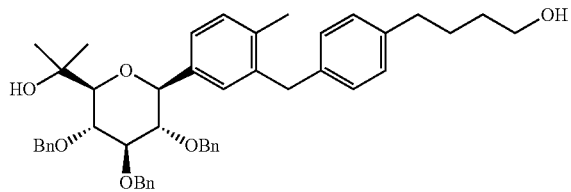 [SMILES: Cc1ccc([C@@H]2O[C@H](C(C)(C)O)[C@@H](OCc3ccccc3)[C@H](OCc3ccccc3)[C@H]2OCc2ccccc2)cc1Cc1ccc(CCCCO)cc1]

2-[(2S,3S,4R,5S,6S)-6-[3-[[4-(4-allyloxybutyl)phenyl]methyl]-4-methyl-phenyl]-3,4,5-tribenzyloxy-tetrahydropyran-2-yl]propan-2-ol (8.3 g, 11 mmol) was dissolved in anhydrous methanol (80 mL), then palladium chloride (1.0 g, 5.6 mmol) was added. The mixture was stirred for 2 hours at room temperature under nitrogen. Then the mixture was concentrated. The residue was purified by a silica gel column chromatography (EtOAc/PE(v/v)=1/2) to give the title compound as colorless oil (6.0 g, 76%).

Step 20

4-[4-[[2-methyl-5-[(2S,3R,4S,5S,6S)-3,4,5-tribenzyloxy-2-hydroxy-6-(1-hydroxy-1-methyl-ethyl)tetrahydropyran-2-yl]phenyl]methyl]phenyl]butyric acid

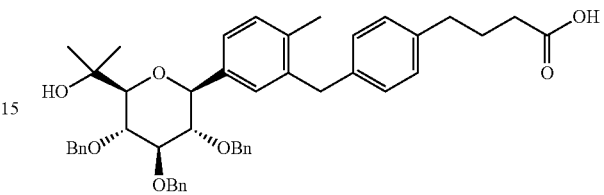

(2S,3R,4S,5S,6S)-3,4,5-tribenzyloxy-2-[4-methyl-3-[[4-(4-hydroxybutyl)phenyl]methyl]phenyl]-6-(1-hydroxy-1-methyl-ethyl)tetrahydropyran-2-ol (2.0 g, 2.8 mmol) was dissolved in dichloromethane(20 mL) at room temperature. Water (4 mL), 2,2,6,6-tetramethylpiperidine oxide (0.14 g, 0.85 mmol) and iodobenzene diacetic acid (2.3 g, 7.0 mmol) were added. The reaction mixture was stirred at room temperature overnight. Then the mixture was separated. The organic phase was dried over anhydrous sodium sulfate, filtered and concentrated. The residue was purified by a silica gel column chromatography (EtOAc/PE(v/v)=1/2) to give the title compound as yellow oil (1.6 g, 78%).

$^1$H NMR (400 MHz, DMSO-$d_6$) δ (ppm): 12.04 (s, 1H), 7.34-7.15 (m, 16H), 7.00 (s, 4H), 6.93 (d, 2H), 4.92-4.72 (m, 4H), 4.32 (d, 1H), 4.26-4.12 (m, 2H), 4.03-3.64 (m, 5H), 3.50-3.30 (m, 5H), 2.20 (s, 3H), 1.79-1.70 (m, 2H), 1.16 (d, 6H).

Step 21

N-(2-dimethylaminoethyl)-2-methyl-2-[4-[4-[[2-methyl-5-[(2S,3S,4R,5S,6S)-3,4,5-tribenzyloxy-6-(1-hydroxy-1-methyl-ethyl)tetrahydropyran-2-yl]phenyl]methyl]phenyl]butanamido]propanamide

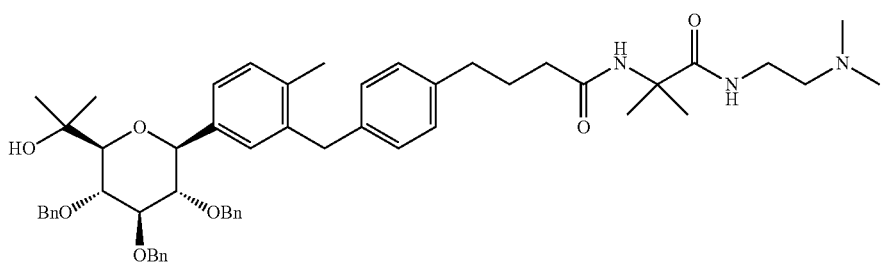 [SMILES: Cc1ccc([C@@H]2O[C@H](C(C)(C)O)[C@@H](OCc3ccccc3)[C@H](OCc3ccccc3)[C@H]2OCc2ccccc2)cc1Cc1ccc(CCCC(=O)NC(C)(C)C(=O)NCCN(C)C)cc1]

4-[4-[[2-methyl-5-[(2S,3R,4S,5S,6S)-3,4,5-tribenzyloxy-2-hydroxy-6-(1-hydroxy-1)-methyl-ethyl)tetrahydropyran-2-yl]phenyl]methyl]phenyl]butyric acid (1.6 g, 2.2 mmol) was dissolved in N,N-dimethylformamide (20 mL) at room temperature. HBTU (1.0 g, 2.6 mmol) and N,N-diisopropylethylamine (2.0 mL, 11 mmol) were added in turn. The reaction mixture was stirred at room temperature for 20 min. Then 2-amino-N-(2-dimethylaminoethyl)-2-methyl-propionyl dihydrochloride (0.70 g, 2.8 mmol) was added. The reaction mixture was stirred at room temperature overnight. The reaction mixture was diluted with water (60 mL). The resulting mixture was extracted with ethyl acetate (100 mL×3). The combined organic layers were washed with brine (200 mL), dried over ahydrous sodium sulfate and filtered. The filtrate was concentrated, and the residue was purified by a silica gel column chromatography (dichloromethane/anhydrous methanol (v/v)=30/1) to give the title compound as colorless oil (1.5 g, 77%).

$^1$H NMR (400 MHz, CDCl$_3$) δ (ppm): 7.98 (s, 1H), 7.41 (s, 1H), 7.31 (m, 8H), 7.22 (m, 6H), 7.12 (t, 1H), 7.02 (m, 6H), 5.24 (s, 1H), 5.11 (d, 1H), 5.02 (d, 1H), 4.86 (d, 1H), 4.75 (d, 1H), 4.38 (d, 1H), 4.25 (d, 1H), 3.99 3.86 (m, 4H), 3.79 (t, 1H), 3.70 3.61 (m, 3H), 3.53 (t, 1H), 3.32 (m, 3H), 2.91 (s, 6H), 2.59 (t, 2H), 2.33 (t, 2H), 2.27 (s, 3H), 1.92 1.83 (m, 2H), 1.43 (s, 6H), 1.29 (s, 3H), 1.25 (s, 3H).

Step 22

N-(2-dimethylaminoethyl)-2-methyl-2-[4-[4-[[2-methyl-5-[(2S,3R,4R,5S,6S)-3,4,5-trihydroxy-6-(1-hydroxy-1-methyl-ethyl)tetrahydropyran-2-yl]phenyl]methyl]phenyl]butanamido]propanamide

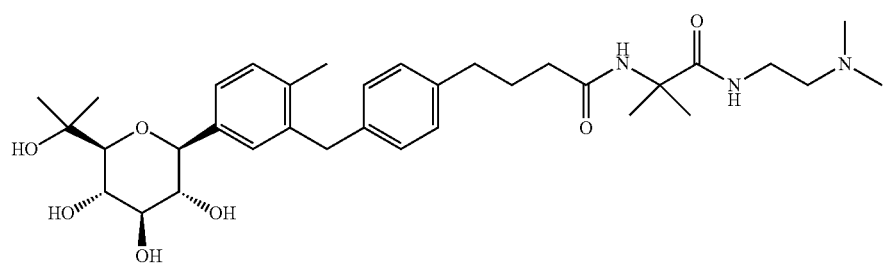 [SMILES: Cc1ccc([C@@H]2O[C@H](C(C)(C)O)[C@@H](O)[C@H](O)[C@H]2O)cc1Cc1ccc(CCCC(=O)NC(C)(C)C(=O)NCCN(C)C)cc1]

N-(2-dimethylaminoethyl)-2-methyl-2-[4-[4-[[2-methyl-5-[(2S,3S,4R,5S,6S)-3,4,5-tribenzyloxy-6-(1-hydroxy-1-methyl-ethyl)tetrahydropyran-2-yl]phenyl]methyl]phenyl]butanamido]propan amide was dissolved in anhydrous methanol (20 mL). 10% palladium/carbon catalyst (0.40 g, 0.38 mmol) was added. The reaction mixture was stirred overnight under hydrogen. Then the mixture was filtered and concentrated. The residue was purified by a silica gel column chromatography (dichloromethane/anhydrous methanol (v/v)=7/1) to give the title compound as colorless oil (0.6 g, 50%).

MS (ESI, pos. ion) m/z: 614.5 [M+H]$^+$.

$^1$H NMR (400 MHz, CD$_3$OD) δ (ppm): 7.17-7.05 (m, 7H), 4.08 (d, 1H), 3.96 (s, 2H), 3.67-3.56 (m, 3H), 3.51 (t, 1H), 3.31-3.16 (m, 4H), 2.95 (s, 6H), 2.62 (t, 2H), 2.29-2.24 (m, 2H), 2.23 (s, 3H), 1.94-1.85 (m, 2H), 1.42 (s, 6H), 1.28 (s, 3H), 1.24 (s, 3H).

Example 2

N-(2-dimethylaminoethyl)-2-methyl-2-[4-[4-[[2-methyl-5-[(1S,2S,3S,4R,5S))-2,3,4-trihydroxy-1-(1-hydroxy-1-methyl-ethyl)-6,8-dioxabicyclo[3.2.1]octane-5-yl]phenyl]methyl]phenyl]butanamido]propionamide

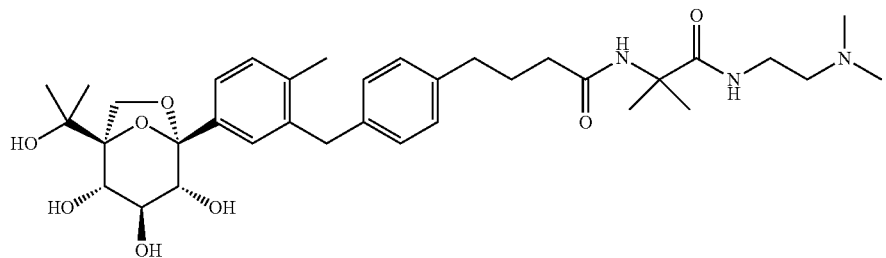 [SMILES: Cc1ccc([C@]23OC[C@](C(C)(C)O)(O2)[C@@H](O)[C@H](O)[C@H]3O)cc1Cc1ccc(CCCC(=O)NC(C)(C)C(=O)NCCN(C)C)cc1]

Step 1

[(2R,3R,4S,5R,6S)-6-[3-[[4-(4-allyloxybutyl)phenyl]methyl]-4-methyl-phenyl]-3,4,5-tribenzyloxy-6-methoxy-tetrahydropyran-2-yl]methanol

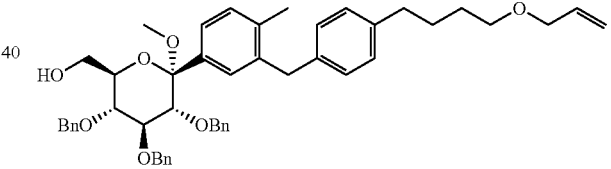

Acetate[(2R,3R,4S,5R,6S)-6-[3-[[4-(4-allyloxybutyl)phenyl]methyl]-4-methyl-phenyl]-3,4,5-tribenzyloxy-6-hydroxy-tetrahydropyran-2-yl]methyl (28.0 g, 35.6 mmol) was dissolved in anhydrous methanol (300 mL), then concentrated hydrochloric acid (9.0 mL, 0.11 mol) was added. The mixture was stirred for 3 hours. Then ethyl acetate (500 mL) was added. The mixture was washed with water (500 mL), saturated sodium bicarbonate (200 mL) and saturated brine (200 mL) in turn, dried over anhydrous sodium sulfate and filtered. The filtrate was concentrated, and the residue was purified by a silica gel column chromatography (EtOAc/PE (v/v)=1/4) to give the title compound as colorless oil (23.0 g, 85%).

¹H NMR (400 MHz, CDCl₃) δ (ppm): 7.46-7.27 (m, 15H), 7.20-7.05 (m, 7H), 5.99 (m, 1H), 5.35 (dd, 1H), 5.25 (t, 1H), 5.02 (dt, 3H), 4.81 (d, 1H), 4.53 (d, 1H), 4.30 (t, 1H), 4.14-3.75 (m, 10H), 3.55-3.44 (m, 3H), 3.24 (s, 3H), 2.67 (t, 2H), 2.34 (s, 3H), 1.79-1.67 (m, 4H)

Step 2

[(2S,3S,4S,5R,6S)-6-[3-[[4-(4-allyloxybutyl)phenyl]methyl]-4-methyl-phenyl]-3,4,5-tribenzyloxy-6-methoxy-tetrahydropyran-2-yl]formaldehyde

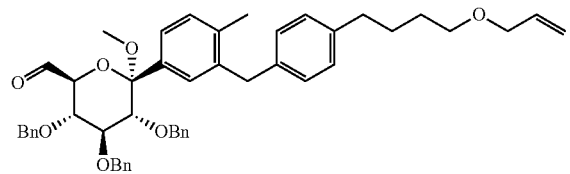 [SMILES: C=CCOCCCCc1ccc(Cc2cc([C@]3(OC)O[C@H](C=O)[C@@H](OCc4ccccc4)[C@H](OCc4ccccc4)[C@H]3OCc3ccccc3)ccc2C)cc1]

To a reaction flask were added [(2R,3R,4S,5R,6S)-6-[3-[[4-(4-allyloxybutyl)phenyl]methyl]-4-methyl-phenyl]-3,4,5-tribenzyloxy-6-methoxy-tetrahydropyran-2-yl]methanol (23.0 g, 30.4 mmol), sodium bicarbonate (16.0 g, 190 mmol), dichloromethane (250 mL) and water (160 mL). The mixture was cooled to 0° C. Potassium bromide (2.4 g, 20 mmol), 2,2,6,6-tetramethylpiperidine oxide (0.75 g, 4.8 mmol) and sodium hypochlorite solution (52 g, available chlorine 5.53%, available chlorine 81 mmol) were added in turn and stirred for 15 minutes. The reaction mixture was separated. The organic phase was washed with saturated brine (200 mL), dried over anhydrous sodium sulfate. The mixture was filtered and concentrated to give the title compound as yellow oil (22 g, 96%).

Step 3

(2R,3S,4S,5R,6S)-6-[3-[[4-(4-allyloxybutyl)phenyl]methyl]-4-methyl-phenyl]-3,4,5-tribenzyloxy-2-(hydroxymethyl)-6-methoxy-tetrahydropyran-2-formaldehyde

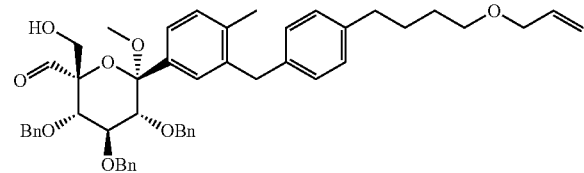 [SMILES: C=CCOCCCCc1ccc(Cc2cc([C@]3(OC)O[C@](C=O)(CO)[C@@H](OCc4ccccc4)[C@H](OCc4ccccc4)[C@H]3OCc3ccccc3)ccc2C)cc1]

[(2S,3S,4S,5R,6S)-6-[3-[[4-(4-allyloxybutyl)phenyl]methyl]-4-methyl-phenyl]-3,4,5-tribenzyloxy-6-methoxy-tetrahydropyran-2-yl]formaldehyde (23.0 g, 30.4 mmol) was dissolved in N,N-dimethylformamide (200 mL) and cooled to 0° C. Then 37% formaldehyde solution (62.0 g, 764 mmol) and DBU (3.1 g, 20 mmol) were added. The mixture was heated to room temperature and stirred overnight. Ethyl acetate (300 mL) was added. The reaction mixture was washed with water (400 mL) and saturated brine (200 mL) in turn, dried over anhydrous sodium sulfate. The mixture was filtered and concentrated to give the title compound as yellow oil (23.0 g, 96%).

Step 4

[(3S,4S,5R,6S)-6-[3-[[4-(4-allyloxybutyl)phenyl]methyl]-4-methyl-phenyl]-3,4,5-tribenzyloxy-2-(hydroxymethyl)-6-methoxy-tetrahydropyran-2-yl]methanol

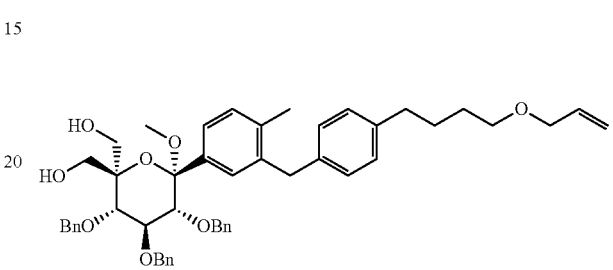

(2R,3S,4S,5R,6S)-6-[3-[[4-(4-allyloxybutyl)phenyl]methyl]-4-methyl-phenyl]-3,4,5-tribenzyloxy-2-(hydroxymethyl)-6-methoxy-tetrahydropyran-2-formaldehyde (23.0 g, 29.3 mmol) was dissolved in methanol (200 mL) and cooled to 0° C. Sodium borohydride (2.8 g, 74 mmol) was added in batches and the mixture was continuously stirred for 10 minutes. Ethyl acetate (500 mL) was added. The reaction mixture was washed with water (500 mL) and saturated brine (200 mL) in turn, dried over anhydrous sodium sulfate. The mixture was filtered and concentrated to give the title compound as yellow oil (23.0 g, 100%).

Step 5

[(1S,2S,3S,4R,5S)-5-[3-[[4-(4-allyloxybutyl)phenyl]methyl]-4-methyl-phenyl]-2,3,4-tribenzyloxy-6,8-dioxabicyclo[3.2.1]octane-1-yl]methanol

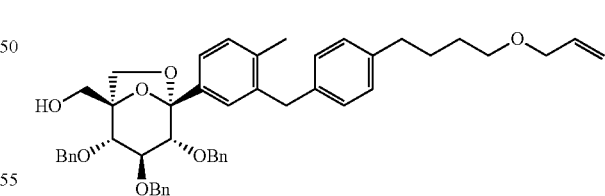

[(3S,4S,5R,6S)-6-[3-[[4-(4-allyloxybutyl)phenyl]methyl]-4-methyl-phenyl]-3,4,5-tribenzyloxy-2-(hydroxymethyl)-6-methoxy-tetrahydropyran-2-yl]methanol (23.0 g, 29.2 mmol) was dissolved in tetrahydrofuran(150 mL). P-toluenesulfonic acid monohydrate (7.0 g, 37 mmol) was added and the mixture was stirred at room temperature overnight. Then the mixture was concentrated. The residue was purified by a silica gel column chromatography (EtOAc/PE(v/v)=1/8) to give the title compound as yellow oil (12.5 g, 57%).

Step 6

(1S,2S,3S,4R,5S)-5-[3-[[4-(4-allyloxybutyl)phenyl]methyl]-4-methyl-phenyl]-2,3,4-tribenzyloxy-6,8-dioxabicyclo[3.2.1]octane-1-formic acid

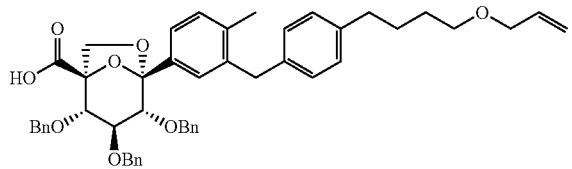 [SMILES: C=CCOCCCCc1ccc(Cc2cc([C@]34OC[C@](C(=O)O)(O3)[C@@H](OCc3ccccc3)[C@H](OCc3ccccc3)[C@H]4OCc3ccccc3)ccc2C)cc1]

[(1S,2S,3S,4R,5S)-5-[3-[[4-(4-allyloxybutyl)phenyl]methyl]-4-methyl-phenyl]-2,3,4-tribenzyloxy-6,8-dioxabicyclo[3.2.1]octane-1-yl]methanol (12.5 g, 16.6 mmol) was dissolved in dichloromethane (130 mL) at room temperature, then cooled to 0° C. Dess-Martin Periodinane (50.0 g, 117 mmol) was added. The reaction mixture was heated to 40° C. and stirred for 2 hours. The mixture was concentrated. The residue was purified by a silica gel column chromatography (EtOAc/PE(v/v)=1/2) to give the title compound as a white solid (10 g, 78%).

Step 7 methyl(1S,2S,3S,4R,5S)-5-[3-[[4-(4-allyloxybutyl)phenyl]methyl]-4-methyl-phenyl]-2,3,4-tribenzyloxy-6,8-dioxabicyclo[3.2.1]octane-1-formate

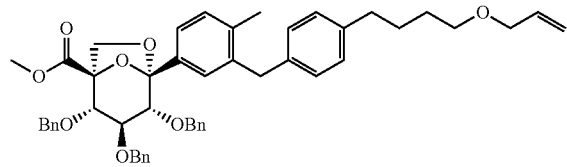 [SMILES: C=CCOCCCCc1ccc(Cc2cc([C@]34OC[C@](C(=O)OC)(O3)[C@@H](OCc3ccccc3)[C@H](OCc3ccccc3)[C@H]4OCc3ccccc3)ccc2C)cc1]

(1S,2S,3S,4R,5S)-5-[3-[[4-(4-allyloxybutyl)phenyl]methyl]-4-methyl-phenyl]-2,3,4-tribenzyloxy-6,8-dioxabicyclo[3.2.1]octane-1-formic acid (10.0 g, 13.0 mmol) was dissolved in anhydrous methanol (100 mL) at room temperature, then concentrated sulphuric acid (1.0 mL, 19 mmol) was added. The mixture was heated to 40° C. and stirred overnight. Then ethyl acetate (200 mL) was added. The mixture was washed with water (300 mL) and saturated sodium bicarbonate (100 mL) in turn, dried over anhydrous sodium sulfate and filtered. The filtrate was concentrated, and the residue was purified by a silica gel column chromatography (EtOAc/PE (v/v)=1/10) to give the title compound as colorless oil (7.5 g, 74%).

Step 8

2-[(1S,2S,3S,4R,5S)-5-[3-[[4-(4-allyloxybutyl)phenyl]methyl]-4-methyl-phenyl]-2,3,4-tribenzyloxy-6,8-dioxabicyclo[3.2.1]octane-1-yl]propan-2-ol

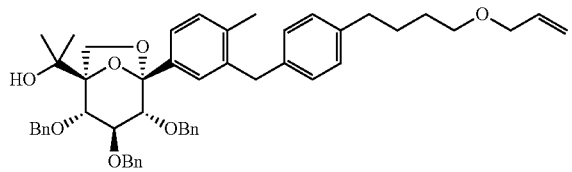 [SMILES: C=CCOCCCCc1ccc(Cc2cc([C@]34OC[C@](C(C)(C)O)(O3)[C@@H](OCc3ccccc3)[C@H](OCc3ccccc3)[C@H]4OCc3ccccc3)ccc2C)cc1]

Methyl(1S,2S,3S,4R,5S)-5-[3-[[4-(4-allyloxybutyl)phenyl]methyl]-4-methyl-phenyl]-2,3,4-tribenzyloxy-6,8-dioxabicyclo[3.2.1]octane-1-formate (7.5 g, 9.6 mmol) was dissolved in tetrahydrofuran (80 mL), then cooled to 0° C. under nitrogen. Methylmagnesium bromide in diethyl ether solution (20 mL, 60 mmol, 3.0 M) was added dropwise. The mixture was heated to room temperature and stirred for 4 hours. The mixture was cooled to 0° C., quenched with dropwise saturated ammonium chloride solution (100 mL) and extracted with ethyl acetate (100 mL×2). The combined organic phases were washed with saturated brines (100 mL), dried over anhydrous sodium sulfate. The mixture was filtered and concentrated to give the title compound as colorless oil (7.5 g, 99%).

Step 9

4-[4-[[2-methyl-5-[(1S,2S,3S,4R,5S)-2,3,4-tribenzyloxy-1-(1-hydroxy-1-)-ethyl)-6,8-dioxabicyclo[3.2.1]octane-5-yl]phenyl]methyl]phenyl]butan-1-ol

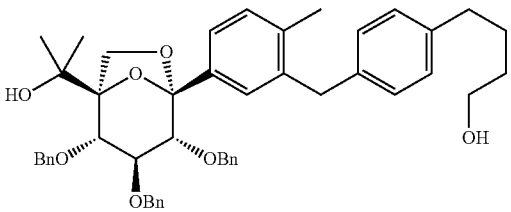 [SMILES: Cc1ccc([C@]23OC[C@](C(C)(C)O)(O2)[C@@H](OCc2ccccc2)[C@H](OCc2ccccc2)[C@H]3OCc2ccccc2)cc1Cc1ccc(CCCCO)cc1]

2-[(1S,2S,3S,4R,5S)-5-[3-[[4-(4-allyloxybutyl)phenyl]methyl]-4-methyl-phenyl]-2,3,4-tribenzyloxy-6,8-dioxabicyclo[3.2.1]octane-1-yl]propan-2-ol (7.0 g, 8.9 mmol) was dissolved in anhydrous methanol (80 mL) at room temperature, then palladium chloride (1.0 g, 5.6 mmol) was added. The mixture was stirred for 2 hours at room temperature under nitrogen. Then the mixture was filtered and concentrated. The residue was purified by a silica gel column chromatography (EtOAc/PE(v/v)=1/2) to give the title compound as colorless oil (5.1 g, 77%).

Step 10

4-[4-[[2-methyl-5-[(1S,2S,3S,4R,5S)-2,3,4-tribenzyloxy-1-(1-hydroxy-1-methyl-ethyl)-6,8-dioxabicyclo[3.2.1]octane-5-yl]phenyl]methyl]phenyl]butyric acid

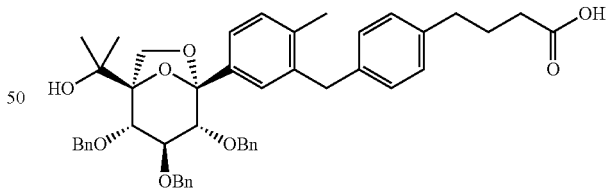

4-[4-[[2-Methyl-5-[(1S,2S,3S,4R,5S)-2,3,4-tribenzyloxy-1-(1-hydroxy-1-methyl-ethyl)-6,8-dioxabicyclo[3.2.1]octane-5-yl]phenyl]methyl]phenyl]butan-1-ol (2.0 g, 2.7 mmol) was dissolved in dichloromethane (20 mL) at room temperature. Water (4 mL), 2,2,6,6-tetramethylpiperidine oxide (0.13 g, 0.79 mmol) and iodobenzene diacetic acid (2.2 g, 6.7 mmol) were added. The reaction mixture was stirred at room temperature overnight. Then the mixture was separated. The organic phase was dried over anhydrous sodium sulfate, filtered and concentrated. The residue was purified by a silica gel column chromatography (EtOAc/PE (v/v)=1/2) to give the title compound as a white solid (1.7 g, 83%).

Step 11

N-(2-dimethylaminoethyl)-2-methyl-2-[4-[4-[[2-methyl-5-[(1S,2S,3S,4R,5S)-2,3,4-tribenzyloxy-1-(1-hydroxy-1-methyl- ethyl)-6,8-dioxabicyclo[3.2.1]octane-5-yl]phenyl] methyl]phenyl]butanamido]propionamide

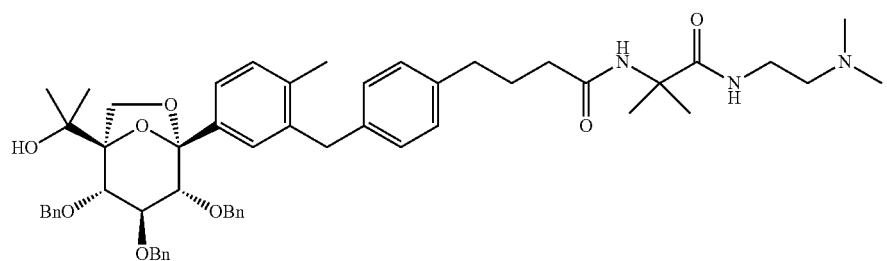 [SMILES: Cc1ccc([C@]23OC[C@](C(C)(C)O)(O2)[C@@H](OCc2ccccc2)[C@H](OCc2ccccc2)[C@H]3OCc2ccccc2)cc1Cc1ccc(CCCC(=O)NC(C)(C)C(=O)NCCN(C)C)cc1]

4-[4-[[2-Methyl-5-[(1S,2S,3S,4R,5S)-2,3,4-tribenzyloxy-1-(1-hydroxy-1-methyl-)ethyl)-6,8-dioxabicyclo[3.2.1]octane-5-yl]phenyl]methyl]phenyl]butyric acid (1.7 g, 2.2 mmol) was dissolved in N,N-dimethylformamide (20 mL) at room temperature, and cooled to 0° C. HBTU (1.0 g, 2.6 mmol) and N,N-diisopropylethylamine (2.0 mL, 11 mmol) were added in turn. The reaction mixture was stirred at room temperature for 20 minutes. Then 2-amino-N-(2-dimethylaminoethyl)-2-methyl-propionyl dihydrochloride (0.72 g, 2.9 mmol) was added. The reaction mixture was stirred at room temperature overnight. The resulting mixture was extracted with water (60 mL) and ethyl acetate (100 mL×3). The combined organic layers were washed with saturated brine (200 mL), dried over ahydrous sodium sulfate and filtered. The filtrate was concentrated, and the residue was purified by a silica gel column chromatography (dichloromethane/anhydrous methanol (v/v)=30/1) to give the title compound as colorless oil (1.8 g, 88%).

Step 12

N-(2-dimethylaminoethyl)-2-methyl-2-[4-[4-[[2-methyl-5-[(1S,2S,3S,4R,5S)-2,3,4-tribenzyloxy-1-(1-hydroxy-1-methyl- ethyl)-6,8-dioxabicyclo[3.2.1]octane-5-yl]phenyl] methyl]phenyl]butanamido]propionamide

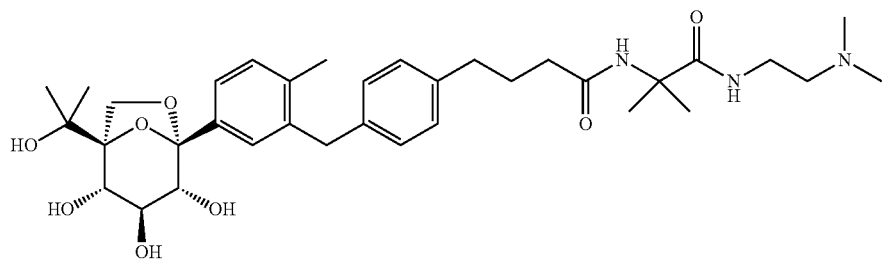 [SMILES: Cc1ccc([C@]23OC[C@](C(C)(C)O)(O2)[C@@H](O)[C@H](O)[C@H]3O)cc1Cc1ccc(CCCC(=O)NC(C)(C)C(=O)NCCN(C)C)cc1]

N-(2-dimethylaminoethyl)-2-methyl-2-[4-[4-[[2-methyl-5-[(1S,2S,3S,4R,5S)-2,3,4-tribenzyloxy-1-(1-hydroxy-1-methyl-ethyl)-6,8-dioxabicyclo[3.2.1]octane-5-yl]phenyl]methyl]phenyl]butanamido]propionamide (1.7 g, 1.9 mmol) was dissolved in anhydrous methanol (20 mL) at room temperature. 10% Palladium hydroxide/carbon (1.6 g, 1.1 mmol) was added. The reaction mixture was stirred overnight under hydrogen. Then the mixture was filtered and concentrated. The residue was purified by a silica gel column chromatography (dichloromethane/anhydrous methanol (v/v)=7/1) to give the title compound as a white solid (0.56 g, 47%).

MS (ESI, pos. ion) m/z: 642.3 [M+H]$^+$.

$^1$H NMR (400 MHz, DMSO-d$_6$) δ (ppm): 8.58 (s, 1H), 8.31 (s, 1H), 7.84 (t, 1H), 7.30 (s, 1H), 7.23 (d, 1H), 7.12-7.04 (m, 5H), 5.50 (d, 1H), 5.01 (d, 1H), 4.88 (d, 1H), 4.20 (s, 1H), 4.04 (d, 1H), 3.91 (s, 2H), 3.81 (d, 1H), 3.75-3.69 (m, 1H), 3.45-3.35 (m, 5H), 3.10 (t, 2H), 2.81 (s, 6H), 2.18 (s, 3H), 2.12 (t, 2H), 1.75 (m, 2H), 1.29 (s, 6H), 1.21 (s, 3H), 1.16 (s, 3H).

Example 3

N-(2-dimethylaminoethyl)-1-[4-[4-[[2-methyl-5-[(2S,3R,4R,5S,6S)-3,4,5-trihydroxy-6-(1-hydroxy-1-methyl-ethyl)tetrahydropyran-2-yl]phenyl]methyl]phenyl]butanamido]cyclopropyl formamide

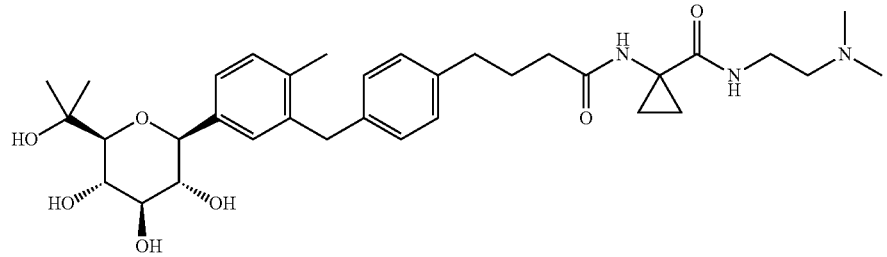 [SMILES: Cc1ccc([C@@H]2O[C@H](C(C)(C)O)[C@@H](O)[C@H](O)[C@H]2O)cc1Cc1ccc(CCCC(=O)NC2(C(=O)NCCN(C)C)CC2)cc1]

Step 1 tert-butyl N-[1-(2-dimethylaminoethylcarbamoyl)cyclopropyl]carbamate

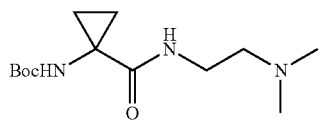 [SMILES: CN(C)CCNC(=O)C1(NC(=O)OC(C)(C)C)CC1]

1-(Tert-butoxycarbonylamino)cyclopropyl formic acid (6.0 g, 30 mmol) was dissolved in chloroform (50 mL) at room temperature. Carbonyldiimidazole (7.3 g, 45 mmol) was added and the mixture was stirred for 45 minutes. N,N-dimethyl-1,2-ethanediamine (4.0 g, 45 mmol) was added and the mixture was stirred at room temperature overnight. The reaction mixture was washed with water (200 mL) and dried over anhydrous sodium sulfate, filtered, and concentrated to give the title compound as yellow oil (8.0 g, 99%).

Step 2

1-amino-N-(2-dimethylaminoethyl)cyclopropyl formamide dihydrochloride

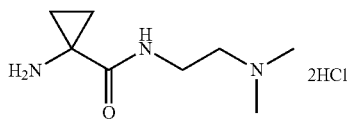

Tert-butyl N-[1-(2-dimethylaminoethylcarbamoyl)cyclopropyl]carbamate (8.0 g, 29 mmol) was dissolved in ethyl acetate (80 mL) at room temperature. A solution of HCl in isopropyl alcohol (20 mL, 5 M) was added. The reaction mixture was stirred for 3.5 hours. The mixture was concentrated. Ethyl acetate (50 mL) was added, stirred overnight and filtered. The filtrate was washed with ethyl acetate and dried in vacuo to give the title compound as a white solid (6.5 g, 90%).

$^1$H NMR (400 MHz, CD$_3$OD) δ (ppm): 3.64 (t, 2H), 3.37 (t, 2H), 2.98 (s, 6H), 1.68 (t, 2H), 1.49 (t, 2H).

Step 3

4-[4-[[2-methyl-5-[(2S,3R,4R,5S,6S)-3,4,5-trihydroxy-6-(1-hydroxy-1-methyl-ethyl)tetrahydropyran-2-yl]phenyl]methyl]phenyl]butyric acid

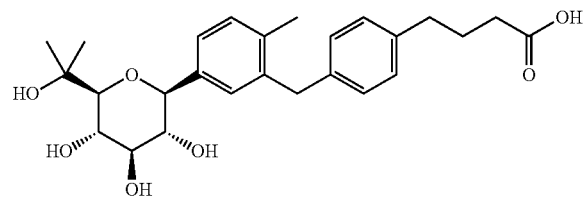 [SMILES: Cc1ccc([C@@H]2O[C@H](C(C)(C)O)[C@@H](O)[C@H](O)[C@H]2O)cc1Cc1ccc(CCCC(=O)O)cc1]

4-[4-[[2-Methyl-5-[(2S,3R,4R,5S,6S)-3,4,5-tribenzyloxy-2-hydroxy-6-(1-hydroxy-1)-methyl-ethyl)tetrahydropyran-2-yl]phenyl]methyl]phenyl]butyric acid was dissolved in the mixture of tetrahydrofuran (2 mL) and anhydrous methanol (20 mL). 10% Palladium hydroxide/carbon (1.2 g, 0.84 mmol) was added. The reaction mixture was stirred overnight under hydrogen. The mixture was filtered and concentrated. The residue was purified by a silica gel column chromatography (EtOAc) to give the title compound as a white solid (0.52 g, 64%).

Step 4

N-(2-dimethylaminoethyl)-1-[4-[4-[[2-methyl-5-[(2S,3R,4R,5S,6S)-3,4,5-trihydroxy-6-(1-hydroxy-1-methyl-ethyl)tetrahydropyran- 2-yl]phenyl]methyl]phenyl]butanamide]cyclopropyl formamide

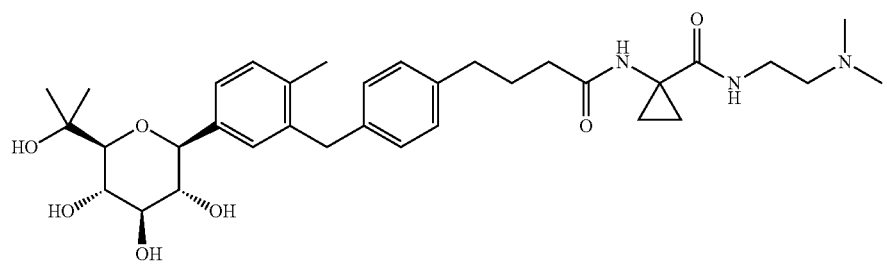 [SMILES: Cc1ccc([C@@H]2O[C@H](C(C)(C)O)[C@@H](O)[C@H](O)[C@H]2O)cc1Cc1ccc(CCCC(=O)NC2(C(=O)NCCN(C)C)CC2)cc1]

4-[4-[[2-Methyl-5-[(2S,3R,4R,5S,6S)-3,4,5-tribenzyloxy-6-(1-hydroxy-1-methyl-ethyl)tetrahydropyran-2-yl]phenyl]methyl]phenyl]butyric acid (0.37 g, 0.81 mmol) was dissolved in acetonitrile (20 mL) at room temperature, then cooled to 0° C. HBTU (0.37 g, 0.97 mmol) and N,N-diisopropylethylamine (0.7 mL, 4 mmol) were added in turn. The reaction mixture was heated to room temperature and stirred for 20 minutes.

1-Amino-N-(2-dimethylaminoethyl)cyclopropylformamide dihydrochloride (0.28 g, 1.1 mmol) was added and the mixture was stirred overnight. Then the mixture was concentrated. The residue was purified by a silica gel column chromatography (dichloromethane/anhydrous methanol (v/v)=7/1) to give the title compound as a white solid (150 mg, 30%).

MS (ESI, pos. ion) m/z: 612.0 [M+H]$^+$.

$^1$H NMR (400 MHz, CD$_3$OD) δ (ppm): 8.61 (s, 1H), 8.17 (s, 1H), 7.16-7.05 (m, 7H), 4.08 (d, 1H), 3.96 (s, 2H), 3.66-3.48 (m, 4H), 3.24 (m, 4H), 2.95 (s, 6H), 2.61 (t, 2H), 2.32-2.26 (m, 2H), 2.23 (s, 3H), 1.95-1.86 (m, 2H), 1.49 (dd, 2H), 1.28 (s, 3H), 1.24 (s, 3H), 1.02 (dd, 2H).

Example 4

N-(2-dimethylaminoethyl)-1-[4-[4-[[2-methyl-5-[(1S,2S,3S,4R,5S)-2,3,4-trihydroxy-1-(1-hydroxy-1-methyl-ethyl)-6,8-dioxabicyclo[3.2.1]octane-5-yl]phenyl]methyl]phenyl]butanamido]cyclopropyl formamide

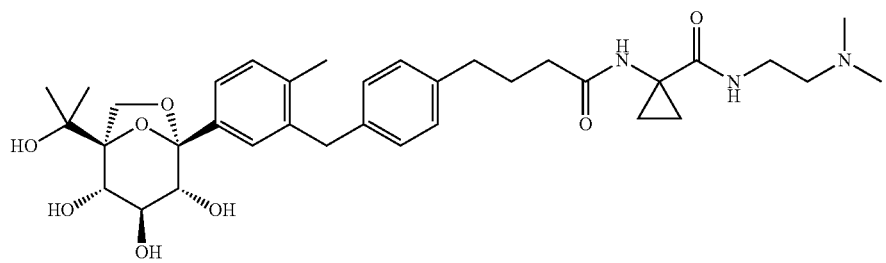 [SMILES: Cc1ccc([C@]23OC[C@](C(C)(C)O)(O2)[C@@H](O)[C@H](O)[C@H]3O)cc1Cc1ccc(CCCC(=O)NC2(C(=O)NCCN(C)C)CC2)cc1]

Step 1

4-[4-[[2-methyl-5-[(1S,2S,3S,4R,5S)-2,3,4-trihydroxy-1-(1-hydroxy-1-methyl-ethyl))-6,8-dioxabicyclo[3.2.1]octane-5-yl]phenyl]methyl]phenyl]butyric acid

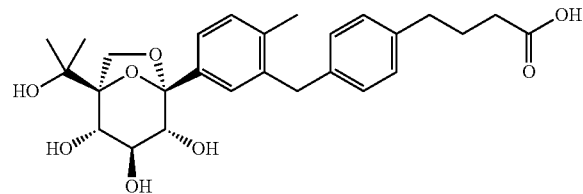 [SMILES: Cc1ccc([C@]23OC[C@](C(C)(C)O)(O2)[C@@H](O)[C@H](O)[C@H]3O)cc1Cc1ccc(CCCC(=O)O)cc1]

4-[4-[[2-Methyl-5-[(1S,2S,3S,4R,5S)-2,3,4-tribenzyloxy-1-(1-hydroxy-1-methyl-ethyl)-6,8-dioxabicyclo[3.2.1]octane-5-yl]phenyl]methyl]phenyl]butyric acid (1.3 g, 1.7 mmol) was dissolved in the mixture of tetrahydrofuran (2 mL) and anhydrous methanol(20 mL). 10% Palladium/carbon catalyst (1.2 g, 0.84 mmol) was added. The reaction mixture was stirred overnight under hydrogen. Then the mixture was filtered and concentrated. The residue was purified by a silica gel column chromatography (EtOAc) to give the title compound as a white solid (0.52 g, 53%).

Step 2

N-(2-dimethylaminoethyl)-1-[2-[4-[[2-methyl-5-[(1S,2S,3S,4R,5S)-2,3,4-trihydroxy-1-(1-hydroxy-1-methyl-ethyl)-6,8-dioxabicyclo[3.2.1]octane-5-yl]phenyl]methyl]phenyl]butylamido]cyclopropyl formamide

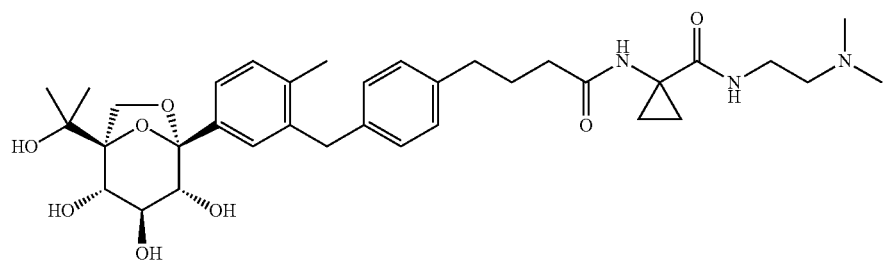 [SMILES: Cc1ccc([C@]23OC[C@](C(C)(C)O)(O2)[C@@H](O)[C@H](O)[C@H]3O)cc1Cc1ccc(CCCC(=O)NC2(C(=O)NCCN(C)C)CC2)cc1]

4-[4-[[2-Methyl-5-[(1S,2S,3S,4R,5S)-2,3,4-trihydroxy-1-(1-hydroxy-1-methyl-)ethyl)-6,8-dioxabicyclo[3.2.1]octane-5-yl]phenyl]methyl]phenyl]butyric acid (0.31 g, 0.64 mmol) was dissolved in acetonitrile (30 mL) at room temperature, and cooled to 0° C. HBTU (0.3 g, 0.8 mmol) and N,N-diisopropylethylamine (0.6 mL, 3 mmol) were added in turn and the mixture was stirred for 20 min. Then 1-amino-N-(2-dimethyl aminoethyl)-cyclopropyl formamide dihydrochloride (0.21 g, 0.86 mmol) was added. The reaction mixture was stirred at room temperature overnight. Then the mixture was concentrated. The residue was purified by a silica gel column chromatography (dichloromethane/anhydrous methanol (v/v)=7/1) to give the title compound as a white solid (180 mg, 44%).

MS (ESI, pos. ion) m/z: 640.4 [M+H]$^+$.
$^1$H NMR (400 MHz, CD$_3$OD) δ (ppm): 8.62 (s, 1H), 8.20 (s, 1H), 7.37-7.30 (m, 2H), 7.16 (d, 1H), 7.08 (m, 4H), 4.22 (d, 1H), 4.00-3.98 (m, 3H), 3.93 (d, 1H), 3.69 (t, 1H), 3.64-3.52 (m, 3H), 3.27-3.22 (m, 2H), 2.94 (s, 6H), 2.61 (t, 2H), 2.32-2.24 (m, 2H), 2.23 (s, 3H), 1.91 (dd, 2H), 1.49 (dd, 2H), 1.36 (s, 3H), 1.31 (s, 3H), 1.02 (dd, 2H).

Example 5

N-[(1R)-2-(2-dimethylaminoethylamino)-1-methyl-2-oxo-ethyl]-4-[4-[[2-methyl-5-[(1S,2S,3S,4R,5S)-2,3,4-trihydroxy-1-(1-hydroxy-1-methyl-ethyl)-6,8-dioxabicyclo[3.2.1]octane-5-yl]phenyl]methyl]phenyl]butanamide

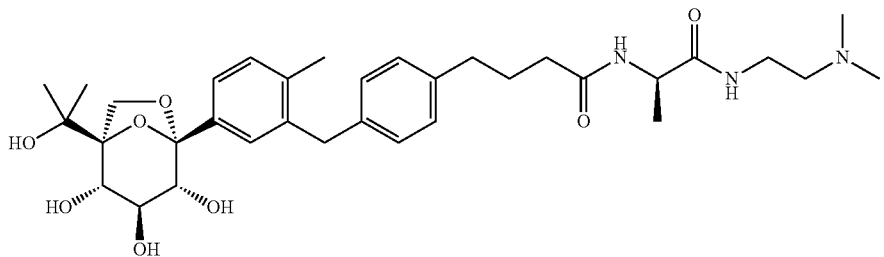 [SMILES: Cc1ccc([C@]23OC[C@](C(C)(C)O)(O2)[C@@H](O)[C@H](O)[C@H]3O)cc1Cc1ccc(CCCC(=O)N[C@H](C)C(=O)NCCN(C)C)cc1]

Step 1

(2R)-2-(tert-oxycarbonylamino)propionic acid

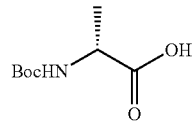

(2R)-2-aminopropionic acid (10 g, 0.11 mol) was dissolved in water (100 mL) at room temperature. Tetrahydrofuran (50 mL) and sodium hydroxide solid (4.9 g, 0.12 mol) were added, then cooled to 0° C. Boc anhydride (27 mL, 0.12 mol) was added. The mixture was heated to room temperature and stirred for 4.5 h. The organic solvent was removed by concentration, and the aqueous phase was adjusted pH to 3 with 1 M hydrochloric acid. The mixture was extracted with ethyl acetate (150 mL×2). The organic phase was washed with saturated salt water (100 mL), dried over anhydrous sodium sulfate, filtered and concentrated to give the title compound as colorless oil (21 g, 98%).

Step 2 tert-butyl N-[(1R)-2-(2-dimethylaminoethylamino)-1-methyl-2-oxo-ethyl]carbamate

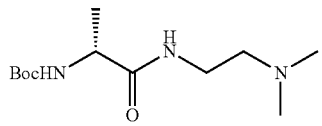 [SMILES: C[C@@H](NC(=O)OC(C)(C)C)C(=O)NCCN(C)C]

(2R)-2-(tert-butoxycarbonylamino)propionic acid (21 g, 0.11 mol) was dissolved in dichloromethane (100 mL) at room temperature and cooled to 0° C. HATU (48 g, 0.12 mol), N,N-diisopropylethylamine (58 mL, 0.33 mol) and N,N-dimethyl-1,2-ethanediamine (13 g, 0.15 mol) were added in turn and the mixture was stirred overnight. Then the mixture was washed with water (200 mL), dried over anhydrous sodium sulfate, filtered and concentrated. The residue was purified by a silica gel column chromatography (dichloromethane/anhydrous methanol (v/v)=10/1) to give the title compound as yellow oil (27 g, 93%).

$^1$H NMR (400 MHz, CDCl$_3$) δ (ppm): 5.66 (s, 1H), 5.20 (s, 1H), 4.01 (m, 1H), 3.27-3.17 (m, 2H), 2.44 (t, 2H), 2.20 (s, 6H), 1.26 (s, 9H), 1.18 (d, 3H).

Step 3

(2R)-2-amino-N-(2-dimethylaminoethyl)propanamide dihydrochloride

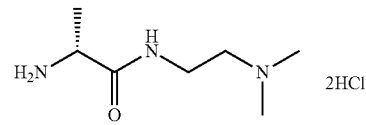

Tert-butyl N-[(1R)-2-(2-dimethylaminoethylamino)-1-methyl-2-oxo-ethyl]carbamate (27 g, 0.11 mol) was dissolved in ethyl acetate (200 mL) at room temperature. A solution of HCl in ethyl acetate (100 mL, 4 M) was added. The reaction mixture was stirred at room temperature overnight. The mixture was filtered, the filter cake was washed with ethyl acetate (200 mL) and dried in vacuo to give the title compound as a white solid (18 g, 74%).

MS (ESI, pos. ion) m/z: 160.2 [M+H]$^+$.

Step 4

N-[(1R)-2-(2-dimethylaminoethylamino)-1-methyl-2-oxo-ethyl]-4-[4-[[2-methyl-5-[(1S,2S,3S,4R,5S)-2,3,4-tribenzyloxy-1-(1-hydroxy-1-methyl-ethyl)-6,8-dioxabicyclo[3.2.1]octane-5-yl]phenyl]methyl]phenyl]butanamide

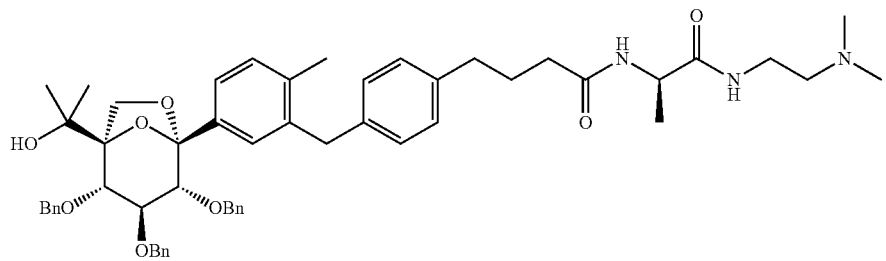 [SMILES: Cc1ccc([C@]23OC[C@](C(C)(C)O)(O2)[C@@H](OCc2ccccc2)[C@H](OCc2ccccc2)[C@H]3OCc2ccccc2)cc1Cc1ccc(CCCC(=O)N[C@H](C)C(=O)NCCN(C)C)cc1]

4-[4-[[2-Methyl-5-[(1S,2S,3S,4R,5S)-2,3,4-tribenzyloxy-1-(1-hydroxy-1-methyl-ethyl)-6,8-dioxabicyclo[3.2.1]octane-5-yl]phenyl]methyl]phenyl]butyric acid (0.52 g, 0.69 mmol) was dissolved in N,N-dimethylformamide (5 mL) at room temperature, and cooled to 0° C. HBTU (0.31 g, 0.80 mmol) and N,N-diisopropylethylamine (0.60 mL, 3.4 mmol) were added and the mixture was stirred for 20 min. Then (2R)-2-amino-N-(2-dimethylaminoethyl)propanamide dihydrochloride (0.20 g, 0.86 mmol) was added. The reaction mixture was stirred overnight. The resulting mixture was extracted with water (60 mL) and ethyl acetate (60 mL×3). The combined organic layers were washed with saturated brine (100 mL), dried over ahydrous sodium sulfate and filtered. The filtrate was concentrated, and the residue was purified by a silica gel column chromatography (dichloromethane/anhydrous methanol (v/v)=30/1) to give the title compound as a white solid (0.60 g, 97%).

Step 5

N-[(1R)-2-(2-dimethylaminoethylamino)-1-methyl-2-oxo-ethyl]-4-[4-[[2-methyl-5-[(1S,2S,3S,4R,5S)-2,3,4-trihydroxy-1-(1-hydroxy-1-methyl-ethyl)-6,8-dioxabicyclo[3.2.1]octane-5-yl]phenyl]methyl]phenyl]butanamide

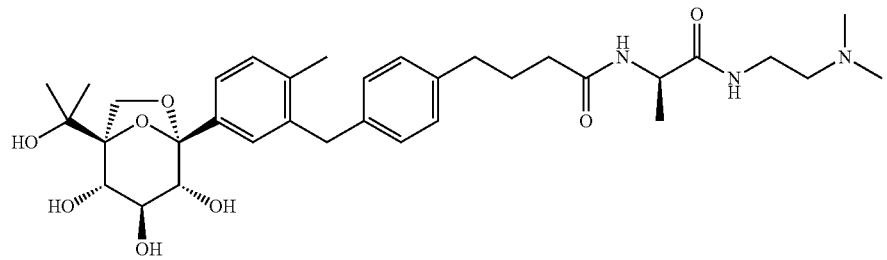 [SMILES: Cc1ccc([C@]23OC[C@](C(C)(C)O)(O2)[C@@H](O)[C@H](O)[C@H]3O)cc1Cc1ccc(CCCC(=O)N[C@H](C)C(=O)NCCN(C)C)cc1]

N-[(1R)-2-(2-dimethylaminoethylamino)-1-methyl-2-oxo-ethyl]-4-[4-[[2-methyl-5-[(1S,2S,3S,4R,5S)-2,3,4-tribenzyloxy-1-(1-hydroxy-1-methyl-ethyl)-6,8-dioxabicyclo[3.2.1]octane-5-yl]phenyl]methyl]phenyl]butanamide (0.60 g, 0.67 mmol) was dissolved in anhydrous methanol (10 mL) at room temperature. 10% Palladium hydroxide/carbon (0.30 g, 0.21 mmol) was added. The reaction mixture was stirred overnight under hydrogen. Then the mixture was filtered and concentrated. The residue was purified by a silica gel column chromatography (dichloromethane/anhydrous methanol (v/v)=7/1) to give the title compound as a white solid (42 mg, 10%).

MS (ESI, pos. ion) m/z: 628.3 [M+H]$^+$.

$^1$H NMR (400 MHz, CD$_3$OD) δ (ppm): 7.42-7.26 (m, 2H), 7.12 (m, 5H), 4.19 (dd, 2H), 3.99-3.93 (m, 4H), 3.73-3.62 (m, 3H), 3.47 (m, 1H), 3.29 (m, 2H), 2.94 (s, 6H), 2.61 (t, 2H), 2.26 (m, 2H), 2.23 (s, 3H), 1.92 (m, 2H), 1.36 (s, 3H), 1.31 (s, 6H).

Example 6

N-[(1S)-2-(2-dimethylaminoethylamino)-1-methyl-2-oxo-ethyl]-4-[4-[[2-methyl-5-[(1S,2S,3S,4R,5S)-2,3,4-trihydroxy-1-(1-hydroxy-1-methyl-ethyl)-6,8-dioxabicyclo[3.2.1]octane-5-yl]phenyl]methyl]phenyl]butanamide

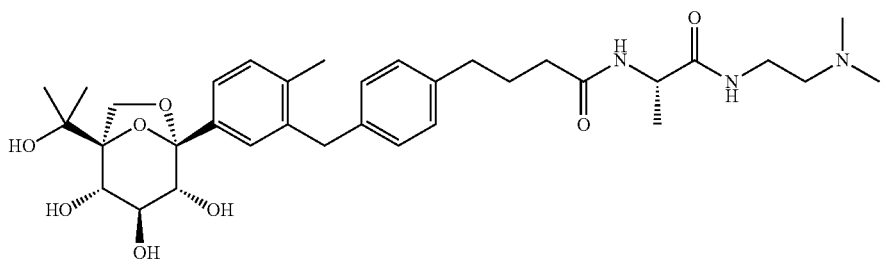 [SMILES: Cc1ccc([C@]23OC[C@](C(C)(C)O)(O2)[C@@H](O)[C@H](O)[C@H]3O)cc1Cc1ccc(CCCC(=O)N[C@@H](C)C(=O)NCCN(C)C)cc1]

Step 1

(2S)-2-(tert-butoxycarbonylamino)propionic acid

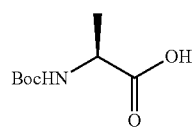

(2S)-2-aminopropionic acid (10 g, 0.11 mol) was dissolved in water (100 mL) at room temperature. Tetrahydrofuran (50 mL) and sodium hydroxide solid (4.9 g, 0.12 mol) were added, and cooled to 0° C. Boc anhydride (27 mL, 0.12 mol) was added. The mixture was heated to room temperature and stirred for 4.5 h. The organic solvent was removed by concentration, and the aqueous phase was adjusted pH to 3 with 1 M hydrochloric acid. The mixture was extracted with ethyl acetate (150 mL×2). The combined organic phases were washed with saturated salt water (100 mL), dried over anhydrous sodium sulfate, filtered and concentrated to give the title compound as colorless oil (21.0 g, 98%).

Step 2 tert-butyl N-[(1S)-2-(2-dimethylaminoethylamino)-1-methyl-2-oxo-ethyl]carbamate

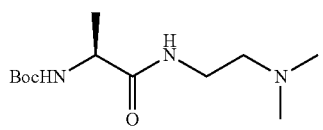 [SMILES: C[C@H](NC(=O)OC(C)(C)C)C(=O)NCCN(C)C]

(2S)-2-(tert-butoxycarbonylamino)propionic acid (21 g, 0.11 mol) was dissolved in dichloromethane (100 mL) at room temperature and cooled to 0° C. HATU (48 g, 0.12 mol), N,N-diisopropylethylamine (58 mL, 0.33 mol) and N,N-dimethyl-1,2-ethanediamine (13 g, 0.15 mol) were added in turn and the mixture was stirred overnight. Then the mixture was washed with water (200 mL), dried over anhydrous sodium sulfate, filtered and concentrated. The residue was purified by a silica gel column chromatography (dichloromethane/anhydrous methanol (v/v)=10/1) to give the title compound as yellow oil (26 g, 90%).

Step 3

(2S)-2-amino-N-(2-dimethylaminoethyl)propanamide dihydrochloride

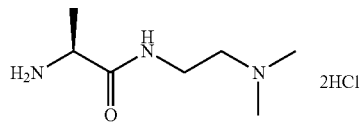

Tert-butyl [(1S)-2-(2-dimethylaminoethylamino)-1-methyl-2-oxo-ethyl] (26 g, 0.10 mol) was dissolved in ethyl acetate (200 mL) at room temperature. A solution of HCl in ethyl acetate (100 mL, 4 M) was added. The reaction mixture was stirred overnight. The mixture was filtered. The filter cake was washed with ethyl acetate (200 mL) and dried in vacuo to give the title compound as a white solid (12 g, 49%).

$^1$H NMR (400 MHz, D$_2$O) δ (ppm): 4.06 (q, 1H), 3.67 (m, 1H), 3.56 (m, 1H), 3.30 (m, 2H), 2.89 (d, 6H), 1.49 (d, 3H).

Step 4

N-[(1S)-2-(2-dimethylaminoethylamino)-1-methyl-2-oxo-ethyl]-4-[4-[[2-methyl-5-[(1S,2S,3S,4R,5S)-2,3,4-tribenzyloxy-1-(1-hydroxy-1-methyl-ethyl)-6,8-dioxabicyclo[3.2.1]octane-5-yl]phenyl]methyl]phenyl]butanamide

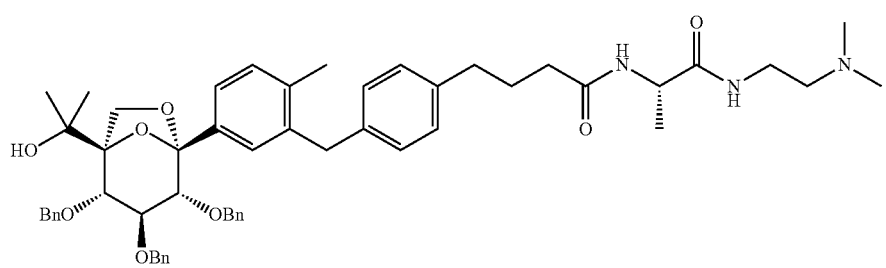

4-[4-[[2-Methyl-5-[(1S,2S,3S,4R,5S)-2,3,4-tribenzyloxy-1-(1-hydroxy-1-methyl-ethyl)-6,8-dioxabicyclo[3.2.1]octane-5-yl]phenyl]methyl]phenyl]butyric acid (0.52 g, 0.69 mmol) was dissolved in N,N-dimethylformamide (5 mL) at room temperature, and cooled to 0° C. HBTU (0.31 g, 0.80 mmol) and N,N-disopropylethylamine (0.60 mL, 3.4 mmol) were added and stirred for 20 min. Then (2S)-2-amino-N-(2-dimethylaminoethyl) propanamide dihydrochloride (0.20 g, 0.86 mmol) was added. The reaction mixture was heated to room temperature and the mixture was stirred overnight. The resulting mixture was extracted with water (60 mL) and ethyl acetate (60 mL×3). The combined organic layers were washed with saturated brine (100 mL), dried over ahydrous sodium sulfate and filtered. The filtrate was concentrated, and the residue was purified by a silica gel column chromatography (dichloromethane/anhydrous methanol (v/v)= 30/1) to give the title compound as a white solid (0.50 g, 80%).

Step 5

N-[1S)-2-(2-dimethylaminoethylamino)-1-methyl-2-oxo-ethyl]-4-[4-[[2-methyl-5-[(1S,2S,3S,4R,5S)-2,3,4-trihydroxy-1-(1-hydroxy-1-methyl-ethyl)-6,8-dioxabicyclo[3.2.1]octane-5-yl]phenyl]methyl]phenyl]butanamide

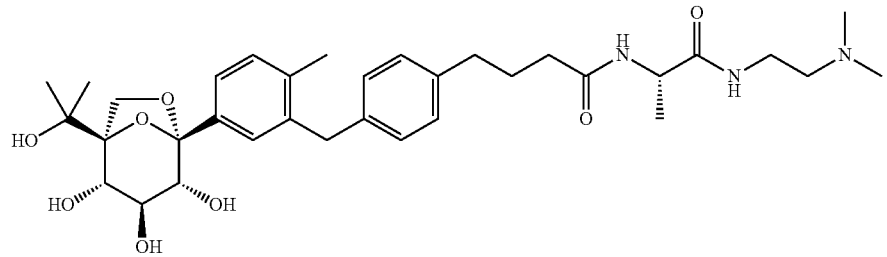 [SMILES: Cc1ccc([C@]23OC[C@](C(C)(C)O)(O2)[C@@H](O)[C@H](O)[C@H]3O)cc1Cc1ccc(CCCC(=O)N[C@@H](C)C(=O)NCCN(C)C)cc1]

N-[(1S)-2-(2-dimethylaminoethylamino)-1-methyl-2-oxo-ethyl]-4-[4-[[2-methyl-5-[(1S,2S,3S,4R,5S)-2,3,4-tribenzyloxy-1-(1-hydroxy-1-methyl-ethyl)-6,8-dioxabicyclo[3.2.1]octane-5-yl]phenyl]methyl]phenyl]butanamide (0.50 g, 0.56 mmol) was dissolved in anhydrous methanol (10 mL) at room temperature. 10% Palladium hydroxide/carbon (0.30 g, 0.21 mmol) was added. The reaction mixture was stirred overnight under hydrogen. Then the mixture was filtered and concentrated. The residue was purified by a silica gel column chromatography (dichloromethane/anhydrous methanol (v/v)=7/1) to give the title compound as a white solid (31 mg, 9%).

MS (ESI, pos. ion) m/z: 628.3 [M+H]$^+$.

$^1$H NMR (400 MHz, CD$_3$OD) δ (ppm): 7.42-7.26 (m, 2H), 7.12 (m, 5H), 4.19 (dd, 2H), 3.99-3.93 (m, 4H), 3.72-3.66 (m, 2H), 3.62 (d, 1H), 3.48 (d, 1H), 3.28 (m, 2H), 2.94 (s, 6H), 2.61 (t, 2H), 2.27 (d, 2H), 2.23 (s, 3H), 1.92 (m, 2H), 1.36 (s, 3H), 1.31 (s, 6H).

Example 7

N-[2-(2-dimethylaminoethylamino)-2-oxo-ethyl]-4-[4-[[2-methyl-5-[(1S,2S,3S,4R,5S)-2,3,4-trihydroxy-1-(1-hydroxy-1-methyl-ethyl)-6,8-dioxabicyclo[3.2.1]octane-5-yl]phenylmethyl]phenyl]butanamide

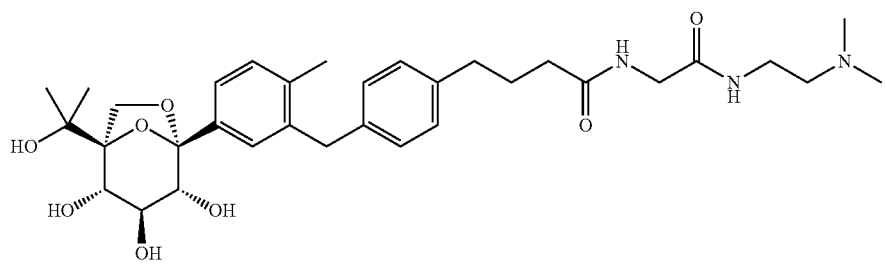 [SMILES: Cc1ccc([C@]23OC[C@](C(C)(C)O)(O2)[C@@H](O)[C@H](O)[C@H]3O)cc1Cc1ccc(CCCC(=O)NCC(=O)NCCN(C)C)cc1]

111

Step 1 tert-butyl N-[2-(2-dimethylaminoethylamino)-2-oxo-ethyl]carbamate

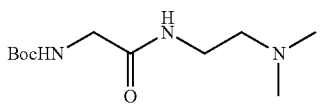 [SMILES: CN(C)CCNC(=O)CNC(=O)OC(C)(C)C]

2-(Tert-butoxycarbonylamino)acetic acid (2.0 g, 11 mmol) was dissolved in dichloromethane (20 mL) at room temperature and cooled to 0° C. HATU (5.0 g, 12 mmol), N,N-diisopropylethylamine (6.0 mL, 34 mmol) and N,N-dimethyl-1,2-ethanediamine (1.3 g, 15 mmol) were added in turn and the mixture was stirred overnight. Then the mixture was concentrated. The residue was purified by a silica gel column chromatography (dichloromethane/anhydrous methanol (v/v)=10/1) to give the title compound as yellow oil (2.6 g, 93%).

112

Step 2

2-amino-N-(2-dimethylaminoethyl)acetamide dihydrochloride

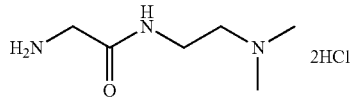

Tert-butyl N-[2-(2-dimethylaminoethylamino)-2-oxo-ethyl]carbamate (2.5 g, 10 mmol) was dissolved in ethyl acetate (30 mL) at room temperature. The solution of HCl in ethyl acetate (6 mL, 4 M) was added. The reaction mixture was stirred overnight. The mixture was filtered, the filter cake was washed with ethyl acetate (20 mL) and dried in vacuo to give the title compound as a white solid (1.8 g, 81%).

MS (ESI, pos. ion) m/z: 146.1 [M+H]$^+$.

$^1$H NMR (400 MHz, D$_2$O) δ (ppm): 3.78 (s, 2H), 3.60 (t, 2H), 3.27 (t, 2H), 2.86 (s, 6H).

Step 3

N-[2-(2-dimethylaminoethylamino)-2-oxo-ethyl]-4-[4-[[2-methyl-5-[(1S,2S,3S,4R,5S)-2,3,4-tribenzyloxy-1-(1-hydroxy-1-methyl-ethyl)-6,8-dioxabicyclo[3.2.1]octane-5-yl]phenyl]methyl]phenyl]butanamide

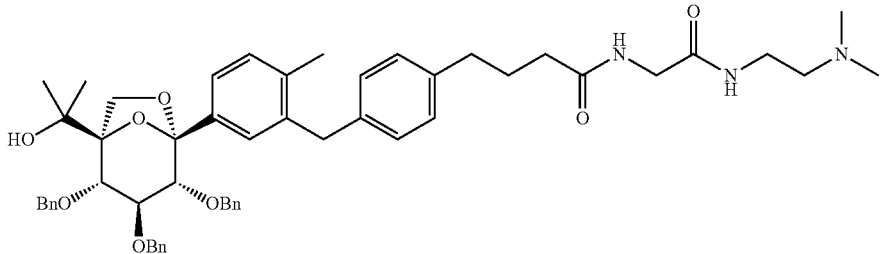 [SMILES: Cc1ccc([C@]23OC[C@](C(C)(C)O)(O2)[C@@H](OCc2ccccc2)[C@H](OCc2ccccc2)[C@H]3OCc2ccccc2)cc1Cc1ccc(CCCC(=O)NCC(=O)NCCN(C)C)cc1]

4-[4-[[2-Methyl-5-[(1S,2S,3S,4R,5S)-2,3,4-tribenzyloxy-1-(1-hydroxy-1-methyl-ethyl)-6,8-dioxabicyclo[3.2.1]octane-5-yl]phenyl]methyl]phenyl]butyric acid (0.80 g, 1.05 mmol) was dissolved in N,N-dimethylformamide (5 mL) at room temperature, and cooled to 0° C. HBTU (0.50 g, 1.3 mmol) and N,N-diisopropylethylamine (1.0 mL, 5.7 mmol) were added and stirred for 20 min. Then 2-amino-N-(2-dimethylaminoethyl)acetamide dihydrochloride (0.30 g, 1.4 mmol) was added. The reaction mixture was stirred overnight. The resulting mixture was extracted with water (60 mL) and ethyl acetate (100 mL×3). The combined organic layers were washed with saturated brine (100 mL), dried over ahydrous sodium sulfate and filtered. The filtrate was concentrated, and the residue was purified by a silica gel column chromatography (dichloromethane/anhydrous methanol (v/v)=30/1) to give the title compound as colorless oil (0.46 g, 49%).

Step 4

N-[2-(2-dimethylaminoethylamino)-2-oxo-ethyl]-4-[4-[[2-methyl-5-[(1S,2S,3S,4R,5S)-2,3,4-trihydroxy-1-(1-hydroxy-1-methyl-ethyl)-6,8-dioxabicyclo[3.2.1]octane-5-yl]phenyl]methyl]phenyl]butanamide

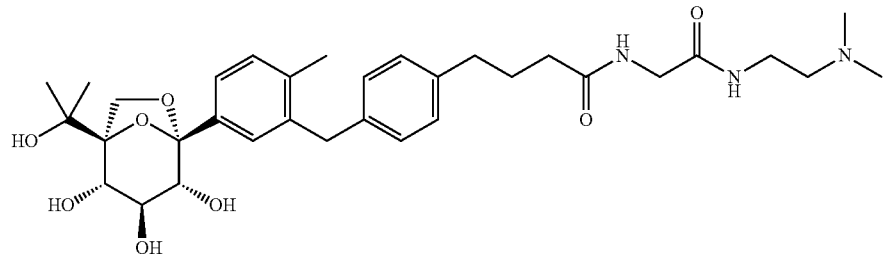 [SMILES: Cc1ccc([C@]23OC[C@](C(C)(C)O)(O2)[C@@H](O)[C@H](O)[C@H]3O)cc1Cc1ccc(CCCC(=O)NCC(=O)NCCN(C)C)cc1]

N-[2-(2-dimethylaminoethylamino)-2-oxo-ethyl]-4-[4-[[2-methyl-5-[(1S,2S,3S,4R,5S)-2,3,4-tribenzyloxy-1-(1-hydroxy-1-methyl-ethyl)-6,8-dioxabicyclo[3.2.1]octane-5-yl]phenyl]methyl]phenyl]butanamide (0.40 g, 0.45 mmol) was dissolved in anisole (5 mL) at room temperature and cooled to 0° C. Anhydrous aluminum trichloride (0.6 g, 4 mmol) was slowly added, stirred for 5 minutes, and then moved to room temperature and stirred for 3 hours. The resulting mixture was poured into ice water (40 mL) and extracted with ethyl acetate (30 mL×6). The combined organic layers were washed with saturated sodium hydrogen carbonate (50 mL) and saturated brine (50 mL), dried over ahydrous sodium sulfate and filtered. The filtrate was concentrated, and the residue was purified by a silica gel column chromatography (dichloromethane/anhydrous methanol (v/v)=7/1) to give the title compound as a white solid (87 mg, 31%).

MS (ESI, pos. ion) m/z: 614.5 [M+H]$^+$.

$^1$H NMR (400 MHz, DMSO-d$_6$) δ (ppm): 8.75 (br.s, 1H), 8.31 (s, 1H), 7.86 (t, 1H), 7.29 (s, 1H), 7.23 (d, 1H), 7.12 7.04 (m, 5H), 5.52 (d, 1H), 5.04 (d, 1H), 4.89 (d, 1H), 4.21 (s, 1H), 4.03 (q, 2H), 3.90 (s, 2H), 3.81 (d, 1H), 3.72 (d, 1H), 3.09 (m, 2H), 2.80 (d, 6H), 2.18 (s, 3H), 2.13 (t, 2H), 1.99 (m, 2H), 1.78 1.72 (m, 4H), 1.62 (m, 2H), 1.21 (s, 3H), 1.15 (s, 3H).

Example 8

N-(2-dimethylaminoethyl)-1-[4-[4-[[2-methyl-5-[(1S,2S,3S,4R,5S)-2,3,4-trihydroxy-1-(1-hydroxy-1-methyl-ethyl)-6,8-dioxabicyclo[3.2.1]octane-5-yl]phenyl]methyl]phenyl]butylamide]cyclopentyl formamide

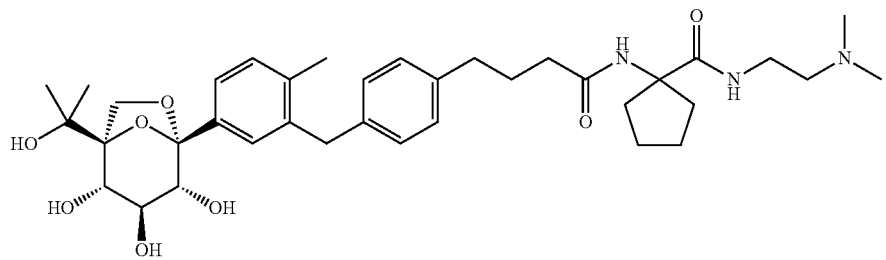 [SMILES: Cc1ccc([C@]23OC[C@](C(C)(C)O)(O2)[C@@H](O)[C@H](O)[C@H]3O)cc1Cc1ccc(CCCC(=O)NC2(C(=O)NCCN(C)C)CCCC2)cc1]

Step 1 tert-butyl N-[1-(2-dimethylaminoethylcarbamoyl)cyclopentyl]carbamate

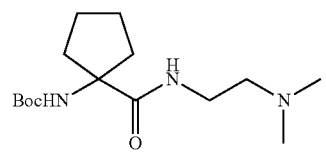 [SMILES: CN(C)CCNC(=O)C1(NC(=O)OC(C)(C)C)CCCC1]

1-(Tert-butoxyformamide)cyclopentyl formic acid (2.0 g, 8.7 mmol) was dissolved in dichloromethane (20 mL) at room temperature and cooled to 0° C. HATU (3.8 g, 9.5 mmol), N,N-diisopropylethylamine (5.0 mL, 29 mmol) and N,N-dimethyl-1,2-ethanediamine (1.0 g, 11 mmol) were added in turn, heated to room temperature and the mixture was stirred overnight. Then the mixture was concentrated. The residue was purified by a silica gel column chromatography (dichloromethane/anhydrous methanol (v/v)=10/1) to give the title compound as yellow oil (2.4 g, 92%).

Step 2

1-amino-N-(2-dimethylaminoethyl)cyclopentylformamide dihydrochloride

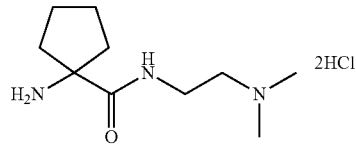

Tert-butyl N-[1-(2-dimethylaminoethylcarbamoyl)cyclopentyl]carbamate (2.5 g, 8.8 mmol) was dissolved in ethyl acetate (30 mL) at room temperature. The solution of HCl in ethyl acetate (6 mL, 4 M) was added. The reaction mixture was stirred overnight. The mixture was filtered, the filter cake was washed with ethyl acetate (20 mL) and dried in vacuo to give the title compound as a white solid (2.2 g, 97%).

Step 3

N-(2-dimethylaminoethyl)-1-[4-[4-[[2-methyl-5-[(1S,2S,3S,4R,5S)-2,3,4-tribenzyloxy-1-(1-hydroxy-1-methylethyl)-6,8- dioxabicyclo[3.2.1]octane-5-yl]phenyl]methyl]phenyl]butanamido]cyclopentyl formamide

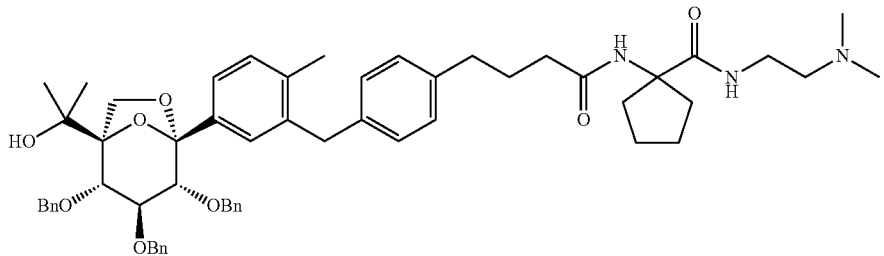 [SMILES: Cc1ccc([C@]23OC[C@](C(C)(C)O)(O2)[C@@H](OCc2ccccc2)[C@H](OCc2ccccc2)[C@H]3OCc2ccccc2)cc1Cc1ccc(CCCC(=O)NC2(C(=O)NCCN(C)C)CCCC2)cc1]

4-[4-[[2-methyl-5-[(1S,2S,3S,4R,5S)-2,3,4-tribenzyloxy-1-(1-hydroxy-1-methyl-ethyl)-6,8-dioxabicyclo[3.2.1]octane-5-yl]phenyl]methyl]phenyl]butyric acid (0.80 g, 1.05 mmol) was dissolved in N,N-dimethylformamide (5 mL) at room temperature, and cooled to 0° C. HBTU (0.50 g, 1.3 mmol) and N,N-diisopropylethylamine (1.0 mL, 5.7 mmol) were added and the mixture was stirred for 20 minutes. Then 1-amino-N-(2-dimethylaminoethyl)cyclopentylcarboxamide dihydrochloride (0.38 g, 1.4 mmol) was added and the mixture was stirred overnight. The resulting mixture was extracted with water (60 mL) and ethyl acetate (100 mL×3). The combined organic layers were washed with saturated brine (100 mL), dried over ahydrous sodium sulfate and filtered. The filtrate was concentrated, and the residue was purified by a silica gel column chromatography (dichloromethane/anhydrous methanol (v/v)=30/1) to give the title compound as colorless oil (0.90 g, 90%).

Step 4

N-(2-dimethylaminoethyl)-1-[4-[4-[[2-methyl-5-[(1S,2S,3S,4R,5S)-2,3,4-trihydroxy-1-(1-hydroxy-1-methyl-ethyl)-6,8-dioxabicyclo[3.2.1]octane-5-yl]phenyl]methyl]phenyl]butanamido]cyclopentyl formamide

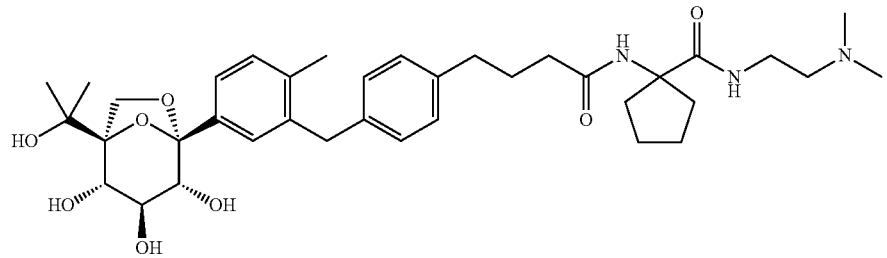 [SMILES: Cc1ccc([C@]23OC[C@](C(C)(C)O)(O2)[C@@H](O)[C@H](O)[C@H]3O)cc1Cc1ccc(CCCC(=O)NC2(C(=O)NCCN(C)C)CCCC2)cc1]

N-(2-dimethylaminoethyl)-1-[4-[4-[[2-methyl-5-[(1S,2S,3S,4R,5S)-2,3,4-tribenzyloxy-1-(1-hydroxy-1-methyl-ethyl)-6,8-dioxacyclic[3.2.1]octane-5-yl]phenyl]butanamido]cyclopentanyl formamide] (0.90 g, 0.96 mmol) was dissolved in anisole (10 mL) at room temperature and cooled to 0° C. Anhydrous aluminum trichloride (1.3 g, 9.7 mmol) was slowly added, stirred for 5 minutes, and then moved to room temperature and stirred for 3 hours. The resulting mixture was poured into ice water (50 mL) and extracted with ethyl acetate (30 mL×6). The combined organic layers were washed with saturated sodium hydrogen carbonate (50 mL) and saturated brine (50 mL) in turn, dried over ahydrous sodium sulfate and filtered. The filtrate was concentrated, and the residue was purified by a silica gel column chromatography (dichloromethane/anhydrous methanol (v/v)=7/1) to give the title compound as a white solid (170 mg, 27%).

MS (ESI, pos. ion) m/z: 668.5 [M+H]$^+$.

$^1$H NMR (400 MHz, DMSO-d$_6$) δ (ppm): 9.28 (br.s, 1H), 8.16-8.02 (m, 2H), 7.28 (s, 1H), 7.22 (d, 1H), 7.08 (m, 5H), 5.50 (br.s, 1H), 5.02 (br.s, 1H), 4.90 (br.s, 1H), 4.22 (s, 1H), 4.03 (d, 2H), 3.90 (s, 2H), 3.81 (d, 1H), 3.69 (dd, 4H), 3.11 (t, 2H), 2.79 (s, 6H), 2.17 (s, 3H), 2.13 (d, 2H), 2.00 (m, 1H), 1.77 (m, 2H), 1.21 (s, 3H), 1.15 (s, 3H).

Example 9

N-[(1R)-1-cyclopropyl-2-(2-dimethylaminoethylamino)-2-oxo-ethyl]-4-[4-[[2-methyl-5-[(1S,2S,3S,4R,5S)-2,3,4-trihydroxy-1-(1-hydroxy-1-methyl-ethyl)-6,8-dioxabicyclo[3.2.1]octane-5-yl]phenyl]methyl]phenyl]butanamide

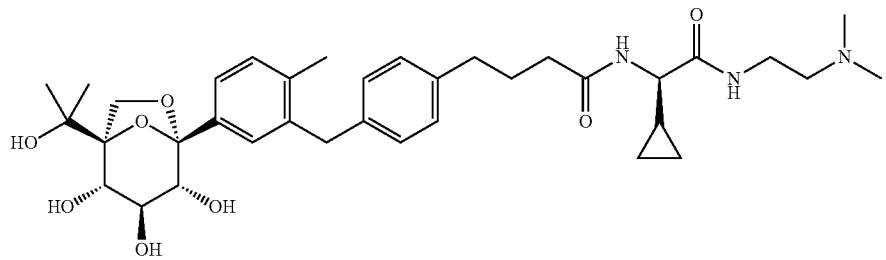 [SMILES: Cc1ccc([C@]23OC[C@](C(C)(C)O)(O2)[C@@H](O)[C@H](O)[C@H]3O)cc1Cc1ccc(CCCC(=O)N[C@@H](C(=O)NCCN(C)C)C2CC2)cc1]

Step 1 tert-butyl N-[(1R)-1-cyclopropyl-2-(2-dimethylaminoethylamino)-2-oxo-ethyl]carbamate

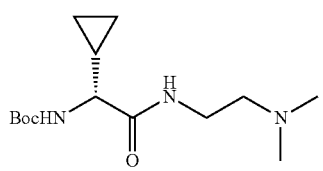 [SMILES: CN(C)CCNC(=O)[C@H](NC(=O)OC(C)(C)C)C1CC1]

(2R)-2-(tert-butoxycarboxamide)-2-cyclopropyl-acetic acid (2.0 g, 9.3 mmol) was dissolved in dichloromethane (20 mL) at room temperature and cooled to 0° C. HATU (4.1 g, 10 mmol), N,N-diisopropylethylamine (5.0 mL, 29 mmol) and N,N-dimethyl-1,2-ethanediamine (1.1 g, 12 mmol) were added in turn, then the mixture was heated to room temperature and stirred overnight. Then the mixture was concentrated. The residue was purified by a silica gel column chromatography (dichloromethane/anhydrous methanol (v/v)=10/1) to give the title compound as yellow oil (2.5 g, 94%).

Step 2

(2R)-2-amino-2-cyclopropyl-N-(2-dimethylaminoethyl)acetamide dihydrochloride

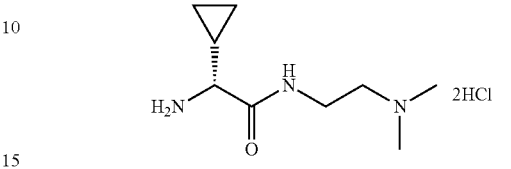

Tert-butyl N-[(1R)-1-cyclopropyl-2-(2-dimethylaminoethylamino)-2-oxo-ethyl]carbamate (25.5 g, 8.8 mmol) was dissolved in ethyl acetate (30 mL) at room temperature. The solution of HCl in ethyl acetate (6 mL, 4 M) was added. The reaction mixture was stirred overnight. The mixture was filtered, the filter cake was washed with ethyl acetate (20 mL) and dried in vacuo to give the title compound as a white solid (1.3 g, 57%).

MS (ESI, pos. ion) m/z: 186.2 [M+H]$^+$.

Step 3

N-[(1R)-1-cyclopropyl-2-(2-dimethylaminoethylamino)-2-oxo-ethyl]-4-[4-[[2-methyl-5-[(1S,2S,3S,4R,5S)-2,3,4-trihydroxy-1-(1-hydroxy-1-methyl-ethyl)-6,8-dioxabicyclo[3.2.1]octane-5-yl]phenyl]methyl]phenyl]butanamide

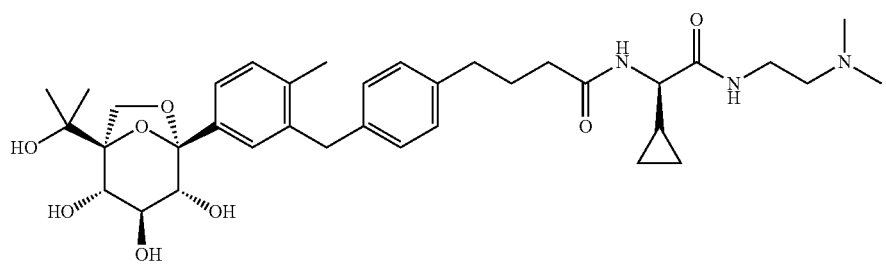 [SMILES: Cc1ccc([C@]23OC[C@](C(C)(C)O)(O2)[C@@H](O)[C@H](O)[C@H]3O)cc1Cc1ccc(CCCC(=O)N[C@@H](C(=O)NCCN(C)C)C2CC2)cc1]

4-[4-[[2-Methyl-5-[(1S,2S,3S,4R,5S)-2,3,4-trihydroxy-1-(1-hydroxy-1-methyl-ethyl))-6,8-dioxabicyclo[3.2.1]octane-5-yl]phenyl]methyl]phenyl]butyric acid (0.40 g, 0.82 mmol) was dissolved in dichloromethane (10 mL) at room temperature, and cooled to 0° C. HBTU (0.38 g, 0.98 mmol) and N,N-diisopropylethylamine (0.72 mL, 4.1 mmol) were added and the mixture was stirred for 20 minutes. Then (2R)-2-amino-2-cyclopropyl-N-(2-dimethylaminoethyl)acetamide dihydrochloride (0.28 g, 1.3 mmol) was added. The reaction mixture was stirred overnight. Then the mixture was concentrated. The residue was purified by a silica gel column chromatography (dichloromethane/anhydrous methanol (v/v)=7/1) to give the title compound as a white solid (0.10 g, 18%).

MS (ESI, pos. ion) m/z: 654.5 [M+H]$^+$.

$^1$H NMR (400 MHz, DMSO-d$_6$) δ (ppm): 8.20 (d, 1H), 8.10 (t, 1H), 7.28 (s, 1H), 7.23 (d, 1H), 7.12-7.03 (m, 5H), 5.50 (d, 1H), 5.32 (t, 1H), 5.02 (d, 1H), 4.88 (d, 1H), 4.22 (s, 1H), 4.03 (d, 1H), 3.90 (s, 2H), 3.81 (d, 1H), 3.72 (m, 1H), 3.53 (m, 2H), 3.05 (br.s, 2H), 2.70 (s, 6H), 2.18 (s, 3H), 2.13 (d, 2H), 2.00 (m, 2H), 1.73 (m, 2H), 1.40 (m, 1H), 1.21 (s, 3H), 1.15 (s, 3H), 1.02 (m, 1H), 0.85 (t, 1H), 0.44 (d, 2H), 0.40 (m, 1H), 0.25 (m, 1H).

Example 10

N-[(1S)-1-cyclopropyl-2-(2-dimethylaminoethylamino)-2-oxo-ethyl]-4-[4-[[2-methyl-5-[(1S,2S,3S,4R,5S)-2,3,4-trihydroxy-1-(1-hydroxy-1-methyl-ethyl)-6,8-dioxabicyclo[3.2.1]octane-5-yl]phenyl]methyl]phenyl]butanamide

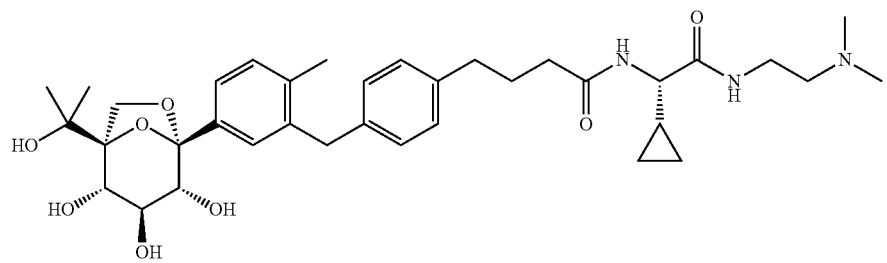 [SMILES: Cc1ccc([C@]23OC[C@](C(C)(C)O)(O2)[C@@H](O)[C@H](O)[C@H]3O)cc1Cc1ccc(CCCC(=O)N[C@H](C(=O)NCCN(C)C)C2CC2)cc1]

Step 1 tert-butyl N-[(1S)-1-cyclopropyl-2-(2-dimethylaminoethylamino)-2-oxo-ethyl]carbamate

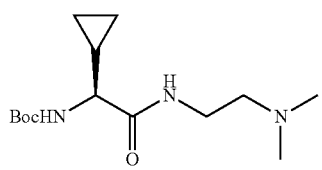 [SMILES: CN(C)CCNC(=O)[C@@H](NC(=O)OC(C)(C)C)C1CC1]

(2S)-2-(Tert-butoxycarboxamide)-2-cyclopropyl-acetic acid (2.0 g, 9.3 mmol) was dissolved in dichloromethane (20 mL) at room temperature and cooled to 0° C. HATU (4.1 g, 10 mmol), N,N-diisopropylethylamine (5.0 mL, 29 mmol) and N,N-dimethyl-1,2-ethanediamine (1.1 g, 12 mmol) were added in turn, then the mixture was heated to room temperature and stirred overnight. Then the mixture was concentrated. The residue was purified by a silica gel column chromatography (dichloromethane/anhydrous methanol (v/v)=10/1) to give the title compound as yellow oil (2.6 g, 98%).

Step 2

(2S)-2-amino-2-cyclopropyl-N-(2-dimethylaminoethyl)acetamide dihydrochloride

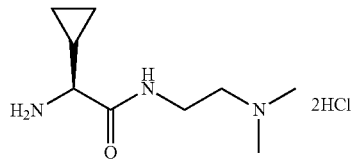

Tert-butyl N-[(1S)-1-cyclopropyl-2-(2-dimethylaminoethylamino)-2-oxo-ethyl]carbamate (25.5 g, 8.8 mmol) was dissolved in ethyl acetate (30 mL) at room temperature. A solution of HCl in ethyl acetate (6 mL, 4 M) was added. The reaction mixture was stirred overnight. The mixture was filtered, the filter cake was washed with ethyl acetate (20 mL) and dried in vacuo to give the title compound as a white solid (1.1 g, 49%).

MS (ESI, pos. ion) m/z: 186.1 [M+H]$^+$.

Step 3

N-[(1S)-1-cyclopropyl-2-(2-dimethylaminoethylamino)-2-oxo-ethyl]-4-[4-[[2-methyl-5-[(1S,2S,3S,4R,5S)-2,3,4-trihydroxy-1-(1-hydroxy-1-methyl-ethyl)-6,8-dioxabicyclo[3.2.1]octane-5-yl]phenyl]methyl]phenyl]butanamide

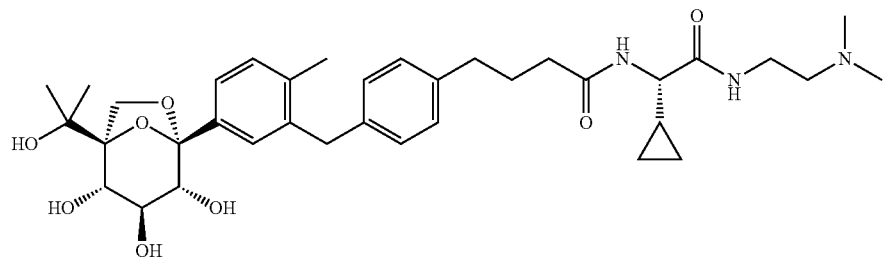 [SMILES: Cc1ccc([C@]23OC[C@](C(C)(C)O)(O2)[C@@H](O)[C@H](O)[C@H]3O)cc1Cc1ccc(CCCC(=O)N[C@H](C(=O)NCCN(C)C)C2CC2)cc1]

4-[4-[[2-Methyl-5-[(S,2S,3S,4R,5S)-2,3,4-trihydroxy-1-(1-hydroxy-1-methyl-ethyl))-6,8-dioxabicyclo[3.2.1]octane-5-yl]phenyl]methyl]phenyl]butyric acid (0.40 g, 0.82 mmol) was dissolved in dichloromethane (10 mL) at room temperature, and cooled to 0° C. HBTU (0.38 g, 0.98 mmol) and N,N-disopropylethylamine (0.72 mL, 4.1 mmol) were added and the mixture was stirred for 20 minutes. (2S)-2-Amino-2-cyclopropyl-N-(2-dimethylaminoethyl)acetamide dihydrochloride (0.28 g, 1.3 mmol) was added. The reaction mixture was stirred overnight. Then the mixture was concentrated. The residue was purified by a silica gel column chromatography (dichloromethane/anhydrous methanol (v/v)=7/1) to give the title compound as a white solid (60 mg, 11%).

MS (ESI, pos. ion) m/z: 654.5 [M+H]$^+$.

$^1$H NMR (400 MHz, DMSO-d$_6$) δ (ppm): 8.20 (d, 1H), 8.10 (t, 1H), 7.28 (s, 1H), 7.23 (d, 1H), 7.11-7.03 (m, 5H), 5.50 (d, 1H), 5.32 (t, 1H), 5.02 (d, 1H), 4.88 (d, 1H), 4.22 (s, 1H), 4.03 (d, 1H), 3.90 (s, 2H), 3.81 (d, 1H), 3.72 (s, 1H), 3.56 (m, 2H), 3.05 (br.s, 2H), 2.74 (s, 6H), 2.18 (s, 3H), 2.13 (d, 2H), 2.00 (m, 2H), 1.73 (m, 2H), 1.40 (m, 1H), 1.21 (s, 3H), 1.15 (s, 3H), 1.02 (m, 1H), 0.85 (m, 1H), 0.45 (d, 2H), 0.40 (m, 1H), 0.25 (m, 1H).

Example 11

N-(2-dimethylaminoethyl)-1-[4-[4-[[2-methyl-5-[(1S,2S,3S,4R,5S)-2,3,4-trihydroxy-1-(1-hydroxy-1-methyl-ethyl)-6,8-dioxabicyclo[3.2.1]octane-5-yl]phenyl]methyl]phenyl]butanamido]cyclobutyl formamide

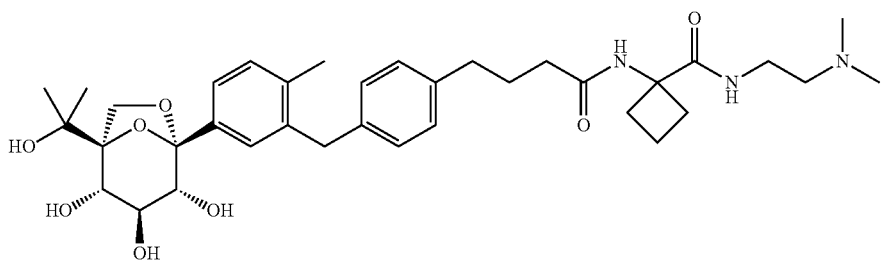 [SMILES: Cc1ccc([C@]23OC[C@](C(C)(C)O)(O2)[C@@H](O)[C@H](O)[C@H]3O)cc1Cc1ccc(CCCC(=O)NC2(C(=O)NCCN(C)C)CCC2)cc1]

Step 1 tert-butyl N-[1-(2-dimethylaminoethylcarbamoyl)cyclobutyl]carbamate

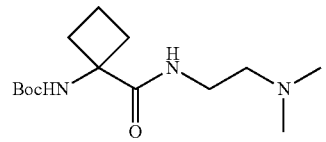 [SMILES: CN(C)CCNC(=O)C1(NC(=O)OC(C)(C)C)CCC1]

1-(Tert-Butoxyformamide)cyclobutyl formic acid (2.0 g, 9.3 mmol) was dissolved in dichloromethane (20 mL) at room temperature and cooled to 0° C. HATU (4.1 g, 10 mmol), N,N-diisopropylethylamine (5.0 mL, 29 mmol) and N,N-dimethyl-1,2-ethanediamine (1.1 g, 12 mmol) were added in turn, heated to room temperature and stirred overnight. Then the mixture was concentrated. The residue was purified by a silica gel column chromatography (dichloromethane/anhydrous methanol (v/v)=10/1) to give the title compound as yellow oil (2.5 g, 94%).

Step 2

1-amino-N-(2-dimethylaminoethyl)cyclobutyl formamide dihydrochloride

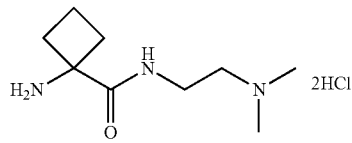

Tert-butyl N-[1-(2-dimethylaminoethylcarbamoyl)cyclobutyl]carbamate (2.5 g, 8.8 mmol) was dissolved in ethyl acetate (30 mL) at room temperature. The solution of HCl in ethyl acetate (6 mL, 4 M) was added and stirred overnight. The mixture was filtered. The filter cake was washed with ethyl acetate (20 mL) and dried in vacuo to give the title compound as a white solid (2.0 g, 88%).

Step 3

N-(2-dimethylaminoethyl)-1-[4-[4-[[2-methyl-5-[(1S,2S,3S,4R,5S)-2,3,4-trihydroxy-1-(1-hydroxy-1-methyl-ethyl)-6,8-dioxabicyclo[3.2.1]octane-5-yl]phenyl]methyl]phenyl]butanamido]cyclobutyl formamide

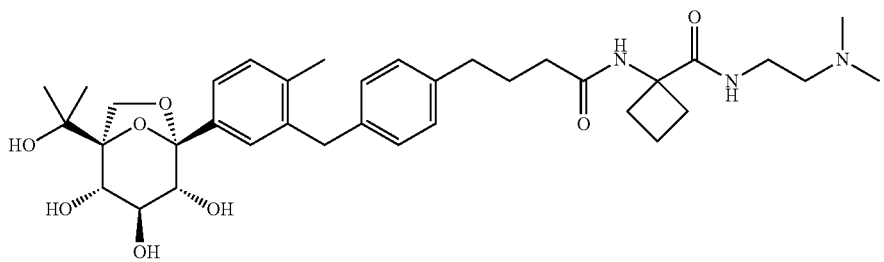 [SMILES: Cc1ccc([C@]23OC[C@](C(C)(C)O)(O2)[C@@H](O)[C@H](O)[C@H]3O)cc1Cc1ccc(CCCC(=O)NC2(C(=O)NCCN(C)C)CCC2)cc1]

4-[4-[[2-Methyl-5-[(1S,2S,3S,4R,5S)-2,3,4-trihydroxy-1-(1-hydroxy-1-methyl-ethyl))-6,8-dioxabicyclo[3.2.1]octane-5-yl]phenyl]methyl]phenyl]butyric acid (0.40 g, 0.82 mmol) was dissolved in dichloromethane (10 mL) at room temperature, and cooled to 0° C. HBTU (0.38 g, 0.98 mmol) and N,N-diisopropylethylamine (0.72 mL, 4.1 mmol) were added and the mixture was stirred for 20 minutes. Then 1-amino-N-(2-dimethyl aminoethyl)cyclobutyl carboxamide dihydrochloride (0.28 g, 1.3 mmol) was added. The mixture was heated to room temperature and stirred overnight. Then the mixture was concentrated. The residue was purified by a silica gel column chromatography (dichloromethane/anhydrous methanol (v/v)=7/1) to give the title compound as a white solid (0.13 g, 24%).

MS (ESI, pos. ion) m/z: 654.5 [M+H]⁺.

¹H NMR (400 MHz, DMSO-d₆) δ (ppm): 8.88 (br.s, 1H), 8.59 (s, 1H), 7.76 (t, 1H), 7.29 (s, 1H), 7.23 (d, 1H), 7.12-7.04 (m, 5H), 5.51 (d, 1H), 5.32 (t, 1H), 5.02 (d, 1H), 4.89 (d, 1H), 4.21 (s, 1H), 4.03 (d, 1H), 3.91 (s, 2H), 3.81 (d, 1H), 3.72 (d, 1H), 3.50 (m, 2H), 3.08 (m, 2H), 2.78 (s, 6H), 2.18 (s, 3H), 2.13 (t, 2H), 2.05-1.96 (m, 4H), 1.86-1.72 (m, 4H), 1.40 (m, 1H), 1.21 (s, 3H), 1.15 (s, 3H), 0.70 (t, 1H).

Example 12

N-(2-dimethylaminoethyl)-2-ethyl-2-[4-[4-[[2-methyl-5-[(1S,2S,3S,4R,5S)-2,3,4-trihydroxy-1-(1-hydroxy-1-methyl-ethyl)-6,8-dioxabicyclo[3.2.1]octane-5-yl]phenyl]methyl]phenyl]butanamido]butanamide

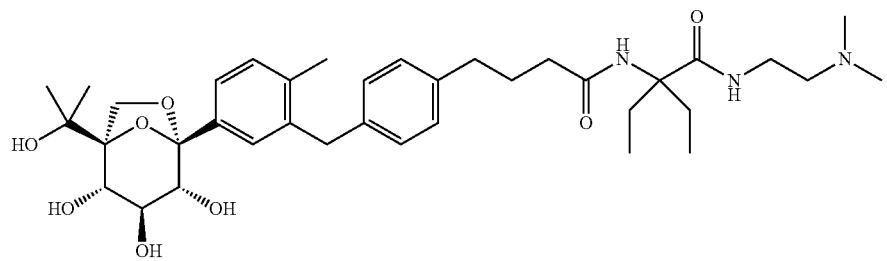 [SMILES: CCC(CC)(NC(=O)CCCc1ccc(Cc2cc([C@]34OC[C@](C(C)(C)O)(O3)[C@@H](O)[C@H](O)[C@H]4O)ccc2C)cc1)C(=O)NCCN(C)C]

Step 1

2-(benzyloxycarboxamido)-2-ethyl-butyric acid

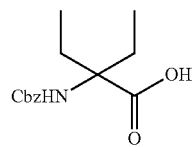

2-Amino-2-ethyl-butyric acid (2.0 g, 15 mmol) was dissolved in dioxane (20 mL) at room temperature, sodium carbonate (4.8 g, 45 mmol) and water (50 mL) were added and cooled to 0° C. Benzyl chloroformate (2.7 mL, 18 mmol) was added dropwise, then the mixture was heated to room temperature and stirred overnight. The mixture was washed with the petroleum ether (100 mL). The aqueous phase was adjusted pH to 1 with 1 M hydrochloric acid. The mixture was extracted with ethyl acetate (100 mL×2). The combined organic phases were washed with saturated salt water (100 mL), dried over anhydrous sodium sulfate, filtered and concentrated to give the title compound as colorless oil (2.1 g, 52%).

MS (ESI, pos. ion) m/z: 266.3 [M+H]⁺.

Step 2 benzyl N-[1-(2-dimethylaminoethylcarbamoyl)-1-ethyl-propyl]carbamate

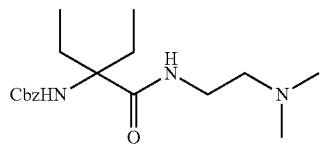 [SMILES: CCC(CC)(NC(=O)OCc1ccccc1)C(=O)NCCN(C)C]

2-(Benzyloxycarboxamido)-2-ethyl-butyric acid (1.84 g, 6.94 mmol) was dissolved in dichloromethane (30 mL) at room temperature and cooled to 0° C. HATU (3.1 g, 7.7 mmol) and N,N-diisopropylethylamine(3.7 mL, 29 mmol) were added, and the mixture was stirred for 20 min. N,N-dimethyl-1,2-ethanediamine (0.80 g, 9.1 mmol) was added, and the mixture was heated to room temperature and stirred overnight. Then the mixture was washed with water. The organic phase was concentrated. The residue was purified by a silica gel column chromatography (dichloromethane/anhydrous methanol (v/v)=30/1) to give the title compound as yellow oil (2.2 g, 95%).

MS (ESI, pos. ion) m/z: 336.4 [M+H]$^+$.

Step 3

2-amino-N-(2-dimethylaminoethyl)-2-ethyl-butanamide

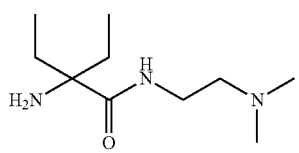

Benzyl N-[1-(2-dimethylaminoethylcarbamoyl)-1-ethyl-propyl]carbamate (2.0 g, 6.0 mmol) was dissolved in a mixed solvent of tetrahydrofuran (2 mL) and anhydrous methanol (20 mL) at room temperature. 10% Palladium/carbon catalyst (0.20 g, 0.19 mmol) was added. The mixture was stirred overnight under hydrogen. The mixture was filtered and concentrated to give the title compound as yellow oil (1.2 g, 99%).

Step 4

2-amino-N-(2-dimethylaminoethyl)-2-ethyl-butanamide dihydrochloride

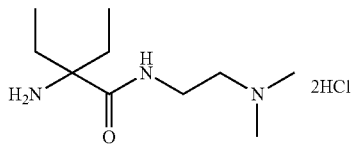

2-Amino-N-(2-dimethylaminoethyl)-2-ethyl-butanamide (1.2 g, 6.0 mmol) was dissolved in ethyl acetate (20 mL) at room temperature. A solution of HCl in isopropyl alcohol (4 mL, 5 M) was added. The mixture was stirred for 1 hour. The mixture was filtered, the filter cake was washed with ethyl acetate (20 mL) and dried in vacuo to give the title compound as a white solid (1.5 g, 92%).

MS (ESI, pos. ion) m/z: 202.3 [M+H]$^+$.

$^1$H NMR (400 MHz, D$_2$O) δ (ppm): 3.58 (t, 2H), 3.25 (t, 2H), 2.86 (s, 6H), 2.76 (s, 2H), 1.89 (q, 4H), 0.85 (t, 6H).

Step 5

N-(2-dimethylaminoethyl)-2-ethyl-2-[4-[4-[[2-methyl-5-[(1S,2S,3S,4R,5S)-2,3,4-tribenzyloxy-1-(1-hydroxy-1-methyl-ethyl)-6,8-dioxabicyclo[3.2.1]octane-5-yl]phenyl]methyl]phenyl]butanamido]butanamide

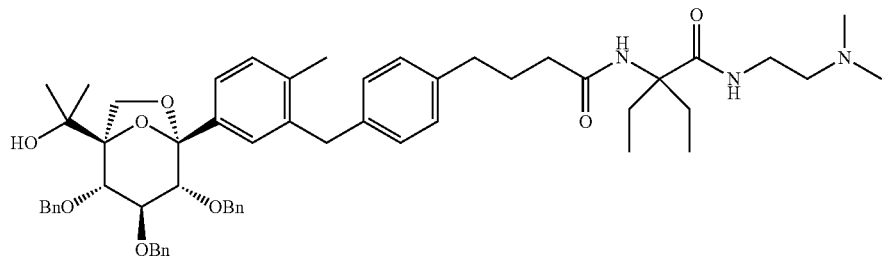 [SMILES: CCC(CC)(NC(=O)CCCc1ccc(Cc2cc([C@]34OC[C@](C(C)(C)O)(O3)[C@@H](OCc3ccccc3)[C@H](OCc3ccccc3)[C@H]4OCc3ccccc3)ccc2C)cc1)C(=O)NCCN(C)C]

4-[4-[[2-Methyl-5-[(1S,2S,3S,4R,5S)-2,3,4-tribenzyloxy-1-(1-hydroxy-1-methyl-)ethyl)-6,8-dioxabicyclo[3.2.1]octane-5-yl]phenyl]methyl]phenyl]butyric acid (0.80 g, 1.05 mmol) was dissolved in N,N-dimethylformamide (6 mL) at room temperature, and cooled to 0° C. HBTU (0.50 g, 1.3 mmol) and N,N-diisopropylethylamine (1.0 mL, 5.7 mmol) were added in turn. The reaction mixture was heated to room temperature and stirred for 20 minutes. Then 2-amino-N-(2-dimethylaminoethyl)-2-ethyl-butanamide dihydrochloride (0.38 g, 1.4 mmol) was added. The reaction mixture was stirred overnight. The resulting mixture was extracted with water (60 mL) and ethyl acetate (100 Ml×3). The combined organic layers were washed with saturated brine (100 mL), dried over ahydrous sodium sulfate and filtered. The filtrate was concentrated, and the residue was purified by a silica gel column chromatography (dichloromethane/anhydrous methanol (v/v)=30/1) to give the title compound as colorless oil (0.99 g, 99%).

Step 5

N-(2-dimethylaminoethyl)-2-ethyl-2-[4-[4-[[2-methyl-5-[(1S,2S,3S,4R,5S)-2,3,4-trihydroxy-1-(1-hydroxy-1-methyl-ethyl)-6,8-dioxabicyclo[3.2.1]octane-5-yl]phenyl] methyl]phenyl]butanamido]butanamide

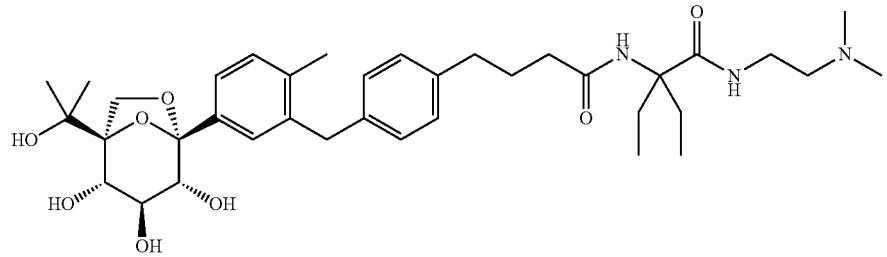 [SMILES: CCC(CC)(NC(=O)CCCc1ccc(Cc2cc([C@]34OC[C@](C(C)(C)O)(O3)[C@@H](O)[C@H](O)[C@H]4O)ccc2C)cc1)C(=O)NCCN(C)C]

N-(2-dimethyl aminoethyl)-2-ethyl-2-[4-[4-[[2-methyl-5-[(1S,2S,3S,4R,5S)-2,3,4-tribenzyloxy-1-(1-hydroxy-1-methyl-ethyl)-6,8-dioxabicyclo[3.2.1]octane-5-yl]phenyl] methyl]phenyl]butanamido]butanamide (0.90 g, 0.45 mmol) was dissolved in anisole (30 mL) at room temperature and cooled to 0° C. Anhydrous aluminum trichloride (1.3 g, 9.7 mmol) was slowly added, and stirred for 5 minutes. The mixture was heated to room temperature and stirred for 3 hours. The resulting mixture was poured into ice water (50 mL) and extracted with ethyl acetate (30 mL×6). The combined organic layers were washed with saturated sodium hydrogen carbonate (100 mL) and saturated brine (100 mL), dried over ahydrous sodium sulfate and filtered. The filtrate was concentrated, and the residue was purified by a silica gel column chromatography (dichloromethane/anhydrous methanol (v/v)=7/1) to give the title compound as a white solid (160 mg, 25%).

MS (ESI, pos. ion) m/z: 670.6 [M+H]$^+$.

$^1$H NMR (400 MHz, DMSO-d$_6$) δ (ppm): 8.00 (s, 1H), 7.93 (t, 1H), 7.29 (s, 1H), 7.23 (d, 1H), 7.16 7.00 (m, 5H), 5.51 (d, 1H), 5.32 (t, 1H), 5.02 (d, 1H), 4.89 (d, 1H), 4.22 (s, 1H), 4.03 (d, 1H), 3.91 (s, 2H), 3.81 (d, 1H), 3.72 (d, 1H), 3.47 (m, 4H), 3.10 (m, 2H), 2.81 (d, 6H), 2.18 (s, 3H), 2.14 (d, 2H), 1.82-1.68 (m, 6H), 1.21 (s, 3H), 1.15 (s, 3H), 0.68 (t, 6H).

Example 13

N-(2-dimethylaminoethyl)-2-methyl-2-[4-[4-[[2-methyl-5-[(1S,2S,3S,4R,5S))-2,3,4-trihydroxy-1-methyl-6,8-dioxabicyclo[3.2.1]octane-5-yl]phenyl]methyl]phenyl]butanamido] propanamide

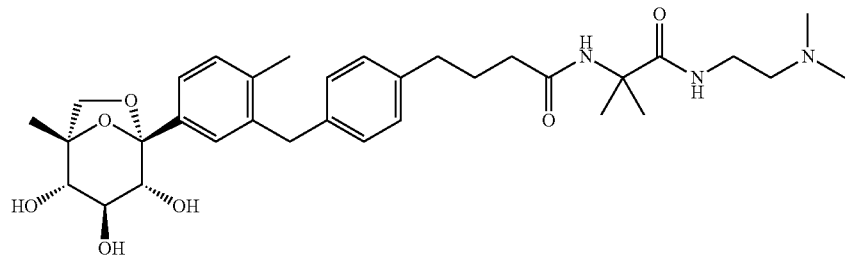 [SMILES: Cc1ccc([C@]23OC[C@](C)(O2)[C@@H](O)[C@H](O)[C@H]3O)cc1Cc1ccc(CCCC(=O)NC(C)(C)C(=O)NCCN(C)C)cc1]

Step 1

(1S,2S,3S,4R,5S)-5-[3-[[4-(4-allyloxybutyl)phenyl]methyl]-4-methyl-phenyl]-2,3,4-tribenzyloxy-1-(iodomethyl)-6,8-dioxabicyclo[3.2.1]octane

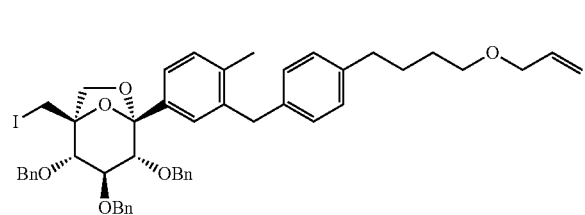 [SMILES: C=CCOCCCCc1ccc(Cc2cc([C@]34OC[C@](CI)(O3)[C@@H](OCc3ccccc3)[C@H](OCc3ccccc3)[C@H]4OCc3ccccc3)ccc2C)cc1]

[(1S,2S,3S,4R,5S)-5-[3-[[4-(4-allyloxybutyl)phenyl]methyl]-4-methyl-phenyl]-2,3,4-tribenzyloxy-6,8-dioxabicyclo[3.2.1]octane-1-yl]methanol (2.0 g, 2.6 mmol) was dissolved in toluene (20 mL) at room temperature, then triphenylphosphine (1.7 g, 6.5 mmol), imidazole (0.90 g, 13 mmol) and iodine seed (1.7 g, 6.6 mmol) was added. The mixture was heated to 80° C. and stirred for 3 hours under nitrogen. The mixture was cooled to room temperature, washed with 5% sodium thiosulfate solution (30 mL), and concentrated under reduced pressure. The residue was purified by a silica gel column chromatography (EtOAc/PE(v/v)=1/10) to give the title compound as a white solid (1.6 g, 70%).

Step 2

4-[4-[[2-methyl-5-[(1S,2S,3S,4R,5S)-2,3,4-tribenzyloxy-1-(iodomethyl)-6,8-dioxabicyclo[3.2.1]octane-5-yl]phenyl]methyl]phenyl]butan-1-ol

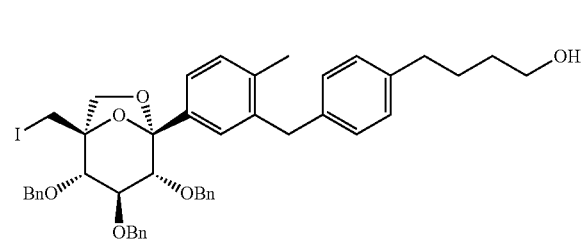 [SMILES: Cc1ccc([C@]23OC[C@](CI)(O2)[C@@H](OCc2ccccc2)[C@H](OCc2ccccc2)[C@H]3OCc2ccccc2)cc1Cc1ccc(CCCCO)cc1]

[(1S,2S,3S,4R,5S)-5-[3-[[4-(4-allyloxybutyl)phenyl]methyl]-4-methyl-phenyl]-2,3,4-tribenzyloxy-1-(iodomethyl)-6,8-dioxabicyclo[3.2.1]octane (1.6 g, 1.9 mmol) was dissolved in methanol (20 mL) at room temperature, then palladium chloride (0.20 g, 1.1 mmol) was added and stirred for 6 hours. The mixture was filtered and concentrated. The residue was purified by a silica gel column chromatography (EtOAc/PE(v/v)=1/2) to give the title compound as a white solid (1.0 g, 66%).

Step 3

4-[4-[[2-methyl-5-[(1S,2S,3S,4R,5S)-2,3,4-tribenzyloxy-1-methyl-6,8-dioxabicyclo[3.2.1]octane-5-yl]phenyl]methyl]phenyl]butan-1-ol

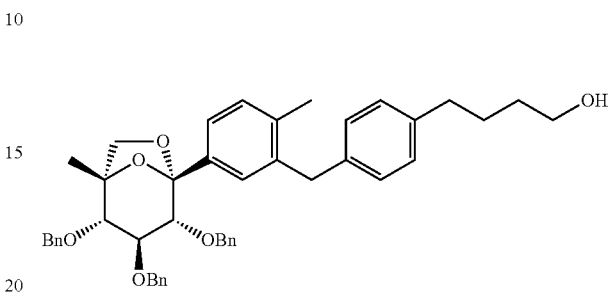

4-[4-[[2-Methyl-5-[(1S,2S,3S,4R,5S)-2,3,4-tribenzyloxy-1-(iodomethyl)-6,8-dioxabicyclo[3.2.1]octane-5-yl]phenyl]methyl]phenyl]butan-1-ol (1.0 g, 1.2 mmol) was dissolved in methanol (10 mL) at room temperature. 10% palladium/carbon (0.10 g, 0.094 mmol) and triethylamine (0.5 mL, 3.6 mmol) was added. The mixture was stirred overnight under hydrogen. Then the mixture was filtered and concentrated. The crude product was purified by a silica gel column chromatography (EtOAc/PE(v/v)=1/2) to give the title compound as colorless oil (0.59 g, 70%).

Step 4

4-[4-[[2-methyl-5-[(1S,2S,3S,4R,5S)-2,3,4-tribenzyloxy-1-methyl-6,8-dioxabicyclo[3.2.1]octane-5-yl]phenyl]methyl]phenyl]butyric acid

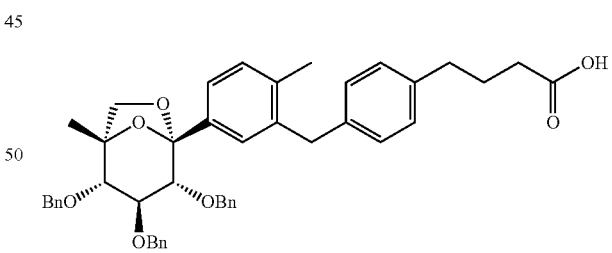

4-[4-[[2-Methyl-5-[(1S,2S,3S,4R,5S)-2,3,4-tribenzyloxy-1-methyl-6,8-dioxabicyclo[3.2.1]octane-5-yl]phenyl]methyl]phenyl]butan-1-ol (0.59 g, 0.84 mmol) was dissolved in dichloromethane (10 mL) at room temperature. Water (1.5 mL), 2,2,6,6-tetramethylpiperidine oxide (42 mg, 0.25 mmol) and iodobenzene diacetic acid (0.69 g, 2.1 mmol) were added. The reaction mixture was stirred at room temperature overnight. Then the mixture was separated. The organic phase was dried over anhydrous sodium sulfate, filtered and concentrated. The crude product was purified by a silica gel column chromatography (EtOAc/PE(v/v)=1/2) to give the title compound as yellow oil (0.44 g, 73%).

Step 11

N-(2-dimethyl aminoethyl)-2-methyl-2-[4-[4-[[2-methyl-5-[(1S,2S,3S,4R,5S)-2,3,4-tribenzyloxy-1-methyl-6,8-dioxabicyclo[3.2.1]octane-5-yl]phenyl]methyl]phenyl]butanamido]propionamide

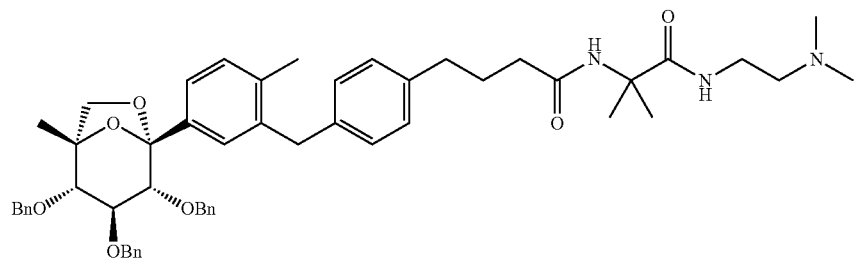 [SMILES: Cc1ccc([C@]23OC[C@](C)(O2)[C@@H](OCc2ccccc2)[C@H](OCc2ccccc2)[C@H]3OCc2ccccc2)cc1Cc1ccc(CCCC(=O)NC(C)(C)C(=O)NCCN(C)C)cc1]

4-[4-[[2-Methyl-5-[(1S,2S,3S,4R,5S)-2,3,4-tribenzyloxy-1-methyl-6,8-dioxabicyclo[3.2.1]octane-5-yl]phenyl]methyl]phenyl]butyric acid (0.44 g, 0.62 mmol) was dissolved in dichloromethane (10 mL) at room temperature. HBTU (0.30 g, 0.75 mmol) and N,N-diisopropylethylamine (0.54 mL, 3.1 mmol) were added and stirred for 20 min. Then 2-amino-N-(2-dimethylaminoethyl)-2-methyl-propionamide dihydrochloride (0.23 g, 0.93 mmol) was added and stirred overnight. The reaction was stopped. The resulted mixture was washed with water (10 mL), dried over anhydrous sodium sulfate, filtered and concentrated. The crude product was purified by a silica gel column chromatography (dichloromethane/methanol (v/v)=10/1) to give the title compound as colorless oil (0.38 g, 71%).

Step 5

N-(2-dimethylaminoethyl)-2-methyl-2-[4-[4-[[2-methyl-5-[(1S,2S,3S,4R,5S))-2,3,4-trihydroxy-1-methyl-6,8-dioxabicyclo[3.2.1]octane-5-yl]phenyl]methyl]phenyl]butanamido]propanamide

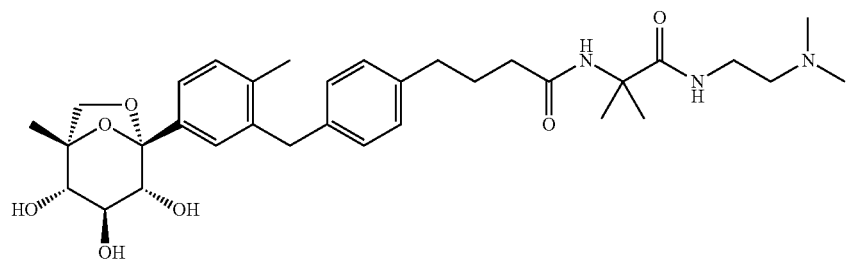 [SMILES: Cc1ccc([C@]23OC[C@](C)(O2)[C@@H](O)[C@H](O)[C@H]3O)cc1Cc1ccc(CCCC(=O)NC(C)(C)C(=O)NCCN(C)C)cc1]

N-(2-dimethylaminoethyl)-2-methyl-2-[4-[4-[[2-methyl-5-[(1S,2S,3S,4R,5S)-2,3,4-tribenzyloxy-1-methyl-6,8-dioxabicyclo[3.2.1]octane-5-yl]phenyl]methyl]phenyl]butanamido]propionamide (0.38 g, 0.44 mmol) was dissolved in methanol (6 mL) at room temperature. 10% Palladium hydroxide/carbon (0.32 g, 0.22 mmol) was added. The reaction mixture was stirred overnight under hydrogen. Then the mixture was filtered and concentrated. The residue was purified by a silica gel column chromatography (dichloromethane/anhydrous methanol (v/v)=7/1) to give the title compound as a white solid (0.11 g, 42%).

MS (ESI, pos. ion) m/z: 598.3 [M+H]$^+$.

$^1$H NMR (400 MHz, DMSO-$d_6$) δ (ppm): 8.66 (br.s, 1H), 8.31 (s, 1H), 7.86 (t, 1H), 7.24 (s, 1H), 7.20 (d, 1H), 7.13-7.03 (m, 5H), 5.50 (d, 1H), 5.01 (d, 1H), 4.88 (d, 1H), 4.08 (d, 1H), 3.92 (s, 2H), 3.45-3.35 (m, 6H), 3.11 (m, 2H), 2.82 (s, 3H), 2.81 (s, 3H), 2.18 (s, 3H), 2.12 (t, 2H), 2.00 (m, 1H), 1.75 (m, 2H), 1.45 (m, 1H), 1.29 (s, 6H), 1.28 (s, 3H).

Example 14

N-(2-dimethylaminoethyl)-2-[4-[4-[[5-[(1S,2S,3S,4R,5S)-1-ethyl-2,3,4-trihydroxy-6,8-dioxabicyclo[3.2.1]octane-5-yl]-2-methyl-phenyl]methyl]phenyl]butanamido]-2-methyl-propionamide

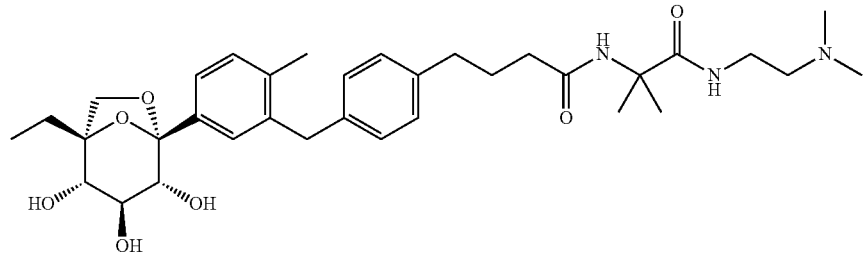 [SMILES: CC[C@@]12CO[C@@](c3ccc(C)c(Cc4ccc(CCCC(=O)NC(C)(C)C(=O)NCCN(C)C)cc4)c3)(O1)[C@H](O)[C@@H](O)[C@@H]2O]

Step 1

(1S,2S,3S,4R,5S)-5-[3-[[4-(4-allyloxybutyl)phenyl]methyl]-4-methyl-phenyl]-2,3,4-tribenzyloxy-6,8-dioxabicyclo[3.2.1]octane-1-formaldehyde

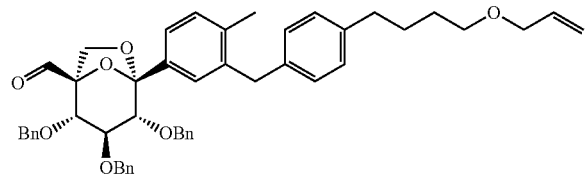 [SMILES: C=CCOCCCCc1ccc(Cc2cc([C@]34OC[C@](C=O)(O3)[C@@H](OCc3ccccc3)[C@H](OCc3ccccc3)[C@H]4OCc3ccccc3)ccc2C)cc1]

(1S,2S,3S,4R,5S)-5-[3-[[4-(4-allyloxybutyl)phenyl]methyl]-4-methyl-phenyl]-2,3,4-tribenzyloxy-6,8-dioxabicyclo[3.2.1]octane-1-yl]methanol (2.5 g, 3.3 mmol) was dissolved in dichloromethane (30 mL). Saturated sodium bicarbonate solution (30 mL) was added, and the mixture was cooled to 0° C. Potassium bromide (0.26 g, 2.2 mmol) and 2,2,6,6-tetramethylpiperidine oxide (78 mg, 0.50 mmol) were added and the mixture was stirred for 1 minute. Sodium hypochlorite solution (2.6 mL, 8.9 mmol, available chlorine 9.70%) was added once and the mixture was continuously stirred for 10 minutes. The reaction mixture was separated. The organic phase was washed with saturated saturated sodium chloride solution (30 mL), dried over anhydrous sodium sulfate. The mixture was filtered and concentrated to give the title compound as yellow oil (2.5 g, 100%).

Step 2

1-[(1R,2S,3S,4R,5S)-5-[3-[[4-(4-allyloxybutyl)phenyl]methyl]-4-methyl-phenyl]-2,3,4-tribenzyloxy-6,8-dioxabicyclo[3.2.1]octane-1-yl]ethanol

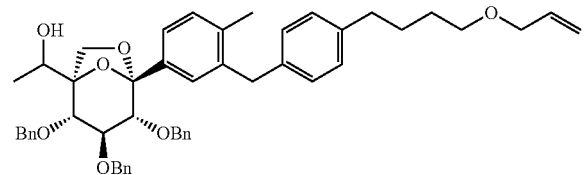 [SMILES: C=CCOCCCCc1ccc(Cc2cc([C@]34OC[C@](C(C)O)(O3)[C@@H](OCc3ccccc3)[C@H](OCc3ccccc3)[C@H]4OCc3ccccc3)ccc2C)cc1]

(1S,2S,3S,4R,5S)-5-[3-[[4-(4-allyloxybutyl)phenyl]methyl]-4-methyl-phenyl]-2,3,4-tribenzyloxy-6,8-dioxabicyclo[3.2.1]octane-1-carbaldehyde (2.5 g, 3.3 mmol) was dissolved in anhydrous tetrahydrofuran (20 mL), then cooled to −5° C. under nitrogen. A solution of methylmagnesium bromide in tetrahydrofuran (7.0 mL, 7.0 mmol, 1.0 mmol/L) was added dropwise. The mixture was stirred at room temperature overnight. The reaction mixture was cooled to 0° C., and quenched with dropwise saturated aqueous ammonium chloride (20 mL). The resulting mixture was extracted with ethyl acetate (50 mL) and concentrated under reduced pressure. The crude product was purified by a silica gel column chromatography (EtOAc/PE(v/v)=1/10) to give the title compound as colorless oil (2.2 g, 86%).

Step 3

(1S,2S,3S,4R,5S)-5-[3-[[4-(4-allyloxybutyl)phenyl]methyl]-4-methyl-phenyl]-2,3,4-tribenzyloxy-1-(1-iodo-ethyl)-6,8-dioxabicyclo[3.2.1]octane

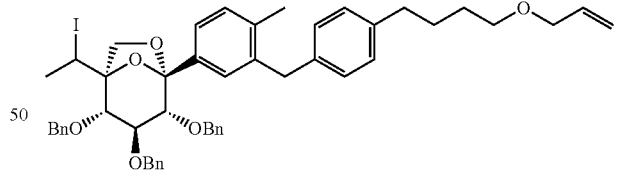

[(1S,2S,3S,4R,5S)-5-[3-[[4-(4-allyloxybutyl)phenyl]methyl]-4-methyl-phenyl]-2,3,4-tribenzyloxy-6,8-dioxabicyclo[3.2.1]octane-1-yl]ethanol (2.0 g, 2.6 mmol) was dissolved in toluene (20 mL) at room temperature, then triphenylphosphine (1.7 g, 6.5 mmol), imidazole (0.90 g, 13 mmol) and iodine seed (1.7 g, 6.6 mmol) were added. The mixture was heated to 80° C. and stirred for 3 hours under nitrogen. The mixture was cooled to room temperature, washed with 5% sodium thiosulfate solution (30 mL), and concentrated under reduced pressure. The residue was purified by a silica gel column chromatography (EtOAc/PE(v/v)=1/10) to give the title compound as a white solid (1.4 g, 61%).

Step 4

4-[4-[[2-methyl-5-[(1S,2S,3S,4R,5S)-2,3,4-tribenzyloxy-1-(1-iodoethyl)-6,8-dioxabicyclo[3.2.1]octane-5-yl]phenyl]methyl]phenyl]butan-1-ol

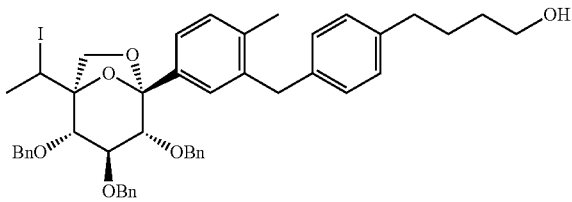 [SMILES: Cc1ccc([C@]23OC[C@](C(C)I)(O2)[C@@H](OCc2ccccc2)[C@H](OCc2ccccc2)[C@H]3OCc2ccccc2)cc1Cc1ccc(CCCCO)cc1]

[(1S,2S,3S,4R,5S)-5-[3-[[4-(4-allyloxybutyl)phenyl]methyl]-4-methyl-phenyl]-2,3,4-tribenzyloxy-1-(1-iodo-ethyl)-6,8-dioxabicyclo[3.2.1]octane (1.4 g, 1.6 mmol) was dissolved in methanol (20 mL) at room temperature, then palladium chloride (0.15 g, 0.85 mmol) was added. The mixture was stirred overnight. Then the mixture was filtered and concentrated. The crude product was purified by a silica gel column chromatography (EtOAc/PE(v/v)=1/2) to give the title compound as colorless oil (0.80 g, 60%).

Step 5

4-[4-[[2-methyl-5-[(1S,2S,3S,4R,5S)-2,3,4-tribenzyloxy-1-ethyl-6,8-dioxabicyclo[3.2.1]octane-5-yl]phenyl]methyl]phenyl]butan-1-ol

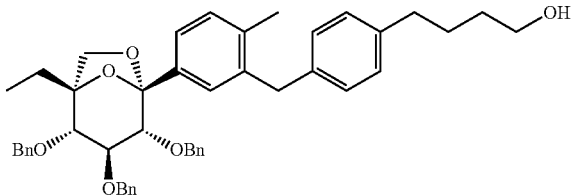 [SMILES: CC[C@@]12CO[C@@](c3ccc(C)c(Cc4ccc(CCCCO)cc4)c3)(O1)[C@H](OCc1ccccc1)[C@@H](OCc1ccccc1)[C@@H]2OCc1ccccc1]

4-[4-[[2-Methyl-5-[(1S,2S,3S,4R,5S)-2,3,4-tribenzyloxy-1-(iodomethyl)-6,8-dioxabicyclo[3.2.1]octane-5-yl]phenyl]methyl]phenyl]butan-1-ol (0.78 g, 0.93 mmol) was dissolved in methanol (6 mL) at room temperature. 10% Palladium/carbon (80 mg, 0.075 mmol) and triethylamine (0.4 mL, 2.9 mmol) were added. The mixture was stirred overnight under hydrogen. Then the mixture was filtered and concentrated. The crude product was purified by a silica gel column chromatography (EtOAc/PE(v/v)=1/2) to give the title compound as colorless oil (0.40 g, 60%).

$^1$H NMR (400 MHz, CDCl$_3$) δ (ppm): 7.45-7.26 (m, 12H), 7.24-7.15 (m, 4H), 7.05-6.92 (m, 6H), 4.98-4.86 (m, 2H), 4.81 (dd, 1H), 4.77-4.70 (m, 1H), 4.33 (dd, 1H), 4.21 (dd, 1H), 4.04-3.93 (m, 3H), 3.87 (d, 1H), 3.79-3.72 (m, 1H), 3.69-3.51 (m, 4H), 2.60 (t, 2H), 2.25 (s, 3H), 1.70-1.55 (m, 7H), 1.29 (q, 2H), 0.99 (t, 1H).

Step 6

4-[4-[[2-methyl-5-[(1S,2S,3S,4R,5S)-2,3,4-tribenzyloxy-1-ethyl-6,8-dioxabicyclo[3.2.1]octane-5-yl]phenyl]methyl]phenyl]butyric acid

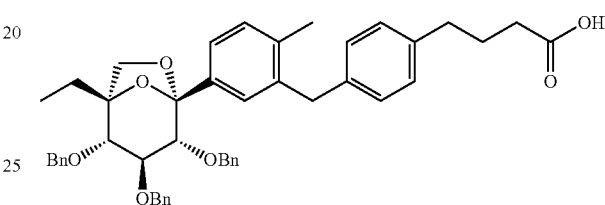

4-[4-[[2-Methyl-5-[(1S,2S,3S,4R,5S)-2,3,4-tribenzyloxy-1-ethyl-6,8-dioxabicyclo[3.2.1]octane-5-yl]phenyl]methyl]phenyl]butan-1-ol (0.37 g, 0.52 mmol) was dissolved in dichloromethane (5 mL) at room temperature. Water (1 mL), 2,2,6,6-tetramethylpiperidine oxide (26 mg, 0.16 mmol) and iodobenzene diacetic acid (0.43 g, 1.3 mmol) were added in turn. The reaction mixture was stirred overnight at room temperature. Then the mixture was separated. The organic phase was dried over anhydrous sodium sulfate, filtered and concentrated. The crude product was purified by a silica gel column chromatography (EtOAc/PE(v/v)=1/2) to give the title compound as a yellow solid (0.30 g, 80%).

Step 7

N-(2-dimethylaminoethyl)-2-methyl-2-[4-[4-[[2-methyl-5-[(1S,2S,3S,4R,5S))-2,3,4-tribenzyloxy-1-ethyl-6,8-dioxabicyclo[3.2.1]octane-5-yl]phenyl]methyl]phenyl]butanamido]propanamide

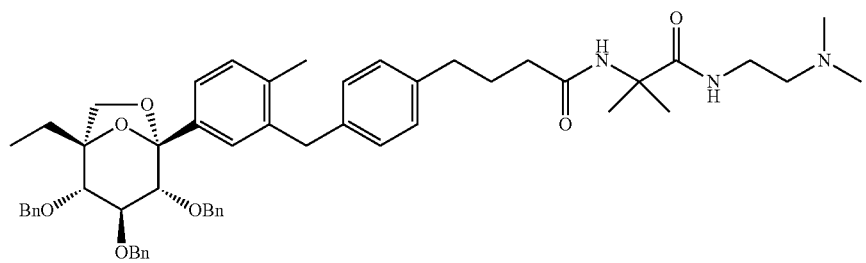 [SMILES: CC[C@@]12CO[C@@](c3ccc(C)c(Cc4ccc(CCCC(=O)NC(C)(C)C(=O)NCCN(C)C)cc4)c3)(O1)[C@H](OCc1ccccc1)[C@@H](OCc1ccccc1)[C@@H]2OCc1ccccc1]

4-[4-[[2-Methyl-5-[(1S,2S,3S,4R,5S)-2,3,4-tribenzyloxy-1-methyl-6,8-dioxabicyclo[3.2.1]octane-5-yl]phenyl]methyl]phenyl]butyric acid (0.30 g, 0.41 mmol) was dissolved in dichloromethane (10 mL) at room temperature. HATU (0.20 g, 0.50 mmol) and N,N-diisopropylethylamine (0.40 mL, 2.3 mmol) were added and stirred for 20 minutes. Then 2-amino-N-(2-dimethylaminoethyl)-2-methyl-propionamide dihydrochloride (0.23 g, 0.93 mmol) was added and the mixture was stirred overnight. The stir was stopped. The resulted mixture was washed with water (10 mL), dried over anhydrous sodium sulfate, filtered and concentrated. The crude product was purified by a silica gel column chromatography (dichloromethane/methanol (v/v)=10/1) to give the title compound as colorless oil (0.30 g, 82%).

Step 8

N-(2-dimethylaminoethyl)-2-[4-[4-[[5-[(1S,2S,3S,4R,5S)-1-ethyl-2,3,4-trihydroxy-6,8-dioxabicyclo[3.2.1]octane-5-yl]-2-methyl-phenyl]methyl]phenyl]butanamido]-2-methyl-propionamide

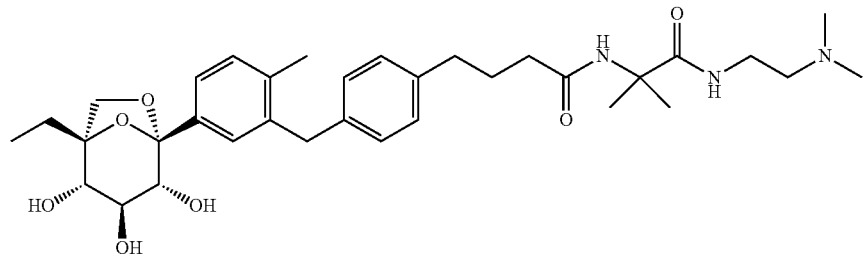 [SMILES: CC[C@@]12CO[C@@](c3ccc(C)c(Cc4ccc(CCCC(=O)NC(C)(C)C(=O)NCCN(C)C)cc4)c3)(O1)[C@H](O)[C@@H](O)[C@@H]2O]

N-(2-dimethylaminoethyl)-2-methyl-2-[4-[4-[[2-methyl-5-[(1S,2S,3S,4R,5S)-2,3,4-tribenzyloxy-1-ethyl-6,8-dioxabicyclo[3.2.1]octane-5-yl]phenyl]methyl]phenyl]butanamido]propionamide (0.30 g, 0.34 mmol) was dissolved in methanol (6 mL) at room temperature. 10% Palladium hydroxide/carbon (0.25 g, 0.17 mmol) was added. The reaction mixture was stirred overnight under hydrogen. Then the mixture was filtered and concentrated. The residue was purified by a silica gel column chromatography (dichloromethane/anhydrous methanol (v/v)=7/1) to give the title compound as a white solid (76 mg, 37%).

MS (ESI, pos. ion) m/z: 612.3 [M+H]$^+$.

$^1$H NMR (400 MHz, DMSO-$d_6$) δ (ppm): 8.80 (br.s, 1H), 8.30 (s, 1H), 7.88 (s, 1H), 7.27 (s, 1H), 7.20 (d, 1H), 7.16-6.99 (m, 5H), 4.03 (d, 1H), 3.91 (s, 2H), 3.45-3.35 (m, 6H), 3.11 (m, 2H), 2.81 (s, 6H), 2.18 (s, 3H), 2.12 (t, 2H), 1.80-1.70 (m, 3H), 1.54 (m, 1H), 1.28 (s, 6H), 1.24 (m, 2H), 0.89 (t, 3H).

Example 15

N-(2-dimethylaminoethyl)-2-methyl-2-[4-[4-[[2-methyl-5-[(1S,2S,3S,4R,5S))-2,3,4-trihydroxy-1-(hydroxymethyl)-6,8-dioxabicyclo[3.2.1]octane-5-yl]phenyl]methyl]phenyl]butanamido]propanamide

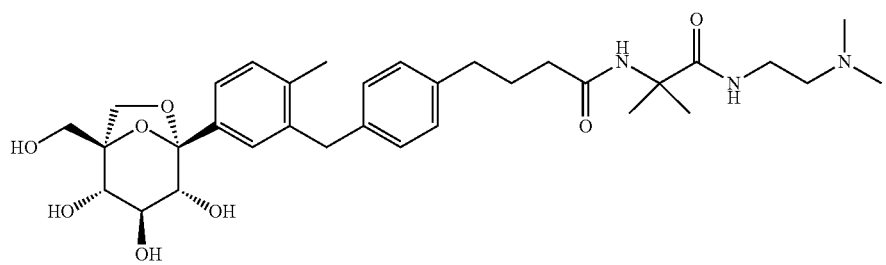 [SMILES: Cc1ccc([C@]23OC[C@](CO)(O2)[C@@H](O)[C@H](O)[C@H]3O)cc1Cc1ccc(CCCC(=O)NC(C)(C)C(=O)NCCN(C)C)cc1]

Step 1

(1S,2S,3S,4R,5S)-5-[3-[[4-(4-allyloxybutyl)phenyl]methyl]-4-methyl-phenyl]-2,3,4-tribenzyloxy-1-(benzyloxymethyl)-6,8-dioxabicyclo[3.2.1]octane

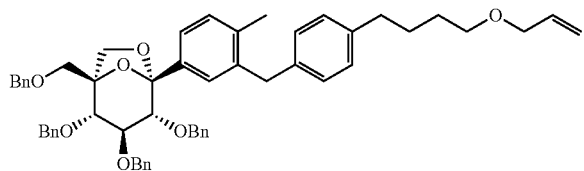 [SMILES: C=CCOCCCCc1ccc(Cc2cc([C@]34OC[C@](COCc5ccccc5)(O3)[C@@H](OCc3ccccc3)[C@H](OCc3ccccc3)[C@H]4OCc3ccccc3)ccc2C)cc1]

[(1S,2S,3S,4R,5S)-5-[3-[[4-(4-allyloxybutyl)phenyl]methyl]-4-methyl-phenyl]-2,3,4-tribenzyloxy-6,8-dioxabicyclo[3.2.1]octane-1-yl]methanol (2.0 g, 2.6 mmol) was dissolved in tetrahydrofuran (20 mL) at room temperature, cooled to 0° C. Sodium hydride (0.21 g, 5.3 mmol, 60%) and tetrabutylammonium iodide (10 mg, 0.03 mmol) were added and stirred for 30 minutes. Benzyl bromide (0.63 mL, 5.3 mmol) was added dropwise and stirred overnight at room temperature. The reaction mixture was cooled to 0° C., and quenched with dropwise water (20 mL). The resulting mixture was extracted with ethyl acetate (20 mL) and concentrated under reduced pressure. The residue was purified by a silica gel column chromatography (EtOAc/PE(v/v)=1/6) to give the title compound as a white solid (2.2 g, 98%).

Step 2

4-[4-[[2-methyl-5-[(1S,2S,3S,4R,5S)-2,3,4-tribenzyloxy-1-(benzyloxymethyl)-6,8-dioxabicyclo[3.2.1]octane-5-yl]phenyl]methyl]phenyl]butan-1-ol

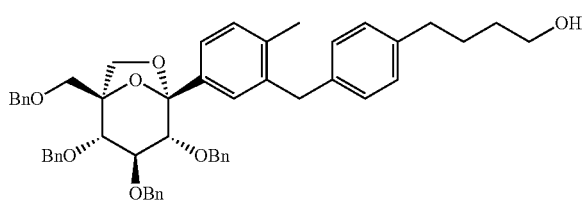 [SMILES: Cc1ccc([C@]23OC[C@](COCc4ccccc4)(O2)[C@@H](OCc2ccccc2)[C@H](OCc2ccccc2)[C@H]3OCc2ccccc2)cc1Cc1ccc(CCCCO)cc1]

[(1S,2S,3S,4R,5S)-5-[3-[[4-(4-allyloxybutyl)phenyl]methyl]-4-methyl-phenyl]-2,3,4-tribenzyloxy-1-(benzyloxymethyl)-6,8-dioxabicyclo[3.2.1]octane (2.2 g, 2.6 mmol) was dissolved in methanol (20 mL) and dichloromethane (4 mL) at room temperature, then palladium chloride (0.23 g, 1.3 mmol) was added. The mixture was stirred for 3 hours. Then the mixture was filtered and concentrated. The crude product was purified by a silica gel column chromatography (EtOAc/PE(v/v)=1/2) to give the title compound as colorless oil (1.5 g, 72%).

Step 3

4-[4-[[2-methyl-5-[(1S,2S,3S,4R,5S)-2,3,4-tribenzyloxy-1-(benzyloxymethyl)-6,8-dioxabicyclo[3.2.1]octane-5-yl]phenyl]methyl]phenyl]butyric acid

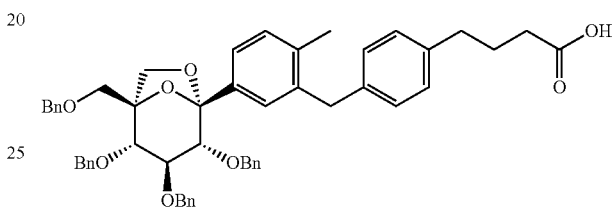

4-[4-[[2-Methyl-5-[(1S,2S,3S,4R,5S)-2,3,4-tribenzyloxy-1-(benzyloxymethyl)-6,8-dioxabicyclo[3.2.1]octane-5-yl]phenyl]methyl]phenyl]butan-1-ol (1.4 g, 1.7 mmol) was dissolved in dichloromethane (20 mL) at room temperature. Water (3 mL), 2,2,6,6-tetramethylpiperidine oxide (92 mg, 0.56 mmol) and iodobenzene diacetic acid (1.5 g, 4.6 mmol) were added in turn. The reaction mixture was stirred overnight at room temperature. Then the mixture was separated. The organic phase was dried over anhydrous sodium sulfate, filtered and concentrated. The crude product was purified by a silica gel column chromatography (EtOAc/PE(v/v)=1/2) to give the title compound as yellow oil (1.0 g, 70%).

Step 4

N-(2-dimethylaminoethyl)-2-methyl-2-[4-[4-[[2-methyl-5-[(1S,2S,3S,4R,5S)-2,3,4-tribenzyloxy-1-(benzyloxymethyl)-6,8-dioxabicyclo[3.2.1]octane-5-yl]phenyl]methyl]phenyl]butanamido]propanamide

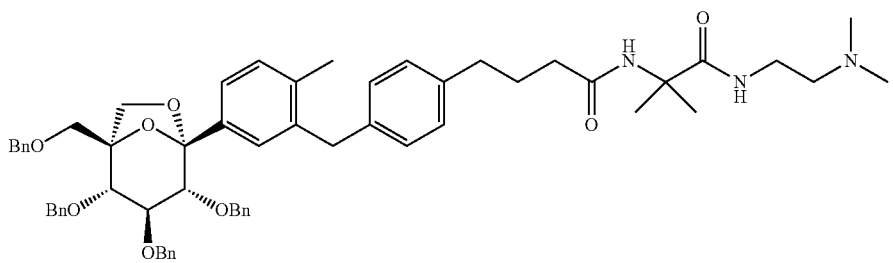 [SMILES: Cc1ccc([C@]23OC[C@](COCc4ccccc4)(O2)[C@@H](OCc2ccccc2)[C@H](OCc2ccccc2)[C@H]3OCc2ccccc2)cc1Cc1ccc(CCCC(=O)NC(C)(C)C(=O)NCCN(C)C)cc1]

4-[4-[[2-Methyl-5-[(1S,2S,3S,4R,5S)-2,3,4-tribenzyloxy-1-(benzyloxymethyl)-6,8-dioxabicyclo[3.2.1]octane-5-yl]phenyl]methyl]phenyl]butyric acid (1.0 g, 1.2 mmol) was dissolved in dichloromethane (10 mL) at room temperature. HATU (0.57 g, 1.5 mmol) and N,N-diisopropylethylamine (1.1 mL, 6.3 mmol) were added, and the mixture was stirred for 20 minutes. Then 2-Amino-N-(2-dimethylaminoethyl)-2-methyl-propionamide dihydrochloride (0.40 g, 1.6 mmol) was added and the mixture was stirred overnight. The reaction was stopped. The resulted mixture was washed with water (10 mL), dried over anhydrous sodium sulfate, filtered and concentrated. The crude product was purified by a silica gel column chromatography (dichloromethane/methanol (v/v)=30/1) to give the title compound as colorless oil (1.0 g, 84%).

Step 5

N-(2-dimethylaminoethyl)-2-methyl-2-[4-[4-[[2-methyl-5-[(1S,2S,3S,4R,5S)-2,3,4-trihydroxy-1-(hydroxymethyl)-6,8-dioxabicyclo[3.2.1]octane-5-yl]phenyl]methyl]phenyl]butanamido]propanamide

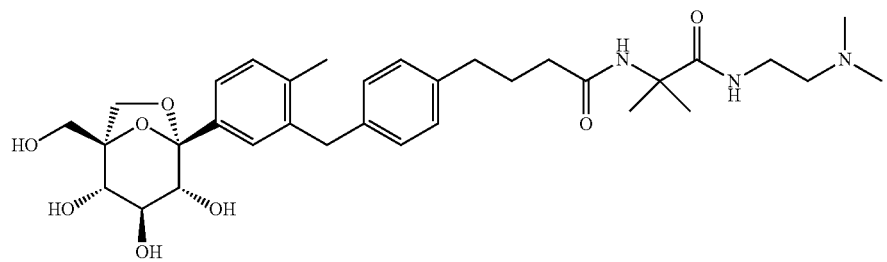 [SMILES: Cc1ccc([C@]23OC[C@](CO)(O2)[C@@H](O)[C@H](O)[C@H]3O)cc1Cc1ccc(CCCC(=O)NC(C)(C)C(=O)NCCN(C)C)cc1]

N-(2-dimethylaminoethyl)-2-methyl-2-[4-[4-[[2-methyl-5-[(1S,2S,3S,4R,5S)-2,3,4-tribenzyloxy-1-(benzyloxymethyl)-6,8-dioxabicyclo[3.2.1]octane-5-yl]phenyl]methyl]phenyl]butanamido]propanamide (1.0 g, 1.0 mmol) was dissolved in methanol (10 mL) at room temperature. 10% Palladium hydroxide/carbon (0.73 g, 0.50 mmol) was added. The reaction mixture was stirred overnight under hydrogen. Then the mixture was filtered and concentrated. The residue was purified by a silica gel column chromatography (dichloromethane/anhydrous methanol (v/v)=7/1) to give the title compound as a white solid (0.24 g, 39%).

MS (ESI, pos. ion) m/z: 614.4 [M+H]$^+$.

$^1$H NMR (400 MHz, DMSO-d$_6$) δ (ppm): 8.66 (br.s, 1H), 8.33 (s, 1H), 7.87 (t, 1H), 7.28 (s, 1H), 7.22 (d, 1H), 7.14-7.02 (m, 5H), 3.98 (d, 1H), 3.92 (s, 2H), 3.64 (d, 1H), 3.57-3.50 (m, 2H), 3.49-3.41 (m, 4H), 3.40-3.34 (m, 2H), 3.10 (m, 2H), 2.82 (s, 3H), 2.81 (s, 3H), 2.18 (s, 3H), 2.11 (t, 2H), 2.05-1.95 (m, 1H), 1.80-1.71 (m, 2H), 1.29 (s, 6H).

Example 16

N-(2-dimethylaminoethyl)-1-[4-[4-[[2-methyl-5-[(1S,2S,3S,4R,5S)-2,3,4-trihydroxy-1-(1-hydroxy-1-methyl-ethyl)-6,8-dioxabicyclo[3.2.1]octane-5-yl]phenyl]methyl]phenyl]butylamide]cyclohexyl carboxamide

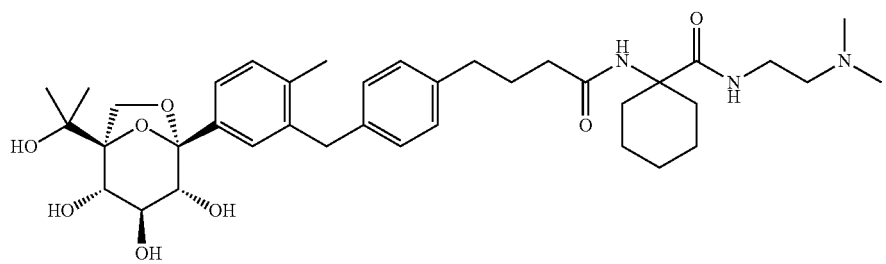 [SMILES: Cc1ccc([C@]23OC[C@](C(C)(C)O)(O2)[C@@H](O)[C@H](O)[C@H]3O)cc1Cc1ccc(CCCC(=O)NC2(C(=O)NCCN(C)C)CCCCC2)cc1]

Step 1 benzyl N-[1-(2-dimethylaminoethylcarbamoyl)cyclohexyl] carbamate

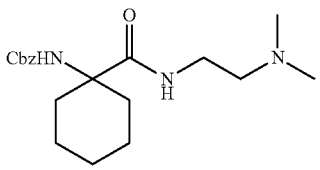 [SMILES: CN(C)CCNC(=O)C1(NC(=O)OCc2ccccc2)CCCCC1]

1-(Benzyloxycarboxamido)-cyclohexyl formic acid (2.5 g, 9.0 mmol) was dissolved in dichloromethane (30 mL) at room temperature and cooled to 0° C. HATU (4.0 g, 10 mmol) and N,N-diisopropylethylamine (5.0 mL, 29 mmol) were added, and the mixture was stirred for 20 min. N,N-dimethyl-1,2-ethanediamine (1.0 g, 11 mmol) was added, and the mixture was heated to room temperature and stirred overnight. The stir was stopped. The reaction mixture was washed with water (20 mL), dried over anhydrous sodium sulfate, filtered and concentrated. The residue was purified by a silica gel column chromatography (dichloromethane/anhydrous methanol (v/v)=30/1) to give the title compound as yellow oil (1.8 g, 57%).

Step 2

1-amino-N-(2-dimethylaminoethyl)cyclohexyl formamide

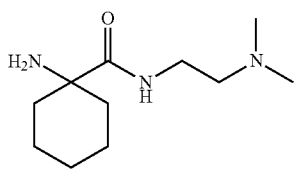

To a reaction flask were added benzyl N-[1-(2-dimethyl-aminoethylcarbamoyl)cyclohexyl]carbamate (1.8 g, 5.2 mmol), 10% palladium/carbon (0.20 g, 0.19 mmol) and methanol (20 mL) in turn at room temperature. The mixture was stirred for 3 hours under hydrogen, Then the mixture was filtered and concentrated to give the title compound as yellow oil (1.1 g, 100%).

MS (ESI, pos. ion) m/z: 214. 1[M+H]$^+$.

Step 3

1-amino-N-(2-dimethylaminoethyl)cyclohexyl formamide dihydrochloride

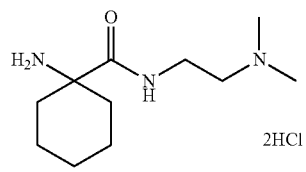

Amino-N-(2-dimethylaminoethyl)cyclohexyl formamide (1.0 g, 4.7 mmol) was dissolved in ethyl acetate (10 mL) at room temperature. A solution of HCl in isopropyl alcohol was added (3 mL, 5 M). The reaction mixture was stirred for 10 minutes, then cooled to 0° C. and stirred for 30 minutes. The mixture was filtered, the filter cake was washed with ethyl acetate (5 mL) and dried in vacuo to give the title compound as a white solid (0.92 g, 65%).

Step 4

N-(2-dimethylaminoethyl)-1-[4-[4-[[2-methyl-5-[(1S,2S,3S,4R,5S)-2,3,4-trihydroxy-1-(1-hydroxy-1-methyl-ethyl)-6,8- dioxabicyclo[3.2.1]octane-5-yl]phenyl]methyl]phenyl] butylamide]cyclobutyl formamide

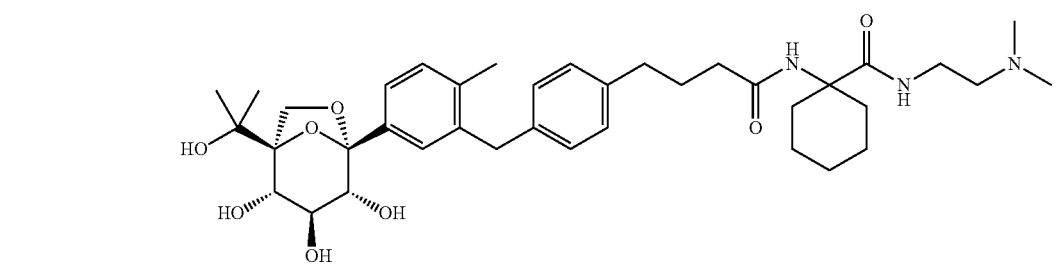 [SMILES: Cc1ccc([C@]23OC[C@](C(C)(C)O)(O2)[C@@H](O)[C@H](O)[C@H]3O)cc1Cc1ccc(CCCC(=O)NC2(C(=O)NCCN(C)C)CCCCC2)cc1]

4-[4-[[2-Methyl-5-[(1S,2S,3S,4R,5S)-2,3,4-trihydroxy-1-(1-hydroxy-1-methyl-ethyl)-6,8-dioxabicyclo[3.2.1]octane-5-yl]phenyl]methyl]phenyl]butyric acid (0.30 g, 0.62 mmol) was dissolved in DMF (0.5 mL) and dichloromethane (4 mL) at room temperature. 1-Amino-N-(2-dimethylamino-ethyl)cyclohexylcarboxamide dihydrochloride (0.28 g, 0.93 mmol), HATU (0.28 g, 0.74 mmol) and N,N-disopropylethylamine (0.54 mL, 3.1 mmol) were added in turn. The mixture was continuously stirred overnight at room temperature. Then the mixture was concentrated under reduced pressure. The residue was purified by a silica gel column chromatography (dichloromethane/methanol (v/v)=10/1-5/1) to give the title compound as a white solid (0.12 g, 28%).

MS (ESI, pos. ion) m/z: 682.5 [M+H]$^+$.

$^1$H NMR (400 MHz, DMSO-d$_6$) δ (ppm): 8.77 (br.s, 1H), 7.97 (s, 1H), 7.82 (t, 1H), 7.30 (s, 1H), 7.23 (d, 1H), 7.13-7.03 (m, 5H), 4.04 (d, 1H), 3.91 (s, 2H), 3.81 (d, 1H), 3.72 (d, 1H), 3.52-3.42 (m, 2H), 3.38 (m, 2H), 3.09 (m, 2H), 2.81 (s, 3H), 2.80 (s, 3H), 2.25 2.15 (m, 5H), 2.01 (m, 1H), 1.89 1.40 (m, 13H), 1.21 (s, 3H), 1.16 (s, 3H).

Example 17

N-(2-dimethylaminoethyl)-1-[4-[4-[[2-methyl-5-[(1S,2S,3S,4R,5S)-2,3,4-trihydroxy-1-methyl-6,8-dioxabicyclo[3.2.1]octane-5-yl]phenyl]methyl]phenyl]butanamido]cyclobutyl carboxamide

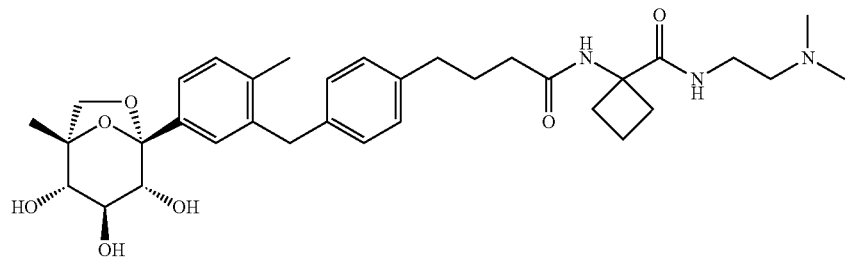

Step 1

N-(2-dimethylaminoethyl)-1-[4-[4-[[2-methyl-5-[(1S,2S,3S,4R,5S)-2,3,4-tribenzyloxy-1-methyl-6,8-dioxabicyclo[3.2.1]octane-5-yl]phenyl]methyl]phenyl]butanamide]cyclobutyl carboxamide

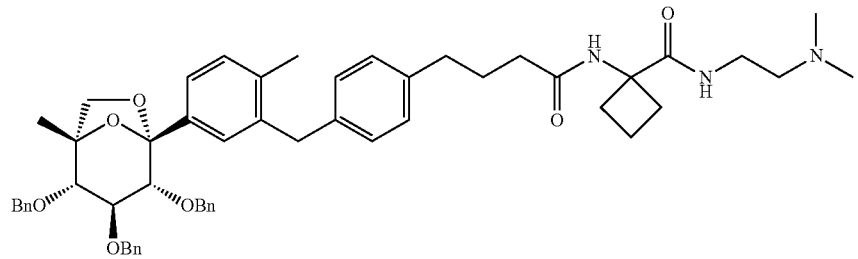

4-[4-[[2-Methyl-5-[(1S,2S,3S,4R,5S)-2,3,4-tribenzyloxy-1-methyl-6,8-dioxabicyclo[3.2.1]octane-5-yl]phenyl]methyl]phenyl]butyric acid (0.35 g, 0.49 mmol) was dissolved in dichloromethane (10 mL) at room temperature. 1-Amino-N-(2-dimethylaminoethyl)cyclohexylcarboxamide dihydrochloride (0.19 g, 0.74 mmol), HATU (0.23 g, 0.60 mmol) and N,N-disopropylethylamine (0.44 mL, 2.5 mmol) were added in turn. The mixture was continuously stirred overnight at room temperature. Then the mixture was concentrated under reduced pressure. The residue was purified by a silica gel column chromatography (dichloromethane/methanol (v/v)=10/1) to give the title compound as colorless oil (0.26 g, 60%).

Step 2

N-(2-dimethylaminoethyl)-1-[4-[4-[[2-methyl-5-[(1S,2S,3S,4R,5S)-2,3,4-trihydroxy-1-methyl-6,8-dioxabicyclo[3.2.2]octane-5-yl]phenyl]methyl]phenyl]butanamido]cyclobutyl carboxamide

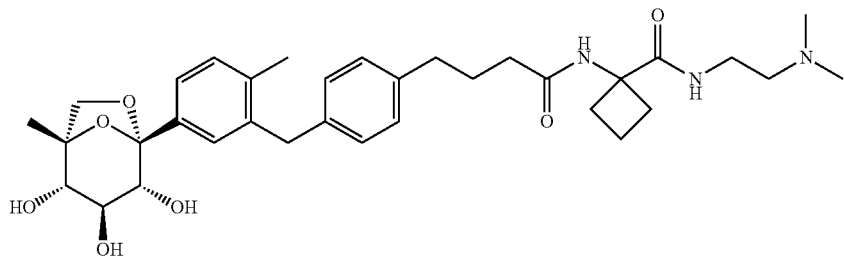

N-(2-dimethylaminoethyl)-1-[4-[4-[[2-methyl-5-[(1S,2S,3S,4R,5S)-2,3,4-tribenzyloxy-1-methyl-6,8-dioxabicyclo[3.2.1]octane-5-yl]phenyl]methyl]phenyl]butanamido]cyclobutyl carboxamide (0.26 g, 0.30 mmol) was dissolved in methanol (5 mL) at room temperature. 10% Palladium hydroxide/carbon (0.22 g, 0.15 mmol) was added. The reaction mixture was stirred overnight under hydrogen. Then the mixture was filtered and concentrated. The residue was purified by a silica gel column chromatography (dichloromethane/anhydrous methanol (v/v)=10/1-5/1) to give the title compound as a white solid (68 mg, 38%).

MS (ESI, pos. ion) m/z: 610.2 [M+H]$^+$.

$^1$H NMR (400 MHz, DMSO-d$_6$) δ (ppm): 8.83 (br.s, 1H), 8.50 (s, 1H), 7.79 (t, 1H), 7.29 (s, 1H), 7.23 (d, 1H), 7.12-7.04 (m, 5H), 4.03 (d, 1H), 3.91 (s, 2H), 3.81 (d, 1H), 3.72 (d, 1H), 3.51-3.41 (m, 2H), 3.39 (m, 2H), 3.07 (m, 2H), 2.81 (s, 3H), 2.70 (s, 3H), 2.27-2.15 (m, 5H), 2.08-1.96 (m, 5H), 1.88-1.73 (m, 4H), 1.43 (m, 1H), 1.21 (s, 3H), 1.16 (s, 3H).

Example 18

N-(2-dimethylaminoethyl)-1-[4-[4-[[2-methyl-5-[(1S,2S,3S,4R,5S)-2,3,4-trihydroxy-1-methyl-6,8-dioxabicyclo[3.2.1]octane-5-yl]phenyl]methyl]phenyl]butanamido]cyclobutyl carboxamide

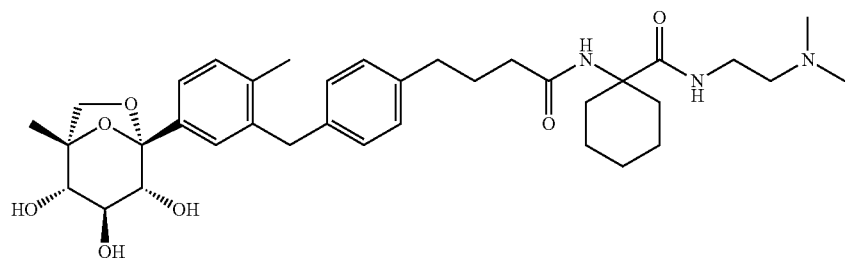

Step 1

N-(2-dimethylaminoethyl)-1-[4-[4-[[2-methyl-5-[(1S,2S,3S,4R,5S)-2,3,4-tribenzyloxy-1-methyl-6,8-dioxabicyclo[3.2.1]octane-5-yl]phenyl]methyl]phenyl]butanamido]cyclobutyl carboxamide

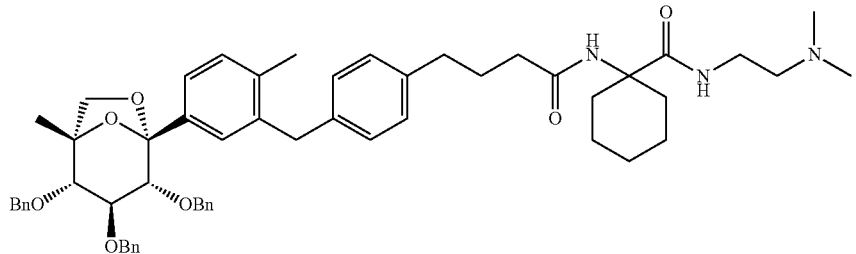

4-[4-[[2-Methyl-5-[(1S,2S,3S,4R,5S)-2,3,4-tribenzyloxy-1-methyl-6,8-dioxabicyclo[3.2.1]octane-5-yl]phenyl]methyl]phenyl]butyric acid (0.35 g, 0.49 mmol) was dissolved in dichloromethane (10 mL) at room temperature. 1-Amino-N-(2-dimethylaminoethyl)cyclohexylcarboxamide dihydrochloride (0.21 g, 0.74 mmol), HATU (0.23 g, 0.60 mmol) and N,N-diisopropylethylamine (0.44 mL, 2.5 mmol) were added in turn. The mixture was continuously stirred overnight at room temperature. Then the mixture was concentrated under reduced pressure. The residue was purified by a silica gel column chromatography (dichloromethane/methanol (v/v)=10/1) to give the title compound as colorless oil (0.29 g, 65%).

Step 2

N-(2-dimethylaminoethyl)-1-[4-[4-[[2-methyl-5-[(1S,2S,3S,4R,5S)-2,3,4-trihydroxy-1-methyl-6,8-dioxabicyclo[3.2.2]octane-5-yl]phenyl]methyl]phenyl]butanamido]cyclobutyl carboxamide

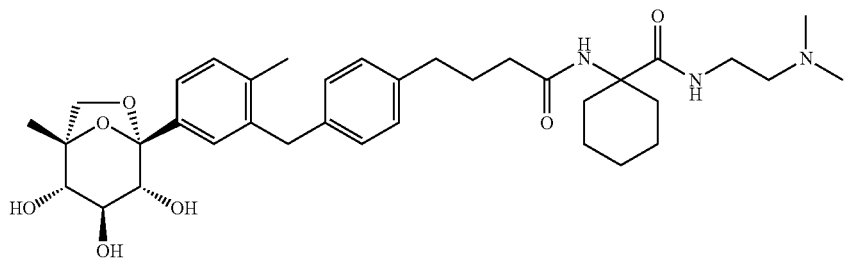

N-(2-dimethylaminoethyl)-1-[4-[4-[[2-methyl-5-[(1S,2S,3S,4R,5S)-2,3,4-tribenzyloxy-1-methyl-6,8-dioxabicyclo[3.2.1]octane-5-yl]phenyl]methyl]phenyl]butanamido]cyclohexyl carboxamide (0.29 g, 0.32 mmol) was dissolved in methanol (5 mL) at room temperature. 10% Palladium hydroxide/carbon (0.23 g, 0.16 mmol) was added. The reaction mixture was stirred overnight under hydrogen. Then the mixture was filtered and concentrated. The residue was purified by a silica gel column chromatography (dichloromethane/anhydrous methanol (v/v)=10/1-5/1) to give the title compound as a white solid (92 mg, 45%).

MS (ESI, pos. ion) m/z: 638.2 [M+H]$^+$.

$^1$H NMR (400 MHz, DMSO-$d_6$) δ (ppm): 8.72 (br.s, 1H), 7.95 (s, 1H), 7.81 (t, 1H), 7.28 (s, 1H), 7.22 (d, 1H), 7.11-7.02 (m, 5H), 4.02 (d, 1H), 3.90 (s, 2H), 3.81 (d, 1H), 3.71 (d, 1H), 3.51-3.40 (m, 2H), 3.37 (m, 2H), 3.06 (m, 2H), 2.80 (s, 3H), 2.79 (s, 3H), 2.25 2.14 (m, 5H), 2.00 (m, 1H), 1.87-1.39 (m, 13H), 1.21 (s, 3H), 1.16 (s, 3H).

Example 19

2-[4-[4-[[2-chloro-5-[(1S,2S,3S,4R,5S)-2,3,4-trihydroxy-1-(1-hydroxy-1-methyl-ethyl)-6,8-dioxabicyclo[3.2.1]octane-5-yl]phenyl]methyl]phenoxy]butanamido]-N-(2-dimethyl-aminoethyl-2-methyl-propionamide

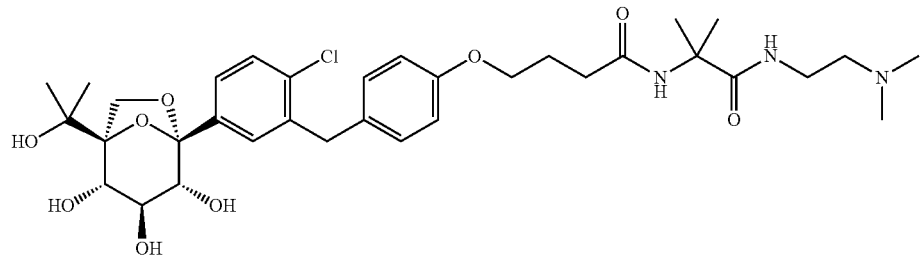 [SMILES: CN(C)CCNC(=O)C(C)(C)NC(=O)CCCOc1ccc(Cc2cc([C@]34OC[C@](C(C)(C)O)(O3)[C@@H](O)[C@H](O)[C@H]4O)ccc2Cl)cc1]

Step 1 ethyl4-[4-[[2-chloro-5-[(1S,2S,3S,4R,5S)-2,3,4-trihydroxy-1-(1-hydroxy-1-methyl-ethyl)-6,8-dioxabicyclo[3.2.1]octane-5-yl]phenyl]methyl]phenoxy]butyrate

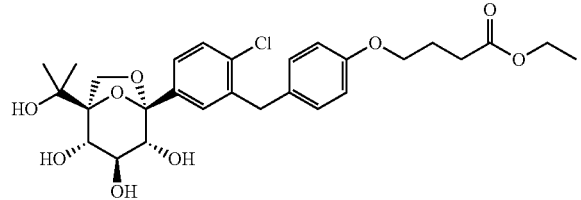 [SMILES: CCOC(=O)CCCOc1ccc(Cc2cc([C@]34OC[C@](C(C)(C)O)(O3)[C@@H](O)[C@H](O)[C@H]4O)ccc2Cl)cc1]

(1S,2S,3S,4R,5S)-5-[4-chloro-3-[(4-hydroxyphenyl)methyl]phenyl]-1-(1-hydroxy-1-methyl-ethyl)-6,8-dioxabicyclo[3.2.1]octane-2,3,4-triol (0.40 g, 0.92 mmol) was dissolved in dimethyl sulfoxide (10 mL) at room temperature. Potassium hydroxide in powder (0.15 g, 2.7 mmol) was added. The mixture was stirred at room temperature for 30 minutes, ethyl 4-bromobutyrate (0.20 g, 1.0 mmol) was added, and the mixture was stirred at room temperature for 3 hours. To the mixture was added ethyl acetate (20 mL) for diluting. The mixture was washed with saturated sodium chloride solution (30 mL×3) and concentrate under reduced pressure to give the title compound as a light yellow solid (0.37 g, 73%).

MS (ESI, pos. ion) m/z: 551.0 [M+H]⁺.

Step 2

4-[4-[[2-chloro-5-[(1S,2S,3S,4R,5S)-2,3,4-trihydroxy-1-(1-hydroxy-1-methyl-ethyl)-6,8-dioxabicyclo[3.2.1]octane-5-yl]phenyl]methyl]phenoxy]butyric acid

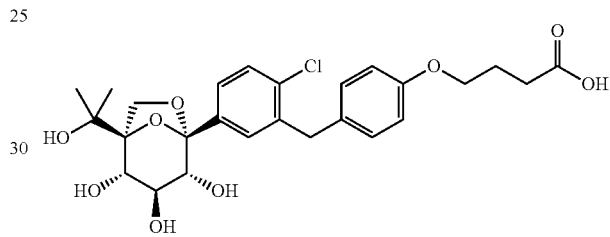

Ethyl 4-[4-[[2-chloro-S-[(1S,2S,3S,4R,5S)-2,3,4-trihydroxy-1-(1-hydroxy-1-methyl-ethyl)-6,8-dioxabicyclo[3.2.1]octane-5-yl]phenyl]methyl]phenoxy]butyrate (0.37 g, 0.67 mmol) was dissolved in the mixed solvent of tetrahydrofuran (2 mL) and methanol (2 mL). A solution of sodium hydroxide (0.12 g, 3.0 mmol) in water (1 mL) was added and the mixture was stirred at room temperature for 2 hours. Concentrated hydrochloric acid was added dropwise to the mixture to adjust pH to 4. The mixture was concentrated under reduced pressure. Water (5 mL) was added to the residue. The resulting mixture was extracted with ethyl acetate (10 mL×2). The combined organic layers were dried over ahydrous sodium sulfate, filtered and concentrated to give the title compound as an off-white white solid (0.29 g, 83%).

MS (ESI, pos. ion) m/z: 523.0 [M+H]⁺

Step 3

2-[4-[4-[[2-chloro-5-[(1S,2S,3S,4R,5S)-2,3,4-trihydroxy-1-(1-hydroxy-1-methyl-ethyl)-6,8-dioxabicyclo[3.2.1]octane-5-yl]phenyl]methyl]phenoxy]butanamido]-N-(2-dimethyl-aminoethyl)-2-methyl-propionamide

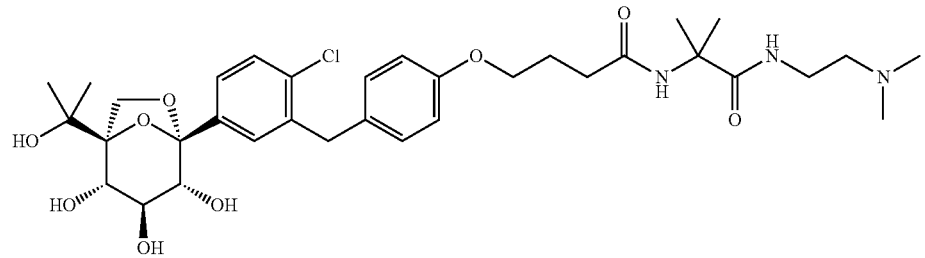 [SMILES: CN(C)CCNC(=O)C(C)(C)NC(=O)CCCOc1ccc(Cc2cc([C@]34OC[C@](C(C)(C)O)(O3)[C@@H](O)[C@H](O)[C@H]4O)ccc2Cl)cc1]

4-[4-[[2-Chloro-5-[(1S,2S,3S,4R,5S)-2,3,4-trihydroxy-1-(1-hydroxy-1-methyl-ethyl))-6,8-dioxabicyclo[3.2.1]octane-5-yl]phenyl]methyl]phenoxy]butyric acid (0.29 g, 0.55 mmol) was dissolved in DMF (0.5 mL) and dichloromethane (4 mL) at room temperature. 2-Amino-N-(2-dimethylaminoethyl)-2-methyl-propionamide dihydrochloride (0.21 g, 0.83 mmol), HATU (0.25 g, 0.66 mmol) and N,N-diisopropylethylamine (0.48 mL, 2.8 mmol) were added in turn. The mixture was continuously stirred at room temperature overnight. Then the mixture was concentrated under reduced pressure. The residue was purified by a silica gel column chromatography (dichloromethane/methanol (v/v) =10/1-5/1) to give the title compound as a white solid (91 mg, 24%).

MS (ESI, pos. ion) m/z: 678.2 [M+H]+.

$^1$H NMR (400 MHz, DMSO-d$_6$) δ (ppm): 8.58 (s, 1H), 8.31 (s, 1H), 7.84 (t, 1H), 7.46 (d, 1H), 7.39 (d, 1H), 7.34 (m, 1H), 7.13 (d, 2H), 6.87 (d, 2H), 4.22 (s, 1H), 4.02-3.83 (m, 4H), 3.77-3.70 (m, 1H), 3.49-3.38 (m, 5H), 3.11 (t, 2H), 2.81 (s, 6H), 2.15 (t, 2H), 1.79 (m, 2H), 1.29 (s, 6H), 1.21 (s, 3H), 1.16 (s, 3H).

Example 20

N-(2-dimethylaminoethyl)-1-[4-[4-[[2-methyl-5-[(1S,2S,3S,4R,5S)-2,3,4-trihydroxy-1-methyl-6,8-dioxabicyclo[3.2.1]octane-5-yl]phenyl]methyl]phenoxy]butanamido]cyclobutyl carboxamide

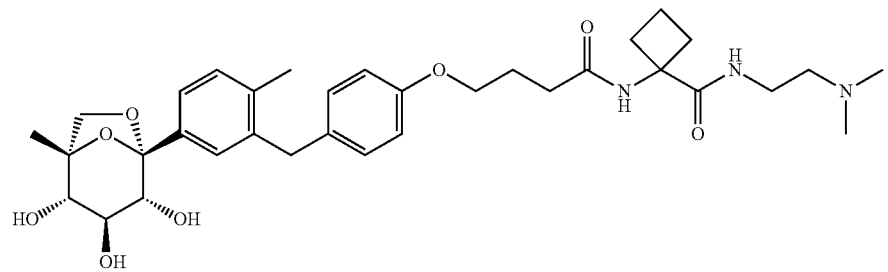

Step 1

(3R,4S,5R,6R)-3,4,5-tribenzyloxy-6-(benzyloxymethyl)tetrahydropyran-2-one

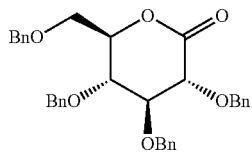

(3R,4S,5R,6R)-3,4,5-tribenzyloxy-6-(benzyloxymethyl)tetrahydropyran-2-ol (100 g, 185 mmol) was dissolved in dichloromethane (600 mL) at room temperature. Saturated sodium bicarbonate solution (1.4 L) was added, and the mixture was cooled to 0° C. Potassium bromide (13.2 g, 111 mmol) and 2,2,6,6-tetramethylpiperidine oxide (2.60 g, 16.6 mmol) were added and the mixture was stirred for 1 minute. Sodium hypochlorite solution (162 mL, 480 mmol, available chlorine 8.42%) was added at a time and the mixture was continuously stirred for 10 minutes. The reaction mixture was separated. The organic phase was washed with saturated brine (500 mL), dried over anhydrous sodium sulfate. The mixture was filtered and concentrated to give the title compound as yellow oil (100 g, 100%).

Step 2

(2R,3S,4R,5R)-2,3,4,6-tetrabenzyloxy-5-hydroxy-1-morpholine-hexane-1-one

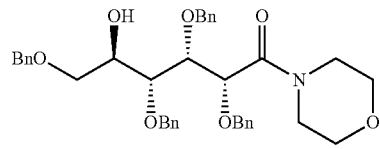 [SMILES: O=C([C@H](OCc1ccccc1)[C@@H](OCc1ccccc1)[C@H](OCc1ccccc1)[C@H](O)COCc1ccccc1)N1CCOCC1]

(3R,4S,5R,6R)-3,4,5-tribenzyloxy-6-(benzyloxymethyl)tetrahydropyran-2-one (63 g, 120 mmol) was dissolved in dichloromethane (300 mL) at room temperature and cooled to 0° C. under nitrogen. Morpholine (20 mL, 230 mmol) was added dropwise and the mixture was stirred at room temperature overnight. The mixture was washed with water (200 mL), 1N dilute hydrochloric acid (100 mL), saturated sodium bicarbonate (100 mL) and saturated sodium chloride (100 mL) in turn, and concentrated under reduced pressure. The residue was purified by a silica gel column chromatography (EtOAc/PE (v/v)=1/3-2/3) to give the title compound as light yellow oil (45 g, 61%)

MS (ESI, pos. ion) m/z: 626.4 [M+H]+. .

Step 3

(2R,3S,4S)-2,3,4,6-tetrabenzyloxy-1-morpholine-hexane-1,5-dione

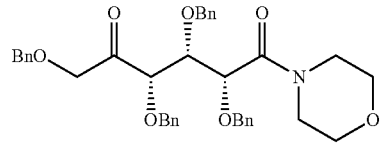 [SMILES: O=C(COCc1ccccc1)[C@@H](OCc1ccccc1)[C@H](OCc1ccccc1)[C@@H](OCc1ccccc1)C(=O)N1CCOCC1]

(2R,3S,4R,5R)-2,3,4,6-tetrabenzyloxy-5-hydroxy-1-morpholine-hexane-1-one (45 g, 72 mmol) was dissolved in toluene (360 mL). DMSO (200 mL) and N,N-diisopropylethylamine (83 mL, 0.50 mol) were added and cooled to 0° C. Sulfur trioxide pyridine complex (40 g, 0.25 mol) were added in batch. The mixture was continuously stirred at 0° C. for 4 hours. The reaction mixture was washed with water (300 mL×2) and saturated sodium chloride solution (300 mL) in turn, and dried over anhydrous sodium sulfate. The mixture was filtered and concentrated to give the title compound as yellow oil (45 g, 100%).

Step 4

(2R,3S,4S)-2,3,4,6-tetrabenzyloxy-5-hydroxy-5-methyl-1-morpholine-hexane-1-one

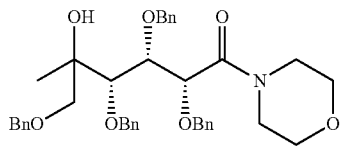 [SMILES: CC(O)(COCc1ccccc1)[C@@H](OCc1ccccc1)[C@H](OCc1ccccc1)[C@@H](OCc1ccccc1)C(=O)N1CCOCC1]

(2R,3S,4S)-2,3,4,6-tetrabenzyloxy-1-morpholine-hexane-1,5-dione (10.0 g, 16.0 mmol) was dissolved in anhydrous tetrahydrofuran (100 mL) at room temperature and cooled to −20° C. under nitrogen. A solution of methyl magnesium bromide in diethyl ether (6.0 mL, 18 mmol, 3.0 mol/L) was added dropwise. After the end of addition, the mixture was continuously stirred at −20° C. for 5 minutes. The mixture was quenched with saturated ammonium chloride solution (50 mL), and extracted with ethyl acetate (50 mL). The organic phase was washed with saturated sodium chloride solution (50 mL) and concentrated under reduced pressure to give the title compound as a yellow syrup (10.3 g, 100%).

MS (ESI, pos. ion) m/z: 640.3 [M+H]$^+$.

Step 5

(2R,3S,4S)-2,3,4,6-tetrabenzyloxy-5-methyl-1-morpholine-5-trimethylsiloxy-hexane-1-one

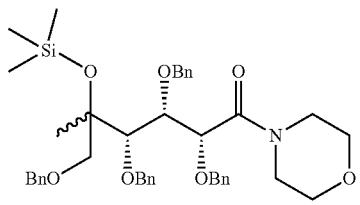 [SMILES: CC(COCc1ccccc1)(O[Si](C)(C)C)[C@@H](OCc1ccccc1)[C@H](OCc1ccccc1)[C@@H](OCc1ccccc1)C(=O)N1CCOCC1]

(2R,3S,4S)-2,3,4,6-tetrabenzyloxy-5-hydroxy-5-methyl-1-morpholine-hexane-1-one (10.3 g, 16.1 mmol) was dissolved in dichloromethane (100 mL) at room temperature and cooled to 0° C. Imidazole (3.9 g, 57 mmol) and trimethylchlorosilane (6.1 mL, 48 mmol) were added and the mixture was stirred at room temperature for 20 minutes. The reaction mixture was washed with water (100 mL×3) and saturated sodium chloride solution (100 mL) in turn, dried over anhydrous sodium sulfate. The mixture was filtered and concentrated to give the title compound as a yellow syrup (11.3 g, 99%). The crude product was directly used for the next reaction.

Step 6

1-Benzyloxy-4-bromo-benzene

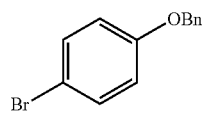 [SMILES: Brc1ccc(OCc2ccccc2)cc1]

p-Bromophenol (120 g, 694 mmol) was dissolved in acetonitrile (500 mL) at room temperature. Potassium carbonate (191 g, 1380 mmol) and benzyl bromide (86 mL, 720 mmol) were added and the mixture was stirred at room temperature for 6 hours. Then the mixture was poured into water (1.0 L) and extracted with ethyl acetate/petroleum ether (v/v=1/10, 800 mL). The organic phase was washed with water (500 mL×2) and saturated sodium chloride solution (500 mL), dried over anhydrous sodium sulfate, and concentrated under reduced pressure. To the residue was added petroleum ether (500 mL) and the mixture was stirred for 1 hour. The mixture was filtered, the filter cake was washed with petroleum ether (100 mL) and dried in vacuo to give the title compound as a white solid (160 g, 88%).

$^1$H NMR (400 MHz, DMSO-$d_6$) δ (ppm): 7.50-7.30 (m, 7H), 6.99 (d, J=8.8 Hz, 2H), 5.10 (s, 2H).

Step 7

(4-benzyloxyphenyl)magnesium bromide

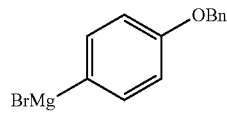

To a dry 500 mL two-necked flask were added magnesium chips (5.3 g, 220 mmol), iodine (10 mg, 0.039 mmol) and added 10 mL of 1-benzyloxy-4-bromo-benzene in anhydrous tetrahydrofuran (200 mL), 1,2-dibromoethane (0.5 mL) under nitrogen. The mixture was heated until the reaction was initiated (the color of the iodine seed disappeared), and then the remaining 1-benzyloxy-4-bromo-benzene in tetrahydrofuran was quickly added dropwise over a period of about 5 minutes. The mixture was further stirred for 10 minutes, and then heated and stirred in an oil bath at 65° C. for 1 hour to give the title compound as a gray-black solution (52 g). The obtained Grignard reagent was cooled to −10° C. and directly used for the next reaction. The yield was calculated as 90%.

Step 8

5-bromo-2-methyl-benzoyl chloride

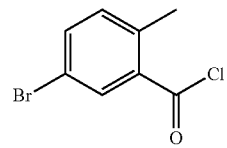

5-Bromo-2-methyl-benzoic acid (50.0 g, 233 mmol) was dissolved in dichloromethane (400 mL) at room temperature, and N,N-dimethylformamide (1.0 mL) was added and the mixture was cooled to 0° C., oxalyl chloride (30 mL, 344 mmol) was added dropwise. After the end of addition, the mixture was stirred at room temperature for 2 hours. Then the mixture was concentrated under reduced pressure to give the title compound as a yellow semi-solid (55 g, 100%). The crude product was directly used for the next reaction.

Step 9

5-bromo-N-methoxy-N,2-dimethyl-benzamide

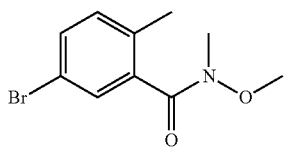

5-Bromo-2-methyl-benzoyl chloride (55 g, 236 mmol) was dissolved in dichloromethane (400 mL) at room temperature, and dimethylhydroxylamine hydrochloride (35 g, 359 mmol) was added. The mixture was cooled to 0° C. under nitrogen, triethylamine (98 mL, 708 mmol) was added dropwise. After addition, the mixture was stirred at room temperature for 2 hours. The mixture was washed with water (300 mL×2), and concentrated under reduced pressure. The residue was dissolved in ethyl acetate/petroleum ether (v/v=1/3, 400 mL), and washed with water (300 mL×2), saturated sodium bicarbonate solution (200 mL) and saturated sodium chloride solution (200 mL) in turn. Then the mixture was concentrated under reduced pressure to give the title compound as yellow oil (60 g, 99%). The crude product was directly used for the next reaction.

Step 10

(4-benzyloxyphenyl)-(5-bromo-2-methyl-phenyl)methanone

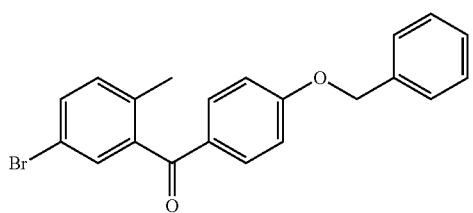 [SMILES: Cc1ccc(Br)cc1C(=O)c1ccc(OCc2ccccc2)cc1]

5-Bromo-N-methoxy-N,2-dimethyl-benzamide (42 g, 163 mmol) was dissolved in anhydrous tetrahydrofuran (60 mL) at room temperature, then added dropwise to a solution of (4-benzyloxyphenyl)magnesium bromide (52 g, 181 mmol) in tetrahydrofuran at −10° C. obtained in step 7. The mixture was stirred at room temperature for 1 hour. The mixture was poured into saturated ammonium chloride solution (200 mL), and quenched with petroleum ether (200 mL). The organic phase was washed with saturated sodium chloride solution (200 mL) and concentrated under reduced pressure. The residue was purified by beating with ethyl acetate/petroleum ether (v/v=1/30, 120 mL) to give the title compound as a yellow solid (50 g, 81%).

Step 11

2-[(4-benzyloxyphenyl)methyl]-5-bromo-1-methyl-benzene

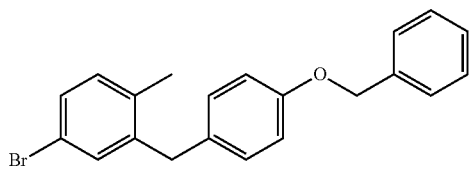 [SMILES: Cc1ccc(Br)cc1Cc1ccc(OCc2ccccc2)cc1]

(4-Benzyloxyphenyl)-(5-bromo-2-methyl-phenyl)methanone (40 g, 105 mmol) was dissolved in in a mixed solvent of dichloromethane (150 mL) and acetonitrile (150 mL) at room temperature. Triethylsilane (100 mL, 630 mmol) was added. The mixture was cooled to 0° C. under nitrogen. Boron trifluoride diethyl ether complex (26 mL, 211 mmol) was added dropwise. The mixture was stirred at room temperature for 2 hours. The reaction mixture was quenched with the dropwise addition of saturated sodium bicarbonate (300 mL), and extracted with ethyl acetate/petroleum ether (v/v=1/10, 400 mL). The organic phase was washed with saturated sodium chloride solution (300 mL) and concentrated under reduced pressure. The residue was purified by a silica gel column chromatography[dichloromethane/petroleum ether (v/v)=1/15] to give the title compound as light yellow oil. To the oil was added petroleum ether (100 mL), and the mixture was stirred for 10 min quickly. Then the mixture was filtered and dried in vacuo give the title compound as a white solid (33.5 g, 87%).

$^1$H NMR (400 MHz, DMSO-$d_6$) δ (ppm): 7.43 (d, 2H), 7.38 (t, 2H), 7.35-7.28 (m, 2H), 7.26 (s, 1H), 7.11 (d, 1H), 7.06 (d, 2H), 6.94 (d, 2H), 5.06 (s, 2H), 3.87 (s, 2H), 2.16 (s, 3H). Step 12 [3-[(4-Benzyloxyphenyl)methyl]-4-methyl-phenyl]-magnesium bromide

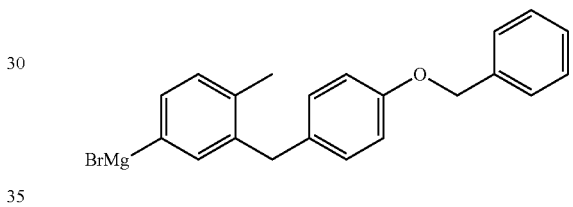

To a dry 250 mL two-necked flask were added magnesium chips (0.19 g, 7.8 mmol), iodine (10 mg, 0.039 mmol) at room temperature and added 2 mL of 2-[(4-benzyloxyphenyl)methyl]-5-bromo-1-methyl-benzene (2.8 g, 7.6 mmol) in anhydrous tetrahydrofuran (15 mL) under nitrogen. The mixture is heated until the reaction is initiated (the color of the iodine disappeared), and then the remaining 2-[(4-benzyloxyphenyl)methyl]-5-bromo-1-methyl-benzenetetrahydrofuran solution was added. The mixture was stirred in an oil bath of 65° C. for 1 hour. The mixture was cooled to room temperature to give the title compound as a brown-black solution (2.4 g, 80%).

Step 13

(2R,3S,4S)-2,3,4,6-tetrabenzyloxy-1-[3-[(4-benzyloxyphenyl)methyl]-4-methyl-phenyl]-5-methyl-5-trimethylsiloxy-hexane-1-one

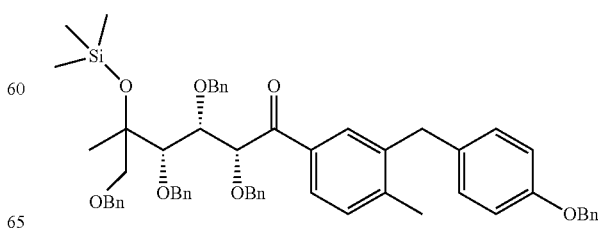

(2R,3S,4S)-2,3,4,6-tetrabenzyloxy-5-methyl-1-morpholine-5-trimethylsiloxy-hexane-1-one (3.3 g, 4.6 mmol) was dissolved in anhydrous tetrahydrofuran (20 mL) at room temperature and cooled to −10° C. under nitrogen. A solution of [3-[(4-benzyloxyphenyl)methyl]-4-methyl-phenyl]-magnesium bromide (2.4 g, 6.1 mmol) in anhydrous tetrahydrofuran obtained in Step 11 was added dropwise completely. After the end of addition, the mixture was stirred at room temperature for 1 hour. The reaction mixture was quenched with saturated aqueous ammonium chloride (20 mL) and extracted with petroleum ether (20 mL). The organic phase was washed with saturated sodium chloride solution (20 mL) and concentrated under reduced pressure. The residue was purified by a silica gel column chromatography[EtOAc/PE(v/v)=1/15] to give the title compound as colorless oil (3.6 g, 86%).

Step 14

(1S,2S,3S,4R,5S)-5-[3-[(4-hydroxyphenyl)methyl]-4-methyl-phenyl]-1-methyl-6,8-dioxabicyclo[3.2.1]octane-2,3,4-triol

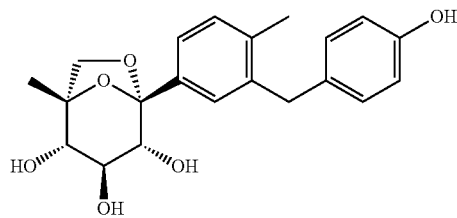

(2R,3S,4S)-2,3,4,6-tetrabenzyloxy-1-[3-[(4-benzyloxyphenyl)methyl]-4-methyl-phenyl]-5-methyl-5-trimethylsiloxy-hexane-1-one (3.6 g, 3.9 mmol) was dissolved in anisole (40 mL) at room temperature and cooled to −10° C. Aluminum trichloride (6.6 g, 49 mmol) was added to the mixture which was then stirred at room temperature for 2 hour. The mixture was cooled to 0° C., quenched with water (100 mL), and extracted with ethyl acetate (100 mL). The organic phase was washed with water (100 mL), saturated sodium bicarbonate solution (100 mL) and saturated sodium chloride (100 mL) in turn. Petroleum ether (100 mL) was added to the residue. The mixture was stirred at 0° C. for 10 minutes and concentrated under reduced pressure. The mixture was filtered and the filtrate was purified by a silica gel column chromatography (EtOAc/PE (v/v)=3/1-3/0) to give the title compound as a white solid (0.35 g, 24%).

MS (ESI, pos. ion) m/z: 373.0 [M+H]+.

Step 15 ethyl4-[4-[[2-methyl-5-[(1S,2S,3S,4R,5S)-2,3,4-trihydroxy-1-methyl-6,8-dioxabicyclo[3.2.1]octane-5-yl]phenyl]methyl]phenoxy]butyrate

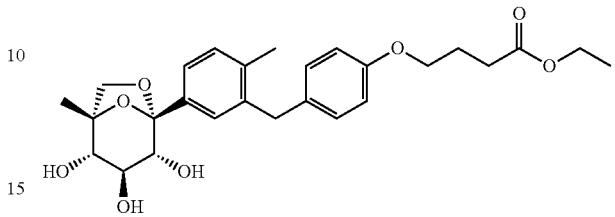

(1S,2S,3S,4R,5S)-5-[3-[(4-hydroxyphenyl)methyl]-4-methyl-phenyl]-1-methyl-6,8-dioxabicyclo[3.2.1]octane-2,3,4-triol (0.35 g, 0.94 mmol) was dissolved in dimethyl sulfoxide (8 mL) at room temperature. Potassium hydroxide in powder (0.16 g, 2.9 mmol) was added. The mixture was stirred at room temperature for 30 minutes, ethyl 4-bromobutyrate (0.20 g, 1.0 mmol) was added, and the mixture was stirred at room temperature for 3 hours. To the mixture was added ethyl acetate (20 mL) for diluting. The mixture was washed with saturated sodium chloride solution (30 mL×3) and concentrated under reduced pressure to give the title compound as a light yellow solid (0.38 g, 83%).

MS (ESI, pos. ion) m/z: 487.1 [M+H]+.

Step 16

4-[4-[[2-methyl-5-[(1S,2S,3S,4R,5S)-2,3,4-trihydroxy-1-methyl-6,8-dioxabicyclo[3.2.1]octane-5-yl]phenyl]methyl]phenoxy]butyric acid

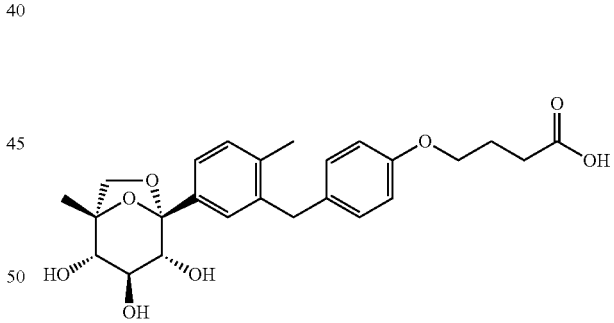

Ethyl 4-[4-[[2-methyl-5-[(1S,2S,3S,4R,5S)-2,3,4-trihydroxy-1-methyl-6,8-dioxabicyclo[3.2.1]octane-5-yl]phenyl]methyl]phenoxy]butyrate (0.38 g, 0.78 mmol) was dissolved in the mixed solvent of tetrahydrofuran (2 mL) and methanol (2 mL). A solution of sodium hydroxide (0.12 g, 3.0 mmol) in water (1 mL) was added and the mixture was stirred at room temperature for 2 hours. Concentrated hydrochloric acid was added dropwise to the mixture to adjust pH to 4. The residue was extracted with water (5 mL) and ethyl acetate (10 mL×2). The combined extracts were dried over anhydrous sodium sulfate, filtered and concentrated to give the title compound as an off-white white solid (0.33 g, 92%).

MS (ESI, pos. ion) m/z: 459.1 [M+H]+.

Step 17

N-(2-dimethylaminoethyl)-1-[4-[4-[[2-methyl-5-[(1S,2S,3S,4R,5S)-2,3,4-trihydroxy-1-methyl-6,8-dioxabicyclo[3.2.1]octane-5-yl]phenyl]methyl]phenoxy]butanamido]cyclobutyl carboxamide

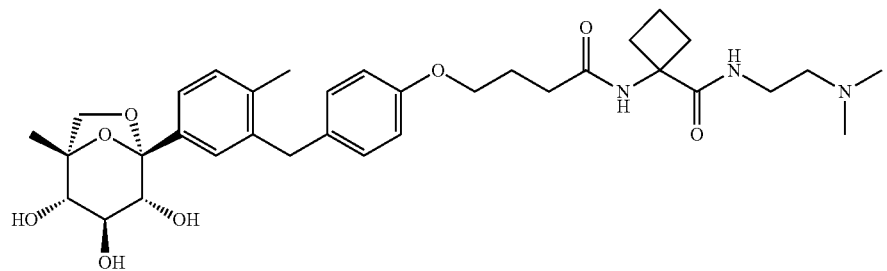

4-[4-[[2-Methyl-5-[(1S,2S,3S,4R,5S)-2,3,4-trihydroxy-1-methyl-6,8-dioxabicyclo[3.2.1]octane-5-yl]phenyl]methyl]phenoxy]butyric acid (0.20 g, 0.44 mmol) was dissolved in DMF (0.5 mL) and dichloromethane (4 mL) at room temperature. 1-Amino-N-(2-dimethylaminoethyl)cyclobutylcarboxamide dihydrochloride (0.17 g, 0.66 mmol), HATU (0.26 g, 0.65 mmol) and N,N-disopropylethylamine (0.38 mL, 2.2 mmol) were added in turn. The mixture was continuously stirred overnight at room temperature. Then the mixture was concentrated under reduced pressure. The residue was purified by a silica gel column chromatography (dichloromethane/methanol(v/v)=10/1-5/1) to give the title compound as a white solid (116 mg, 42%).

MS (ESI, pos. ion) m/z: 626.6 [M+H]⁺.

¹H NMR (400 MHz, CD₃OD) δ (ppm): 7.31 (s, 1H), 7.28 (d, 1H), 7.13 (d, 1H), 7.04 (d, 2H), 6.82 (d, 2H), 4.21 (d, 1H), 3.98 (t, 2H), 3.93 (s, 2H), 3.63-3.56 (m, 2H), 3.53 (t, 2H), 3.46 (dd, 2H), 3.17 (t, 2H), 2.89 (s, 6H), 2.67-2.57 (m, 2H), 2.46 (t, 2H), 2.20 (s, 3H), 2.18-2.10 (m, 2H), 2.08-2.01 (m, 2H), 1.99-1.87 (m, 2H), 1.37 (s, 3H).

Example 21

N-(2-dimethylaminoethyl)-1-[4-[4-[[2-methyl-5-[(1S,2S,3S,4R,5S)-2,3,4-trihydroxy-1-methyl-6,8-dioxabicyclo[3.2.1]octane-5-yl]phenyl]methyl]phenoxy]butanamido]cyclohexylcarboxamide

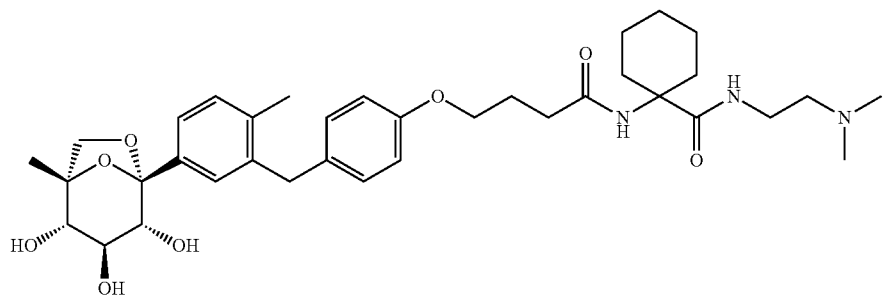 [SMILES: Cc1ccc([C@]23OC[C@](C)(O2)[C@@H](O)[C@H](O)[C@H]3O)cc1Cc1ccc(OCCCC(=O)NC2(C(=O)NCCN(C)C)CCCCC2)cc1]

4-[4-[[2-Methyl-5-[(1S,2S,3S,4R,5S)-2,3,4-trihydroxy-1-methyl-6,8-dioxabicyclo[3.2.1]octane-5-yl]phenyl]methyl]phenoxy]butyric acid (0.20 g, 0.44 mmol) was dissolved in DMF (0.5 mL) and dichloromethane (4 mL) at room temperature. 1-Amino-N-(2-dimethylaminoethyl)cyclohexylcarboxamide dihydrochloride (0.19 g, 0.66 mmol), HATU (0.26 g, 0.65 mmol) and N,N-diisopropylethylamine (0.38 mL, 2.2 mmol) were added in turn. The mixture was continuously stirred at room temperature overnight. Then the mixture was concentrated under reduced pressure. The residue was purified by a silica gel column chromatography (dichloromethane/methanol(v/v)=10/1-5/1) to give the title compound as a white solid (0.10 g, 35%).

MS (ESI, pos. ion) m/z: 654.5[M+H]$^+$;

$^1$H NMR (400 MHz, CD$_3$OD) δ (ppm): 7.31 (s, 1H), 7.28 (d, 1H), 7.13 (d, 1H), 7.03 (d, 2H), 6.81 (d, 2H), 4.21 (d, 1H), 3.97 (t, 2H), 3.92 (s, 2H), 3.58 (d, 2H), 3.55 (t, 2H), 3.50-3.43 (m, 2H), 3.19 (t, 2H), 2.89 (s, 6H), 2.49 (t, 2H), 2.20 (s, 3H), 2.07 2.00 (m, 2H), 1.91 (m, 2H), 1.78 (m, 2H), 1.64-1.49 (m, 5H), 1.39 (s, 3H), 1.31 (m, 1H).

Test Cases

1. Test of Inhibitory Activity on SGLT1

Test Purpose

The following methods can be used to determine the inhibitory activity of the compound of the invention on SGLT-1.

Test Materials $^{14}$C-AMG solution was purchased from PerkinElmer, Cat. No. NEZ080001MC.

α-Methylglucoside was purchased from Sigma, Cat. No. M9376-100G

N-methyl-D-glucosamine was purchased from Sigma, Cat. No. M2004-100G

Phloridzin was purchased from Sigma, Cat. No. P3449-1G

96-Well cell culture plate was purchased from Corning, Cat. No. 3903.

Test Method

Mock-transfected FIP-in CHO cells (3×10$^4$ cells) and expressing human SGLT1 CHO cells were seeded into 96-well plates respectively. The cells were incubated for 12 hours. Each well of the 96-well plate was washed with 150 μL of sodium-free buffer once. To each well was added 50 μL of sodium-containing buffer containing test compounds having different concentrations and 0.5 μM [$^{14}$C]-AMG. The incubation mixture was incubated at 37° C. for 1 hour. To each well was added 150 μL of precooled sodium-free buffer to terminate the reaction. The cell pellet was washed with sodiumfree buffer three times and the residual liquid in well was removed. To each well was added 20 μL of precooled 100 mM NaOH. The 96-well plate was vibrated at 900 rpm for 5 minutes. Scintillation fluid (80 μL) was added to each well which was then vibrated at 600 rpm for 5 minutes. The amount of $^{14}$C-AMG was quantitatively detected using liquid scintillation. The results are shown in table 1:

TABLE 1

Inhibitory activity on SGLT1 of the compound provided by the examples of the present invention

| Example No. | IC$_{50}$(SGLT1)/nM |
|---|---|
| Example 8 | 0.24 |
| Example 10 | 1.61 |
| Example 11 | 0.23 |
| Example 12 | 1.51 |
| Example 13 | 2.90 |

TABLE 1-continued

Inhibitory activity on SGLT1 of the compound provided by the examples of the present invention

| Example No. | IC$_{50}$(SGLT1)/nM |
|---|---|
| Example 14 | 0.57 |
| Example 16 | 0.47 |
| Example 17 | 0.40 |
| Example 18 | 0.43 |
| Example 20 | 0.55 |
| Example 21 | 0.60 |

The test results show that the compound of the present invention has a significant inhibitory effect on SGLT1.

2. Oral Glucose Tolerance Test and Urinary Glucose Excretion Test

Test Purpose

The following methods were used to evaluate the effects of the compound of the invention on improving oral glucose tolerance and glycosuria excretion.

Test Materials

The glucose was purchased from Cheng Du Kelong Chemical Reagent Company.

Roche Biochemical Analyzer: for urine sugar detection

Roche Excellence Blood Glucose Detector: for blood glucose detection

Test Method 1:

The weight and the fasting blood glucose levels of C57BL/6 mice were measured after an overnight 15-hours fast. The mice were grouped by their weights and fasting plasma glucose levels. Each test group was administered with the corresponding test compound once by gavage at a dose of 1 mg/Kg, and the blank control group was administered solvent. After 15 minutes, the blood glucose level (i.e. zero point blood glucose) of each group was measured, and each group was immediately administered glucose (2.5 g/kg) once by gavage. The blood was drawn from the caudal vein of the C57BL/6 mice at 15, 30, 60 and 120 minutes after glucose administration and the blood glucose levels were measured continuously on blood-glucose meter. The decline rate of the area under the blood sugar curve within 120 minutes (AUC$_{Glu\ 0\text{-}120\ min}$) after sugar loading was calculated.

After blood glucose level at 120 minutes time point was measured, each group was placed in a metabolism cage, and the urine was collected during 2.25 hours to 6 hours and 6 hours to 24 hours after drug administration with the metabolism cage as the unit. The urine volume of each metabolism cage at each point was recorded. The mice had free access to food and water during the urine collection. The urine was collected and centrifuged to obtain the supernatant. The urine glucose concentration of C57BL/6 mice at each time point was determined on automatic biochemical analyzer.

Test Method 2:

The weights and the fasting blood glucose levels of male SD rats were measured after an overnight 15-hours fast. The rats were grouped by their weights and fasting plasma glucose levels. Each test group was administered with the corresponding test compound once by gavage at a dose of 1 mg/Kg, and the blank control group was administered solvent. After 30 minutes, the blood glucose level (i.e., zero point blood glucose) of each group was measured, and then each group was immediately administered glucose (4.0 g/kg) once by gavage. The blood was drawn from the caudal vein of the C57BL/6 mice at 15, 30 and 60 minutes after glucose administration and the blood glucose levels were measured continuously on blood-glucose meter. The decline rate of the area under the blood sugar curve within 60 minutes (AUC$_{Glu\ 0\text{-}60min}$) after sugar loading was calculated.

After blood glucose level at 60 minutes time point was measured, each group was placed in a metabolism cage, and the urine was collected during 1.5 hours to 24 hours and 24 hours to 48 hours after drug administration with the metabolism cage as the unit. The urine volume of each metabolism cage at each point was recorded. The urine was collected and centrifuged to obtain the supernatant. The mice had free access to food and water during the urine collection. The urine glucose concentration of SD rats at each time point was determined on automatic biochemical analyzer. Results were as shown in table 2.

TABLE 2

Results of the effect of the compound provided in the examples of the present invention on blood glucose of SD rats

| Example No. | dosage (mg/kg) | hypoglycemic rate (%) |
|---|---|---|
| Example 2 | 1 | 31.64 |
| Example 6 | 1 | 33.19 |
| Example 16 | 0.1 | 30.93 |

The test results show that the compound of the present invention has remarkable effect on reducing blood sugar level.

The test results show that the compound of the present invention has remarkable effect on promoting urinary sugar excretion.

3. Pharmacokinetic Evaluation of the Compound of the Invention After Intravenous and Oral Quantification Test Purpose The following test was used to evaluate the pharmacokinetic properties of the compound of the invention in animals.

Test Method

The weights of SD rats were measured after an overnight 15-hours fast. The rats were grouped by their weights. The test compound was administered by dissolving in 5% DMSO and 5% Koliphor HS 15 and 90% Saline vehicle. For the experimental group administered intravenously, the test animals were administered with a dose of 1 mg/kg, 2 mg/kg or 5 mg/kg; for the experimental group administered orally, the test animals were administered with a dose of 5 mg/kg. Then, venous blood (about 0.2 mL) was taken at 0.083 hours before drug administration and at 0.083 (intravenous group only), 0.25, 0.5, 1.0, 2.0, 5.0, 7.0, and 24 hours after drug administration, and placed in EDTAK2 anticoagulant tubes, centrifuged at 21,000 rpm for 2 minutes. The plasma was collected, and stored at 20° C. or 70° C. until LC/MS/MS analysis. The plasma drug concentration was measured at each time point. The pharmacokinetic parameters were calculated by the method of WinNonlin 6.3 software non-compartmental model, and the drug-time curve was drawn.

The test results show that the compound provided by the present invention exhibits excellent pharmacokinetic properties when administered intravenously or orally.

In the description of the present specification, the reference terms to "one embodiment," "some embodiments," "an example," "a specific example," or "some examples," and the like means that a particular feature, structure, material, or characteristic described in connection with the embodiment or example is included in at least one embodiment or example of the present disclosure. In the present specification, the schematic representation of the above terms is not necessarily directed to the same embodiment or example. Furthermore, the particular features, structures, materials, or characteristics may be combined in any suitable manner in one or more embodiments or examples. In addition, those skilled in the art can integrate and combine different embodiments, examples or the features of them as long as they are not contradictory to one another.

Although explanatory embodiments have been shown and described, it would be appreciated by those skilled in the art that the above embodiments cannot be construed to limit the present disclosure, and changes, alternatives, and modifications can be made in the embodiments without departing from spirit, principles and scope of the present disclosure.

What is claimed is:

1. A compound having Formula (I) or a pharmaceutically acceptable salt thereof,

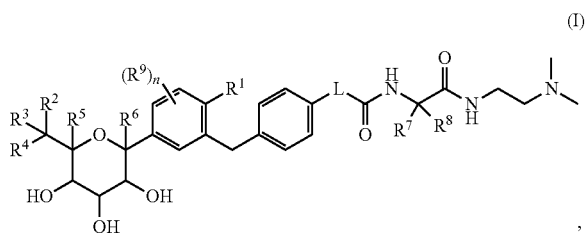

(I)

wherein,

L is $C_{1-8}$ alkylene or —Y—Z—, wherein the $C_{1-8}$ alkylene is unsubstituted or substituted with 1, 2, 3 or 4 substituents independently selected from D, F, Cl, Br, I, CN, NO$_2$, OH, NH$_2$, —C(=O)OH or —SH;

Y is —O—, —NH—, —S—, —S(=O)— or —S(=O)$_2$—;

Z is $C_{1-8}$ alkylene, wherein the $C_{1-8}$ alkylene is unsubstituted or substituted with 1, 2, 3 or 4 substituents independently selected from D, F, Cl, Br, I, CN, NO$_2$, OH, NH$_2$, —C(=O)OH or —SH;

$R^1$ is H, D, F, Cl, Br, I, OH, CN, NO$_2$, NH$_2$, $C_{1-6}$alkyl, $C_{1-6}$ alkoxy, $C_{1-6}$ hydroxyalkyl, $C_{1-6}$ haloalkyl or $C_{1-6}$ haloalkoxy, wherein each of the $C_{1-6}$ alkyl, $C_{1-6}$ alkoxy, $C_{1-6}$ hydroxyalkyl, $C_{1-6}$ haloalkyl and $C_{1-6}$ haloalkoxy is independently unsubstituted or substituted with 1, 2, 3 or 4 substituents independently selected from D, F, Cl, Br, I, CN, NO$_2$, OH, NH$_2$, —C(=O)OH or —SH;

$R^2$ is H, D, CN, =O, $C_{1-6}$ alkyl, $C_{1-6}$ alkoxy, $C_{1-6}$ alkylthio or $C_{1-6}$ alkylamino, wherein each of the $C_{1-6}$ alkyl, $C_{2-6}$ alkenyl, $C_{2-6}$ alkynyl, $C_{1-6}$ alkoxy, $C_{1-6}$ alkylthiol and $C_{1-6}$ alkylamino is independently unsubstituted or substituted with 1, 2, 3 or 4 substituents independently selected from D, F, Cl, Br, I, CN, NO$_2$, OH, NH$_2$, —C(=O)OH, —SH or =O;

$R^3$ is H, D, CN, =O, $C_{1-6}$ alkyl, $C_{1-6}$ alkoxy, $C_{1-6}$ alkylthio or —$C_{1-6}$ alkylamino, wherein each of the $C_{1-6}$ alkyl, $C_{1-6}$ alkoxy, $C_{1-6}$ alkylthiol and $C_{1-6}$ alkylamino is independently unsubstituted or substituted with 1, 2, 3 or 4 substituents independently selected from D, F, Cl, Br, I, CN, NO$_2$, OH, NH$_2$, —C(=O)OH, —SH or =O;

or $R^2$ and $R^3$, together with the carbon atom they are attached to, form a $C_{3-6}$ carbocycle or 3-6 membered heterocyclic ring, wherein each of the $C_{3-6}$ carbocycle and 3-6 membered heterocyclic ring is independently unsubstituted or substituted with 1, 2, 3 or 4 substituents independently selected from D, F, Cl, Br, I, CN, NO₂, OH, NH₂, —C(═O)OH, —SH or ═O;

R⁴ is H, D or —OR⁴ᵃ;

R⁴ᵃ is H, D, C₁₋₆ alkyl, C₃₋₆ cycloalkyl or 3-6 membered heterocyclyl, wherein each of the C₁₋₆ alkyl, C₃₋₆ cycloalkyl and 3-6 membered heterocyclyl is independently unsubstituted or substituted with 1, 2, 3 or 4 substituents independently selected from D, F, Cl, Br, I, CN, NO₂, OH, NH₂, —C(═O)OH, —SH or ═O;

each of R⁵ and R⁶ is independently H, D, F, Cl, Br, I, OH, CN, NO₂, NH₂, C₁₋₆ alkyl or C₁₋₆ alkoxy, wherein each of the C₁₋₆ alkyl and C₁₋₆ alkoxy is independently unsubstituted or substituted with 1, 2, 3 or 4 substituents independently selected from D, F, Cl, Br, I, OH, CN, NH₂ or ═O;

or R⁵ and R⁶, together with the carbon atom they are attached to respectively, form a 5 membered heterocyclyl ring or 6 membered heterocyclyl ring, wherein each of the 5 membered heterocyclyl ring and 6 membered heterocyclyl ring is independently unsubstituted or substituted with 1, 2, 3 or 4 substituents independently selected from D, F, Cl, Br, I, OH, CN, NH₂ or ═O;

R⁹ is H, D, F, Cl, Br, I, CN, NO₂, NH₂ or C₁₋₆ alkyl;

each of R⁷ and R⁸ is independently H, D, F, Cl, Br, I, CN, NO₂, OH, NH₂, C₁₋₆ alkyl, C₁₋₆ alkoxy, C₁₋₆ alkylamino, C₁₋₆ haloalkyl, C₁₋₆ haloalkoxy or C₃₋₈ cycloalkyl, wherein each of the C₁₋₆ alkyl, C₁₋₆ alkoxy, C₁₋₆ alkylamino, C₁₋₆ haloalkyl, C₁₋₆ haloalkoxy and C₃₋₈ cycloalkyl is independently unsubstituted or substituted with 1, 2, 3 or 4 substituents independently selected from D, F, Cl, Br, I, CN, NO₂, OH, NH₂, ═O, —C(═O)OH or —C(═O)NH₂;

or R⁷ and R⁸, together with the carbon atom they are attached to respectively, form a C₃₋₈ carbocycle, wherein each of the C₃₋₈ carbocycle is independently unsubstituted or substituted with 1, 2, 3 or 4 substituents independently selected from D, F, Cl, Br, I, CN, NO₂, OH, NH₂, ═O, —C(═O)OH or —C(═O)NH₂; and n is 0, 1, 2 or 3.

2. The compound of claim 1 having Formula (II),

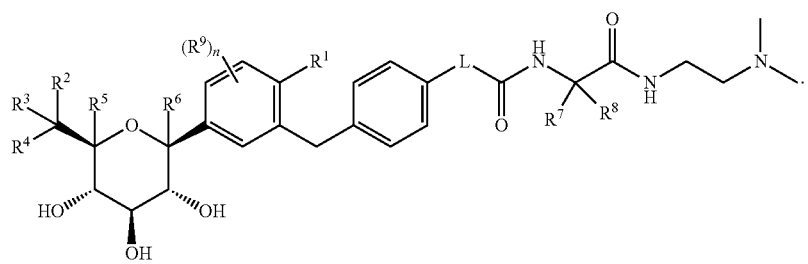

(II)

3. The compound of claim 1, wherein

L is C₁₋₆ alkylene or —Y—Z—, wherein the C₁₋₆ alkylene is unsubstituted or substituted with 1, 2, 3 or 4 substituents independently selected from D, F, Cl, Br, I, CN, NO₂, OH, NH₂, —C(═O)OH or —SH;

Y is —O—, —NH—, —S—, —S(═O)— or —S(═O)₂—; and

Z is C₁₋₆ alkylene, wherein the C₁₋₆ alkylene is unsubstituted or substituted with 1, 2, 3 or 4 substituents independently selected from D, F, Cl, Br, I, CN, NO₂, OH, NH₂, —C(═O)OH or —SH.

4. The compound of claim 1, wherein

L is —CH₂—, —CH₂CH₂—, —CH₂CH₂CH₂—, —CH(CH₃)CH₂—, —CH₂(CH₂)₂CH₂—, —C(CH₃)₂CH₂—, —CH₂(CH₂)₃CH₂—, —CH₂(CH₂)₄CH₂— or —Y—Z—, wherein each of the —CH₂—, —CH₂CH₂—, —CH₂CH₂CH₂—, —CH(CH₃)CH₂—, —C(CH₂)₂CH₂—, —C(CH₃)₂CH₂—, —CH₂(CH₂)₃CH₂— and —CH₂(CH₂)₄CH₂— is independently unsubstituted or substituted with 1, 2, 3 or 4 substituents independently selected from D, F, Cl, Br, I, CN, NO₂, OH, NH₂, —C(═O)OH or —SH;

Y is —O—, —NH—, —S—, —S(═O)— or —S(═O)₂—; and

Z is —CH₂—, —CH₂CH₂—, —CH₂CH₂CH₂—, —CH(CH₃)CH₂—, —CH₂(CH₂)₂CH₂⁻, —C(CH₃)₂CH₂—, —CH₂(CH₂)₃CH₂— or —CH₂(CH₂)₄CH₂⁻, wherein each of the —CH₂—, —CH₂CH₂⁻, —CH₂CH₂CH₂—, —CH(CH₃)CH₂—, —CH₂(CH₂)₂CH₂—, —C(CH₃)₂CH₂—, —CH₂(CH₂)₃CH₂— and —CH₂(CH₂)₄CH₂— is independently unsubstituted or substituted with 1, 2, 3 or 4 substituents independently selected from D, F, Cl, Br, I, CN, NO₂, OH, NH₂, —C(═O)OH or —SH.

5. The compound of claim 1, wherein

R¹ is H, D, F, Cl, Br, I, OH, CN, NO₂, NH₂, methyl, ethyl, n-propyl, isopropyl, methoxy, ethoxy, hydroxymethyl, trifluoromethyl, trifluoroethyl, monofluoromethyl, trifluoromethoxy or difluoromethoxy, wherein each of the methyl, ethyl, n-propyl, isopropyl, methoxy, ethoxy, hydroxymethyl, trifluoromethyl, trifluoroethyl, monofluoromethyl, trifluoromethoxy and difluoromethoxy is independently unsubstituted or substituted with 1, 2, 3 or 4 substituents independently selected from D, F, Cl, Br, I, CN, NO₂, OH, NH₂, —C(═O)OH or —SH; and R⁹ is H, D, F, Cl, Br, I, CN, NO₂, NH₂, methyl, ethyl, n-propyl or isopropyl.

6. The compound of claim 1, wherein

R² is H, D, CN, ═O, C₁₋₄ alkyl, C₁₋₄ alkoxy, C₁₋₄ alkylthio or C₁₋₄ alkylamino, wherein each of the C₁₋₄ alkyl, C₁₋₄ alkoxy, C₁₋₄ alkylthio and C₁₋₄ alkylamino is independently unsubstituted or substituted with 1, 2, 3 or 4 substituents independently selected from D, F, Cl, Br, I, CN, NO₂, OH, NH₂, —C(═O)OH, —SH or ═O;

R³ is H, D, CN, ═O, C₁₋₄ alkyl, C₁₋₄ alkoxy, C₁₋₄ alkylthio or C₁₋₄ alkylamino, wherein each of the C₁₋₄ alkyl, C₁₋₄ alkoxy, C₁₋₄ alkylthio and C₁₋₄ alkylamino is independently unsubstituted or substituted with 1, 2, 3 or 4 substituents independently selected from D, F, Cl, Br, I, CN, NO₂, OH, NH₂, —C(═O)OH or —SH;

or R² and R³, together with the carbon atom they are attached to, form a C₃₋₆ carbocycle or 5-6 membered heterocyclic ring, wherein each of the C₃₋₆ carbocycle and 5-6 membered heterocyclic ring is independently unsubstituted or substituted with 1, 2, 3 or 4 substituents independently selected from D, F, Cl, Br, I, CN, $NO_2$, OH, $NH_2$, —C(=O)OH, —SH or =O.

7. The compound of claim 1, wherein
$R^2$ is H, D, CN, =O, methyl, ethyl, n-propyl, isopropyl, methoxy, ethoxy, methylthio or methylamino, wherein each of the methyl, ethyl, n-propyl, isopropyl, methoxy, ethoxy, methylthio and methylamino is independently unsubstituted or substituted with 1, 2, 3 or 4 substituents independently selected from D, F, Cl, Br, I, CN, $NO_2$, OH, $NH_2$, —C(=O)OH or —SH;
$R^3$ is H, D, CN, =O, methyl, ethyl, n-propyl, isopropyl, methoxy, ethoxy, methylthio or methylamino, wherein each of the methyl, ethyl, n-propyl, isopropyl, methoxy, ethoxy, methylthio and methylamino is independently unsubstituted or substituted with 1, 2, 3 or 4 substituents independently selected from D, F, Cl, Br, I, CN, $NO_2$, OH, $NH_2$, —C(=O)OH, —SH or =O;
or $R^2$ and $R^3$, together with the carbon atom they are attached to, form a cyclopropane, cyclobutane, cyclopentane, cyclohexane or 5-6 membered heterocyclic ring, wherein each of the cyclopropane, cyclobutane, cyclopentane, cyclohexane and 5-6 membered heterocyclic ring is independently unsubstituted or substituted with 1, 2, 3 or 4 substituents independently selected from D, F, Cl, Br, I, CN, $NO_2$, OH, $NH_2$, —C(=O)OH, —SH or =O.

8. The compound of claim 1, wherein
$R^4$ is H, D or —$OR^{4a}$;
$R^{4a}$ is H, D, methyl, ethyl, n-propyl, isopropyl, cyclopropyl, cyclobutyl, cyclopentyl, cyclohexyl, tetrahydrofuranyl, tetrahydrothiophenyl, tetrahydropyranyl, piperidyl, morpholinyl, thiomorpholinyl or piperazinyl, wherein each of the methyl, ethyl, n-propyl, isopropyl, cyclopropyl, cyclobutyl, cyclopentyl, cyclohexyl, tetrahydrofuranyl, tetrahydrothiophenyl, tetrahydropyranyl, piperidyl, morpholinyl, thiomorpholinyl and piperazinyl is independently unsubstituted or substituted with 1, 2, 3 or 4 substituents independently selected from D, F, Cl, Br, I, CN, $NO_2$, OH, $NH_2$, —C(=O)OH or —SH.

9. The compound of claim 1, wherein
each of $R^7$ and $R^8$ is independently H, D, F, Cl, Br, I, CN, $NO_2$, OH, $NH_2$, $C_{1-4}$ alkyl, $C_{1-4}$ alkoxy, $C_{1-4}$ alkylamino, $C_{1-4}$ haloalkyl or $C_{1-4}$ haloalkoxy, $C_{3-6}$ cycloalkyl or $C_{3-6}$ cycloalkyl—$C_{1-2}$ alkylene, wherein each of the $C_{1-4}$ alkyl, $C_{1-4}$ alkoxy, $C_{1-4}$ alkylamino, $C_{1-4}$ haloalkyl, $C_{1-4}$ haloalkoxy, $C_{3-6}$ cycloalkyl and $C_{3-6}$ cycloalkyl-$C_{1-2}$ alkylene is independently unsubstituted or substituted with 1, 2, 3 or 4 substituents independently selected from D, F, Cl, Br, I, CN, $NO_2$, OH, $NH_2$, =O, —C(=O)OH or —C(=O)$NH_2$;
or $R^7$ and $R^8$, together with the carbon atom they are attached to respectively, form a $C_{3-6}$ carbocycle, wherein each of the $C_{3-6}$ carbocycle is independently unsubstituted or substituted with 1, 2, 3 or 4 substituents independently selected from D, F, Cl, Br, I, CN, $NO_2$, OH, $NH_2$, =O, —C(=O)OH or —C(=O)$NH_2$.

10. The compound of claim 1, wherein
each of $R^7$ and $R^8$ is independently H, D, F, Cl, Br, I, CN, $NO_2$, OH, $NH_2$, methyl, ethyl, n-propyl, isopropyl, n-butyl, tert-butyl, methoxy, ethoxy, methylamino, trifluoromethyl, trifluoromethoxy, difluoromethoxy, cyclopropyl, cyclobutyl, cyclopentyl, cyclohexyl or $C_{3-6}$ cycloalkyl-$C_{1-2}$ alkylene, wherein each of the methyl, ethyl, n-propyl, isopropyl, n-butyl, tert-butyl, methoxy, ethoxy, methylamino, difluoromethoxy, cyclopropyl, cyclobutyl, cyclopentyl, cyclohexyl and $C_{3-6}$ cycloalkyl-$C_{1-2}$ alkylene is independently unsubstituted or substituted with 1, 2, 3 or 4 substituents independently selected from D, F, Cl, Br, I, CN, $NO_2$, OH, $NH_2$, =O, —C(=O)OH or —C(=O)$NH_2$;
or $R^7$ and $R^8$, together with the carbon atom they are attached to respectively, form a cyclopropyl, cyclobutyl, cyclopentyl or cyclohexyl, wherein each of the cyclopropyl, cyclobutyl, cyclopentyl and cyclohexyl is independently unsubstituted or substituted with 1, 2, 3 or 4 substituents independently selected from D, F, Cl, Br, I, CN, $NO_2$, OH, $NH_2$, =O, —C(=O)OH or —C(=O)$NH_2$.

11. The compound of claim 1 having Formula (III) or Formula (IV),

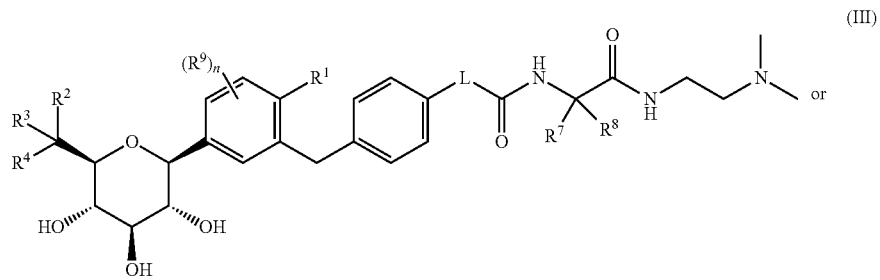

(III)

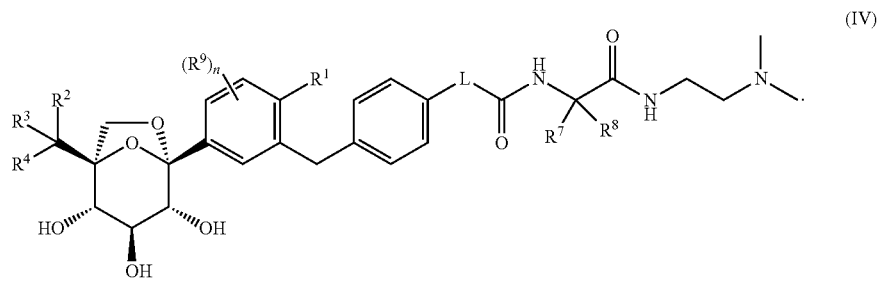

(IV)

12. The compound of claim 1 having one of the following structures:
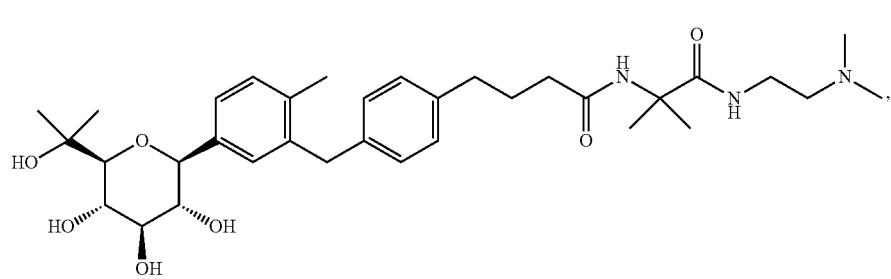
(1)
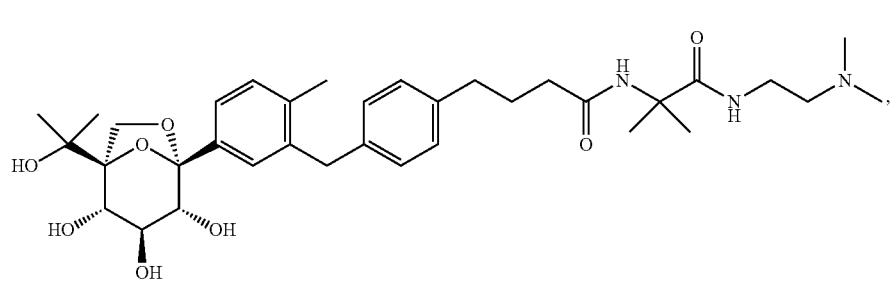
(2)
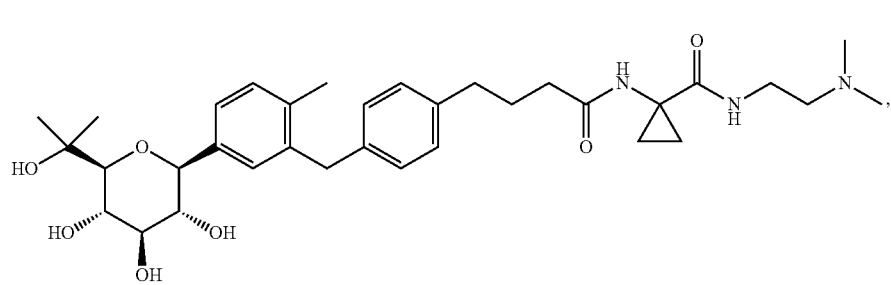
(3)
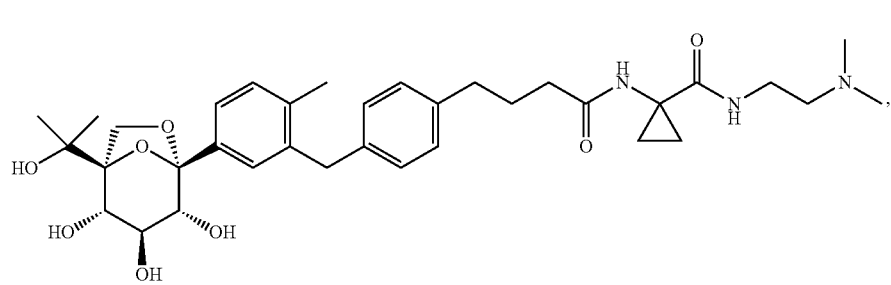
(4)
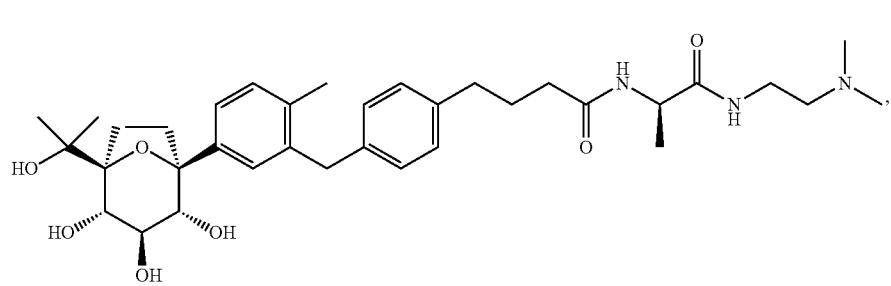
(5)

-continued
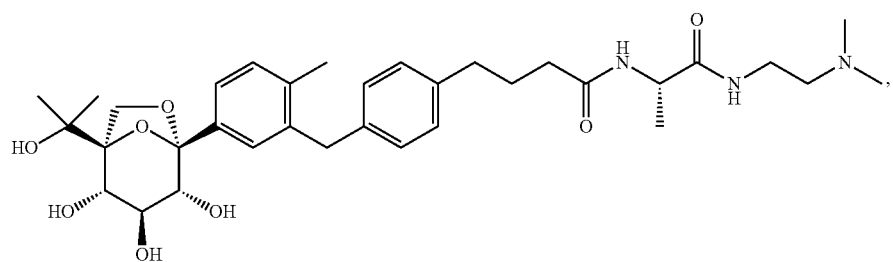
(6)
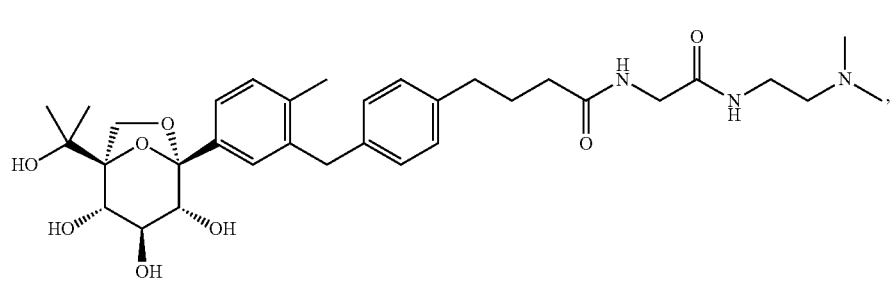
(7)
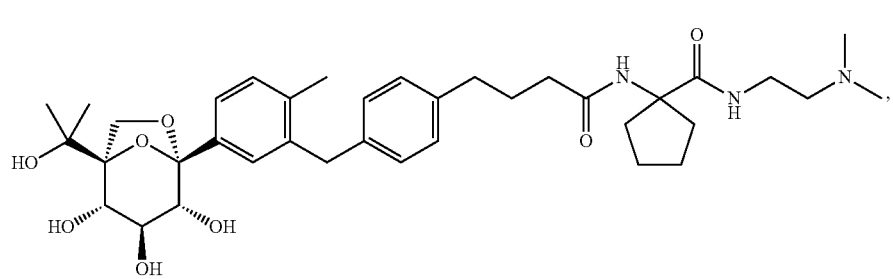
(8)
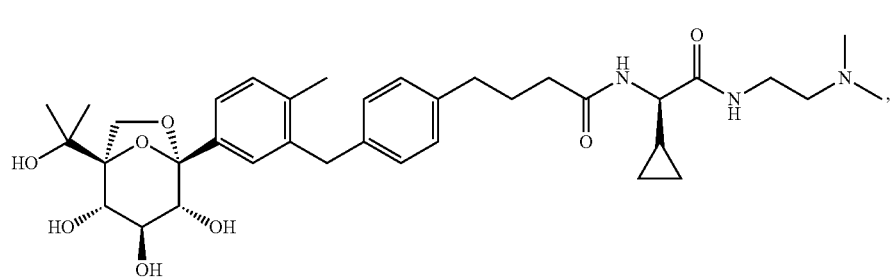
(9)
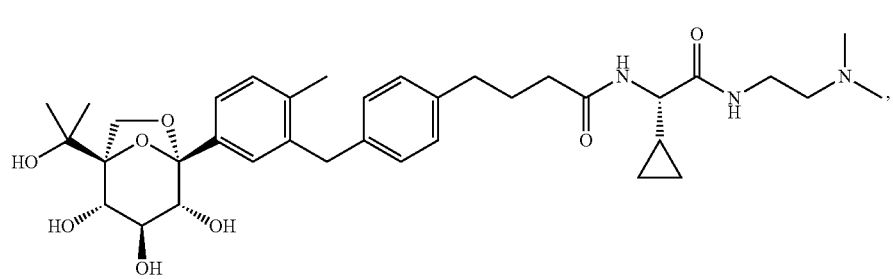
(10)
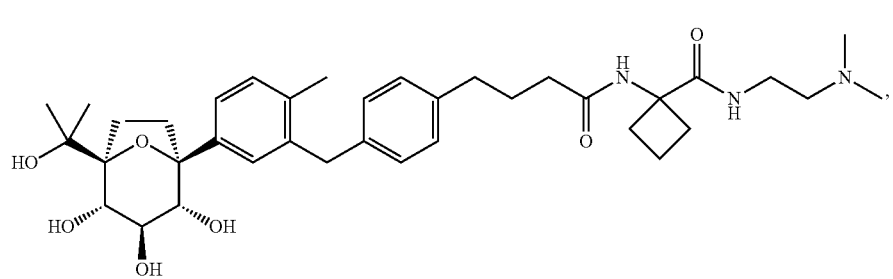
(11)

-continued
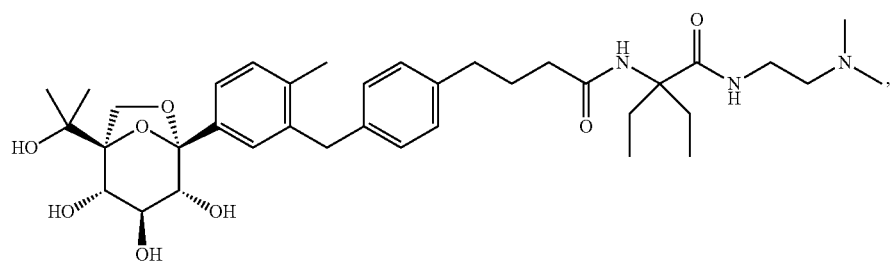
(12)
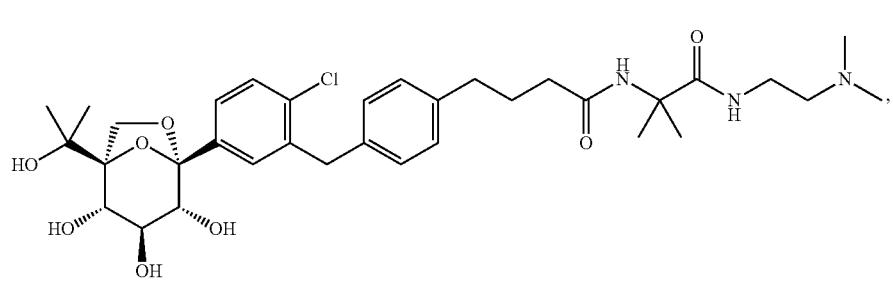
(13)
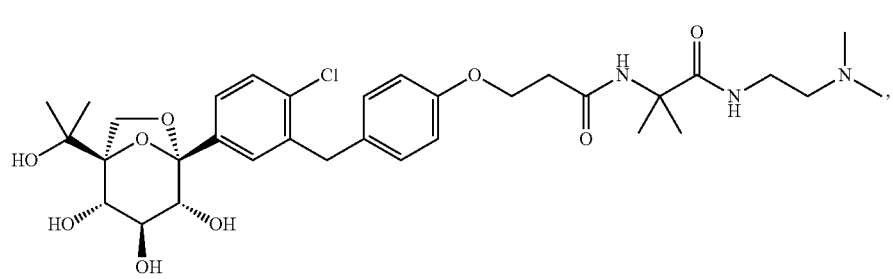
(14)
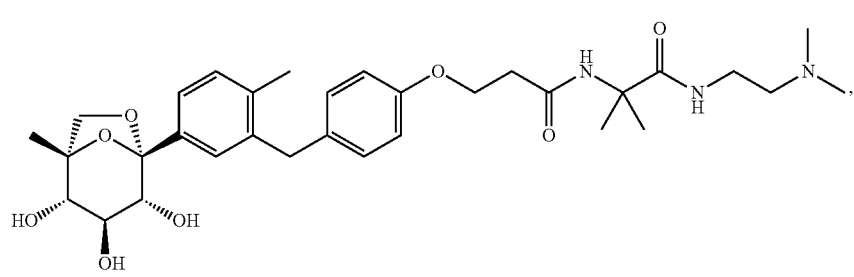
(15)
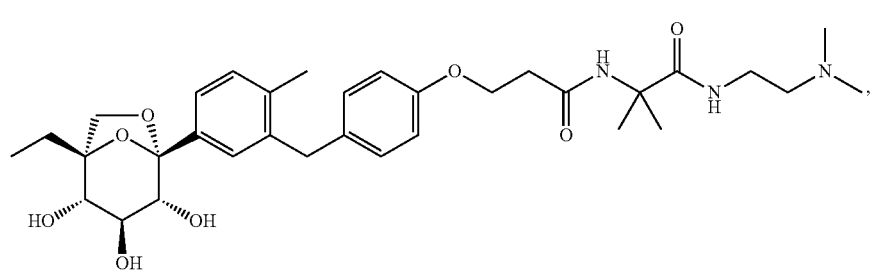
(16)
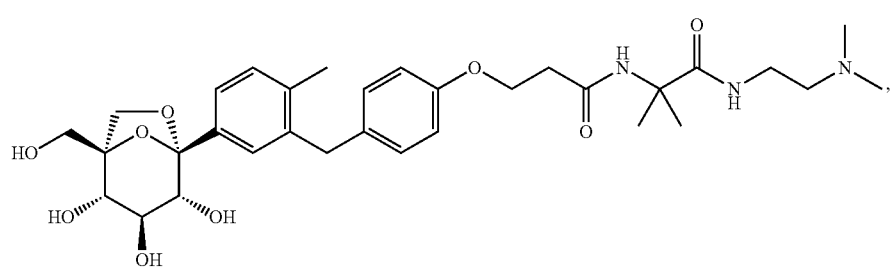
(17)

-continued
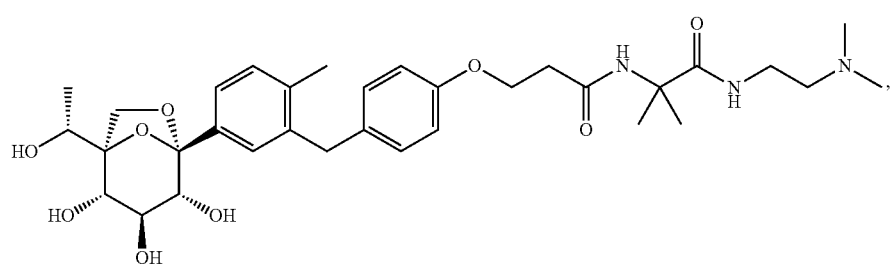
(18)
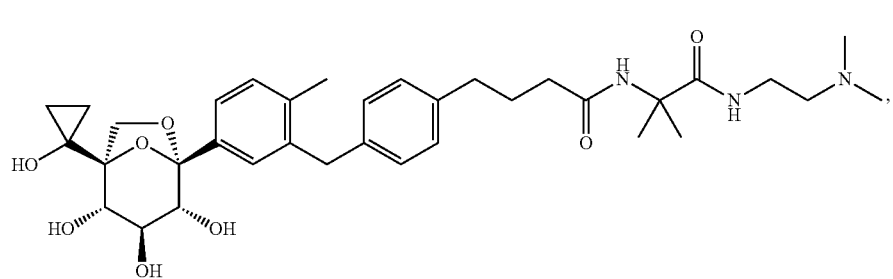
(19)
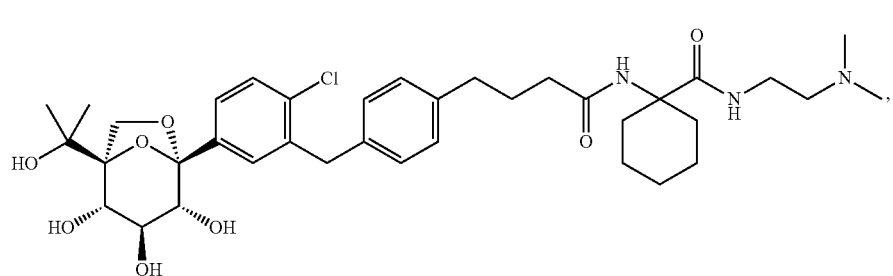
(20)
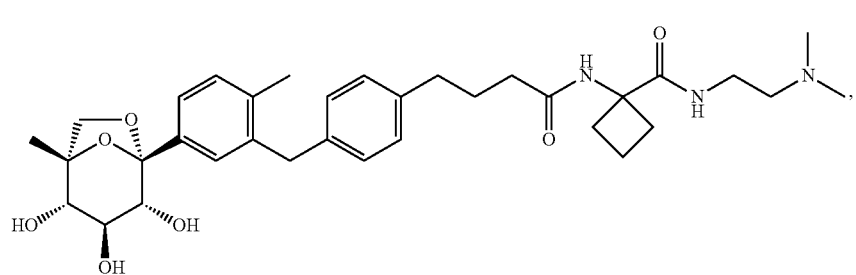
(21)
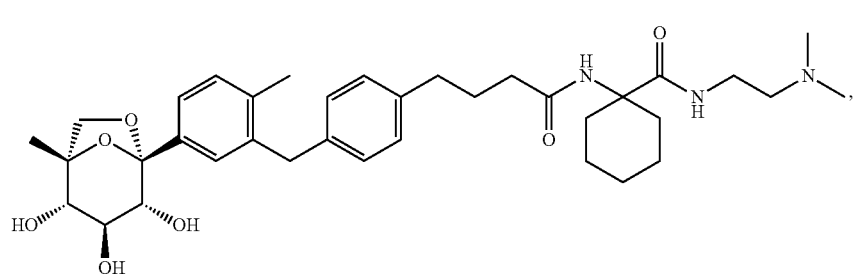
(22)
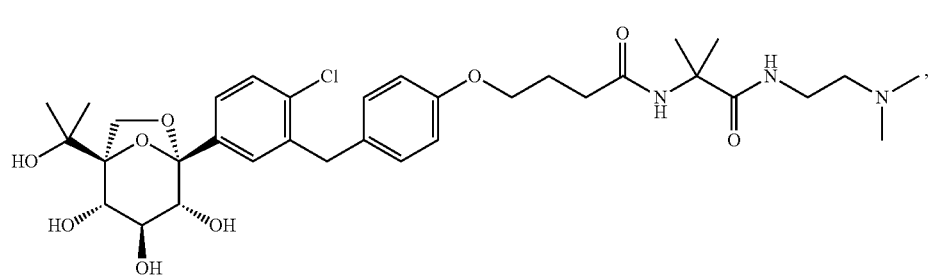
(23)

(24)

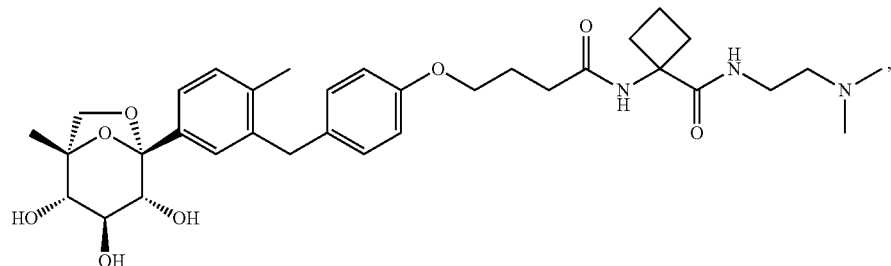

(25)

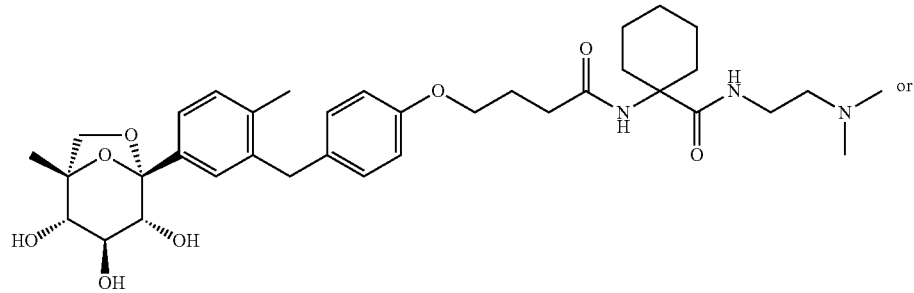

(26)

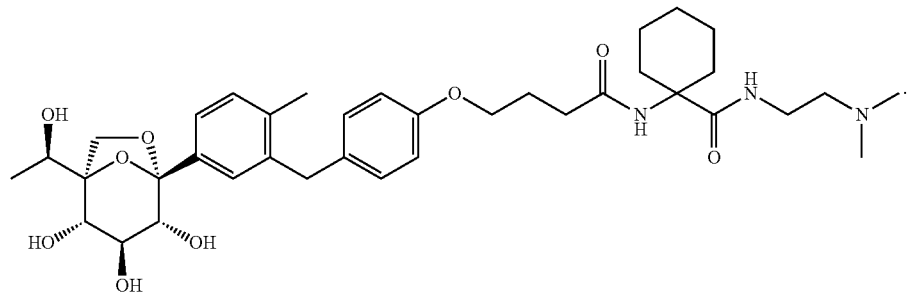

or a pharmaceutically acceptable salt thereof.

13. The compound of claim 1, wherein $R^5$ and $R^6$, together with the carbon atom they are attached to respectively, form a 5 membered heterocyclyl ring or 6 membered heterocyclyl ring, wherein each of the 5 membered heterocyclyl ring and 6 membered heterocyclyl ring is independently unsubstituted or substituted with 1, 2, 3 or 4 substituents independently selected from D, F, Cl, Br, I, OH, CN, $NH_2$ or $=O$.

14. A pharmaceutical composition comprising a compound of claim 1, and at least one selected from the group consisting of a pharmaceutically acceptable carrier, an excipient, an adjuvant, and a vehicle.

15. The pharmaceutical composition of claim 14, further comprising one or more additional therapeutic agents, wherein the additional therapeutic agent is selected from an anti-diabetic agent, an antihyperglycemic agent, an antiobesity agent, an antihypertensive agent, an appetite suppressant, a lipid-lowering agent or a combination thereof.

16. The pharmaceutical composition of claim 15, wherein each of the anti-diabetic agent and antihyperglycemic agent is independently selected from a SGLT2 inhibitor a biguanide, a sulfonylurea, a glucosidase inhibitor a PPAR agonist, a αP2 inhibitor a PPARα/γ double activator a dipeptidyl peptidase IV inhibitor a glinide, an insulin, a glucagon-like peptide-1 inhibitor a PTP1B inhibitor a glycogen phosphorylase inhibitor a glucose-6-phosphatase inhibitor or a combination thereof;

the anti-obesity drug is selected from a central anti-obesity agent, a MCH receptor antagonist, a neuropeptide Y receptor antagonist, a cannabinoid receptor antagonist, a brain-gut peptide antagonist, a lipase inhibitor a β3 agonist, a 11β-HSD1 inhibitor a DGAT-1 inhibitor a peptide appetite suppressant, a cholecystokinin agonist, a feeding inhibitor or a combination thereof;

the lipid-lowering drug is selected from a MTP inhibitor a HMGCoA reductase inhibitor a squalene synthetase inhibitor a betabutyric lipid-lowering drug, an ACAT inhibitor a lipoxygenase inhibitor a cholesterol absorption inhibitor an ileal sodium ion/bile acid cotransporter inhibitor an upregulator of LDL receptor activity, a niacin hypolipidemic drug, a bile acid chelate or a combination thereof; or the lipid-lowering drug is selected from pravastatin, simvastatin, atorvastatin, fluvastatin, cerivastatin, atorvastatin, rosuvastatin or a combination thereof.

17. A method of inhibiting SGLT1, or treating a disease, lessening symptoms of the disease or delaying progression or onset of the disease, comprising administering a therapeutically effective amount of the compound of claim 1 to the patient, wherein the disease is diabetes, diabetic complications, insulin resistance, hyperglycemia, hyperinsulinemia, hyperlipidemia, obesity, syndrome X, atherosclerosis, cardiovascular disease, congestive heart failure, hypomagnesemia, hyponatremia, renal failure, disorders associated with blood concentration, constipation or hypertension;

wherein the diabetic complications are diabetic retinopathy, diabetic neuropathy or diabetic nephropathy; the hyperlipidemia is hypertriglyceridemia.

18. A method of inhibiting SGLT1, or treating a disease, lessening symptoms of the disease or delaying progression or onset of the disease, comprising administering a therapeutically effective amount of the compound of the pharmaceutical composition of claim 14 to the patient, wherein the disease is diabetes, diabetic complications, insulin resistance, hyperglycemia, hyperinsulinemia, hyperlipidemia, obesity, syndrome X, atherosclerosis, cardiovascular disease, congestive heart failure, hypomagnesemia, hyponatremia, renal failure, disorders associated with blood concentration, constipation or hypertension; wherein the diabetic complications are diabetic retinopathy, diabetic neuropathy or diabetic nephropathy; the hyperlipidemia is hypertriglyceridemia.

\* \* \* \* \*